US006821955B2

(12) United States Patent
Orson et al.

(10) Patent No.: US 6,821,955 B2
(45) Date of Patent: Nov. 23, 2004

(54) MACROAGGREGATED PROTEIN CONJUGATES AS ORAL GENETIC IMMUNIZATION DELIVERY AGENTS

(75) Inventors: Frank M. Orson, Houston, TX (US); Berma M. Kinsey, Houston, TX (US); Balbir S. Bhogal, The Woodlands, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/827,688

(22) Filed: Apr. 6, 2001

(65) Prior Publication Data

US 2003/0165476 A1 Sep. 4, 2003

Related U.S. Application Data

(60) Provisional application No. 60/195,680, filed on Apr. 7, 2000.

(51) Int. Cl.$^7$ ........................ A01N 43/04; A61K 31/70; C12N 15/00; C12N 15/63; C12N 15/87

(52) U.S. Cl. ...................... 514/44; 435/320.1; 435/455; 435/465

(58) Field of Search ......................... 514/44; 435/320.1, 435/455, 465; 536/23.1, 53.4, 23.7, 23.72, 23.74

(56) References Cited

U.S. PATENT DOCUMENTS

| | | | | |
|---|---|---|---|---|
| 4,069,352 A | * | 1/1978 | Parsons, Jr. ..................... | 427/2 |
| 5,703,057 A | | 12/1997 | Johnston et al. | |
| 6,348,449 B1 | * | 2/2002 | Weiner et al. ................ | 514/44 |

OTHER PUBLICATIONS

Chattergoon et a. FASEB J. 11:753–763, 1997.*
Miller et al. FASEB J. 9:190–199, 1995.*
Verma et al. Nature 389:239–242, 1997.*
Denonarain, MP. Exp. Opin. Ther. Patents 8:53–69, 1998.*
McCluskie et al. Mol. Med. 5:287–300, 1999.*
Kircheis, R. et al. Coupling of cell–binding ligands to polyethyleninmine for targeted gene delivery; Gene Therapy (1997) 4, pp. 409–418.
Ogris, M. et al. The size of DNA/transferrin–PEI complexes is an important factor for gene expression in cultured cells; Gene Therapy (1998) 5, pp. 1425–1433.
Song, Li, et al. Targeted gene delivery to pulmonary endothelium by anti–PECAM antibody; Am. J. Physiol. Lun Cell. Mol. Physiol. 2000.
Wojda, Urszula, et al. Surface Membrane biotinylation Efficiently Mediates the Endocytosis of Avidin Bioconjugates into Nucleated Cells; Bioconjugate Chem. 10, 1044–1050, 1999.

Kircheis, R. et al. Coupling of cell–binding ligaands to polyethylenimine for targeted gene delivery; Gene Therapy 4, 409–418, 1997.
Erbacher, Patrick et al. Transfection and Physical Properties of Various Saccaride, Poly(ethylene glycol), and Antibody–derivatized Polyethylenimines (PEI); Physiology & Biophysic, 1999.
Piedrafita, David et al. Protective Immune Responses Induced by Vaccination with an Expression Genomic Library of Leishmania Major; The American Association of Immunologists, 1999.
Manoutcharian, Karen et al. Protection against murine cysticercosis using cDNA expression library immunization; Immunology Letters 62, 131–36; 1998.
Tan, Yadi et al. The Inhibitory Role of CpG Immunostimulatory Motifs in Cationic Lipid Vector–Mediated Transgene Expression in Vivo; Human Gene Therapy 10; 2153–2161; 1999.
Leitner, W.W. et al. DNA and RNA–based vaccines: principles, progress and prospects; Elsevier Science Ltd. Vaccine 18 765–777, 2000.
McCluskie, M. J. et al. Route and Method of Delivery of DNA Vaccine Influence Immune Responses in Mice and Non–Human Primates; Molecular Medicine 5; 287–300, 1999.
Wu, Y et al. Deoxyribonucleic Acid Vaccines Encoding Antigens with Rapid Proteasome–Dependent Degradation Are Highly Efficient Inducers of Cytolytic T Lymphocytes; The American Association of Immunologists; 6037–6043; 1997.
Densmore, C. L. et al. Aerosol Delivery of Robust Polyethyleneimine–*DNA* Complexes for Gene Therapy and Genetic Immunication; Molecular Therapy vol. 1, No. 2, 2000.
Orson, F. M. Genetic Immunization with Lung–Targeting Macroaggregated Polyethyleneimine–Albumin Conjugates Elicits Combined Systemic and Mucosal Immune Responses; The American Association of Immunologists; 6313–6321; 2000.

* cited by examiner

*Primary Examiner*—David Guzo
*Assistant Examiner*—Quang Nguyen
(74) *Attorney, Agent, or Firm*—Fulbright & Jaworski, LLP

(57) ABSTRACT

This invention relates to the development of an expression vector containing an antigenic genomic sequence, which is bound to an aggregated protein-polycationic polymer conjugate. More particularly it relates to the use of the expression vector as an oral DNA vaccine or to induce immune response. In specific embodiments, the expression vector is bound to a protein-polycationic polymer suspension.

35 Claims, 24 Drawing Sheets

A.

B.

MACROAGGREGATED PROTEIN CONJUGATES AS ORAL GENETIC IMMUNIZATION DELIVERY AGENTS

This application claims the benefit of U.S. Provisional Application No. 60/195,680 filed on Apr. 7, 2000.

The work herein was supported by grants from the United States Government. The United States Government may have certain rights in the invention

FIELD OF INVENTION

This invention relates to the use of aggregated protein-polycationic polymer conjugates in genetic vaccines. More particularly it relates to the use of macroaggregated albumin conjugates for oral delivery of vaccines.

BACKGROUND OF THE INVENTION

The mucosal immune system is extremely important in human resistance to microbial pathogens, but complicating the picture is the role of the mucosal immune system in suppressing undesirable antigenic responses to inhaled and ingested antigens in order to avoid massive allergic sensitivity (Mowat, 1987). In addition, systemic immunization usually does not elicit significant mucosal immune responses (Mestecky et al., 1994). In the context of HIV, the genital surface is the most important target tissue for immunity, and it is particularly difficult to immunize directly, especially in the male. Hence, an HIV vaccine aimed at inducing mucosal immunity will almost certainly have to be administered elsewhere (e.g., the gut), but it must still result in the accumulation of immune effector cells and molecules in the genital mucosa. Airway immunization (e.g., intranasal and intratracheal) and gut immunization have both been shown to produce responses with effector cells spilling over to other mucosal surfaces, especially the genital tract. Recent work has revealed that antigens (and particles) are delivered across the mucosal surface relatively unchanged to antigen presenting cells underneath the surface via specialized cells (membranous cells or M cells) that are derived from the normal epithelium. It is generally believed that antigens taken up by the M cells, which cover the mucosal inductive sites, are channeled to parenchymal macrophages, dendritic cells, B lymphocytes and even mast cells. Under some conditions, such as viral infection, or perhaps genetic immunization, the antigen can be processed and perhaps presented directly by the epithelial cells to the underlying B and T cells. Hence, regardless of how the antigen is administered, antigen (or antigen expressed via plasmid DNA) that can be delivered to these antigen presenting cells should result in mucosal immune responses.

In genetic immunization, a simple mammalian expression plasmid containing the gene for an antigen is administered to the animal rather than the antigen itself. Expression of the antigen gene in this manner produces the antigen intracellularly, making it a substrate for major histocompatibility (MHC) class I presentation (Schirmbeck et al., 1995) thereby enabling strong cellular immune responses to be produced. The mechanisms of antigen presentation include transfection and expression of the antigen within professional antigen presenting cells (e.g., macrophages or dendritic cells), or transfer of peptides from a different expressing cell (e.g., cytoplasm transfer from muscle cells) to a professional antigen presenting cell (Doe et al., 1996, Huang et al., 1994). Anti-HIV envelope cytotoxic T-lymphocytes (CTL) have been induced in mice and nonhuman primates by genetic immunization (Wang et al., 1994). Furthermore, intramuscular genetic vaccination with influenza nucleoprotein expressing plasmids has produced long-lived $CD8^+$ CTL mediating cross-strain protection against flu (Ulmer et al., 1994). Humoral responses, e.g., to HIV-1 envelope protein (Wang et al., 1993, Lu et al., 1995), are also produced by such immunizations, either by the target cells themselves acting as antigen presenting cells, or by shedding of the protein products from the cell surface and subsequent processing of the peptides by professional antigen presenting cells through the MHC class II pathway. In fact, repeated intramuscular injections of plasmids have resulted in a conversion of the dominant CTL response into a humoral response, with waning of the cellular cytotoxicity response in some reports (Fuller et al., 1994). Hence, the appropriate dose, timing, and route(s) for administration are critical to producing an optimal genetic immunization response.

Inefficient DNA delivery remains one of the main impediments to successful gene therapy and DNA immunizations (Thierry et al., 1997). Transfection in vivo has been accomplished using cationic lipid/DNA complexes administered by injection intravenously (Zhu et al., 1993) and intramuscularly (Mitchell et al., 1995), and by application to mucosal surfaces (Schmid et al., 1994). Naked DNA has also been used intravenously, but it has a very brief half-life (Lew et al., 1995 and Kawabata, et al. 1995) and thus is extremely inefficient. However, intramuscular and intradermal injection of naked DNA has been effective in a variety of animal models. Viral vectors can be very efficient transiently, but the induction of antiviral immune responses prevents repeated administrations and may result in lowered transgene expression (Weichselbaum et al., 1997). In addition, toxicity may result from either cationic lipids or viral vectors in some cases. Microencapsulated plasmids containing reporter genes given orally penetrate the gastrointestinal tract surfaces and cause expression of the foreign genes in the cells of the gut and associated lymphoid tissue (Mathiowitz et al., 1997). Microspheres can also penetrate lymphoid tissue given by other routes as well, as has been observed in studies of protein antigen delivery (Marx et al., 1993 and Jenkins et al., 1995). Delivery of DNA to cutaneous tissues using a gene gun (Williams et al., 1991) has produced humoral systemic immunization (Tang et al., 1992) and cellular responses that were protective in the lung against *Mycoplasma pulmonis* infection (Barry et al., 1995). Despite all of these different, methods, none has proved to be broadly efficient in gene transfection application in vivo.

Mucosal immunity has been induced by nasal administration of plasmid DNA expression vectors, e.g., protective immunity to flu virus challenge with a vector encoding the influenza hemagglutinin protein (Fynan et al., 1993). Packaging with viral vectors (e.g., adeno-associated viruses), or incorporating antigenic genes into vaccinia virus has been frequently used, but has the disadvantage of inducing an immune reaction to the associated viral proteins as well, limiting the potential for boosting, or for administration of other antigens by the same route.

Expression library immunization (ELI) is a novel vaccine approach that weds the power of recombinant DNA technology to genetic immunization (Barry et al., 1995). In ELI, a pathogen's genome is broken into small fragments and cloned into mammalian expression plasmids to create a vaccine representing all or most of the antigens of the pathogen. The expression plasmids contain a strong promoter (e.g., CMV) and expression of the protein products can be controlled by fusion to targeting sequences, i.e., the carboxy terminus of ubiquitin, which directs the protein to the proteasome for MHC class I presentation, a signal sequence for secretion, which directs the product to be secreted for antibody induction for MHC class II presentation, or without an additional sequence, which the protein is processed based on the native properties of the protein sequence. ELI was first demonstrated effective against the bacterial pathogen *Mycoplasma pulmonis* by Michael Barry and colleagues (Barry et al., 1995). Expression libraries were generated by fusing fragments of *M. pulmonis* genomic DNA to the carboxy-termini of human growth hormone (containing a signal sequence for secretion) or ubiquitin. Ubiquitin fusions were recently reported to produce CTL, but reduce antibody induction (Gillanders et al., 1997); however, gene gun vaccination with these ELI vaccines for *M. pulmonis* produced both CTL and antibody protection against mycoplasma infection at least an order of magnitude better than the best traditional mycoplasma vaccine available. ELI appears useful for generating multiple immune responses simultaneously, in a manner analogous to that of a live/attenuated pathogen vaccine. Given the pattern of responses seen in the resistant sexually exposed individuals in HIV infections, the broad range of antigen specificities that can be delivered by the expression library approach is particularly attractive. ELI vaccines are also safer than live-attenuated vaccines, because the genome of the pathogen is fragmented and scattered across large numbers of separate plasmids precluding reassembly of a pathogenic viral genome.

This invention demonstrates for the first time the use of an oral delivery system for a genetic vaccine in which the DNA is conjugated to an aggregated protein and a polycationic polymer. It is noteworthy that although the prior art in genetic vaccines have utilized other modes of delivery, the strategy of using oral delivery for a DNA vaccine has not been developed, suggesting that this invention is indeed nonobvious.

SUMMARY OF THE INVENTION

An embodiment of the present invention is a composition comprising an expression vector bound to an aggregated protein-polycationic polymer conjugate, wherein the expression vector comprises a promoter polynucleotide sequence operatively linked to a polynucleotide sequence encoding an antigen.

In a specific embodiment of the present invention, the polynucleotide sequence encoding the antigen is a fragment of a genome or gene selected from the group of genomes or genes associated with a disease consisting of infectious disease, cancer and autoimmune disease.

In another specific embodiment of the present invention, the polynucleotide sequence encoding the antigen is a fragment of a genome or gene selected from the group of pathogenic genomes consisting of virus, bacterium, fungus and protozoa. In specific embodiments, the polynucleotide sequence encoding the antigen is a fragment of a genome selected from the group viral genomes consisting of human immunodeficiency virus (HIV), herpes simplex virus (HSV) hepatitis C virus (HCV), influenza virus and respiratory syncytial virus (RSV).

In a specific embodiment of the present invention, the polynucleotide sequence encoding the antigen is a fragment of a gene selected from the group of genes associated with an autoimmune disease consisting of rheumatoid arthritis, vaculitis, and multiple sclerosis.

A further embodiment of the present invention is a composition wherein the expression vector comprises a heterologous mammalian targeting sequence. In specific embodiments, the mammalian targeting sequence is ubiquitin or a signal sequence for secretion.

Another specific embodiment of the present invention is a method of producing a DNA vaccine comprising the step of incubating an expression vector with an aggregated protein-polycationic polymer conjugate to form DNA particles wherein the expression vector comprises a promoter polynucleotide sequence operatively linked to a polynucleotide sequence encoding an antigen. In specific embodiments, the DNA vaccine is administered to a mucosal (e.g., intranasal surface, oral surface, gastrointestinal surface and genitourinary tract surface) or parenteral surface (e.g., intraperitoneal, intravenous, subcutaneous, intramusclar and intradermal) of an organism. Organisms that may be treated using the method of the invention include, but are not limited to humans, cows, horses, pigs, dogs, cats, sheep goats, rabbits, rats, mice, birds, monkeys, chickens or fish.

An additional embodiment of the present invention is the method of inducing an immune response in an organism comprising the step of administering to an organism the expression vector bound to an aggregated protein-polycationic polymer conjugate wherein the expression vector is comprises a promoter polynucleotide sequence operatively linked to a polynucleotide sequence encoding an antigen.

In specific embodiments, the method of inducing an immune response comprises the step of co-administering to an organism the expression vector bound to an aggregated protein-polycationic polymer conjugate and a cytokine expression vector.

In further embodiments, the method of inducing an immune response comprises the step of administering to an organism one expression vector bound to an aggregated protein-polycationic polymer conjugate, wherein the expression vector comprises a promoter polynucleotide sequence operatively linked to a first polynucleotide sequence encoding an antigen and a second polynucleotide sequence encoding a cytokine. In specific embodiments, the first and second polynucleotide sequences are under transcriptional control of the same promoter polynucleotide sequence. In other embodiments, the first and second polynucleotide sequences are under transcriptional control of different promoter polynucleotide sequences. One skilled in the art realizes that the polynucleotide sequences may be in tandem under control of the same promoter sequence or the polynucleotides are under control of separate promoter sequences.

A further embodiment of the present invention is the method of introducing genes into a cell comprising the steps of forming a DNA particle comprising an expression vector bound to an aggregated protein-polycationic polymer conjugate wherein the expression vector comprises a promoter polynucleotide sequence operatively linked to a polynucleotide sequence encoding an antigen, and incubating the cells with the DNA particle under conditions wherein the cells take in the DNA particle.

Another embodiment of the present invention is a composition comprising an expression vector incubated with a protein-polycationic polymer suspension, wherein the expression vector comprises a promoter polynucleotide sequence operatively linked to a polynucleotide sequence encoding an antigen.

Yet further, an additional embodiment of the present invention is the method of inducing an immune response in an organism comprising the step of administering to an organism an expression vector incubated with a protein-polycationic polymer suspension, wherein the expression vector is comprises a promoter polynucleotide sequence operatively linked to a polynucleotide sequences encoding an antigen.

Other and further objects, features and advantages would be apparent and eventually more readily understood by reading the following specification and by reference to the company drawings forming a part thereof, or any examples of the present preferred embodiments of the invention are give for the purpose of the disclosure.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A shows the cells under visible light. FIG. 2B shows the same cells under UV light illuminating the fluorescent protein.

FIG. 4A illustrates the total specific anti-hGH antibody. FIG. 4B shows serial dilution of the individual serum from each mouse described in FIG. 4A. In FIGS. 4A and 4B, the triangles represent the control samples, the diamonds represent the MAA-PEI-hGH samples and the squares represent the IM-hGH samples. FIG. 4C shows the serial dilution as in FIG. 4B from different set of experiments. In FIG. 4C, the triangles represent the control samples, the diamonds represent the MAA-PEI-hGH samples and the squares represent the IV-hGH samples.

FIG. 5A illustrates the isotype specific antibody responses from 8 week pooled serum samples from the particle, intramusclar and control unimmunized groups. The gray bars represent control, the black bars represent MAA-PEI-hGH and the white bars represent IM-hGH. FIG. 5B demonstrates the kinetics of the immune response with respect to isotype pooled samples from the 2, 6, and 12 week serum samples from the particle group. The gray bars represent 2 weeks, the black bars represent 6 weeks and the white bars represent 12 week serum samples.

FIG. 6A illustrates the isotype specific anti-hGH antibody for IgA in the lavage fluid after 8 weeks in the following groups: control unimmunized mice and mice immunized with MAA-PEI-hGH plasmid, naked hGH plasmid, or PEI-hGH plasmid complexes. The triangles represent the control samples, the diamonds represent the MAA-PEI-hGH samples and the squares represent the IV-hGH samples. FIG. 6B illustrates both IgA (white bars) and IgG (black bars) antibodies to hGH assayed in the bronchoalvedar lavage fluids.

FIG. 7A illustrates the p18 Specific splenic cytotoxic T-lymphocytes. Direct CTL assays were performed with spleen cells at 8 weeks. FIG. 7B shows the p18 specific IEL CTL elicited by MAA-PEI-CMV-UB#23 in intestinal epithelial lymphocytes. The triangles represent p18 targets and the squares represent no peptide targets.

FIG. 12A shows the mean and standard deviation of baseline (Week 0, white bars) and 9 week samples (black bars) from 6 monkeys. FIG. 12B shows the baseline (white bars) and 12 week samples (3 weeks after boost, black bars) under similar conditions.

FIG. 15A shows the dose response curve for the quantity of injected DNA. FIG. 15B shows the range of N:P ratios.

FIG. 16A shows the gene expression over time, 24 hrs, 48 hrs, 72 hrs and 96 hrs. FIG. 16A shows the gene expression for 48 hrs with one, two or three injections within the 48 hrs.

FIG. 17A shows the gene expression in the presence of a range of concentrations of HSA. FIG. 17A shows the gene expression in the presence of other soluble proteins.

FIG. 18A shows the distribution of gene expression using DNA bound to non-conjugated HSA/PEI. FIG. 18B shows the distribution of gene expression using DNA bound to conjugated MAA-PEI.

DETAILED DESCRIPTION

Figure 1:
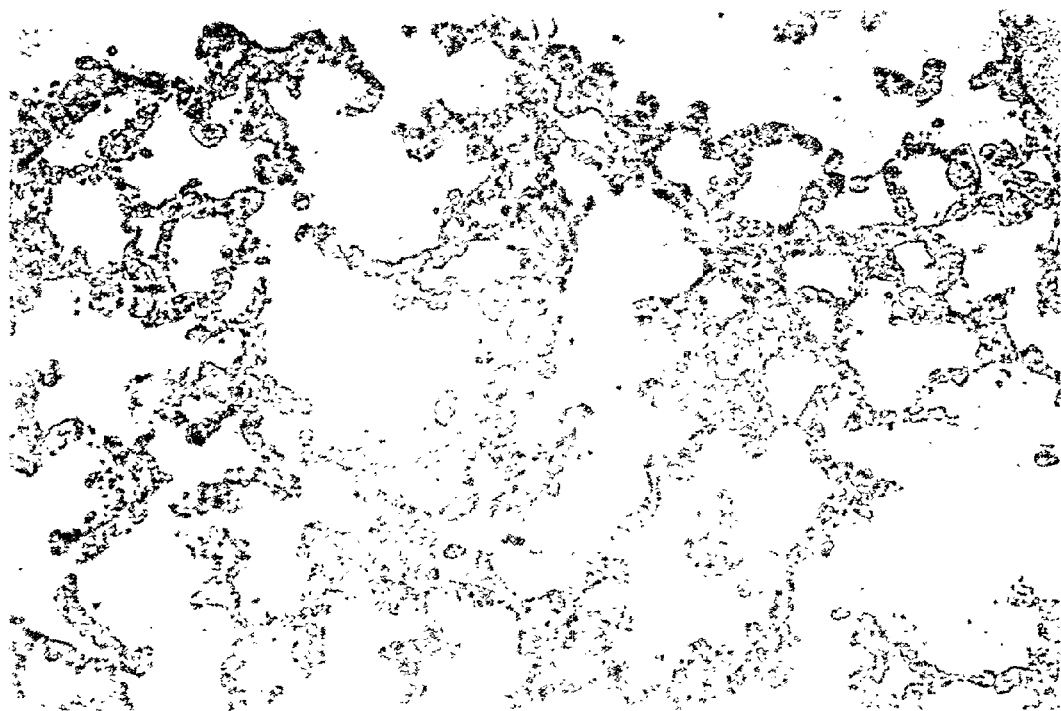
FIG. 1 shows the distribution of macroaggregated polyethyleneimine fluorescent particles in cross sections of lung tissue isolated from mice.

It is readily apparent to one skilled in the art that various embodiments and modifications may be made to the invention disclosed in this Application without departing from the scope and spirit of the invention.

As used herein the specification, "a" or "an" may mean one or more. As used herein in the claim(s), when used in conjunction with the word "comprising", the words "a" or "an" may mean one or more than one. As used herein "another" may mean at least a second or more.

The term "aggregated protein" as used herein is defined as a protein that has been combined to form a large amorphous particle. Heat and chemical denaturation are the most common methods used to aggregate proteins. Exemplary proteins that can be a aggregated include but are not limited to, albumin, lysozyme, immunoglobulins, ribonuclease, alcohol dehydrogenase and human chorionic gonadotropin.

The term "antibody" as used herein is defined as a serum immunoglobulin that has specific binding sites to combine with antigens.

The term "antigen" as used herein is defined as a molecule that provokes an immune response. This immune response may involve either antibody production, the activation of specific immunologically-competent cells, or both. An antigen can be derived from organisms, subunits of proteins/antigens, killed or inactivated whole cells or lysates. Therefore, a skilled artisan realizes that any macromolecule, including virtually all proteins, can serve as antigens. Furthermore, antigens can be derived from recombinant DNA. A skilled artisan realizes that any recombinant DNA, which contains sequences or partial sequences of a pathogenic genome or a gene for a protein that elicits an immune response can result in synthesis of an antigen.

The term "autoimmune disease" as used herein is defined as a disorder that results from autoimmune responses. Autoimmunity is an inappropriate and excessive response to self-antigens. Examples include but are not limited to, Addision's disease, Graves' disease, Type I-Diabetes mellitus, Multiple sclerosis, Myxedema, Pernicious anemia, Rheumatic fever, Rheumatoid arthritis, Systemic lupus erythematous, and ulcerative colitis.

The term "cancer" as used herein is defined as a malignant cellular neoplasm (tumor) that invades other cells. Examples include but are not limited to, breast cancer, prostate cancer, ovarian cancer, cervical cancer, skin cancer, pancreatic cancer, colorectal cancer and lung cancer.

The terms "cell," "cell line," and "cell culture" as used herein may be used interchangeably. All of these terms also include their progeny, which are any and all subsequent generations. It is understood that all progeny may not be identical due to deliberate or inadvertent mutations.

The term "conjugate" as used herein is defined as molecules bound to each other via a covalent bond. One skilled in the art recognizes that the terms "conjugate" and "cross-link" are interchangeable.

The term "cytotoxic T-lymphocytes" as used herein is defined as cells that destroy cells displaying a specific antigen recognized by their surface receptors. These cytotoxic T-lymphocytes also release lymphotoxin.

The term "DNA" as used herein is defined as deoxyribonucleic acid.

The term "DNA particle" as used herein is defined as DNA bound to a protein-polycationic polymer conjugate. The DNA may be in the form of an expression vector or plasmid or a linear DNA fragment. One of skill in the art is cognizant that the DNA is bound to the conjugate via a non-covalent bond.

The term "expression" as used herein is defined as the transcription and/or translation of a particular polynucleotide sequence driven by its promoter.

The term "expression vector" as used herein refers to a vector containing a polynucleotide sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of control sequences, which refer to polynucleotide sequences necessary for the transcription and possibly translation of an operatively linked coding sequence in a particular host organism. In addition to control sequences that govern transcription and translation, vectors and expression vectors may contain polynucleotide sequences that serve other functions as well and are described infra. One skilled in the art realizes that an "expression vector" and a "plasmid" are interchangeable.

The term "expression library immunization" or "ELI" as used herein is defined as a library constructed by cloning overlapping fragments of a particular genome into a mammalian expression plasmid. Exemplary genomes include but are not limited to, Helicobacters, Campylobacters, Clostridia, *Corynebacterium diphtheriae*, *Bordetella pertussis*, influenza virus, parainfluenza viruses, respiratory syncytial virus, hepatitis viruses, *Borrelia burgdorfei*, Plasmodium, herpes simplex viruses, human immunodeficiency virus, papilloma virus, *Vibrio cholera, E. coli*, measles virus, rotavirus, shigella, *Salmonella typhi, Neisseria gonorrhea*.

The term "immunoglobulin" or "Ig", as used herein is defined as a class of proteins, which functions as antibodies. Two members in this class of proteins are IgA and IgG. IgA functions as the primary antibody that is present in body secretions, such as saliva, tears, breast milk, gastrointestinal secretions and mucus secretions of the respiratory and genitourinary tracts. IgG functions as the most common circulating antibody.

The term "pharmaceutically acceptable carrier" as used herein includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289–1329, incorporated herein by reference). Except insofar as any conventional carrier is incompatible with the active ingredient, its use in the therapeutic or pharmaceutical compositions is contemplated.

The term "polycationic polymer" as used herein is defined as a water-soluble positively charged compound. The polycationic polymer neutralizes the negative charge of the nucleic acids allowing close proximity of the nucleic acids to the negatively charge cell membrane. Exemplary polycationic polymers include but are not limited to, polylysine, polyethyleneimine, polyhistidine, protamine, polyvinylamines, polyvinylpyridine, polymethacrylates, and polyomithine. One of skill in the art is cognizant that polyehyleneimine and polyethylenimine are interchangeable.

The term "polynucleotide" as used herein is defined as a chain of polynucleotides. Furthermore, nucleic acids are polymers of polynucleotides. Thus, nucleic acids and polynucleotides as used herein are interchangeable. One skilled in the art has the general knowledge that nucleic acids are polynucleotides, which can be hydrolyzed into the monomeric "polynucleotides." The monomeric polynucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means. Furthermore, one skilled in the art is cognizant that polynucleotides include, without limitation, mutations of the polynucleotides, including but not limited to, mutation of the polynucleotides, or nucleosides by methods well known in the art.

The term "promoter" as used herein is defined as the region of polynucleotide sequence, which regulates transcription of a specific polynucleotide sequence. The term promoter includes enhancers, silencers and other cis-acting regulatory elements. One of skill in the art is cognizant that the "promoter" refers to the nucleotide sequence recognized by the synthetic machinery of the cell, or introduced synthetic machinery, required to initiate the specific transcription of a gene.

The term "RNA" as used herein is defined as ribonucleic acid.

The term "recombinant DNA" as used herein is defined as DNA produced by joining pieces of DNA from different sources.

The term "recombinant polypeptide" as used herein is defined as a hybrid protein produced by using recombinant DNA methods.

The term "transfected" or "transformed" or "transduced" as used herein refers to a process by which exogenous nucleic acid is transferred or introduced into the host cell. A transformed cell includes the primary subject cell and its progeny.

The phrase "under transcriptional control" or "operatively linked" as used herein means that the promoter is in the correct location and orientation in relation to the polynucleotide sequence to control RNA polymerase initiation and expression of the gene.

The term "vaccine" as used herein is defined as material used to provoke an immune response (e.g., the production of antibodies) on administration of the materials and thus conferring immunity.

The term "virus" as used herein is defined as a particle consisting of polynucleotide sequences (RNA or DNA) enclosed in a protein coat, with or without an outer lipid envelope, which is only capable of replicating within a whole cell and spreading from cell to cell.

One embodiment of the present invention is a composition comprising an expression vector bound to an aggregated protein-polycationic polymer conjugate, wherein the expression vector comprises a promoter polynucleotide sequence operatively linked to a polynucleotide sequence encoding an antigen.

In preferred embodiments, the polynucleotide sequence encoding an antigen product is under transcriptional control of a promoter. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a polynucleotide sequence encoding an antigen is not believed to be important, so long as it is capable of expressing the polynucleotide sequence in the targeted cell. Thus, where a human cell is targeted, it is preferable to position the polynucleotide sequence coding region adjacent to and under the control of a promoter that is capable of being expressed in a human cell. Generally speaking, such a promoter might include either a human or viral promoter.

In various embodiments, the human cytomegalovirus (CMV) immediate early gene promoters, the SV40 early promoter and the Rous sarcoma virus long terminal repeat can be used to obtain high-level expression of the antigen of interest. The use of other viral or mammalian cellular bacterial phage promoters which are well-known in the art to achieve expression of a specific antigen are contemplated as well, provided that the levels of expression are sufficient for a given purpose.

By employing a promoter with well-known properties, the level and pattern of expression of a specific gene can be optimized. For example, selection of a promoter which is active specifically in lung cells, such as tyrosinase (melanoma), alpha-fetoprotein and albumin (liver tumors), CC10 (lung tumor) and prostate-specific antigen (prostate tumor) will permit tissue-specific expression of a specific gene. Further, selection of a promoter that is regulated in response to specific physiologic signals can permit inducible expression of a specific gene. Several elements/promoters which may be employed, in the context of the present invention, to regulate the expression of a specific gene.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

In specific embodiments of this invention, the expression vector is bound to an aggregated protein-polycationic polymer conjugate. The conjugate of an aggregated protein and a polycationic polymer makes an attractive delivery vehicle. Polycations, which are water-soluble complexes, are known in the art and have been utilized as a delivery system for DNA plamids. This strategy employs the use of a soluble system, which will convey the DNA into the cells via a receptor-mediated endocytosis (Wu & Wu 1988). For prior art to be successful, however, specific ligands or receptors must be conjugated to a polycation. The present invention is different and one skilled in the art realizes that the combination of the polycation will help neutralize the negative charge of the nucleic acid allowing increased endocytic uptake and the aggregated protein will aid in the particulate formation allowing the DNA to be taken up by the endothelial cells in the capillary bed; thus eliminating the necessity of targeting a specific cell surface receptor.

One embodiment of the present invention is that the bond between the aggregated protein-polycationic polymer is a covalent bond. For example, but not limited to, the protein is conjugated to the polycationic polymer via cross-linking an amine group to a thiol group. One skilled in the art realizes that there are several methods available to conjugate molecules. Exemplary conjugating or cross-linking methods include, but are not limited to thiol-thiol cross-linking, amine-amine cross-linking and amine-thiol cross-linking. After the conjugate is formed, the protein is aggregated.

A further embodiment of the present invention is that the expression vector is bound to the aggregated protein-polycationic polymer conjugate. One skilled in the art is cognizant that the bond between the conjugate and the expression vector or DNA is a non-covalent bond. Exemplary non-covalent bonds include, but are not limited to charge-charge interaction, charge-dipole interaction, dipole-dipole interaction, charge-induced dipole interaction, dipole-induced dipole interaction, dispersion, and hydrogen bond. In specific embodiments, the non-covalent bond is a charge-charge interaction.

In further specific embodiments, the expression vector is bound to a suspension of a protein and a polycationic polymer. The protein and the polycationic polymer are not conjugated, however, they are bound via a charge-charge interaction. Thus, a skilled artisan realizes that conjugation of the protein and polycationic polymer is not essential under all circumstances for efficient delivery of the DNA. The expression vector or DNA is combined under appropriate conditions in a suspension with a protein and a polycationic polymer and the suspension can be administered to the animal. In specific embodiments, the protein is not aggregated.

Furthermore, skilled artisans recognize that a particulate form of a DNA vaccine can be used to more efficiently target antigen-presenting cells. In general, the range of possible targets for a particulate DNA vaccine is dependent on the route of injection (e.g., intravenous or intra-arterial, subcutaneous, intra-peritoneal, intrathecal or oral). For systemic injections, the specificity of this particulate delivery system is affected by the accessibility of the target to blood borne particles, which in turn, is affected by the size range of the particles. Temperature, particle concentration, and pH affect the size of the particles. The particles can also be size-fractionated (e.g., by sucrose gradient ultracentrifugation). Particles with size less than 150 nanometers can access the interstitial space by traversing through the fenestrations that line most blood vessels walls. Hydrophilic particles with sizes greater than 0.2 microns may cross the capillary wall by endocytosis at the luminal surface, vesicular transport through cytoplasm and exocytosis at the other side where the molecule passes through the interstitial space to target macrophages and dendritic cells. In the present invention, the target size of the particles is within the range of about 0.05–50 microns.

For oral delivery, the target cells include but are not limited to, the M cells or absorptive epithelial cells. A skilled artisan realizes that the particulate DNA is engulfed by the M cells, which covers the mucosal inductive sites, and is channeled to parenchymal macrophages, dendritic cells, B lymphocytes, mast cells, and/or they can be processed and perhaps presented directly by the epithelial cells to the underlying B and T cells. Furthermore, a skilled artisan recognizes the inductive sites of the mucosal surface include the Peyer's patches in the small intestine, the appendix and solitary follicles in the large intestine and rectum, the nasal mucosa and the tonsils in the upper aerodigestive tract (Czerkinsky et al., 1999). These sites serve as the primary sources of precursor cells that migrate through the lymphatic and circulatory system.

Furthermore, the ratio of nucleic acids to conjugate can vary within a wide range, and it is not absolutely necessary to neutralize all the charges of the nucleic acids. This ratio will have to be adjusted for each individual case depending on criteria such as the size and structure of the nucleic acids, the size of the polycation and the number and distribution of its charges, so as to achieve a ratio of transportability and biological activity of the nucleic acids which is favorable to the particular application. This ratio can first of all be adjusted coarsely, for example by using the delay in the speed of migration of the DNA in a gel (e.g., using the mobility shift on an agarose gel) or by density gradient centrifugation. Once this provisional ratio has been obtained, it may be expedient to carry out transporting tests with labeled complexes, e.g., radioactive isotopes, stable isotopes, or fluorescent tags, with respect to the maximum available activity of the nucleic acid in the cell and then reduce the proportion of conjugate if necessary so that the remaining negative charges of the nucleic acid are not an obstacle to transportation into the cell.

In a specific embodiment of the present invention, the polynucleotide sequence encoding the antigen is a fragment of a genome or gene selected from the group of genomes or genes associated with a disease consisting of infectious disease, cancer and autoimmune disease. More particularly, the polynucleotide sequence encoding the antigen is a fragment of a genome selected from the group of pathogenic genomes consisting of virus, bacterium, fungus and protozoa. In specific embodiments, the polynucleotide sequence encoding the antigen is a fragment of a genome selected from the group viral genomes consisting of human immunodeficiency virus (HIV), herpes simplex virus (HSV), hepatitis C virus (HCV), influenza virus and respiratory syncytial virus (RSV). In a further embodiment of the present invention, the polynucleotide sequence encoding the antigen is a fragment of a gene selected from the group of genes associated with an autoimmune disease consisting of rheumatoid arthritis, vaculitis, and multiple sclerosis.

The following polynucleotide sequences are representative sequences corresponding to HIV, HSV, HCV, influenza virus or RSV genomes or fragments of the genomes and are within the scope of the invention and some are referenced with the corresponding GenBank Accession Numbers U23 (SEQ.ID.NO:1); AF041850: SHIV-HXBc2P 3.2, complete (SEQ.ID.NO:3); U12055: HIV-1, isolate LW12.3, lab worker, complete genome (SEQ.ID.NO:4); M76764: SHIV clone 1A11, complete genome (SEQ.ID.NO:5); NC_001433: Hepatitis C virus, complete genome (SEQ.ID.NO:6); AF290978: Hepatitis C virus isolate colonel complete genome (SEQ.ID.NO:7); NC_001798: Human herpesvirus 2, complete genome (SEQ.ID.NO:8); NC_001781: Human respiratory syncytial virus, complete genome (SEQ.ID.NO:10); AF321523: HIV-1 clone MJ4 from Botswana, complete genome (SEQ.ID.NO:11) and K02007: HIV-1, isolate ARV-2/SF2, complete proviral genome; (SEQ.ID.NO:12). One of skill in the art is cognizant that the above sequences are representative sequences of several pathogenic genomes. It is well known and understood that standard methods of molecular biology can be used to isolate and clone a sequence of any pathogen of interest and to use this sequence in the present invention.

This invention utilizes the technique of expression library immunization to construct the recombinant plasmids that are used to induce an immune response. This technique has been used to produce immunologic responses similar to live vaccines without the risk of reversion to pathogenic viruses. The ELI is constructed by cloning overlapping fragments of the antigenic genome or gene (genomic DNA or cDNA) of interest into mammalian expression plasmids. Therefore, a skilled artisan realizes that any genome, gene and fragments of genomes and genes associated with infectious disease, cancer or autoimmune disease can be used to construct an ELI and this DNA plasmid or plasmids can be used in the present invention to induce an immune response. In addition to the above-mentioned possibilities for ELI, another possibility is the use of a gene that is important in regulatory processes at the mucosal surface. For example, interleukin 5 and interleukin 13 are thought to play a regulatory role in asthma. Therefore, an ELI could be constructed to IL-5 or IL-13 and used as a potential vaccine to treat asthma.

A further embodiment of the present invention is a composition wherein the expression vector comprises a heterologous mammalian targeting sequence. In specific embodiments, the mammalian targeting sequence is ubiquitin or a signal sequence for secretion. Skilled artisans recognize that the use of particular targeting sequences direct the antigen to particular compartments within the cell. It has been documented that the insertion downstream of a ubiquitin sequence enhanced the cytotoxic lymphocyte response because the ubiquitin sequence targets the antigen to the proteasome for degradation and presentation via the MHC class I pathway. However, the addition of a signal sequence for secretion, specifically targets the antigen for secretion, which allows for presentation via the MHC type II pathway or B lymphocytes. Exemplary proteins, which contain signal sequences for secretion, that could be used to target the antigen for secretion include but are not limited to, hormones, cytokines, neurotransmitters, and immunoglobulins. Thus, skilled artisans realize that any targeting sequence can be substituted in the present invention to achieve the desired response.

Another specific embodiment of the present invention is a method of producing a DNA vaccine comprising the step of forming a DNA particle comprising an expression vector bound to an aggregated protein-polycationic polymer conjugate. In specific embodiments, the DNA vaccine will be administered to a mucosal (e.g., intranasal surface, oral surface, gastrointestinal surface and genitourinary tract surface) or parenteral surface (e.g., intraperitoneal, intravenous, subcutaneous, intramusclar and intradermal) of an organism. A skilled artisan recognizes the importance of developing mucosal immunization methods because the majority of deaths from infectious diseases are caused by organisms that first make contact with and either colonize or cross the mucosal surface to infect the host. Therefore, for many infections, such as HIV, a vaccine that does not prevent the initial infection of the host will unlikely succeed in resolving the infection before the disease ensues. Mucosal immunization induces IgA antibodies, which are directed against specific pathogens of mucosal surfaces. It is suggested in the art that greater than 80% of all the antibodies produced in mucosal-associated lymphoid tissues may block attachment of bacteria and viruses. This blockade neutralizes bacterial toxins and inactivates invading viruses inside the epithelial cells. Therefore, a skilled artisan can readily recognize that mucosal immunization would actually prevent the initial infection resulting in a decrease in the morbidity caused by pathogens.

An additional embodiment of the present invention is the method of inducing an immune response comprising the step of administering to an organism the expression vector bound to an aggregated protein-polycationic polymer conjugate wherein the expression vector comprises a promoter polynucleotide sequence, and a polynucleotide sequence encoding an antigen, operatively linked.

In specific embodiments, the method of inducing an immune response comprises the step of co-administering to an organism the expression vector and a cytokine expression vector. A number of studies have shown that the responses to individual plasmids can be enhanced by co-administration of a cytokine expressing plasmid. It should be noted that picogram to nanogram quantities of locally synthesized cytokine from the expression vector are too low to have systemic effects on the whole animal, but can still strongly influence the local cytokine environment and thus the immune response to the administered antigen. A skilled artisan readily recognizes that the polynucleotide sequences for a cytokine and the polynucleotide sequences for the antigen can be incorporated into one expression vector; thus eliminating the use of two separate vectors. In addition to cytokines, plasmids that contain ummethylated CpG sequences enhance the cell mediated (Th1) response (Carson et al., 1997). CpG sequence motifs include but are not limited to, RRCpGYY. Thus, a skilled artisan realizes that supplementation of a cytokine with the expression vector or addition of a CpG sequence motif in the present invention would result in the enhancement of the immune response.

A further embodiment of the present invention is the method of introducing genes into a cell comprising the steps of forming a DNA particle comprising an expression vector bound to an aggregated protein-polycationic polymer conjugate wherein the expression vector comprises a promoter polynucleotide sequence, and a polynucleotide sequence encoding an antigen, operatively linked and incubating the cells with the DNA particle under conditions wherein the cells take in the DNA particle.

Dosage and Formulation

The compounds (active ingredients) of this invention can be formulated and administered to treat a variety of disease states by any means that produces contact of the active ingredient with the agent's site of action in the body of the organism. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

The dosage administered will be a therapeutically effective amount of active ingredient and will, of course, vary depending upon known factors such as the pharmacodynamic characteristics of the particular active ingredient and its mode and route of administration; age, sex, health and weight of the recipient; nature and extent of symptoms; kind of concurrent treatment, frequency of treatment and the effect desired.

The active ingredient can be administered orally in solid dosage forms such as capsules, tablets and powders, or in liquid dosage forms such as elixirs, syrups, emulsions and suspensions. The active ingredient can also be formulated for administration parenterally by injection, rapid infusion, nasopharyngeal absorption or dermoabsorption. The agent may be administered intramuscularly, intravenously, or as a suppository.

Gelatin capsules contain the active ingredient and powdered carriers such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium Ethylenediaminetetraacetic acid (EDTA). In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly (lactic acid) or ethylenevinylacetate copolymers. In addition to being incorporated, these agents can also be used to trap the compound in microcapsules.

Useful pharmaceutical dosage forms for administration of the compounds of this invention can be illustrated as follows.

Capsules: Capsules are prepared by filling standard two-piece hard gelatin capsulates each with 100 milligram of powdered active ingredient, 175 milligrams of lactose, 24 milligrams of talc and 6 milligrams magnesium stearate.

Soft Gelatin Capsules: A mixture of active ingredient in soybean oil is prepared and injected by means of a positive displacement pump into gelatin to form soft gelatin capsules containing 100 milligrams of the active ingredient. The capsules are then washed and dried.

Tablets: Tablets are prepared by conventional procedures so that the dosage unit is 100 milligrams of active ingredient. 0.2 milligrams of colloidal silicon dioxide, 5 milligrams of magnesium stearate, 275 milligrams of microcrystalline cellulose, 11 milligrams of cornstarch and 98.8 milligrams of lactose. Appropriate coatings may be applied to increase palatability or to delay absorption.

Injectable: A parenteral composition suitable for administration by injection is prepared by stirring 1.5% by weight of active ingredients in 10% by volume propylene glycol and water. The solution is made isotonic with sodium chloride and sterilized.

Suspension: An aqueous suspension is prepared for oral administration so that each 5 milliliters contain 100 milligrams of finely divided active ingredient, 200 milligrams of sodium carboxymethyl cellulose, 5 milligrams of sodium benzoate, 1.0 grams of sorbitol solution U.S.P. and 0.025 milliliters of vanillin.

Accordingly, the pharmaceutical composition of the present invention may be delivered via various routes and to various sites in an animal body to achieve a particular effect (see, e.g., Rosenfeld et al. (1991), supra; Rosenfeld et al., Clin. Res., 39(2), 311A (1991a); Jaffe et al., supra; Berkner, supra). One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The composition of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and animal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular host.

These methods described herein are by no means all-inclusive, and further methods to suit the specific application will be apparent to the ordinary skilled artisan. Moreover, the effective amount of the compositions can be further approximated through analogy to compounds known to exert the desired effect.

Gene Therapy Administration

One skilled in the art recognizes that the mode of DNA delivery of this invention could potentially be used to deliver DNA to specific cells for gene therapy. For gene therapy, a skilled artisan would be cognizant that the vector to be utilized must contain the gene of interest operatively limited to a promoter. For antisense gene therapy, the antisense sequence of the gene of interest would be operatively linked to a promoter. One skilled in the art recognizes that in certain instances other sequences such as a 3' UTR regulatory sequences are useful in expressing the gene of interest. Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds. A sufficient amount of vector containing the therapeutic nucleic acid sequence must be administered to provide a pharmacologically effective dose of the gene product.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein the vector is complexed to another entity, such as a liposome, aggregated protein or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

It is possible that cells containing the therapeutic gene may also contain a suicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter although the product of the suicide gene remains harmless in the absence of a prodrug. Once the therapy is complete or no longer desired or needed, administration of a prodrug causes the suicide gene product to become lethal to the cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Strains of Mice and Treatment of Mice

Female BALB/c mice were used for most studies where mucosal immune responses in the genital tract required collection of surface fluids for antibodies and effector cells for CTL assay from the target tissues. Male mice were used in limited studies. C57BL/6, SKH and CD-1 mouse strains were also studied in a limited number of experiments. Serum samples were obtained by tail bleeds, and vaginal and intestinal secretion samples were obtained by the wick method (Haneberg et al., 1994). Mice were sacrificed at the desired time points by lethal anesthesia and exsanguination via cardiac puncture. Intestinal IELs and splenocytes were recovered by standard techniques, mincing the tissue by forcing it though cell strainer (Becton-Dickinson, Franklin Lakes, N.J.). Mucosal tissues were subjected to a brief incubation with collagenase, and then mononuclear cells were separated by centrifugation over ficoll/hypaque. Genital mucosa lymphocyte isolation used similar methods, $3 \times 10^6$ mononuclear cells were recovered from the genital tissues excised from a group of 4 female mice.

Example 2

Macroaggregated Albumin and Plasmid Binding

Macroaggregated albumin (MAA) was prepared following a standard protocol (Colombetti et al., 1975). In brief, N-succinimidyl 3-(2-pyridyldithio)propionate (SPDP) was added to bovine serum albumin (BSA) or human serum albumin (HSA) and to polyethyleneimine (PEI) 750 kD; other sizes were treated in a similar manner) in a 15:1 mole ratio at pH 8 or above, reducing the PEI-SPDP at pH 7–7.5 with Reductacryl and adding it to BSA-SPDP at pH 7–7.5 in a 1:2 mole ratio. Aggregation was done at pH 5.5–6, and the aggregates were gently centrifuged, resuspended and rinsed with PBS for final use. In detail, 25 µL of a 20 mg/mL solution of SPDP in DMSO was added to 10 mL of a 10 mg/mL solution of BSA in 0.1 M NaHCO$_3$. Stirring was continued for 2 h. A solution of 144 mg of a 50% (w/w) of PEI in 2 mL of 0.1 M NaHCO$_3$ was prepared, and treated with 25 µL of the SPDP solution. After 2 h of stirring, the PEI solution was divided and put over 2 NAP-10 columns which was equilibrated in phosphate buffered saline (PBS), pH 7.4. The combined effluents (3 mL) were stirred with 10 mg of Reductacryl for 1 h. The pH of 5 mL of the BSA-SPDP solution was adjusted to 7–7.5 (pH 4.5–10 test strips) with HCl, and 0.75 mL of the reduced, filtered PEI solution was added. The pH was further adjusted if necessary and the combined solutions incubated for 3 h. The pH was adjusted to 6–6.5 with 10% HCl, and the aggregation was accomplished at 70–75° C. (thermometer in solution) for 5–10 min. The MAA-PEI particles were centrifuged down gently in microfuge tubes, and rinsed twice with PBS, pH 7.4. For plasmid binding, the particles were diluted in PBS to the desired volume, and the plasmid (diluted in PBS to 200 ng/µL) was added dropwise with gentle vortexing of the particle suspension. The suspension was then incubated at room temperature (RT) for 20 minutes before administration to the mice.

SPDP is a heterobifunctional crosslinking reageant. It crosslinks an amine group on one molecule, i.e., polyethyleneimine, to a thiol group on a second molecule, i.e., albumin. However, one skilled in the art recongizes that there are several methods available to conjugate molecules. Exemplary crosslinking methods include, but are not limited to, thiol-thiol crosslinking, i.e., fluorescent cross-linkers; amine-amine crosslinking, i.e., formaldehyde and glutaraldehyde, fluoescent bis(succinimidyl ester); and amine-thiol crosslinking, i.e., SPDP.

Example 3

Macroaggregated Albumin (MAA) Distribution in Mouse Lung

To determine where functionalized MAA localized in lung tissue, MAA conjugated to low molecular weight polylysine was prepared using polylysine labeled with fluorescein isothiocyanate by standard methods (Colombetti et al., 1975). Briefly, 5 mL of a 10 mg/mL solution of bovine serum albumin (BSA) was prepared. The particles were gently centrifuged, and resuspended twice in 0.1 M NaHCO$_3$. The particles were transferred to a flask and gently stirred while adding 30 µL of a solution of N-succinimidyl 3-(2-pyridyldithio) propionate (SPDP) (30 mg/mL, ca. 3:1 molar ratio SPDP:BSA). After the particles had stirred for 1 h, they were washed with 10 mM phosphate buffer pH 7.4, 0.150 M NaCl (PBS) using gentle centrifugation and resuspended to a volume of 4 mL. Solutions of polyethyleneimine (PEI) and polylysine (MW 10–20,000) were prepared in 0.1 M NaHCO3 and functionalized with SPDP and fluorescein isothiocyanate (FITC), using a 3:1 and 1:1 molar ratio respectively. These solutions were rid of unreacted SPDP and FITC by elution from a NAP-5 column (Pharmacia). The SH groups were released by treatment with dithiothreitol (DTT) at pH 4.5 for 1 hr. The excess DTT was removed and the buffer changed to PBS by elution from a NAP-5 column. The SH functionalized polycation was immediately added to the SPDP functionalized MAA with gentle stirring. The molar ratio of BSA to polycation was ca. 1:1. The brightly fluorescent green particles were washed with PBS before use. When the polycation was not functionalized with FITC, the release of the SH groups was accomplished with Reductacryl (CalBiochem) in PBS, and the solution added directly to the MAA.

To demonstrate successful conjugation of the MAA without FITC and binding of DNA, an oligopolynucleotide labeled with FITC was added at 1 µM to the particle suspensions, and then washed and examined under UV illumination. Fluorescent particles in the range of 10 to 100 µm diameter were present in the MAA-PEI and MAA-polylysine conjugates, while unconjugated MAA incubated with the oligopolynucleotide showed no fluorescence.

Once the MAA particles were prepared by the above procedure, BALB/c mice were injected via tail vein with 200 µL of the particulate suspension ($2 \times 10^4$ particles/mL in the 50 to 100 µm size range), and then sacrificed after either 20 or 120 minutes. The lungs were prepared by inflating with embedding medium, and 40 µm thick frozen sections were examined by fluorescence microscopy. Brightly fluorescent particles were readily appreciated in alveolar septae where loose collections of macrophages and lymphocytes reside in the interstitial space (Hasleton et al., 1996). The low level autofluorescence of lung tissue was not apparent with partial visual light illumination, but was easily distinguished from the bright fluorescence of the MAA particles under UV illumination alone (FIG. 1). Examination of samples from multiple lung areas demonstrated a similar pattern, corresponding to the expected blood flow in the mouse, with relatively even distribution of the particles throughout the lung fields. There were no differences in particle appearance between samples obtained from mice sacrificed 20 minutes and 120 minutes after injection.

Example 4

Transfection of Cell Lines by MAA—Plasmid Particles Using Serum Free Medium

MAA was prepared and conjugated to polyethyleneimine according to Example 2, and then diluted to approximately $10^4$ particles/mL in PBS. Plasmid DNA (pCMVβGal) was added at 2 µg/50 µL of particulate suspension and briefly incubated before diluting into serum free medium (Optimem, Gibco) at 50 µL/1.5 mL. T47D breast carcinoma cells grown to confluence in 6 well plates were washed with PBS, and then incubated for 24 h with the MAA suspension in Optimem, and compared with liposome transfection using Lipofectin (Gibco) complexed with the plasmid. The cells were assayed for β-galactosidase, and roughly 20–30% of cells in the MAA cultures showed enzymatic activity, compared to about 50% of the cells transfected by liposomes.

In a similar experiment, MAA was prepared and conjugated to polyethyleneimine, and then diluted to approximately $10^4$ particles/mL in PBS. To bind pEGFP (encoding green fluorescnet protein, GFP) plasmid to MAA-PEI, the particles were diluted in PBS, and then an appropriate concentration of plasmid in PBS (1 microgram/40 microliters of particle suspension) was added to the suspension during gentle vortexing. After a 20 minute incubation at room temperature, the particle complexes were added to the cultures with swirling to distribute the particles evenly.

Figure 2A:
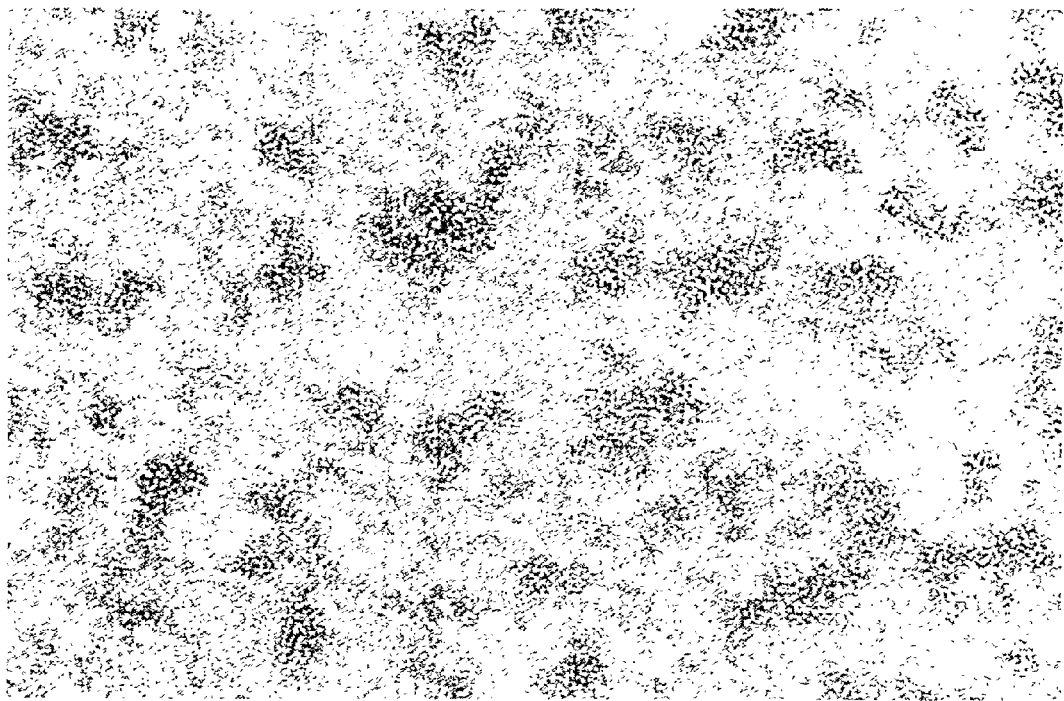
FIGS. 2A and 2B show cells in which green fluorescent protein (GFP) has been expressed.
Figure 2B:
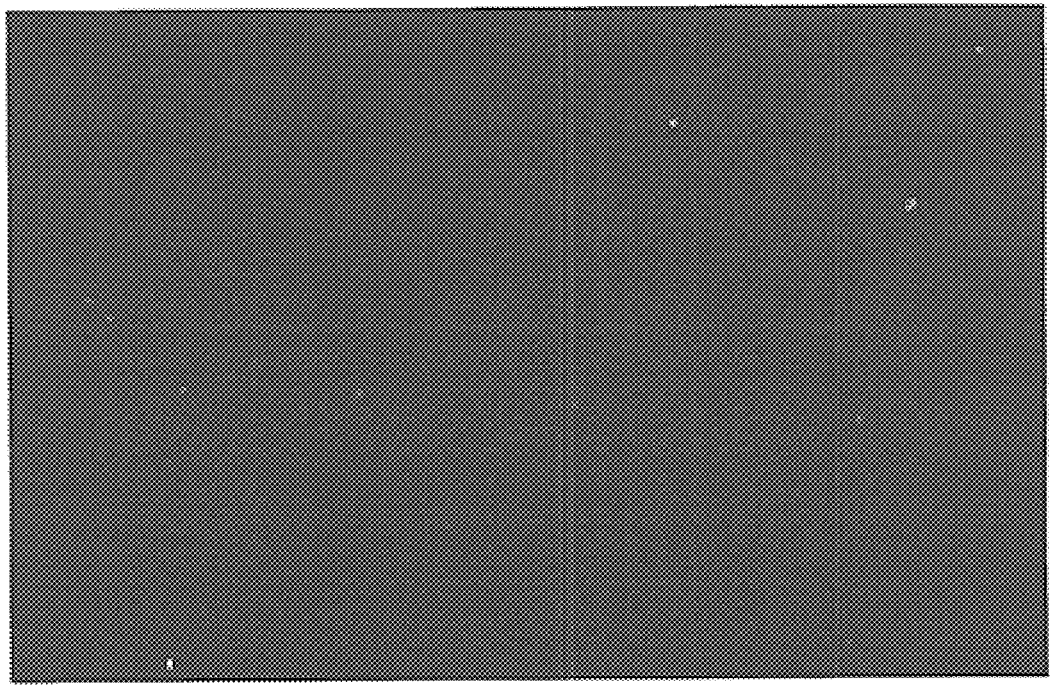

RAW264.7 monocyte/macrophage lineage cells were grown to confluence in 24 well plates were washed with PBS, and then incubated for 24 h with the MAA suspension in RPMI containing 10% FCS. Cells in which GFP has been expressed from the pEGFP plasmid were examined by UV microscopy at appropriate time points after culture initiation (usually 24 h), and photographed under both visible light and UV illumination conditions as shown in FIG. 2A and FIG. 2B. Approximately 25% of the treated cells showed high level GFP expression.

Example 5

Comparison of Transfection Efficiency MAA-PEI and Lipofectin in Serum and Serum Free Medium To determine the efficiency of in vitro transfection in the presence or absence of serum in the medium, cells were transfected with a DNA conjugated to MAA-PEI or Lipofectin. Similar protocols were followed as in Example 4; however, a monocyte/macrophage lineage murine cell line (RAW) was transfected with a luciferase construct under cytomegalovirus (CMV) promoter regulation conjugated to MAA-PEI and was compared to plasmid/Lipofectin conjugates. In this experiment, the efficiency of transfection in the presence of 10% fetal calf serum (FCS) supplemented culture medium was tested. The positive control was transfection with lipofectin+1 μg of plasmid in serum free medium. Negative controls included untreated cells, cells exposed to plasmid alone, and cells exposed to MAA-PEI alone. Test cultures were exposed to a concentration curve of plasmid+MAA-PEI, from a maximum of 2 μg to a minimum of 0.25 μg of plasmid. The full curve was done under identical conditions to the positive control, and two concentration points were done in which the cells were exposed in the presence of 10% fetal calf serum.

Figure 3:
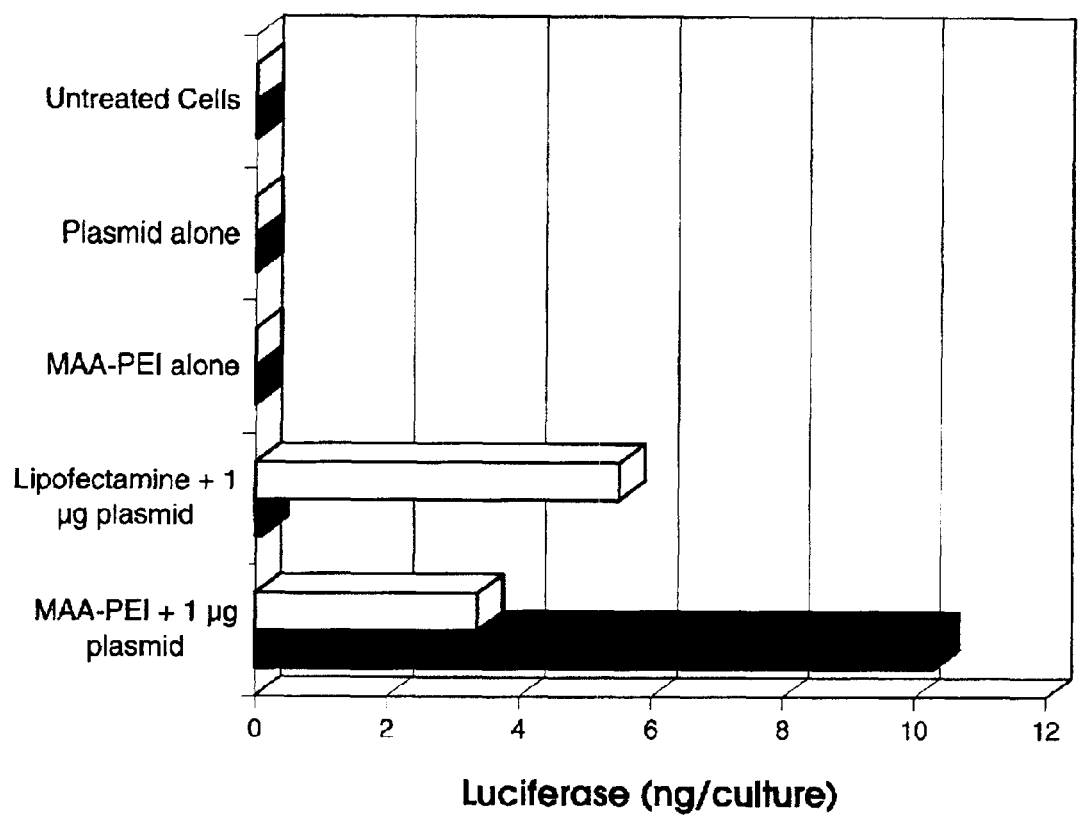
FIG. 3 shows a graphical representation of the comparison between the transfection efficiency of MAA-PEI compared to Lipofectin. The black bars indicate that 10% fetal calf serum (FCS) was used in the medium. The white bars indicate that the medium was serum free.

The results are expressed in lumens, and represent ¹⁄₁₀₀ of the total culture cell extract from 1 ml culture in a 24 well plate. FIG. 3 is a bar graph representation of the data illustrated below in Table 1.

TABLE 1

| SERUM FREE MEDIUM | LUMENS |
| --- | --- |
| Untreated cells | 0.00 |
| Plasmid alone | 0.00 |
| MAA-PEI alone | 0.00 |
| Lipofectin + 1 μg Plasmid | 551.0 |
| MAA-PEI + 2 μg Plasmid | 711.0 |
| MAA-PEI + 1 μg Plasmid | 336.0 |
| MAA-PEI + 0.5 μg Plasmid | 57.5 |
| MAA-PEI + 0.25 μg Plasmid | 5.7 |
| IN 10% SERUM MEDIUM | IN 10% SERUM MEDIUM |
| MAA-PEI + 1 μg Plasmid | 1029.0 |
| MAA-PEI + 0.25 μg Plasmid | 76.3 |

This data illustrated that the MAA-PEI bound plasmids were as efficient as Lipofectin (one of the most widely used agents for serum free transfections). Furthermore, the data illustrated that the MAA-PEI conjugates were equally or more efficient in the presence of serum. Most agents are inefficient in vivo because of the presence of serum proteins. Therefore, a skilled artisan realizes the enormous implications of this data and its use for in vivo DNA trasfection strategies.

Example 6

Humoral Immune Responses Elicited by Intravenously Injected MAA-PEI Bound Plasmid To evaluate immune responses to antigens expressed in the lung tissue, mice were injected intravenously with 5 μg of pCMV-hGH (SEQ.ID.NO:13) loaded on MAA-PEI particles, or intravenously with 50 μg of pCMV-hGH. At biweekly intervals, serum was collected from each mouse via tail bleed. At the end of the experiment, the mice were sacrificed and bronchoalveolar lavage was performed to evaluate antibody responses in pulmonary secretions.

Figure 4A:
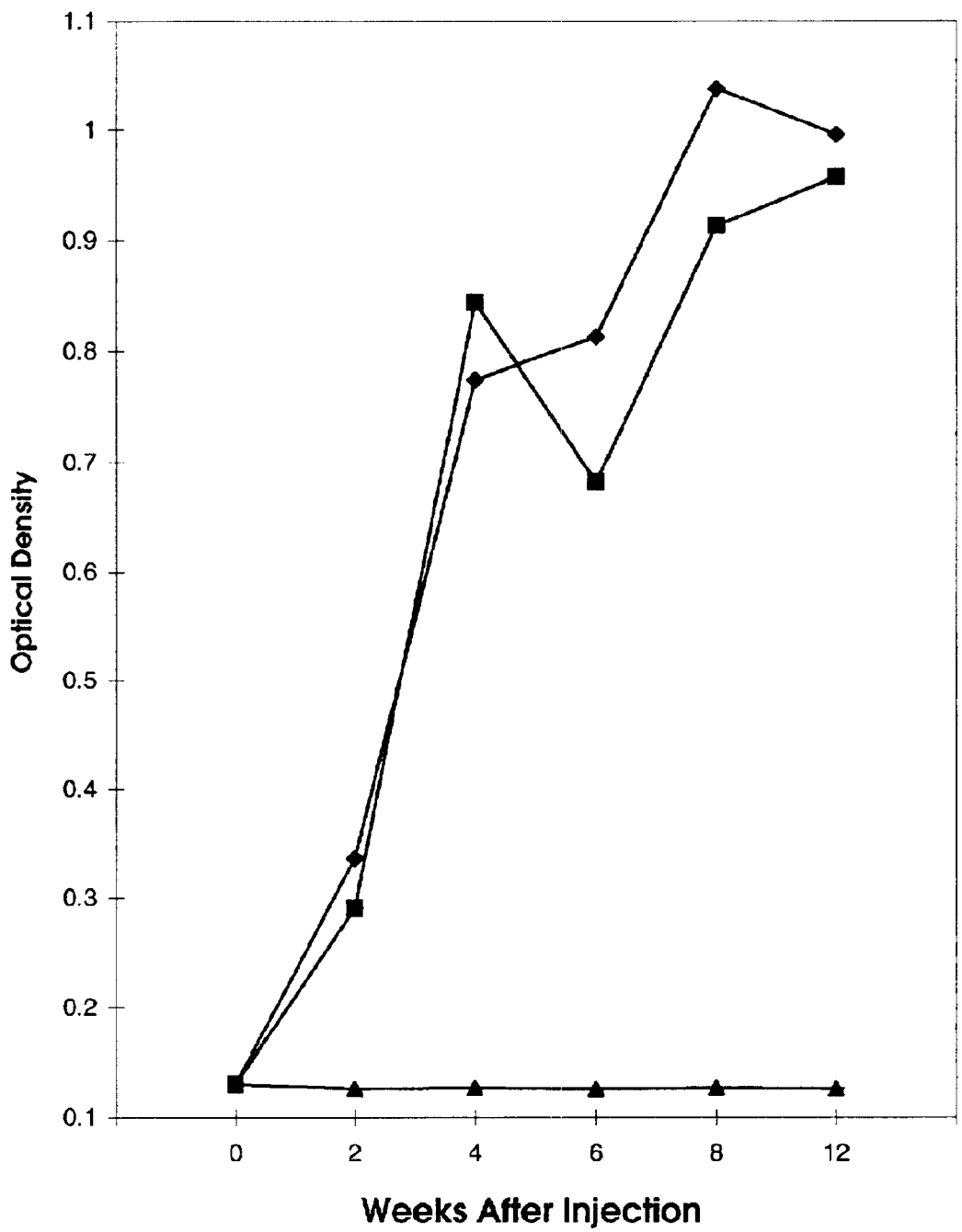
FIGS. 4A, 4B and 4C show the total systemic humoral immune response to injection of pCMV-hGH bound to macroaggregated polyethyleneimine MAA-PEI.
Figure 4B:
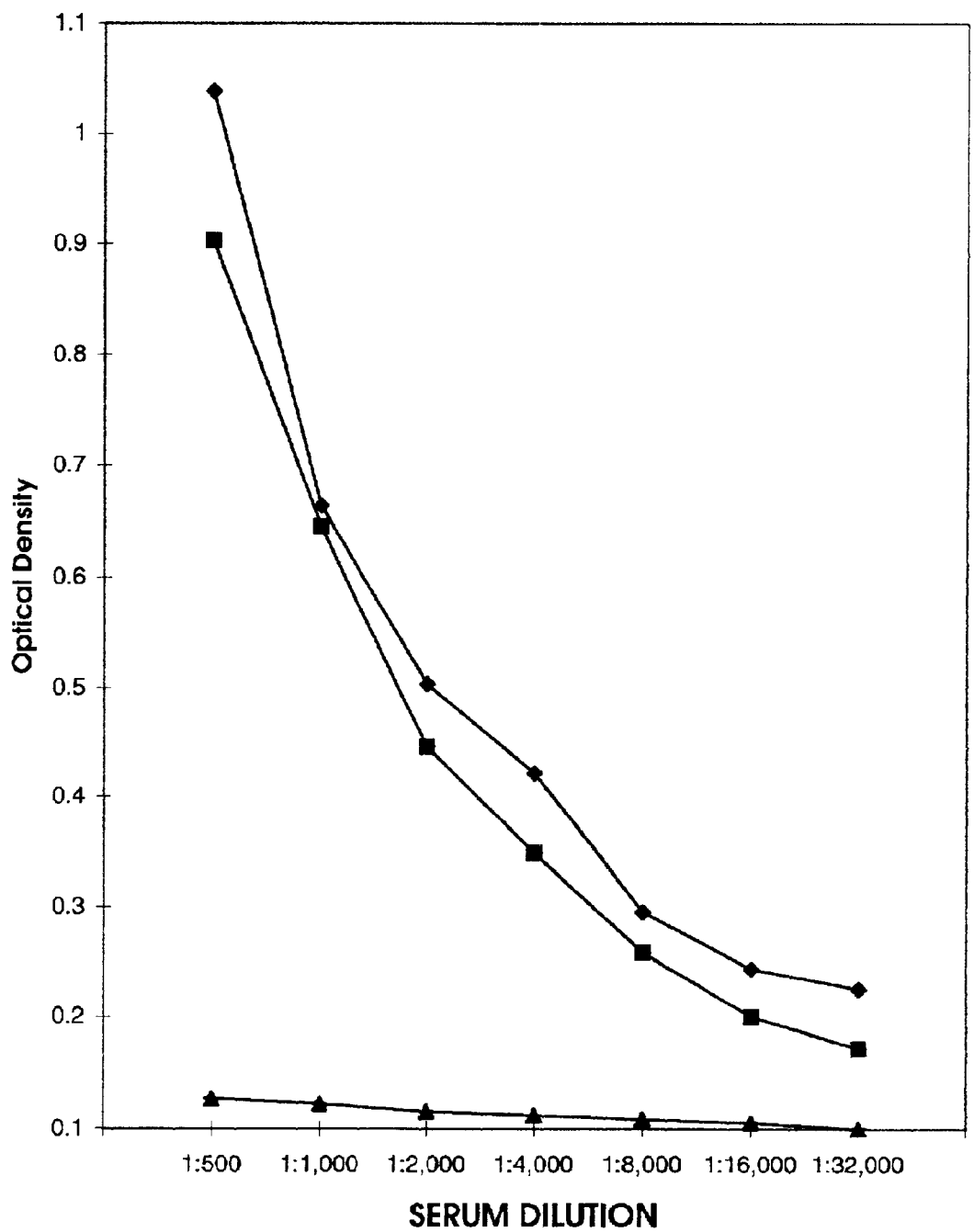
Figure 4C:
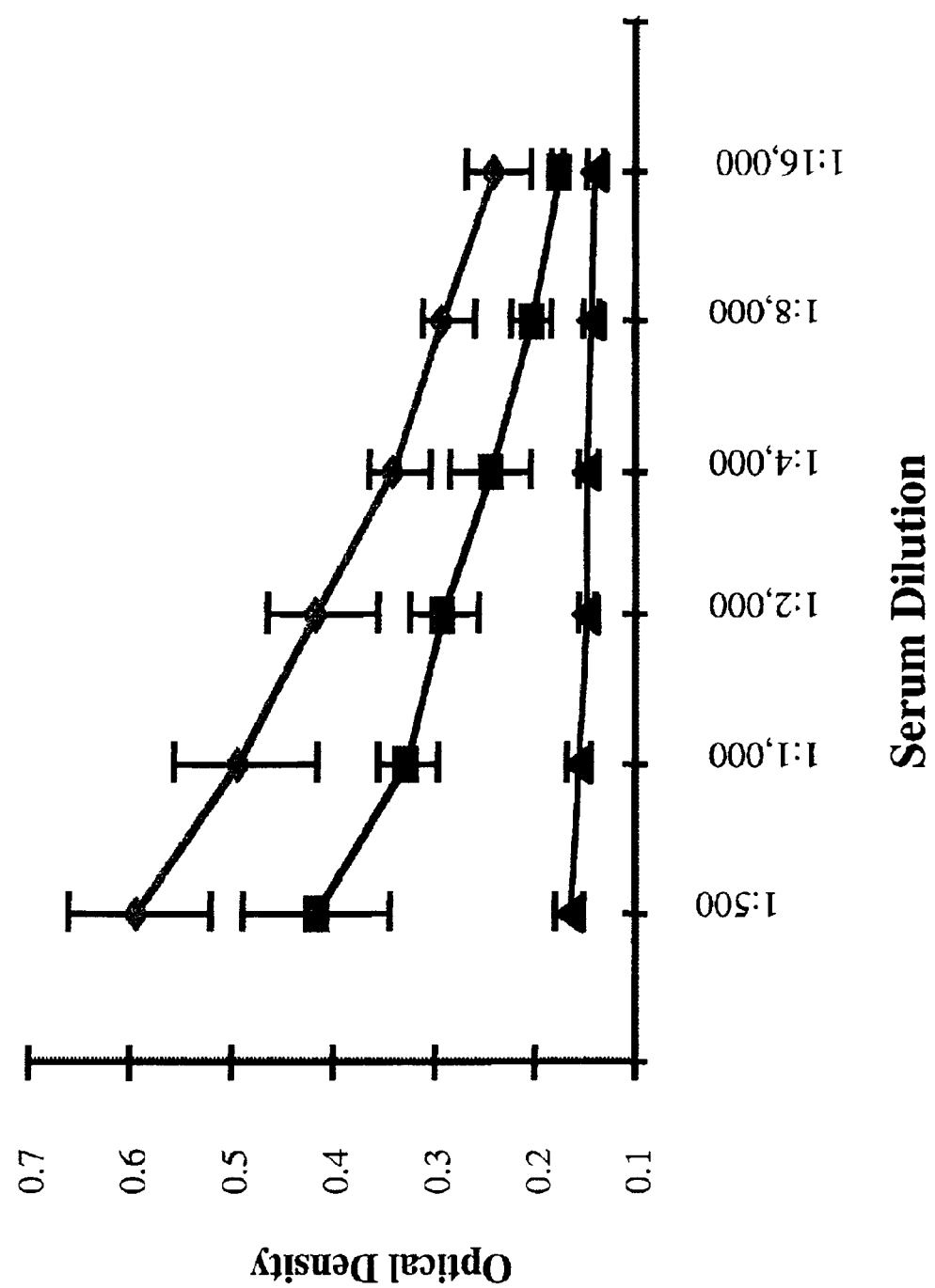

Controls included uninjected animals and animals in which naked hGH plasmid were injected intramuscularly. FIG. 4A illustrates the total systemic antibody response to hGH elicited by the MAA-PEI plasmid through 12 weeks in one group of mice, showing a rapid and strong response from the single dose of plasmid, which appeared to plateau after 4 weeks. Intramuscular injection of naked DNA showed essentially the same level of antibody response systemically, and the differences from uninjected control animals for both immunized groups were statistically significant at all time points ($p<0.02$ at all time points). FIG. 4B shows a dilution curve of serum at 12 weeks illustrating that the antibody dilutes out to a titer of >1:32,000 in the MAA-PEI and intramuscularly injected animals, with the optical density at each dilution being statistically different from controls ($p<0.01$). FIG. 4C shows a second set of mice injected with MAA-PEI bound hGH plasmid and compared with other controls: the same quantity of hGH plasmid injected intravenously as naked DNA or as PEI-DNA complexes. MAA-PEI-hGH responses showed high titer systemic antibody, with somewhat higher levels than seen with naked DNA intravenously alone.

Figure 5A:
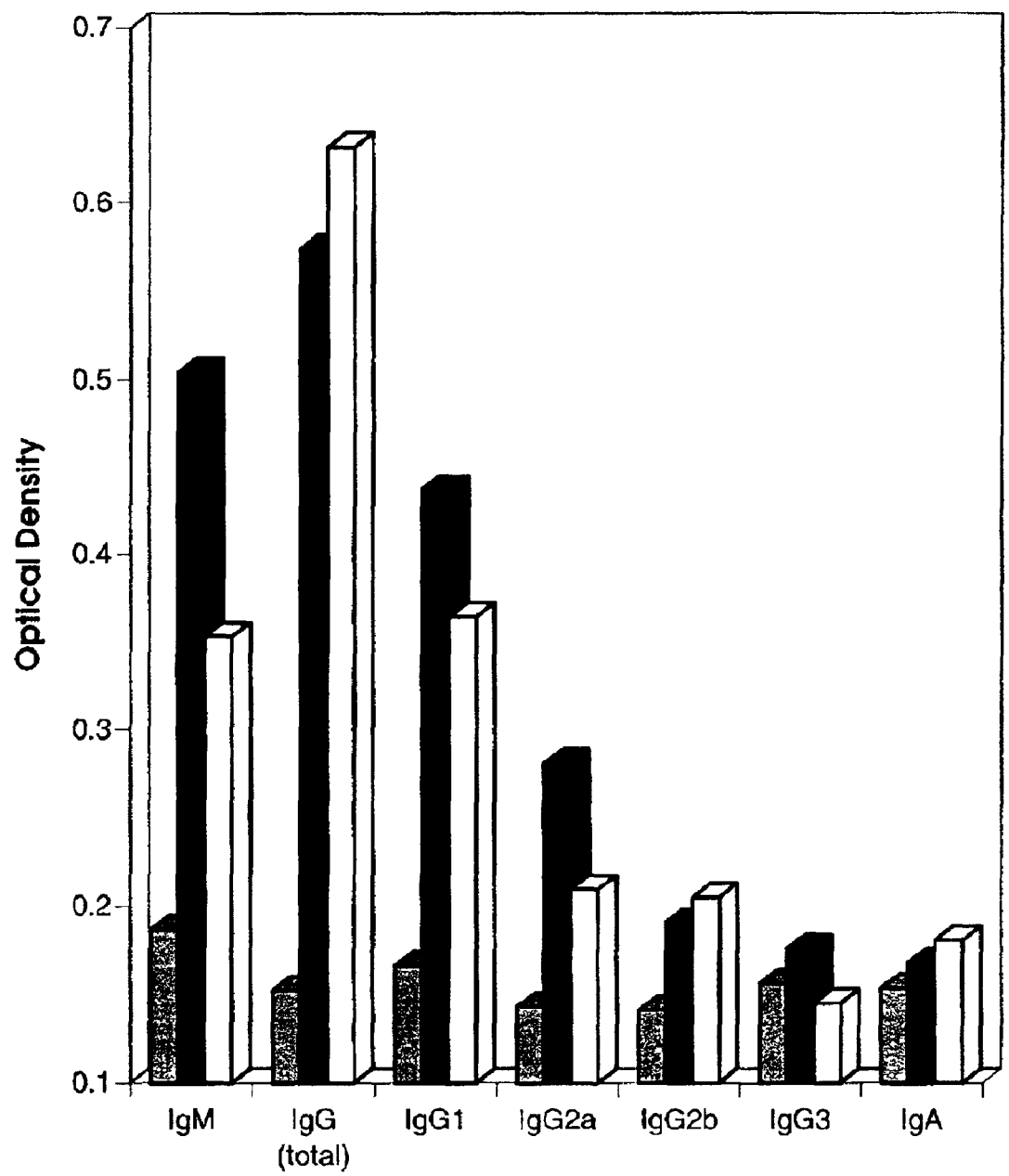
FIGS. 5A and 5B show the isotype distribution of the humoral response.
Figure 5B:
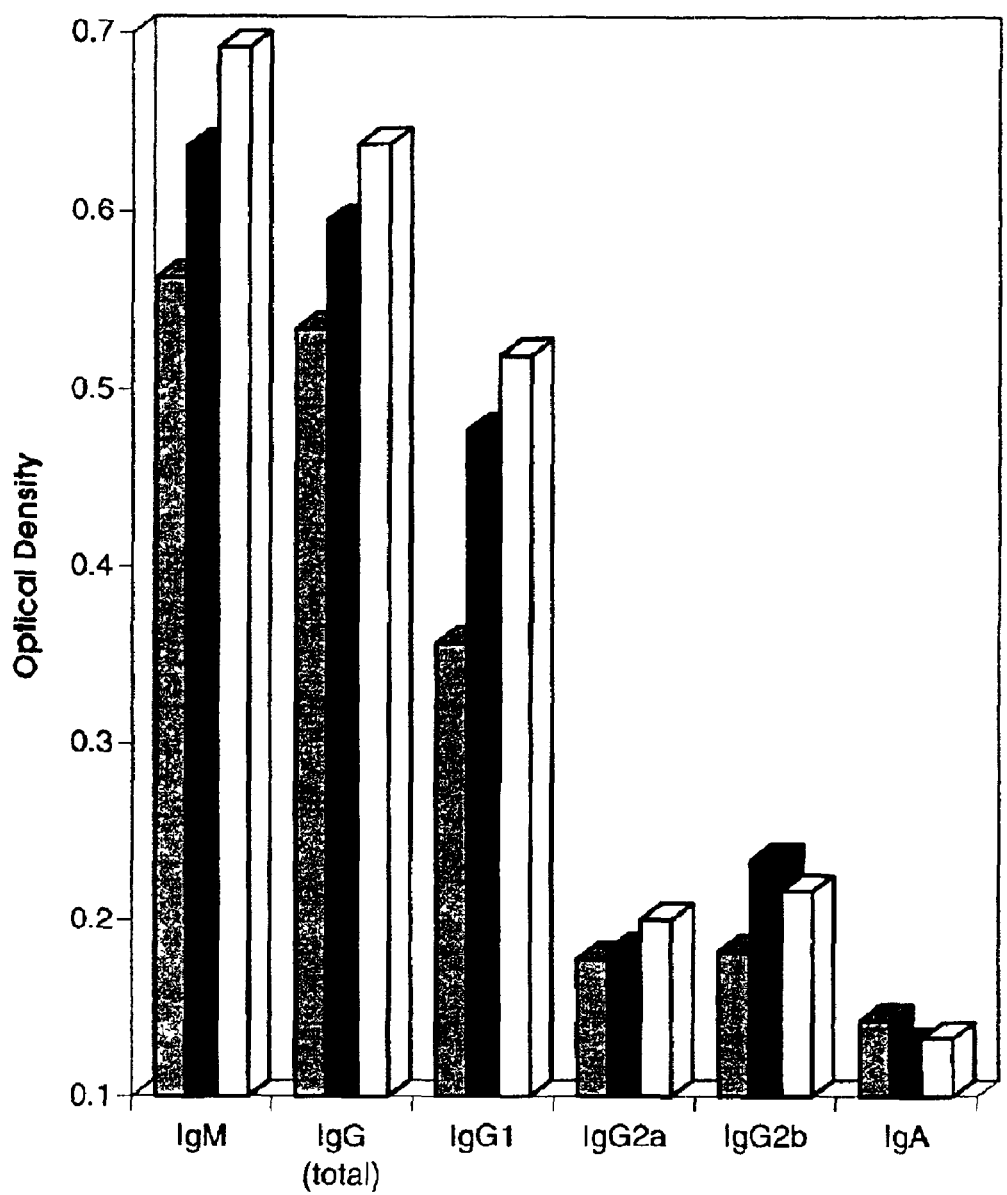

The isotype distribution of the humoral response at 8 weeks to MAA-PEI-hGH plasmid injection group is shown in FIG. 5A, along with intramuscularly hGH and naive control groups, demonstrating strong IgM and total IgG response, which was dominantly IgG1, with modest IgG2a and little IgG2b or IgG3. This isotype distribution was also essentially the same at 2, 4, and 12 weeks (FIG. 5B).

Figure 6A:
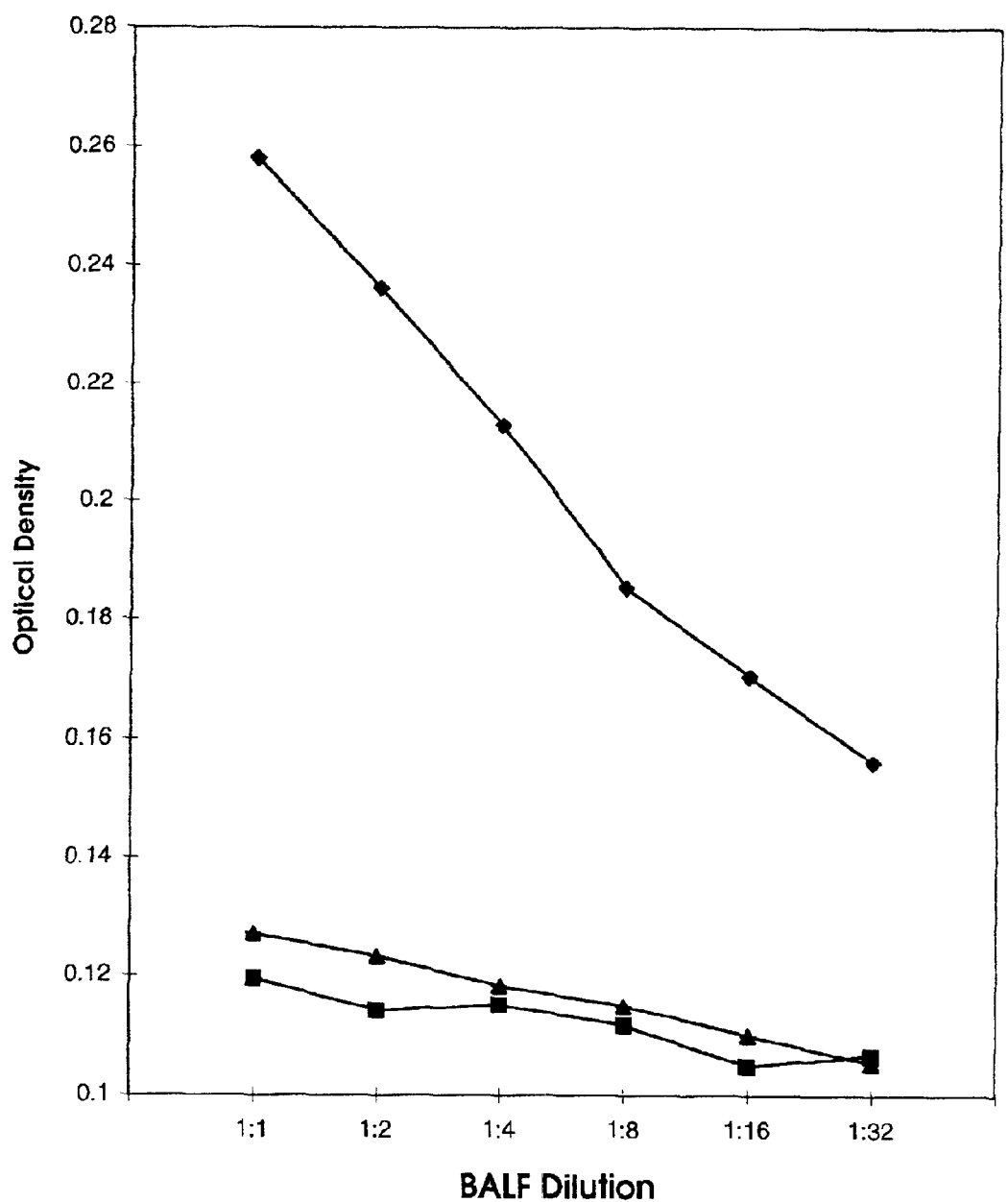
FIGS. 6A and 6B show pulmonary mucosal IgA response.
Figure 6B:
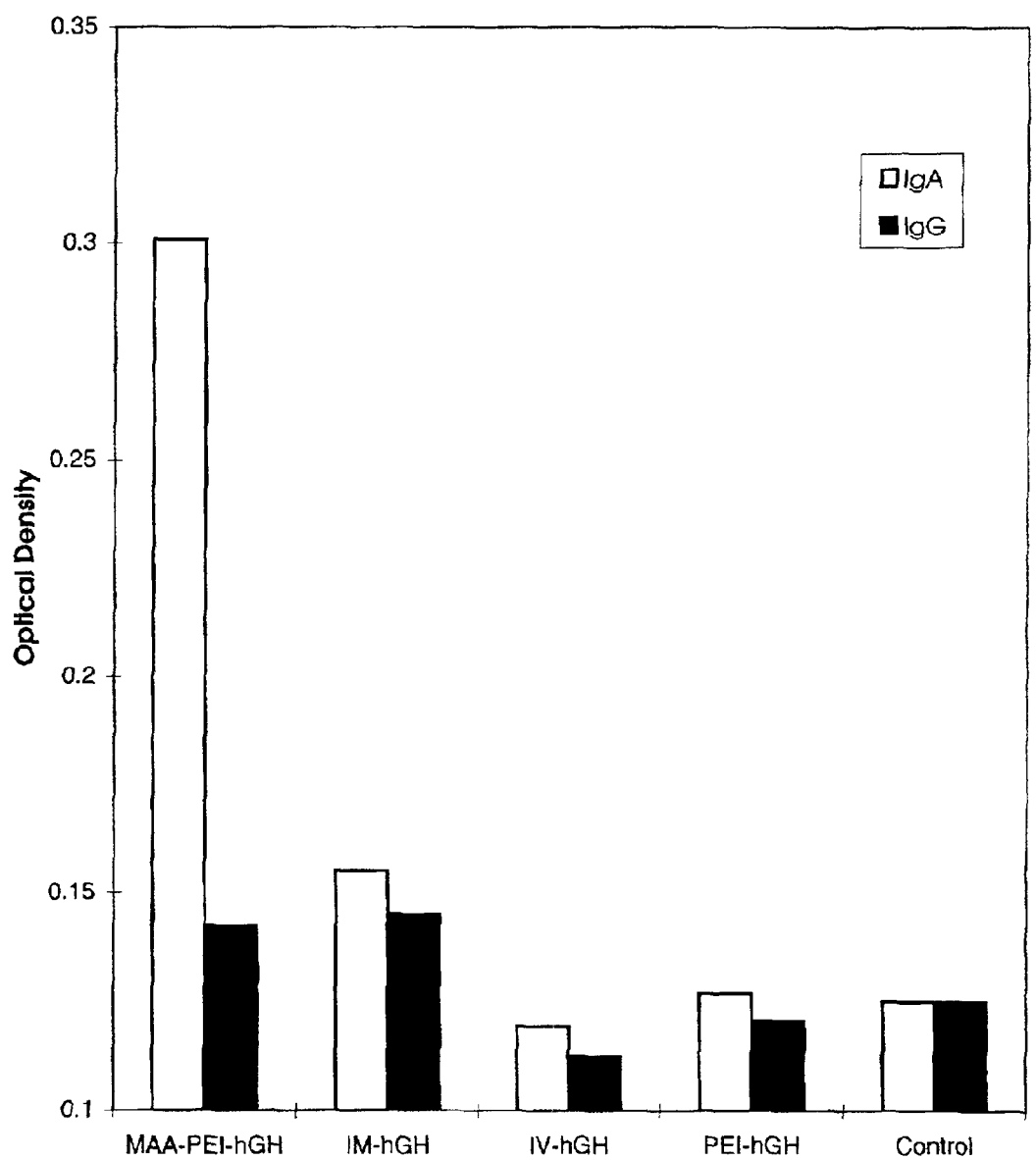

Mucosal antibody responses are shown in FIG. 6A, demonstrating that high titer IgA anti-hGH antibody is present in the lung secretions of only MAA-PEI-hGH plasmid immunized mice. FIG. 6B shows the composite data from 2 experiments comparing particle-mediated immunization with different controls. Although a substantial systemic response was present from immunization with naked DNA administered intravenously or intramuscularly (FIGS. 4B and 4C), no significant quantity of specific IgA or IgG antibody was present in either group in lung secretions (FIG. 6B). The quantity of IgA measured in the bronchoalveolar lavage fluids of the particle-immunized group was significantly different from the levels of IgA in the other groups ($p<0.01$), as well as from those for IgG in its own bronchoalveolar lavage fluids and that of all other groups ($p<0.01$).

Therefore, a skilled artisan recognizes that intravenous injection of conjugated plasmid to MAA-PEI elicited an equal or a stronger immune response compared to intramuscular injection of plasmid DNA alone. Furthermore, only the MAA-PEI plasmid induced a mucosal response suggesting that this delivery system (MAA-PEI) via a systemic route induces a mucosal response, which is not typical of systemic immunizations.

Example 7

Figure 8:
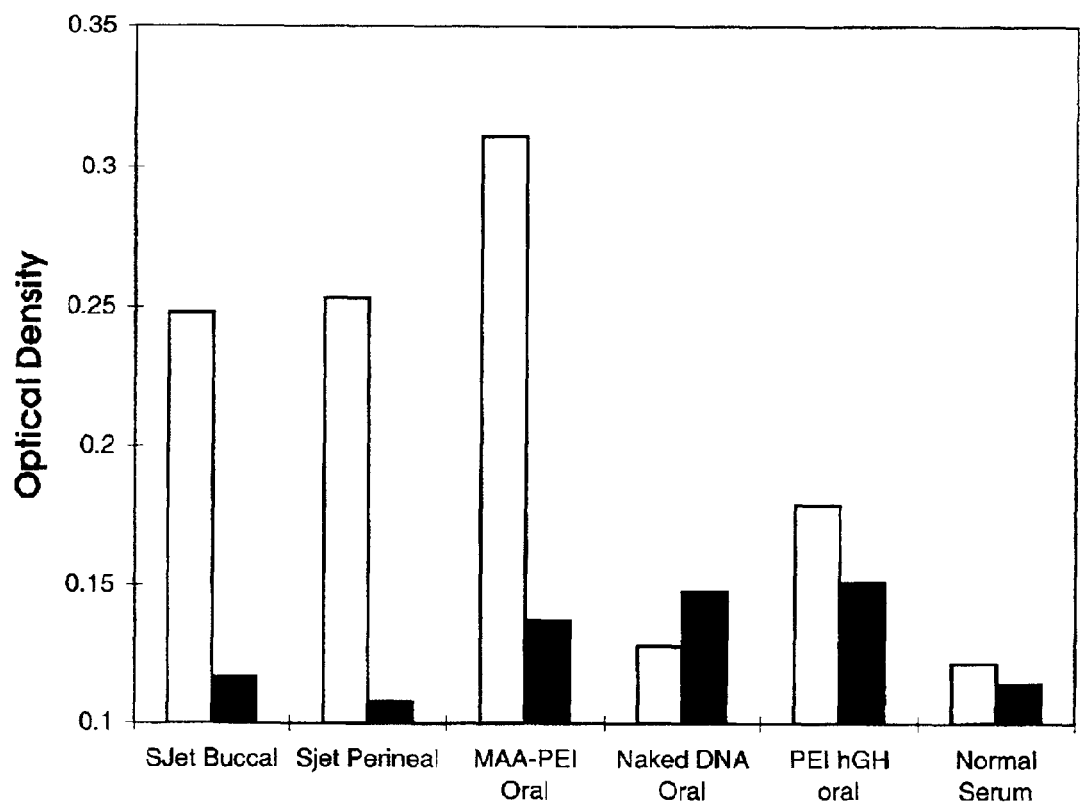
FIG. 8 shows genital mucosal IgA (black bars) induced by oral and syrijet plasmid administration. IgG is shown in the white bars.

Oral Administration of Particle Bound hGH Plasmid and Syrijet Injection Elicit Mucosal Antibody Mice were orally immunized with 15 μg of pCMV-hGH (SEQ.ID.NO:13) plasmid in single doses, and controls included mice orally exposed to 15 μg of pCMV-hGH plasmid alone (naked DNA), 15 μg of pCMV-hGH plasmid complexed with MAA-PEI, and PBS alone. As shown in the FIG. 8, particle immunized mice developed specific vaginal IgA antibody, while controls failed to develop significant antibody responses.

Mice were also immunized with a jet injection device (Syrijet, Inc., Cherry Hill, N.J.). Mice were injected with 30 μg of pCMV-hGH in 15 μL of PBS in the buccal tissue or the perineal tissue. After 4 weeks, vaginal secretions were collected by the wick method and pooled secretions were assayed at 1:2 for IgA and IgG. Comparable levels of anti-hGH IgA were present in vaginal secretions in the Syrijet immunized mice. The particle group secretions were positive to >1:16 dilution, while the Syrijet group secretions were positive to 1:8.

Groups of five mice were injected with 30 μg of pCMV-hGH in 15 μL of PBS in the buccal tissue or the perineal tissue, or orally treated with 15 μg plasmid bound to MAA-PEI particles, 15 μg complexed with free PEI, or 15 μg naked DNA. Vaginal secretions were collected by the wick method 4 weeks later, and pooled secretions were assayed at 1:2 for IgA and IgG.

Therefore, the data suggested that oral administration of MAA-PEI particles elicited a stronger immune response than particles administered via a Syrijet or bound to only a polycationic polymer.

Example 8

Construction of an Expression Library Immunization

Figure 7A:
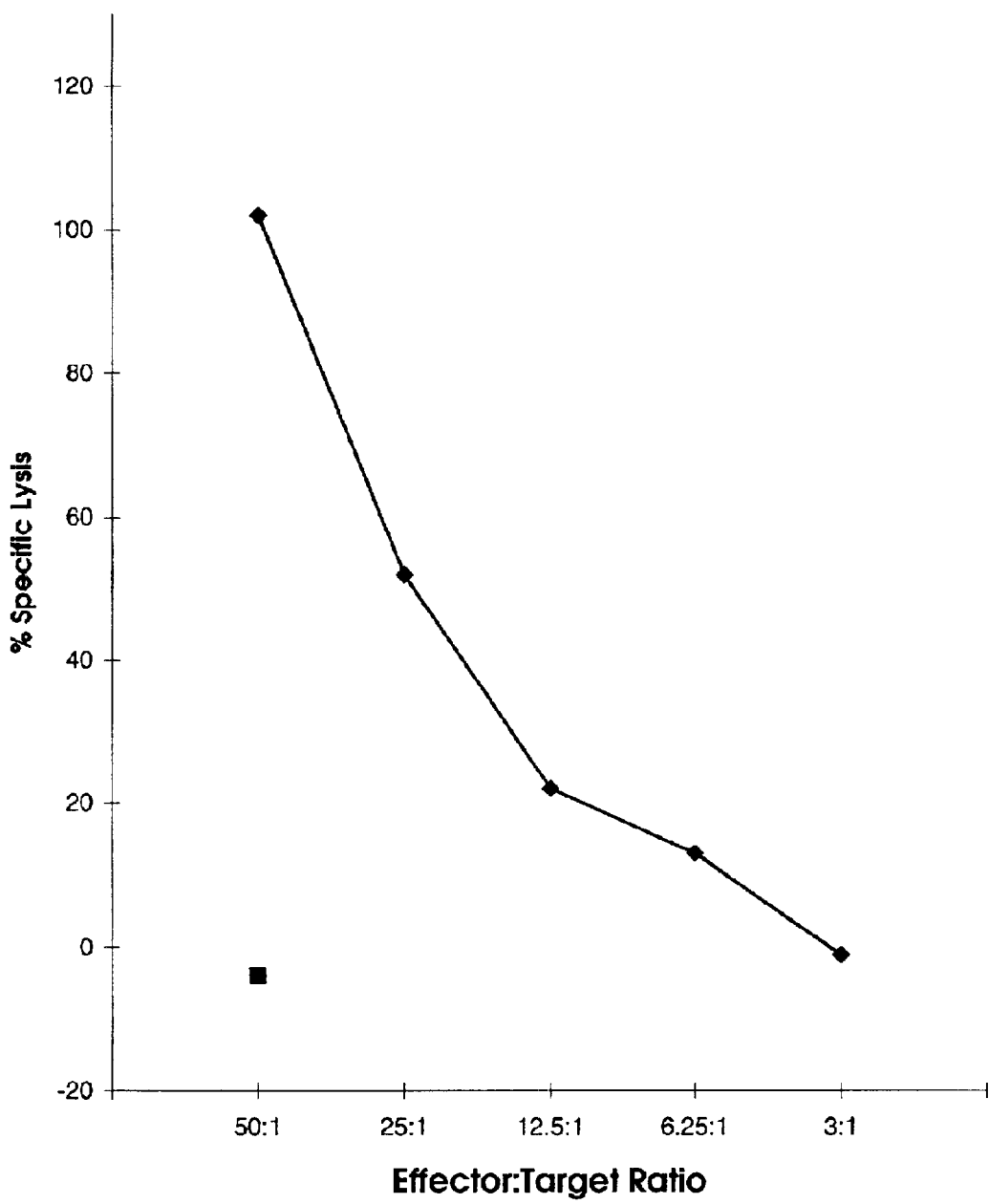
FIGS. 7A and 7B show p18 specific CTL elicited by MAA-PEI-CMV-UB#23.
Figure 7B:
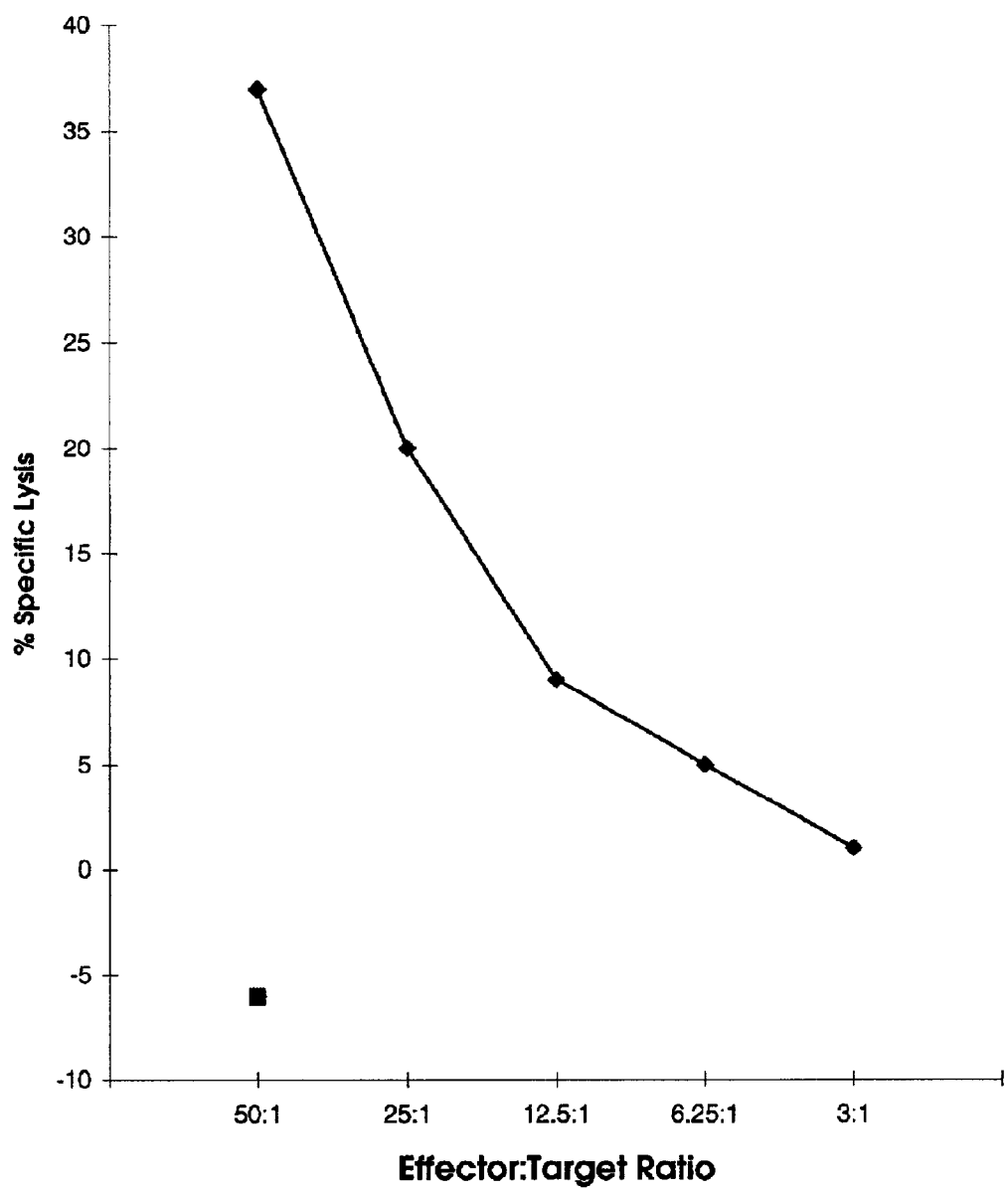
Figure 9:
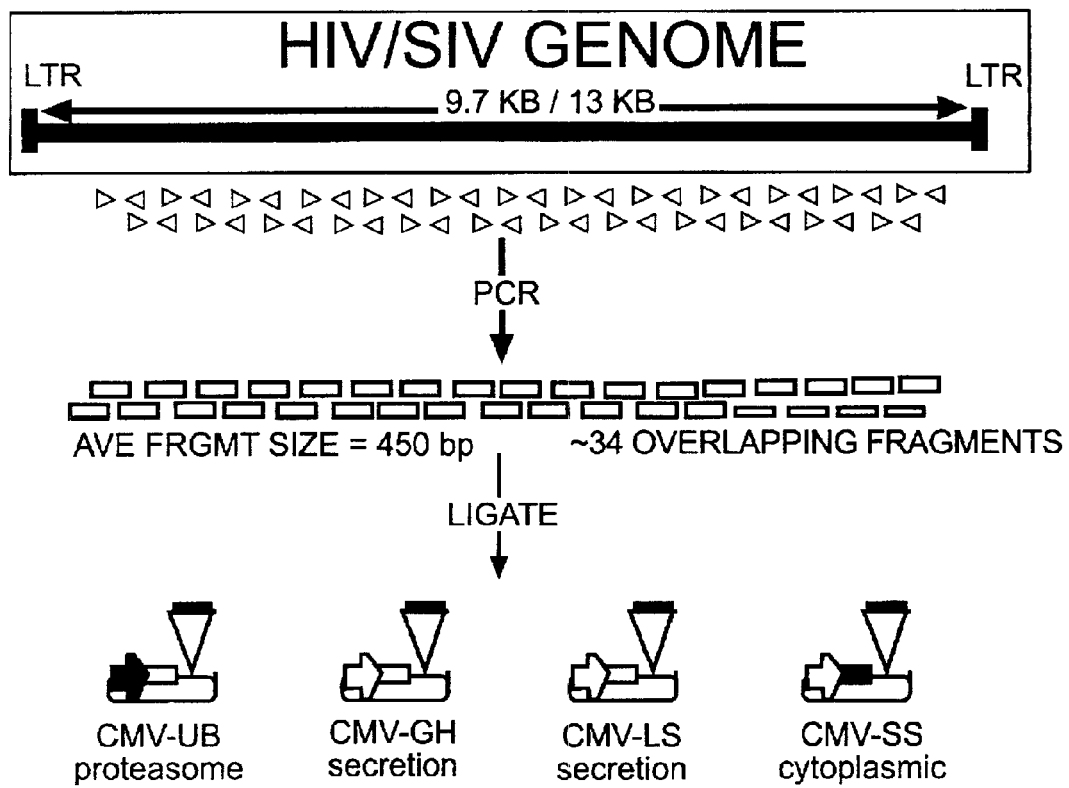
FIG. 9 shows the structure of HIV expression libraries. Expression immunization libraries were constructed by creating overlapping PCR fragments (400–600 bp) from each open reading frame in the HIV genome (Wang et al., 1993). These fragments were then inserted into pCMV expression vectors as shown, with fusion to ubiquitin or hGH coding sequences, or without fusion to another expressed sequence.

There were several reasons why it was thought that this approach might be effective. First, the library would theoretically express all of the pathogen antigens and might therefore promote broader, better protection, since epitopes are presented independently. Second, the libraries truncate each protein rendering it inactive and reducing its potential toxicity to mammalian cells. Third, to better "reveal" the pathogen to the immune system, each fragment in two of the libraries was fused to heterologous mammalian sequences to "target" the antigens within the mammalian cells (FIG. 9). Breaking down the proteins and fusing them to heterologous sequences appears to elicit potent immune responses. For example, fusion of a 602 base pair fragment of gp120 to ubiquitin produces CTL responses in mice when the plasmid (UB#23) is used for immunization with particles (FIGS. 7A and 7B).

Immunization libraries were constructed by creating overlapping PCR fragments (400–600 bp) from each open reading frame in the HIV genome (Wang et al., 1993) (FIG. 9). These fragments were then inserted into pCMV expression vectors as shown, with fusion to ubiquitin or hGH coding sequences, or without fusion to another expressed sequence. The carboxy terminus of ubiquitin directs the fusion product to the proteasome, where it is degraded to peptides which are presented on MHC class I molecules. Fusion to hGH results in secretion of the fused product directing the antigen to be presented on MHC class II molecules.

Furthermore, a skilled artisan realizes that the ELIs can be constructed using either genomic DNA or cDNA (Manoutcharian, 1998). Therefore, the utilization of this technology, and variations thereof, such as those described by U.S. Pat. Nos. 5,989,553 and 5,703,057, each incorporated herein by reference, are exemplary methods of construction of ELIs and their use in DNA vaccines.

Example 9

Enzyme Linked Immunosorbent Assay (ELISA)

Serum, vaginal secretions, and intestinal secretions were assayed by ELISA for total and isotype specific antibody to HIV antigens (purified HIV proteins are obtained from ABI, Columbia, Md.). The desired antigen was coated onto microtiter plates (Immunlon II, Dynex Technologies, Chantilly, Va.) at 0.5 μg/mL (50 ng/well) in PBS buffer (pH 7.3) overnight at 4° C. This loading quantity was the most cost effective, shown by comparison of various concentrations with serial dilutions of a positive control antiserum. The wells were then blocked with 5% non-fat milk in PBS. Sera and mucosal secretions were diluted in PBS and aliquots added to the wells were incubated overnight at 4° C. Sera and secretions from age matched, unimmunized Balb/C mice served as negative controls in each assay. After 5 washes with PBS-Tween (0.1%), bound antibodies were detected with horseradish peroxidase-conjugated goat or rabbit anti mouse immunoglobulin (Bio-Rad, Hercules, Calif.), or anti-mouse IgA, IgM (Sigma), IgG1, IgG2a, or IgG2b (Serotec, Raleigh, N.C.) diluted in PBS-Tween. Reactions were developed using TMB substrate (Calbiochem) and the optical density was measured at 405 nm with an SLT microplate reader (TELAC Inc., Research Triangle Park, N.C.) with a maximal O.D. for linear reading of 1.4, with the background reagent only (no serum) well having an O.D. of 0.1. Results of the isotype specific assays were normalized for equivalent signal strength from dilution curves of bound antigen for each isotype.

Example 10

Cytotoxicity Assay

Mice were exposed to plasmid encoded antigens using particles or jet injections. Single cell suspensions were prepared from mouse spleen or mucosal tissues as described in Example 1. For pCMV-UB-#23 (SEQ.ID.NO:1) immunized animals, P815 target cells were loaded with the desired peptide, e.g., p18 (RIQRGPGRAFVTIGK) (SEQ.ID.NO:9), by incubation at 37° C. for 1 h at 1 μM. Splenocytes (variable numbers) and targets (10,000 cells/well) were co-cultured at desired effector/target ratios, and control cultures included splenocytes with target cells loaded with irrelevant peptide or no peptide. Maximum release was determined by lysing target cells alone, and spontaneous release from both target cells and effector cells was measured from other wells with these cells cultured individually. After a 4 h incubation, supernatant aliquots were harvested, substrate was added for LDH activity released by lysed cells, and optical density measurements were made after 30 minutes (Cytotox96 Assay, Promega).

Example 11

MAA-PEI Bound HIV Plasmid Elicits CTL in Spleen and Gut

Mice were immunized as described in Example 6, except a plasmid from the HIV library constructed with ubiquitin to enhance CTL induction (Wu et al., 1997, Fu et al., 1998) was used. The plasmid (CMV-UB-#23, (SEQ.ID.NO:1)) encodes a protein containing ubiquitin fused to a protein fragment containing the immunodominant epitope for gp120 in Balb/C mice, p18 (Takahashi et al., 1988) and conjugated to MAA-PEI as shown in Example 2. Eight weeks after vaccination, the spleens and intestines were harvested, the tissues minced through a fine screen (intestinal tissue was also briefly incubated with collagenase), and the mononuclear cells collected by density gradient centrifugation. These cells were assayed directly for CTL activity with various effector:target (E:T) ratios. As shown in FIG. 7A, cytolytic T cells were present in splenocytes of the UB#23 immunized mice, and there was no nonspecific lytic activity toward the target cells without peptide loading. The lytic activity at E:T ratios of 25:1, 12.5:1 and 6.25:1 were significantly different from the control wells containing an E:T ratio of 25:1 using target cells not loaded with peptide (p<0.01 for each). FIG. 7B shows intestinal epithelial lymphocytes (IELs) tested in a similar manner. Lytic activity was significant in the IELs with 37% target cell lysis at a 50:1 E:T ratio.

Example 12

CTL Responses to Oral Administration of Particle Bound Plasmid

Groups of mice were orally immunized with MAA-PEI bound UB#23 (SEQ.ID.NO:1), a plasmid encoding a 450 base pair region of the HIV-1 gp120 gene containing the V3 loop with both antibody epitopes and the 15 mer amino acid sequence (p18) that is the strong immunodominant CTL envelope epitope in H-2d mice (Takahashi et al., 1988). This plasmid is one member of the HIV-1 library constructed with the viral sequence fragment fused to the carboxy terminus of ubiquitin (thus directing the fusion product to the proteasome, where it is degraded to peptides which are then presented on MHC class I molecules (Michalek et al., 1993). Mice were given an oral booster dose at 6 weeks and then the mice were sacrificed at 8 weeks for CTL assays. Total gut mononuclear cells were harvested by mincing the tissue, briefly digesting with collagenase, and subjecting the cells to density gradient centrifugation. Total intestinal mononuclear cells were chosen because the yield from the intestine is sufficient to permit full assays to be performed with a limited number of animals pooled. Direct CTL assays on these cells (i.e., assays done with the fresh cells and no prestimulation) and on splenocytes were performed with p18 loaded P815 target cells or control cells without peptide loading.

Figure 10:
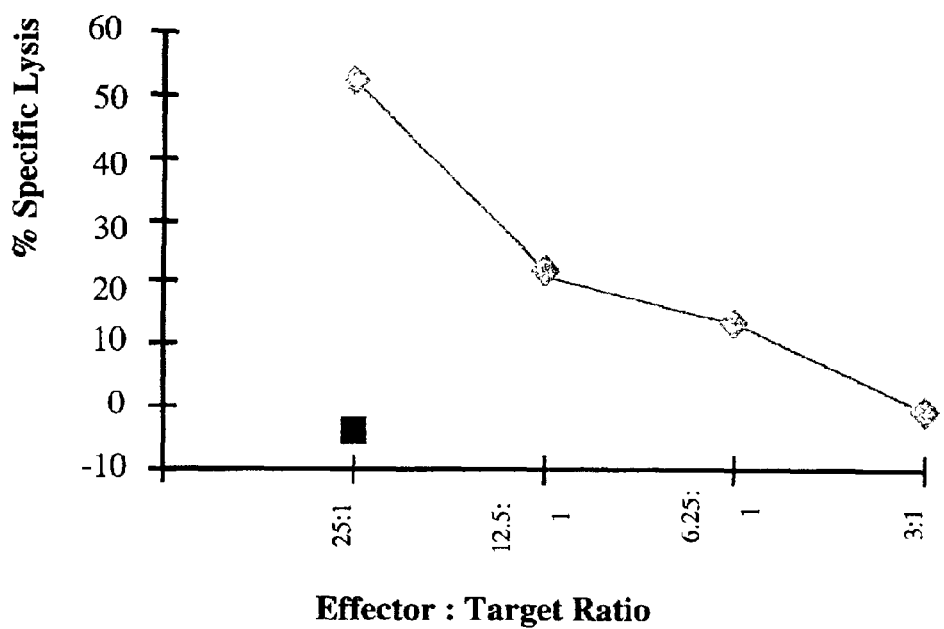
FIGS. 10A and 10B shows the oral MAA-PEI bound UB23 plasmid elicits CTL in splenocytes (FIG. 10A) and intestinal mononuclear cells (FIG. 10B). The triangles represent p18 targets and the squares represent no peptide targets.
Figure 10:
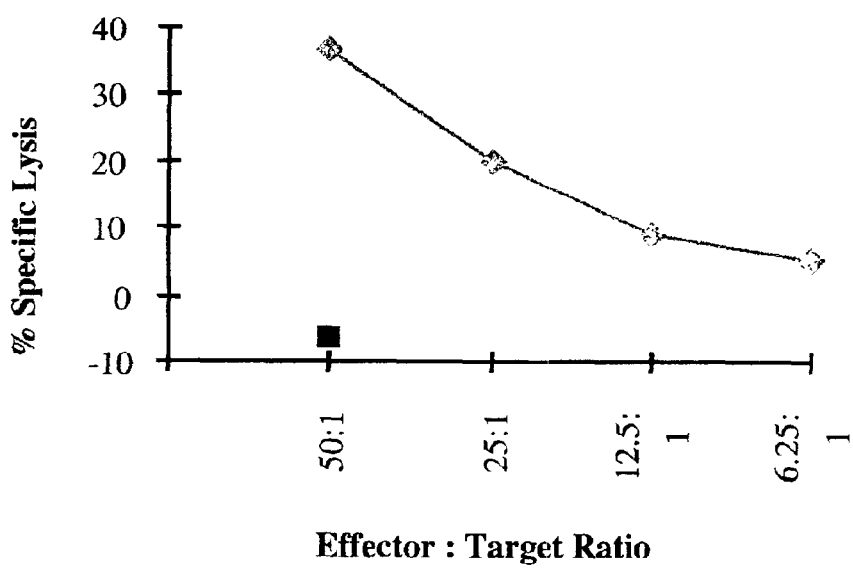

FIG. 10A shows high level spleen cytotoxic activity present at the time of sacrifice with 52% lysis of the target cells after 4 h of incubation at a 25:1 E:T ratio. In the intestinal mononuclear cell population, substantial lytic activity was also present (FIG. 10B) with 37% target cell lysis at a 50:1 E:T ratio. Lysis was specific, since no lytic activity was found in cultures of the mononuclear cell population and P815 cells that were not loaded with the p18 peptide. Hence, this experiment demonstrates that oral immunization is capable of eliciting the accumulation of active cytotoxic effector cells in the gut tissue.

Example 13

Evaluation of CTL in Genital Tissue

Cytolytic activity in mononuclear cells isolated from the vagina and cervical tissues was detected in immunized mice.

Briefly, five mice were injected intradermally in the perineal skin with 25 µg UB23 plasmid (SEQ.ID.NO: 1) in 25 µL PBS, and then boosted with the same dose 4 weeks later. Tissues were harvested and pooled from all the mice at 8 weeks and a single cell mononuclear cell preparation was assayed for cytolytic activity against p18 loaded target cells. Control cultures at a 25:1 E:T ratio contained tissue cells co-cultured with target cells not loaded with peptide.

Figure 11:
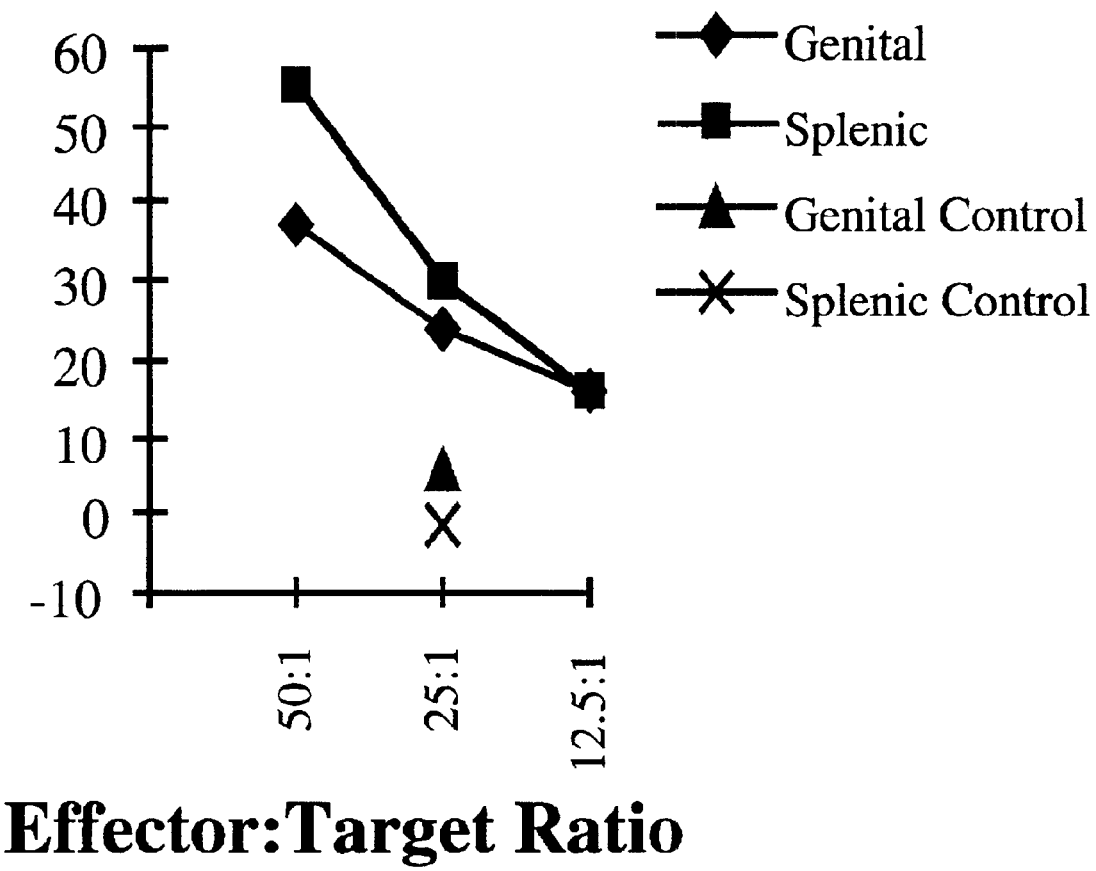
FIG. 11 shows the intradermal injection of UB23 plasmid elicits CTL in total genital mononuclear cells.

As shown in FIG. 11, mice that were immunized and boosted with the single plasmid have active CTL in freshly isolated total mononuclear cells from genital tissues and the spleen. The genital cells preparation contained slightly higher levels of nonspecific lytic activity (7%) that has been seen with other samples, but the lysis of p18 peptide loaded cells was substantially higher (37%). This experiment demonstrates that lytic activity is elicited by genetic immunization.

Example 14

Humoral Immune Responses Elicited by Intravenously Injected MAA-PEI Bound Plasmid in Macaques Six female macaques were immunized by intravenous injection of particle bound plasmids. A library of SHIV antigens fused to ubiquitin were used with the intent of maximizing T cell responses.

The cloned HIV-1$_{IIIB}$ (SEQ.ID.NO:4) isolate were used to construct expression libraries for each open reading frame with sequence fragments of 400–600 bp. Plasmids were constructed with each viral sequence fragment fused to the carboxy terminus of ubiquitin. Control plasmids were the backbone plasmid used in construction of the library but without coding sequence inserts.

The monkeys were immunized intradermally with 160 µg of plasmid (equal quantities of each of the 32 different plasmids bound to MAA-PEI (containing 500 µg of HSA and 215 µg of PEI)). After immunization of the monkeys, sera and secretions (vaginal, oral, and endobronchial) were collected at intervals and assayed for antibody responses to HIV antigens, including envelope (using gp160), p24, and p66 (reverse transcriptase).

Figure 12:
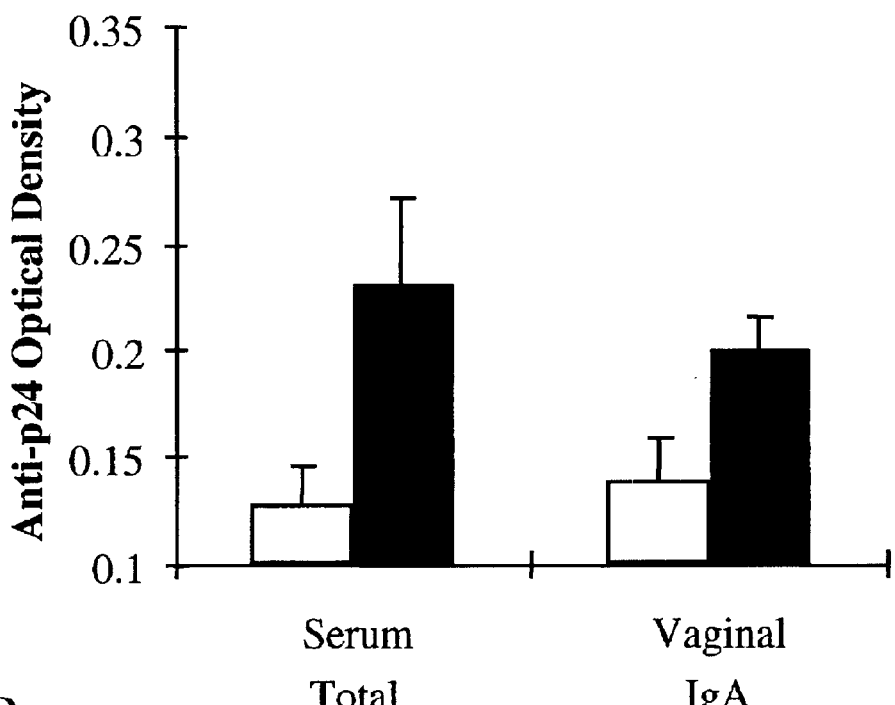
FIGS. 12A and 12B illustrate the systemic and mucosal anti-p24 response after a single injection of particle associated plasmids.
Figure 12:
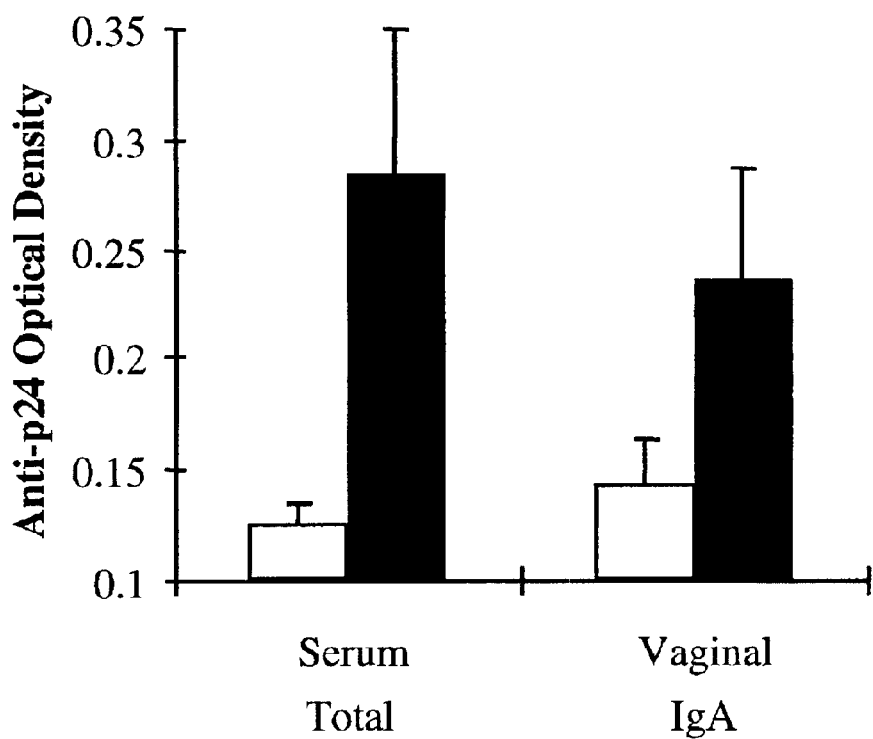

As shown in FIG. 12A, a significant serum antibody response to p24 was present after a single injection in all six monkeys, with an average titer of 1:3000. Anti-p24 IgA antibody was demonstrable in oral, endobronchial, and, most importantly, in vaginal secretions. In vaginal secretions, the anti-p24 IgA titer was estimated to be at least 1:32. In addition, 6/6 had a similar response to envelope and 3/6 had a response to p66 in both serum and vaginal secretions after the first injection.

Samples collected at 12 weeks (3 weeks after boosting IV with the same MAA-PEI-plasmid dose, FIG. 12B) showed an increase in anti-p24 antibody in serum in 5/6 monkeys with an average titer of 1:6800 in serum, and 1:128 in vaginal secretions. All the boosted monkeys showed a response to gp 160 of 1:1000 or greater in serum and 1:32 or greater in vaginal secretions (anti-p66 assays were not performed). Similar responses were also found in oral and endobronchial secretion samples. Therefore both systemic and mucosal antibody responses were elicited to particle bound library plasmids with a prime and single boost regimen.

Example 15

T Cell Responses Elicited by Intravenously Injected MAA-PEI Bound Plasmid in Macaques To assess T cell responses in this pilot experiment, the proliferative and cytokine production of peripheral blood cells to stimulation in vitro with HIV antigens was examined.

Six macaques were immunized at week 0 and boosted at week 9. Peripheral mononuclear blood cells (PBMCs) were isolated and stimulated in vitro with selected peptides and assayed to IFNγ production and T cell proliferative responses.

ELISPOT assay for single cells with IFN-γ release was used as a measure of T cell responses. This assay is known to correlate closely with CTL responses assessed by limiting dilution cytotoxicity assays and MHC tetramer-peptide binding (Tan et al., 1999), thus one skilled in the art recognizes that this represents a technique to evaluate multiple T cell epitope responses.

Briefly, the ELISPOT assay is used for both detection and quantitation of cytokine-secreting cells in response to antigen. CD4$^+$ and CD8$^+$ T cell populations are separated from freshly isolated PBMCs by a magnetic bead procedure and then stimulated in duplicate wells of 96 well plates (polyvinylidene difluoride backed plates, MAIP S 45, Millipore, Bedford, Mass.). The wells are precoated with anti-IFNγantibody (5 μg/mL) in 0.1 M bicarbonate buffer (pH 9.6) by overnight incubation at 4° C. Subsequently, the plates are washed 4 times with PBS, and serial dilutions of the cells, in complete RPMI 1640 medium, are mixed with stimulator cells and added to duplicate wells. The stimulator cells are either autologous PBMC or dendritic cells infected with recombinant vaccinia virus expressing HIV antigens, and fixed with 1% paraformaldehyde. After incubation for 40 h at 37° C. the cells are removed, and the wells are thoroughly washed with PBS and incubated with 100 μL of biotynylated second IFNγ antibody (detection antibody) for 3 h at 37° C. Avidin peroxidase is added and incubated for another 30 minutes. Spots representing IFNγ-secreting cells are developed using freshly prepared substrate (0.3 mg/mL of 3-amino-9-ethyl-carbazole) in 0.1 M sodium acetate buffer, containing 0.015% hydrogen peroxide. Plates are washed to stop color development, and spots are counted using a dissecting microscope. Only spots with fuzzy borders and diffused are scored as positive.

Figure 13:
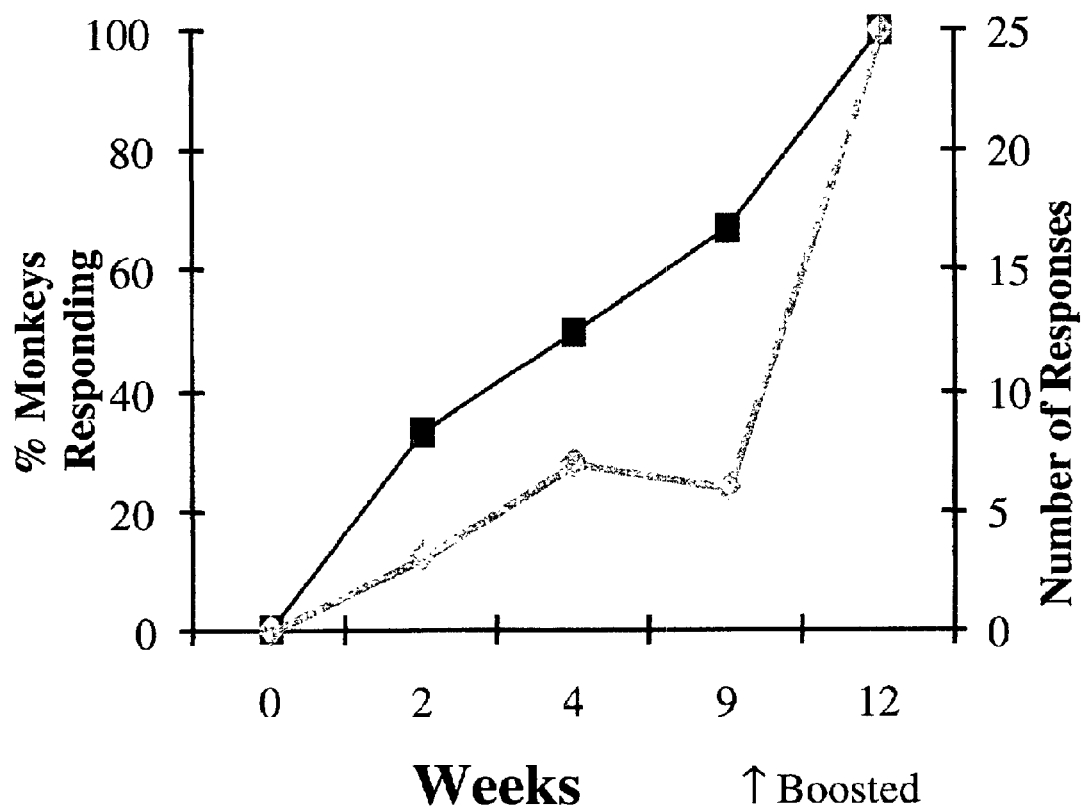
FIG. 13 illustrates the T cell proliferative and cytokine production responses to peptide stimulation. The plot shows the percentage of monkeys responding to one or more peptides over the time course of the experiment (squares), and the total number of individual responses to the different stimulating peptides and proteins in the group of monkeys at the different time points (diamonds).

As shown in FIG. 13, half of the monkeys responded to some T cell epitopes by 4 weeks after the first immunization, and all the monkeys responded after the booster immunization. Responses to several different peptides were detectable after the priming dose, but boosting recruited many other responses that were initially below the level of detection.

After boosting, 5/6 monkeys demonstrated T cell proliferative responses to multiple peptides, and 4/6 released IFNγ after stimulation with one or more peptides.

Figure 14:
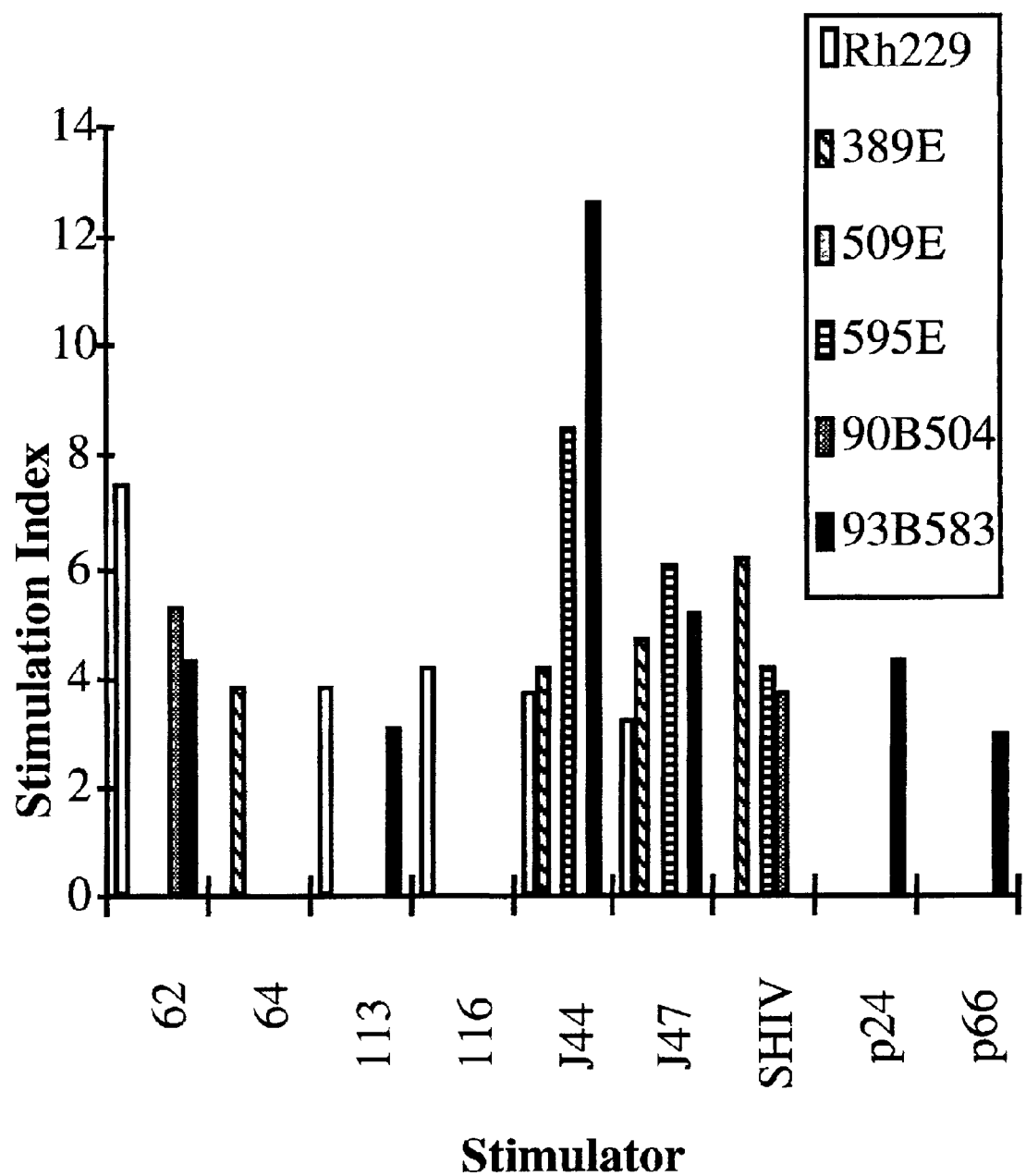
FIG. 14 shows the Rhesus macaque immune responses generated by two immunizations with the HIV-1 ELI vaccine.

FIG. 14 shows the distribution of proliferative responses by the individual monkeys to specific peptides. Briefly, the isolated PBMCs were stimulated with the indicated HIV-1 envelope peptides, intact HIV-1 p24 or p66 protein, or with heat inactivated SHIV and proliferation was assayed by $^3$H thymidine uptake.

$$\text{Stimulation index} = \frac{\text{antigen-stimulated }^3H\text{ uptake}}{\text{media-stimulated }^3H\text{ uptake}}$$

Example 16

Evaluation of Humoral and Cellular Responses to Oral Administration

Monkeys are orally immunized similar methods described herein. Of note is that for the orally immunized monkeys, gastric acidity is suppressed by prior administration of omeprazole (a proton pump inhibitor). One skilled in the art recognizes that this may not be essential since the vaccine is a suspension of the particle bound plasmids. Yet further, it is contemplated that the particles can be dried and incorporated into food or capsules. By selection of appropriate encapsulation materials, the gastric environment can be bypassed.

The immunological monitoring is necessarily limited by the quantity of blood that can be collected in these animals. Humoral immunity is assessed using the ELISPOT assay for IFNγ release as the principal measure of T cell responses.

After a booster regime, the monkeys are challenged by intravaginal administration of SHIV$_{ku\text{-}2}$ (SEQ.ID.NO:3). The intravaginal challenge is with a total volume of 1 mL SHIV$_{ku2}$ (10$^4$ TCID$_{50}$) from a needle-less syringe followed by gentle spread of the inoculum with the plunger of a 1 mL syringe. Virus infection in the animals is ascertained by monitoring virus load in the plasma as well as PBMCs. After challenge, the monkeys are closely followed clinically by the veterinarians responsible for their care, so that the clinical course of illness in infected monkeys is thoroughly documented, in addition to the assessment of the virologic assays. For viral load determination, quantitative competitive PCR is used. Other methods can be used to determine viral load included, but not limited to real time QC RT-PCR.

From this data, one skilled in the art recognizes that the present invention provides a new vaccine for autoimmune deficiency syndrome (AIDS).

Example 17

Evaluation of the Humoral and Cellular Immune Response to Plasmids of Three Different Modes of Expression Using Oral and Jet Injection Routes of Administration To determine whether oral administration of particle bound DNA elicits mucosal humoral and cellular immune responses equivalent or better than jet injection of naked DNA, animals are immunized with an expression vector containing the HIV gp120 protein fragment (the plasmid consists of a 450 base pair region containing the V3 loop with both antibody epitopes and the 15 mer amino acid sequence (p18) that is the strong immunodominant CTL envelope epitope in H-2$^d$ mice (Takahashi et al., 1988)). The p18 epitope is also recognized by H2$^b$ and a number of other murine haplotypes (Shirai et al., 1997). Antibody responses to gp120 are well characterized in mice, and therefore plasmids expressing this protein are valuable tools for evaluating genetic immunization responses to the different administration conditions. Vectors are used expressing the protein fragment alone (unfused, for natural expression dependent on the properties of the native amino acid sequence) or vectors that have been designed specifically for induction of either antibody or cytolytic T cells (Sykes et al, 1999). In the latter plasmids, the gp120 fragment is fused to either the carboxy terminus of ubiquitin (thus directing the fusion product to the proteasome, where it is degraded to peptides which are then presented on MHC class I molecules (Michalek et al, 1993)), or to human growth hormone (for secretion of the fused product and presentation on MHC class II molecules and B lymphocytes; the hGH also provides a separate positive control for immunization in mice). All plasmids are conjugated to MAA-PEI as shown in Example 2.

Mice are immunized with a dose range of particle preparations (1 pg to 50 μg, since gp120 expression levels will not necessarily be identical with those of the hGH reporter plasmid), and assays for systemic and mucosal humoral immune responses by isotype specific ELISA (Haneberg et al., 1994) are performed at intervals (4, 8, and 12 weeks). Assays for cytotoxic T lymphocytes in spleen cells and mucosal lymphocytes isolated from intestinal tissue, genital organs, and pelvic lymph nodes are performed at 4, 8, and 12 weeks on separate groups of animals using p18 loaded target cells in a standard CTL assays. For each group, blood and vaginal secretions are collected at 4 and 8 weeks, and intestinal secretions are collected at 12 weeks for humoral response evaluation similar to Examples 6 and 9.

Example 18

Enhancement of Single Plasmid Oral Immunizations

To determine the enhancement of a booster regimen, mice were orally immunized with the UB#23 plasmid (SEQ.ID.NO: 1) bound to MAA-PEI. Assays of CTLs showed cytotoxicity of 17% for p18 loaded P815 target cells at a ratio of 50:1 at 8 weeks. An oral booster dose was followed by an assay 10 days later and showed an increase in lytic activity to 43% at the 50:1 E:T ratio. Hence, CTLs are elicited by oral immunization, and optimization of the vaccination conditions with boosting or other enhancements (i.e., co-administration with a cytokine) will substantially improve the activity level.

To determine the enhancement of co-administration with cytokine expression vectors, immunizations are performed using methods similar to Example 17. Mice are immunized with the gp120 vector and a cytokine expression vector. Assays are performed for each group to determine the humoral and cellular immune responses. Blood and vaginal secretions are collected at 4, 8 and 12 weeks, and intestinal secretions are collected at 8 weeks for humoral response evaluation similar to the above Example 17. CTL responses are evaluated in spleen cells, and in mucosal lymphocytes isolated from genital and intestinal tissues collected at 4, 8 and 12 weeks.

Furthermore, a dose response experiment for intradermal injection of luciferase plasmid showed that low dose (10 ng) priming followed by a high dose plasmid booster (50 μg), resulted in a higher response than with any other combination. Therefore, a skilled artisan recognizes that these issues will need to be established for oral administration and jet injection. Possible experiments include but are not limited to, low, medium or high dose priming and single high dose booster at 4 weeks with assays done at 4, 8 and 12 weeks for humoral responses, and at 12 weeks for cellular responses.

Example 19

Dosage Determination for Oral or Jet Injected Immunizations with ELIs Eliciting an Immune Response Similar to Single Plasmid Administration To evaluate the possibility that co-administration of multiple plasmids (immunization with libraries containing multiple plasmids, not a single plasmid) may interfere with eliciting immune responses to an individual epitope, expression libraries were constructed as in Example 8. It has been observed that immunization with complex protein mixtures (Maceda et al., 1985, Hammerl et al., 1988) interferes with the elicitation of immune responses. Furthermore, immunizations with ELIs have only been delivered via a gene gun or intramuscularly or subcutaneous. Therefore, a skilled artisan realizes the necessity of determining the effective dose for an expression library to elicit the maximum immune response, especially the dose to be delivered orally.

The plasmid dose required to elicit equivalent immune responses to single plasmid administration was determined from the above examples, from gene gun and intramuscular studies (Barry et al., 1997) and from intradermal injection studies with reporter genes showing that low doses of plasmid (approximately 100 ng) can produce equivalent responses if injected with a sufficient amount of noncoding vector. The additional noncoding plasmid was required both for protection of the plasmid from too rapid enzymatic breakdown and for the immune response enhancement of the local Th1cytokine inducing effects of the CpG sequences in plasmid DNA.

Mice are immunized with a dose range of particle preparations (25 μg to 100 μg) prepared similar to Example 8 and bound to MAA-PEI. Assays for systemic and mucosal humoral immune responses are measured by isotype specific ELISA (Haneberg et al., 1994) are performed at intervals (4, 8, and 12 weeks). Assays for cytotoxic T lymphocytes in spleen and IEL from the gut, genital organs, and pelvic lymph nodes are performed at 4, 8, and 12 weeks on separate groups of animals using p18 loaded target cells in a standard CTL assays.

With these results, the effects of boosting and cytokine enhancing plasmid administration under optimal conditions are evaluated. Assays are performed at 8 and 12 weeks on boost/cytokine treated groups of mice.

Furthermore, a skilled artisan recognizes that immunizations using ELIs are not limited to injecting only one library. Mixtures of libraries can be injected. For example, if 5 libraries were constructed from a particular genome of a parasite, then equal mixtures of the 5 individual libraries can be used for immunization studies. In addition, if one particular library is found to elicit a strong immune response, then sublibraries (libraries containing fewer clones) can be developed to enrich the library resulting in possibly a more potent vaccine (Piedrafita, 1999).

Example 20

Immune Responses in Additional Mouse Strains

To ensure that the murine immune responses are not restricted to a single mouse strain, two additional mouse strains are studied. C57BL/6 mice ($H2^b$) produce CTL responses to the same HIV-1 V3 loop epitope (p18) (Shirai et al., 1997), as well as making antibodies to this region of the envelope protein (Staats et al., 1996). Hence, the same #23 plasmids from Example 8 was used to examine immune responses in this strain. CD-1 mice, a strain that is outbred and thus more analogous to human MHC variation, was also tested. This mouse has not been studied in terms of its actual histocompatibility types (according to Harlan-Sprague-Dawley, the source for these mice).

Example 21

Evaluation of Immune Response in Regional Lymph Nodes

Regional lymph nodes cells with and without perineal boosting with the DNA expression vectors are examined. Although lymph nodes would not be the most optimal location to prove mucosal activity, the association of mucosal effector cells and regional node effector cells is well appreciated (Klavinskis et al., 1996), and furthermore, the first locations beyond the mucosa for HIV replication are the local and regional lymph nodes. The pelvic nodes in two orally immunized mice were pooled. CTL activity was demonstrated 8 weeks after a single oral immunization in both a direct assay (13% at a 50:1 E:T ratio) and in an in vitro restimulation assay (28%, 50:1 E:T ratio).

Example 22

Antigen Binding Using Tetramer/Peptide Complexes

Genital tissue T cells are examined for antigen binding using soluble tetramer/peptide complexes to detect display of antigen specific receptors. This technology is well established in the art (Dunbar et al., 1998, Gillanders et al, 1997, Kuroda et al, 1999, Lefrancois, et al., 1999 and Murali-Krishana, et al. 1998). Tetrameric peptide-MHC class I complexes are prepared by combining the recombinant fusion protein β2-microblobulin-MHC class I extracellular heavy chain and the desired peptide under denaturing conditions in urea. Dilution of the denaturing conditions permits refolding of the monomeric class I complex around the peptide which is then biotinylated, chromatographically purified. Tetramers of the complex are formed by addition of fluorescein labelled avidin. Peptide specific CTL are identified by incubation of the complexes with cells at 37° C. with or without labelled antibody to other cell surface antigens, washed, and analyzyed by flow cytometry.

A skilled artisan realizes that this strategy can be applied to any antigen to determine the antibody response in genital tissue after immunization.

Example 23

HSA/PEI Combination for Gene Expression

For preparation of plasmids for delivery by soluble protein and polyethylenimine, human serum albumin (HSA) (or other proteins) was mixed in PBS to the desired stock concentration with polyethyleneimine (PEI (750 kD), suspended in PBS, and pH adjusted to 7.4, in a mole ratio between approximately 1.5:1 and 150:1 (usually 15:1). For plasmid binding, the HSA/PEI stock solution is diluted in PBS to the desired volume for combination with the plasmid at an N:P ratio between 10:1 and 20:1 (usually 15:1), and the plasmid (diluted in PBS to 200 ng/$\mu$L) was added dropwise with gentle vortexing of the solution. The solution was then incubated at room temperature (RT) for 20 minutes before administration.

Figure 15:
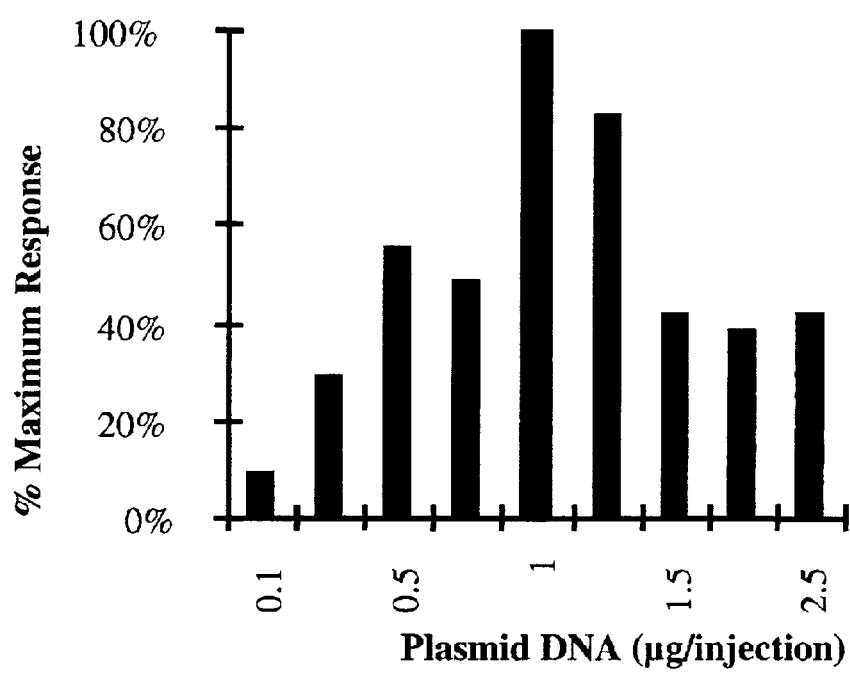
FIGS. 15A and 15B demonstrate the gene expression of a plasmid bound to non-conjugated HSA/PEI.
Figure 15:
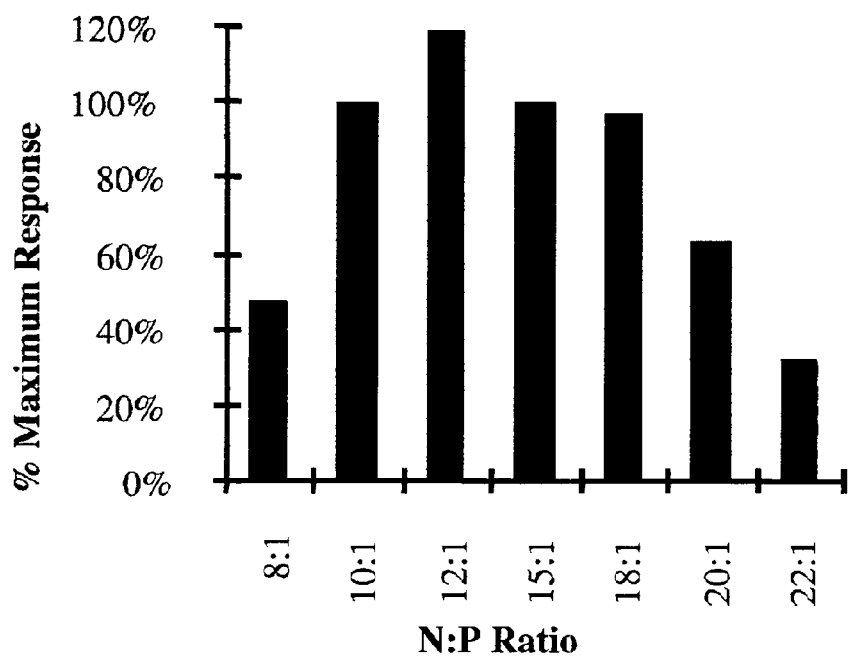

Mice were injected intravenously with pCMV-Luc bound HSA/PEI (non-conjugated), and then were sacrificed at 24 h for luciferase assay of the lungs. In these experiments, all conditions tested were compared with the standard condition of 1 $\mu$g of DNA combined the HSA/PEI at an N:P ratio of 15:1, expressed as a 100% response. The albumin content of each preparation was at a molar ratio of 15 HSA to 1 PEI. In FIG. 15A illustrates a dose response curve for the quantity of DNA injected (each condition in a consistent volume of 200 $\mu$L). This demonstrated that the maximal response was achieved near 1 $\mu$g of plasmid injected under these conditions. In FIG. 15B, 1 $\mu$g was injected in each animal with a range of N:P ratios. Ratios between 1:10 and 1:20 showed good transfection, and in this experiment, 1:12 showed a slightly higher level of transfection than 1:15. In parallel experiments, pCMV-Luc bound to PEI over a range of N:P ratios in the absence of added HSA showed luciferase activity <<1% of that achieved with standard HSA/PEI conditions.

Thus, the present invention provides a new gene delivery system, HSA/PEI, that does not have to be conjugated.

Example 24

Kinetics of Gene Expression and Repeated injections

Mice were injected with 1 $\mu$g pCMV-Luc and HSA/PEI at an N:P ratio of 1:15, and then assayed for luciferase activity in ng of enzyme per whole lung preparation. After a single injection, FIG. 16A shows that gene expression is maximal at 24 h and 48 h, but has a marked decline at 72 h and thereafter.

Figure 16:
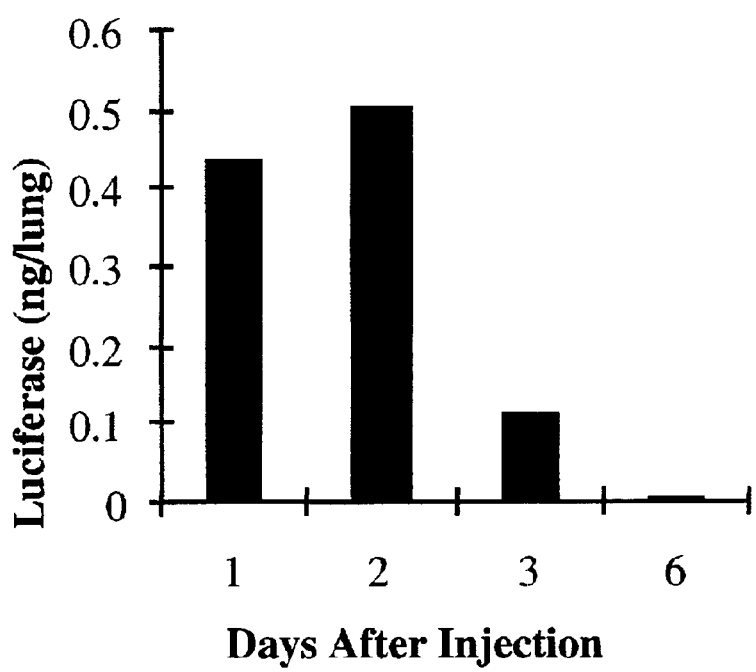
FIGS. 16A and 16B illustrates the kinetics of gene expression in repeated injections.
Figure 16:
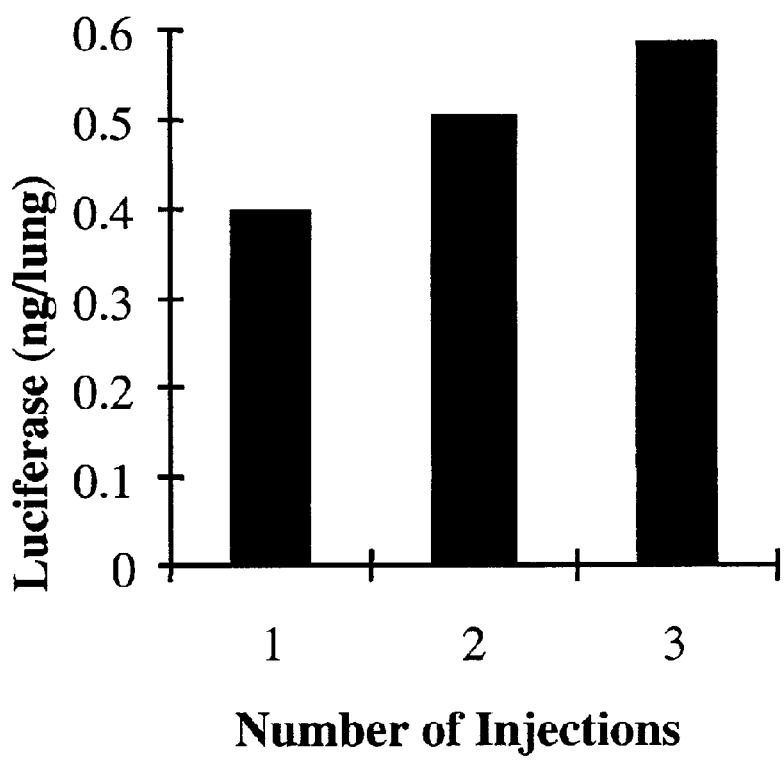

In FIG. 16B, mice were injected with the same preparation as in FIG. 16A either one, two or three times at spaced intervals over 48 h, and then assayed for luciferase activity.

Example 25

Effects of Different Proteins and Concentrations of Proteins on PEI Based Gene Delivery Mice were injected with 1 $\mu$g of pCMV-Luc bound to PEI (N:P of 15) in the presence of different concentrations of HSA (FIG. 17A) or different proteins (FIG. 17B), and then assayed for luciferase activity at 48 h.

Figure 17:
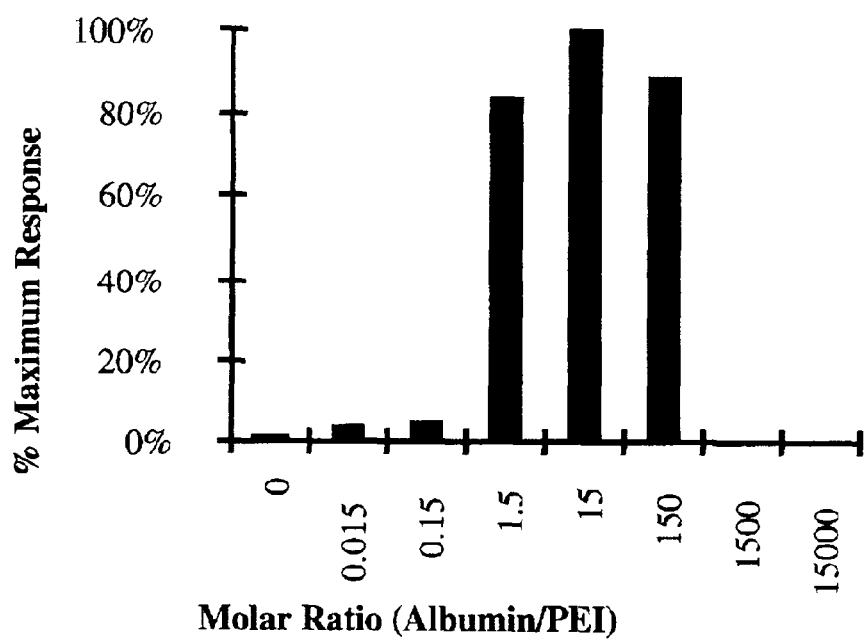
FIGS. 17A and 17B shows the effects of different proteins and concentrations of proteins on PEI based gene delivery.
Figure 17:
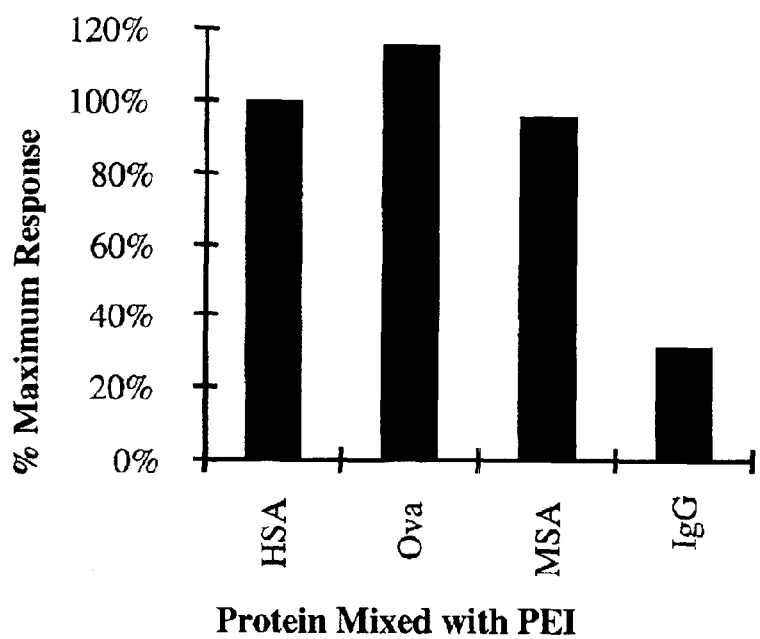

In these experiments, the luciferase activity was expressed as the percentage of the maximal response obtained under the standard conditions of an HSA:PEI molar ratio of 15. FIG. 17A shows that there is a broad range of tolerance for protein quantities between a molar ratio of 1.5 to 150, while FIG. 17B shows that other soluble proteins can also be used to enhance gene delivery by PEI in vivo.

Example 26

Organ Distribution Studies

Gene expression using the luciferase expression vector pCMV-Luc was examined comparing IV injection of HSA/PEI bound plasmid with MAA-PEI bound plasmid.

Figure 18:
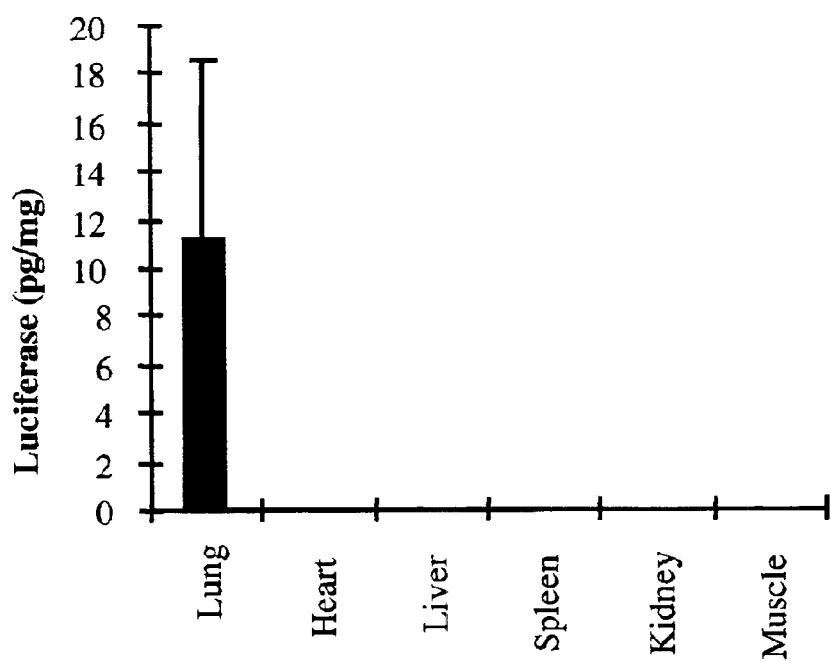
FIGS. 18A and 18B illustrates the organ distribution of gene expression.
Figure 18:
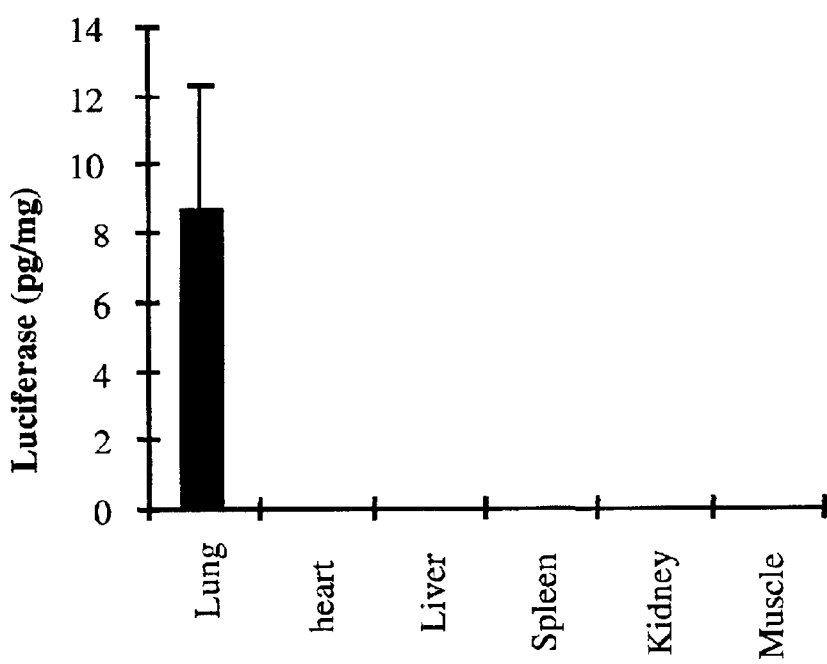

Mice were injected with 1 $\mu$g of plasmid bound at a 15:1 N:P ratio to the PEI present in either preparation, and then they were sacrificed at 48 h and the organs harvested. Equivalent weight samples (whole lung in these mice was an average of 70 mg in mass) for each organ were harvested and assayed for luciferase activity, with gene activity expressed in luciferase enzyme/mg of tissue (FIG. 18A and FIG. 18B). Although none of the other organs had high levels of activity, the organs with HSA/PEI showed that roughly 2–3% of luciferase activity may be distributed outside the lung. With MAA-PEI, in contrast, the luciferase activity outside the lung is <<1% of the total.

Thus, the present invention provides a new gene delivery system for lung tissue using non-conjugated bound plasmids.

References

All patents and publications mentioned in the specification are indicative of the level of those skilled in the art to which the inventions pertains. All publications are herein incorporated by reference to the same extent as if each individual publication was specifically and individually indicated to be incorporated by reference.

Allan et al., 1995. J Acquir Immune Defic Syndr. 9:429–441
Altman et al., 1996. Science. 274(5284):94–6
An et al., 1997. J Virol. 71(3):2292–302.
Baba et al., 1999. Nature Med. 5(2):194–203
Barry and Johnston. 1997. Vaccine. 15:788–791
Barry et al., 1995. Nature. 377:632–635

Benson et al., 1998. J Virol. 72:4170–4182
Bloom. 1996. A perspective on AIDS vaccines. Science. 272:1888–1890.
Boyer et al., 1997. Nature Med. 3:526–532
Brayton et al., 1998. Ann NY Acad Sci. 849:369–371.
Bryson et al., N Engl J Med. 332:833–838
Carson et al., 1997. J Exp Med. 186:1621–1622
Chen et al., 1998. J Immunol. 160:2425–2432
Chow et al., 1998. J Immunol. 160:1320–1329
Chu et al., 1997. J Exp Med. 186:1623–1631
Colombetti et al., 1975. Internatl J Nuclear Med Biol. 2:180–184.
Czerkinsky et al., 1999. Immunological Reviews 170:197–222
Daniel et al., 1992. Science. 258:1938–1941
Doe et al., 1996. Proc Natl Acad Sci (USA). 93:8578–8583
Dolin 1995. J Inf Dis. 172:1175–1183
Donnelly et al., 1997. DNA Vaccines, p. 617–648. In W. E. Paul, C. G. Fathman, and H. Metzger (ed.), Annual Review of Immunology, vol. 15. Annual Reviews, Inc., Palo Alto, Calif.
Dunbar et al., 1998. Curr Biol. 8(7):413–6
Fattom et al., 1999. Vaccine. 17(2):126–33
Fu et al., 1998. Vaccine. 16(18):1711–7
Fuller and Haynes 1994. AIDS Res Hum Retrovir. 10:1433–1441
Fynan et al., 1993. Proc Natl Acad Sci (USA). 90:11478–11482
Gallichan and Rosenthal 1996. J Exp Med. 184(5):1879–1890
Gilkeson et al., 1993. Clin Immunopathol. 68:283–292
Gilkeson et al., 1996. J Exp Med. 183:1389–1397
Gillanders et al., 1997. Int Immunol. 9(1):81–9
Grifantini et al., 1998. Eur J Immunol. 28(4):1225–32
Hammerl et al., 1988. Mol Immunol. 25(3):313–20
Haneberg et al., 1994. Infect Immun. 62:15–23
Hartl et al., 1999. J Allergy Clin Immunol. 103(1 Pt 1):107–13
Hasleton and Curry 1996. Anatomy of the lung, p. 1–55. In P. S. Hasleton (ed.), Spencer's Pathology of the Lung, Fifth ed. McGraw-Hill, New York.
Hu et al., 1992. Science. 255:456–459
Huang et al., 1994. Science. 264:961–965
Hunt et al., 1995. Vaccine. 13(17):1649–57
Ishikawa et al., 1977. Immunology. 32(5):755–66
Jenkins et al., Davis S S. 1995. J Drug Targeting. 3:79–81.
Kawabata et al., 1995. Pharm Res. 12:825–830.
Kim et al., 1998. Eur J Immunol. 28:1089–1103
Kim et al., 1997. Nature Biotechnol. 15:641–646
Klavinskis et al., 1996. Journal of Immunology. 157(6):2521–7
Klavinskis et al., 1997. Vaccine. 15(8):818–20
Klinman et al., 1997. J Immunol. 158(8):3635–9
Kuroda et al., 1999. J Virol. 73(2):1573–9
Lefrancois et al., 1999. J Exp Med. 190(9):1275–1284
Lehner et al., 1992. Science. 258:1365–1369
Lehner et al., 1996. Nature Medicine. 2(7):767–75
Lew et al., 1995. Hum Gene Ther. 6:553–564.
Livingston et al., 1998. Infect Immun. 66(1):322–9
London and Rubin 1998. p. 643–653. In P. L. Ogra, J. Mestecky, M. E. Lamm, W. Strober, J. Bienenstock, and J. R. McGhee (ed.), Mucosal Immunology, 2nd ed. Academic Press, New York
Lu et al., 1995. Virology. 209:147–154
Maceda Soares et al., 1985. Int Arch Allergy Appl Immunol. 78(4):449–51
Mancini et al., 1996. Proc. Nat. Acad. Sci. U.S.A. 93(22):12496–501
Manoutcharian et al., Immunol Lett. 62(3):131–6
Marx et al., 1993. Science. 260:1323–1327
Mathiowitz et al., 1997. Nature. 386:410–414
Mattapallil et al., 1998. J Virol. 72:6421–6429
Mazzoli et al., 1997. Nature Med. 3:1250–1257
McMichael and Phillips 1997. Escape of human immunodeficiency virus from immune control, p. 271–296. In W. E. Paul, C. G. Fathman, and H. Metzger (ed.), Annual Review of Immunology, vol. 15. Annual Reviews, Inc., Palo Alto, Calif.
Mestecky et al., 1994. AIDS Res Hum Retroviruses. 10S2:S11–S20
Michalek et al., 1993. Nature. 363:552–555
Miller et al., 1992. Lab Invest. 68:129–145
Mitchell et al., 1995. Immunotechnology. 1:211–219.
Mowat 1987. Immunol Today. 8:93–98
Murali-Krishna et al., 1998. Immunity. 8(2):177–87
Ogra et al., 1968. N Engl J Med. 279:893–900
Oxford and Jeffs 1996. Vaccine. 14:1712–1717
Pantaleo et al., 1995. N Engl J Med. 332:209–216
Piedrafita et al., 1999. J Immunol. 163(3):1467–72
Roy et al., 1999. Nat Med. 5(4):387–91
Schirmbeck et al., 1995. J Virol. 69:5929–5934
Schmid et al., 1994. Acta Gastroenterol. 32:665–670.
Shirai et al., 1997. J Immunol. 158:3181–3188
Staats et al., 1996. J Immunol. 157:462–472
Sykes and Johnston 1999. DNA Cell Biol. 18(7):521–31
Takahashi et al., 1988. Proc Natl Acad Sci (USA). 85:3105–3109
Tan et al., 1999. Human Gene Ther. 10:2153–2161
Tang et al., 1992. Nature. 356:152–154.
Thierry et al., 1997. Gene Ther. 4:226–237.
Thomson et al., 1998. J Immunol. 160:1717–1723
Ulmer et al., 1994. Vaccine. 12:1541–1544
Wang et al., 1994. AIDS Res Human Retroviruses. 10:S35–S41
Wang et al., 1993. Proc Natl Acad Sci (USA). 90:4156–4160
Weichselbaum and Kufe. 1997. Lancet. 349:SII 10–12.
Weiner et al., 1997. Proc Natl Acad Sci U S A. 94(20):10833–7
Whelan et al., 1999. J Immunol. 163(8):4342–8
Williams et al., 1991. Proc Natl Acad Sci (USA). 88:2726–2730.
Wolff et al., 1992. Hum Mol Genet. 1(6):363–9
Wu and Kipps. 1997. J Immunol. 159(12):6037–43
Zhu et al., 1993. Science. 261:209–211.

One skilled in the art readily appreciates that the present invention is well adapted to carry out the objectives and obtain the ends and advantages mentioned as well as those inherent therein. Methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A composition comprising an expression vector bound to an aggregated protein-polycationic polymer conjugate which forms a DNA particulate composition, wherein the aggregated protein is not a ligand targeted to a cell surface receptor, and the expression vector comprises a promoter polynucleotide sequence operatively linked to a polynucleotide sequence encoding an antigen.

2. The composition of claim 1 wherein the polynucleotide sequence encoding the antigen is a fragment of a genome or gene selected from the group of genomes or genes associated with a disease consisting of infectious disease, cancer, and autoimmune disease.

3. The composition of claim 2 wherein the polynucleotide sequence encoding the antigen is a fragment of a genome or gene selected from the group of pathogenic genomes consisting of virus, bacterium, fungus and protozoa.

4. The composition of claim 3 wherein the polynucleotide sequence encoding the antigen is a fragment of a genome selected from the group of viral genomes consisting of human immunodeficiency virus (HIV), herpes simplex virus (HSV), hepatitis C virus (HCV), influenza and respiratory syncytial virus (RSV).

5. The composition of claim 1 wherein the aggregated protein is albumin.

6. The composition of claim 1 wherein the polycationic polymer is selected from the group consisting of polyamino acids, polyimines or a combination thereof.

7. The composition of claim 6 wherein the polyimine is polyethyleneimine.

8. The composition of claim 1 wherein the expression vector contains a heterologous mammalian targeting sequence.

9. The composition of claim 8 wherein the heterologous mammalian targeting sequence is ubiquitin or a signal sequence for secretion.

10. The composition of claim 9 wherein the signal sequence for secretion is human growth hormone.

11. A method of producing a DNA particulate composition comprising the step of incubating an expression vector with an aggregated protein-polycationic polymer conjugate to form the DNA particulate composition, wherein the aggregated protein is not a ligand targeted to a cell surface receptor, and the expression vector comprises a promoter polynucleotide sequence operatively linked to a polynucleotide sequence encoding an antigen.

12. The method of claim 11 wherein the polynucleotide sequence encoding the antigen is a fragment of a genome or gene selected from the group of genomes or genes associated with a disease consisting of infectious disease, cancer, and autoimmune disease.

13. The method of claim 12 wherein the polynucleotide sequence encoding the antigen is a fragment of a genome selected from the group of pathogenic genomes consisting of virus, bacterium, fungus and protozoa.

14. The method of claim 13 wherein the polynucleotide sequence encoding the antigen is a fragment of a genome selected from the group of viral genomes consisting of HIV, HSV, HCV, influenza and RSV.

15. The method of claim 11 wherein the expression vector contains a heterologous mammalian targeting sequence.

16. The method of claim 15 wherein the heterologous mammalian targeting sequence is ubiquitin or a signal sequence for secretion.

17. The method of claim 16 wherein the signal sequence for secretion is human growth hormone.

18. The method of claim 11 wherein the polycationic polymer is selected from the group consisting of polyamino acids, polyimines or a combination thereof.

19. The method of claim 17 wherein the polyimine is polyethyleneimine.

20. The method of claim 11 wherein the aggregated protein is albumin.

21. A method of inducing an immune response in a mammal comprising the step of administering to the mammal an expression vector bound to an aggregated protein-polycationic polymer conjugate which forms a DNA particulate composition, wherein the aggregated protein is not a ligand targeted to a cell surface receptor, and the expression vector comprises a promoter polynucleotide sequence operatively linked to a polynucleotide sequence encoding an antigen.

22. The method of claim 21 wherein the immune response is systemic.

23. The method of claim 21 wherein the immune response is mucosal.

24. The method of claim 21 wherein the immune response is both systemic and mucosal.

25. A method of inducing an immune response in a mammal comprising the step of co-administering to the mammal two expression vectors, both bound to an aggregated protein-polycationic polymer conjugate which forms DNA particulate compositions, wherein the aggregated protein is not a ligand targeted to a cell surface receptor, and the first expression vector comprises a promoter polynucleotide sequence operatively linked to a polynucleotide sequence encoding an antigen and the second vector comprises a cytokine polynucleotide sequence.

26. The method of claim 25 wherein the cytokine polynucleotide sequence contains the sequence encoding GM-CSF.

27. The method of claim 25 wherein the cytokine polynucleotide sequence contains the sequence encoding IL12.

28. The method of claim 25 wherein the co-administration is to a mucosal surface.

29. The method of claim 28 wherein the mucosal surface is selected from the group consisting of intranasal surface, oral surface, gastrointestinal surface and genitourinary tract surface.

30. The method of claim 25 wherein the co-administration is parenterally.

31. The method of claim 30 wherein the co-administration is intramuscular or intradermal.

32. A method of inducing an immune response in a mammal comprising the step of administering to the mammal an expression vector bound to an aggregated protein-polycationic polymer conjugate which forms a DNA particulate composition, wherein the aggregated protein is not a ligand targeted to a cell surface receptor, and the expression vector comprises a first promoter polynucleotide sequence operatively linked to a first polynucleotide sequence encoding an antigen and a second polynucleotide sequence encoding a cytokine.

33. The method of claim 32, wherein the first and second polynucleotide sequences are under transcriptional control of the same promoter polynucleotide sequence.

34. The method of claim 32, wherein the expression vector comprises the first promoter polynucleotide sequence operatively linked to the first polynucleotide sequence encoding an antigen and a second promoter polynucleotide sequence linked to the second polynucleotide sequence encoding a cytokine and the first and second promoter polynucleotide sequences are different.

35. A method of introducing a polynucleotide into a cell comprising the steps of: forming a DNA particulate composition comprising an expression vector bound to an aggregated protein-polycationic polymer conjugate, wherein the aggregated protein is not a ligand targeted to a cell surface receptor, and the expression vector comprises a promoter polynucleotide sequence operatively linked to a polynucleotide sequence encoding an antigen; and incubating the cell with the DNA particulate composition under conditions wherein the cell takes in the DNA particulate composition.

* * * * *

SEQUENCE LISTING

<160> NUMBER OF SEQ ID NOS: 13

<210> SEQ ID NO 1
<211> LENGTH: 708
<212> TYPE: DNA
<213> ORGANISM: HIV U#23

<400> SEQUENCE: 1

```
aaggtatcct ttgagccaat tcccatacat tattgtgccc cggctggttt tgcgatttta      60
aaatgtaata ataagacgtt caatggaaca ggaccatgta caaatgtcag cacagtacaa     120
tgtacacatg gaattaggcc agtagtatca actcaactgc tgttaaatgg cagtctagca     180
gaagaagagg tagtaattag atctgtcaat ttcatggaca atgctaaaac cataatagta     240
cagctgaaca catctgtaga aattaattgt acaagaccca gcaacaatac aataaaaaga     300
atccgtatcc agagaggacc agggagagca tttgttacaa tgggaaaaat aggagatatg     360
agacaagcac attgtaacat tagtagagca aaatggaata cactttaaa acagatagct      420
agcaaattaa gagaacaatt tggaaataat aaaacaataa tctttaagca atcctcagga     480
ggggacccag aaattgtaac gcacagtttt aattgtggag gggaatttt ctactgtaat       540
tcaacacaac tgtttaatag tacttggttt aatagtactt ggagtactga agggtcaaat     600
aacactgaag gaagtgacac aatcaccctc ccatgcagaa taaaacaaat tataaacatg     660
tggcagaaag taggaaaagc aatgtatgcc cctcccatca gtggacaa                  708
```

<210> SEQ ID NO 2
<211> LENGTH: 236
<212> TYPE: PRT
<213> ORGANISM: HIV U#23

<400> SEQUENCE: 2

```
Lys Val Ser Phe Glu Pro Ile Pro Ile His Tyr Cys Ala Pro Ala Gly
1               5                   10                  15

Phe Ala Ile Leu Lys Cys Asn Asn Lys Thr Phe Asn Gly Thr Gly Pro
            20                  25                  30

Cys Thr Asn Val Ser Thr Val Gln Cys Thr His Gly Ile Lys Pro Val
        35                  40                  45

Val Ser Thr Gln Leu Leu Asn Gly Ser Leu Ala Glu Glu Val
    50                  55                  60

Val Ile Arg Ser Ala Asn Leu Thr Asp Asn Val Lys Thr Ile Ile Val
65                  70                  75                  80

Gln Leu Asn Gln Ser Val Glu Ile Asn Cys Thr Arg Pro Asn Asn
                85                  90                  95

Thr Arg Lys Arg Ile Arg Ile Gln Arg Gly Pro Gly Arg Thr Phe Val
            100                 105                 110

Thr Ile Gly Lys Ile Gly Asn Met Arg Gln Ala His Cys Asn Ile Ser
        115                 120                 125

Arg Ala Lys Trp Asn Asn Thr Leu Lys Gln Ile Ala Ser Lys Leu Arg
    130                 135                 140

Glu Gln Tyr Gly Asn Asn Lys Thr Ile Ile Phe Lys Gln Ser Ser Gly
145                 150                 155                 160

Gly Asp Leu Glu Ile Val Thr His Ser Phe Asn Cys Gly Gly Glu Phe
                165                 170                 175

Phe Tyr Cys Asn Ser Thr Gln Leu Phe Asn Ser Thr Trp Phe Asn Ser
            180                 185                 190
```

```
Thr Trp Ser Thr Glu Gly Ser Asn Asn Thr Glu Gly Ser Asp Thr Ile
        195                 200                 205

Thr Leu Pro Cys Arg Ile Lys Gln Ile Ile Asn Met Trp Gln Glu Val
        210                 215                 220

Gly Lys Ala Met Tyr Ala Pro Pro Ile Ser Gly Gln
225                 230                 235

<210> SEQ ID NO 3
<211> LENGTH: 10006
<212> TYPE: DNA
<213> ORGANISM: HIV (Simian)

<400> SEQUENCE: 3
cagtcgctct gcggagaggc tggcagattg agccctggga ggttctctcc agcactagca      60
ggtagagcct gggtgttccc tgctagactc tcaccagcac ttggccggtg ctgggcagag     120
tgactccacg cttgcttgct taaagccctc ttcaataaag ctgccatttt agaagtaagc     180
tagtgtgtgt tcccatctct cctagccgcc gcctggtcaa ctcggtactc aataataaga     240
agacccggt ctgttaggac cctttctgct ttgggaaacc gaagcaggaa atccctagc      300
agattggcgc ctgaacaggg acttgaagga gagtgagaga ctcctgagta cggctgagtg     360
aaggcagtaa gggcggcagg aaccaaccac gacggagtgc tcctataaag gcgcgggtcg     420
gtaccagacg gcgtgaggag cgggagagga agaggcctcc ggttgcaggt aagtgcaaca     480
caaaaagaa atagctgtct tttatccagg aagggtaat aagatagagt gggagatggg     540
cgtgagaaac tccgtcttgt cagggaagaa agcagatgaa ttagaaaaaa ttaggctacg     600
acccaacgga agaaaaagt acatgttgaa gcatgtagta tgggcagcaa atgaattaga     660
tagatttgga ttagcagaaa gcctgttgga gaacaaagaa ggatgtcaaa aaatactttc     720
ggtcttagct ccattagtgc caacaggctc agaaaattta aaaagccttt ataatactgt     780
ctgcgtcatc tggtgcattc acgcagaaga gaaagtgaaa cacactgagg aagcaaaaca     840
gatagtgcag agacacctag tggtggaaac aggaacaaca gaaactatgc caaaaacaag     900
tagaccaaca gcaccatcta gcggcagagg aggaaattac ccagtacaac aaataggtgg     960
taactatgtc cacctgccat taagcccgag aacattaaat gcctgggtaa aattgataga    1020
ggaaaagaaa tttggagcag aagtagtgcc aggatttcag gcactgtcag aaggttgcac    1080
cccctatgac attaatcaga tgttaaattg tgtgggagac catcaagcgg ctatgcagat    1140
tatcagagat attataaacg aggaggctgc agattggac ttgcagcacc cacaaccagc    1200
tccacaacaa ggacaactta gggagccgtc aggatcagat attgcaggaa caactagttc    1260
agtagatgaa caaatccagt ggatgtacag acaacagaac cccataccag taggcaacat    1320
ttacaggaga tggatccaac tggggttgca aaaatgtgtc agaatgtata cccaacaaa    1380
cattctagat gtaaaacaag gccaaaaaga gccatttcag agctatgtag acaggttcta    1440
caaaagttta agagcagaac agacagatgc agcagtaaag aattggatga ctcaaacact    1500
gctgattcaa aatgctaacc cagattgcaa gctagtgctg aagggctggg tgtgaatcc    1560
caccctagaa gaaatgctga cggcttgtca aggagtaggg gggccgggac agaaggctag    1620
attaatggca gaagccctga agaggccct cgcaccagtg ccaatccctt ttgcagcagc    1680
ccaacagagg ggaccaagaa agccaattaa gtgttggaat tgtgggaaag agggacactc    1740
tgcaaggcaa tgcagagccc caagaagaca gggatgctgg aaatgtggaa aatggacca    1800
tgttatggcc aaatgcccag acagacaggc gggttttta ggccttggtc catggggaaa    1860
```

-continued

```
gaagccccgc aatttcccca tggctcaagt gcatcagggg ctgatgccaa ctgctcccccc      1920 agaggaccca gctgtggatc tgctaaagaa ctacatgcag ttgggcaagc agcagagaga      1980
aaagcagaga gaaagcagag agaagcctta caaggaggtg acagaggatt tgctgcacct      2040
caattctctc tttggaggag accagtagtc actgctcata ttgaaggaca gcctgtagaa      2100
gtattactgg atacaggggc tgatgattct attgtaacag gaatagagtt aggtccacat      2160
tataccccaa aaatagtagg aggaatagga ggttttatta atactaaaga atacaaaaat      2220
gtagaaatag aagttttagg caaaaggatt aagggacaa tcatgacagg gacacccccg       2280
attaacattt tggtagaaa tttgctaaca gctctgggga tgtctctaaa ttttcccata      2340
gctaaagtag agcctgtaaa agtcgcctta aagccaggaa aggatggacc aaaattgaag     2400
cagtggccat tatcaaaaga aaagatagtt gcattaagaa aaatctgtga aaagatggaa     2460
aaggatggtc agttggagga agctcccccg accaatccat acaacacccc cacatttgct    2520
ataaagaaaa aggataagaa caaatggaga atgctgatag atttttaggga actaaatagg   2580 gtcactcagg actttacgga agtccaatta ggaataccac accctgcagg actagcaaaa    2640
aggaaaagaa ttacagtact ggatataggt gatgcatatt tctccatacc tctagatgaa    2700
gaatttaggc agtacactgc ctttacttta ccatcagtaa ataatgcaga gccaggaaaa    2760
cgatacattt ataaggttct gcctcaggga tggaagggt caccagccat cttccaatac     2820
actatgagac atgtgctaga acccttcagg aaggcaaatc cagatgtgac cttagtccag    2880 tatatgatg acatcttaat agctagtgac aggacagacc tggaacatga cagggtagtt     2940
ttacagtcaa aggaactctt gaatagcata gggttttcta ccccagaaga gaaattccaa    3000
aaagatcccc catttcaatg gatggggtac gaattgtggc caacaaaatg gaagttgcaa    3060
aagatagagt tgccacaaag agagacctgg acagtgaatg atatacagaa gttagtagga   3120
gtattaaatt gggcagctca aatttatcca ggtataaaaa ccaaacatct ctgtaggtta    3180
attagaggaa aaatgactct aacagaggaa gttcagtgga ctgagatggc agaagcagaa    3240
tatgaggaaa ataaaataat tctcagtcag gaacaagaag gatgttatta ccaagaaggc   3300
aagccattag aagccacggt aataaagagt caggacaatc agtggtctta taaaattcac   3360
caagaagaca aaatactgaa agtaggaaaa tttgcaaaga taagaatac acataccaat    3420 ggagtgagac tattagcaca tgtaatacag aaaataggaa aggaagcaat agtgatctgg   3480
ggacaggtcc caaaattcca cttaccagtt gagaaggatg tatgggaaca gtggtggaca   3540
gactattggc aggtaacctg gataccggaa tgggatttta tctcaacacc accgctagta    3600
agattagtct tcaatctagt gaaggaccct atagagggag aagaaaccta ttatacagat    3660
ggatcatgta ataaacagtc aaaagaaggg aaagcaggat atatcacaga tagggcaaa    3720 gacaaagtaa aagtgttaga acagactact aatcaacaag cagaattgga agcatttctc    3780
atggcattga cagactcagg gccaaaggca atatattatg tagattcaca atatgttatg    3840
ggaataataa caggatgccc tacagaatca gagagcaggc tagttaatca aataatagaa    3900
gaaatgatta aaagtcaga aatttatgta gcatgggtac cagcacacaa aggtatagga    3960
ggaaaccaag aaatagacca cctagttagt caagggatta acaagttct cttcttggaa    4020 aagatagagc cagcacaaga agaacatgat aaataccata gtaatgtaaa agaattggta    4080
ttcaaatttg gattacccag aatagtggcc agacagatag tagacacctg tgataaatgt   4140
catcagaaag gagaggctat acatgggcag gcaaattcag atctagggac ttggcaaatg    4200
gattgtaccc atctagaggg aaaaataatc atagttgcag tacatgtagc tagtggattc   4260
```

```
atagaagcag aggtaattcc acaagagaca ggaagacaga cagcactatt tctgttaaaa    4320
ttggcaggca gatggcctat tacacatcta cacacagata atggtgctaa ctttgcttcg    4380
caagaagtaa agatggttgc atggtgggca gggatagagc acacctttgg ggtaccatac    4440
aatccacaga gtcagggagt agtggaagca atgaatcacc acctgaaaaa tcaaatagat    4500
agaatcaggg aacaagcaaa ttcagtagaa accatagtat taatggcagt tcattgcatg    4560
aattttaaaa gaaggggagg aataggggat atgactccag cagaaagatt aattaacatg    4620
atcactacag aacaagagat acaatttcaa caatcaaaaa actcaaaatt taaaaatttt    4680
cgggtctatt acagagaagg cagagatcaa ctgtggaagg gacccggtga gctattgtgg    4740
aaaggggaag gagcagtcat cttaaaggta gggacagaca ttaaggtagt acccagaaga    4800
aaggctaaaa ttatcaaaga ttatggagga ggaaaagagg tggatagcag ttcccacatg    4860
gaggataccg gagaggctag agaggtggca tagcctcata aaatatctga aatataaaac    4920
taaagatcta caaaaggttt gctatgtgcc ccattttaag gtcggatggg catggtggac    4980
ctgcagcaga gtaatcttcc cactacagga aggaagccat ttagaagtac aagggtattg    5040
gcatttgaca ccagaaaaag ggtggctcag tacttatgca gtgaggataa cctggtactc    5100
aaagaacttt tggacagatg taacaccaaa ctatgcagac attttactgc atagcactta    5160
tttcccttgc tttacagcgg gagaagtgag aagggccatc aggggagaac aactgctgtc    5220
ttgctgcagg ttcccgagag ctcataagta ccaggtacca agcctacagt acttagcact    5280
gaaagtagta agcgatgtca gatcccaggg agagaatccc acctgaaaac agtggagaag    5340
agacaatagg agaggccttc gaatggctaa acagaacagt agaggagata aacagagagg    5400
cggtaaacca cctaccaagg gagctaattt tccaggtttg gcaaaggtct tgggaatact    5460
ggcatgatga acaagggatg tcaccaagct atgtaaaata cagatacttg tgtttaatac    5520
aaaaggcttt atttatgcat tgcaagaaag gctgtagatg tctagggaa ggacatgggg     5580 caggggatg gagaccagga cctcctcctc ctccccctcc aggactagca taaatggaag    5640
aaagacctcc agaaaatgaa ggaccacaaa gggaaccatg ggatgaatgg gtagtggagg    5700
ttctggaaga actgaaagaa gaagctttaa aacattttga tcctcgcttg ctaactgcac    5760
ttggtaatca tatctataat cgtcacggag acactctaga gggagcagga gaactcatta    5820
gaatcctcca acgagcgctc ttcatgcatt tcagaggcgg atgcatccac tccagaatcg    5880
gccaacctgg gggaggaaat cctctctcag ctataccgcc ctctagaagc atgctgtaga    5940
gcaagaaatg gagccagtag atcctagact agagccctgg aagcatccag gaagtaagcc    6000
taaaactgct tgtaccaatt gctattgtaa aaagtgttgc tttcattgcc aagtttgttt    6060
cataacaaaa gccttaggca tctcctatgg caggaagaag cggagacagc gacgaagagc    6120
tcatcagaac agtcagactc atcaagcttc tctatcaaag cagtaagtag tacatgtaat    6180
gcaacctata caaatagcaa tagtagcatt agtagtagca ataataatag caatagttgt    6240
gtggtccata gtaatcatag aatataggaa aatattaaga caagaaaaa tagacaggtt    6300 aattgataga ctaatagaaa gagcagaaga cagtggcaat gagagtgaag gagaaatatc    6360
agcacttgtg gagatggggg tggagatggg gcaccatgct ccttgggatg ttgatgatct    6420
gtagtgctac agaaaaattg tgggtcacag tctattatgg ggtacctgtg tggaaggaag    6480
caaccaccac tctatttgt gcatcagatg ctaaagcata tgatacagag gtacataatg    6540
tttgggccac acatgcctgt gtacccacag accccaaccc acaagaagta gtattggtaa    6600
atgtgacaga aaattttaac atgtggaaaa atgacatggt agaacagatg catgaggata    6660
```

-continued

```
taatcagttt atgggatcaa agcctaaagc catgtgtaaa attaacccca ctctgtgtta    6720
gtttaaattg cactgatttg aagaatgata ctaataccaa tagtagtagc gggagaatga    6780
taatggagaa aggagagata aaaaactgct ctttcaatat cagcacaagc ataagaggta    6840
aggtgcagaa agaatatgca tttttttata aacttgatat aataccaata gataatgata    6900
ctaccagcta tacgttgaca agttgtaaca cctcagtcat ttcacaggcc tgtccaaagg    6960
tatcctttga gccaattccc atacattatt gtgcccggc tggttttgcg attttaaaat     7020
gtaataataa gacgttcaat ggaacaggac catgtacaaa tgtcagcaca gtacaatgta    7080
cacatggaat taggccagta gtatcaactc aactgctgtt aaatggcagt ctagcagaag    7140
aagaggtagt aattagatct gtcaatttca tggacaatgc taaaaccata atagtacagc    7200
tgaacacatc tgtagaaatt aattgtacaa gacccagcaa caatcaata aaagaatcc     7260 gtatccagag aggaccaggg agagcatttg ttacaatggg aaaaatagga gatatgagac    7320
aagcacattg taacattagt agagcaaaat ggaataacac tttaaaacag atagctagca    7380
aattaagaga acaatttgga aataataaaa caataatctt taagcaatcc tcaggagggg    7440
acccagaaat tgtaacgcac agttttaatt gtggagggga atttttctac tgtaattcaa    7500
cacaactgtt taatagtact tggtttaata gtacttggag tactgaaggg tcaaataaca    7560
ctgaaggaag tgacacaatc accctcccat gcagaataaa acaaattata acatgtggc     7620 agaaagtagg aaaagcaatg tatgcccctc ccatcagtgg acaaattaga tgttcatcaa    7680
atattacagg gctgctatta acaagagatg gtggtaaagg caacaatgag tccgagatct    7740
tcagacctgg aggaggagat atgagggaca attggagaag tgaattatat aaatataaag    7800
tagtaaaaat tgaaccatta ggagtagcac ccaccaaggc aaagagaaga gtggtgcaga    7860
gagaaaaaag agcagtggga ataggagctt tgttccttgg gttcttggga gcagcaggaa    7920
gcactatggg cgcagcgtca atgacgctga cggtacaggc cagacaatta ttgtctggta    7980
tagtgcagca gcagaacaat ttgctgaggg ctattgaggc gcaacagcat ctgttgcaac    8040
tcacagtctg gggcatcaag cagctccagg caagaatcct ggctgtggaa agatacctaa    8100
aggatcaaca gctcctgggg atttggggtt gctctggaaa actcatttgc accactgctg    8160
tgccttggaa tgctagttgg agtaataaat ctctggaaca gatttggaat cacatgacct    8220
ggatggagtg ggacagagaa attaacaatt acacaagctt aatacactcc ttaattgaag    8280
aatcgcaaaa ccagcaagaa aagaatgaac aagaattatt ggaattagat aaatgggcaa    8340
gtttgtggaa ttggtttgac ataacaaatt ggctgtggta tataaaatta ttcataatga    8400
tagtaggagg cttggtaggt ttaagaatag ttttgctgt actttctata gtgaatagag    8460
ttaggcaggg atattcacca ttatcgtttc agacccacct cccaaccccg aggggacccg    8520
acaggcccga aggaatagaa gaagaggtg gagagagaga cagagacaga tccattcgat    8580
tagtgaacgg atccttggca cttatctggg acgatctgcg gagcctgtgc ctcttcagct    8640
accaccgctt gagagactta ctcttgattg taacgaggat tgtggaactt ctgggacgca    8700
gggggtggga agccctcaaa tattggtgga atctcctaca gtattggagt caggaactaa    8760
agaatagtgc tgttagcttg ctcaatgcca cagccatagc agtagctgag gggacagata    8820
gggttataga agtagtacaa ggagcttgta gagctattcg ccacatacct agaagaataa    8880
gacagggctt ggaaaggatt ttgctataag acggaccgac ctacaatatg ggtggagcta    8940
tttccatgag gcggtccagg ccgtctggag atctgcgaca gagactcttg cgggcgcgtg    9000
gggagactta tgggagactc ttaggagagg tggaagatgg atactcgcaa tccccaggag    9060
```

```
gattagacaa gggcttgagc tcactctctt gtgagggaca gaaatacaat cagggacagt    9120
atatgaatac tccatggaga aacccagctg aagagagaga aaaattagca tacagaaaac    9180
aaaatatgga tgatatagat gaggaagatg atgacttggt aggggtatca gtgaggccaa    9240
aagttcccct aagaacaatg agttacaaat tggcaataga catgtctcat tttataaaag    9300 aaaaggggggg actggaaggg atttattaca gtgcaagaag acatagaatc ttagacatat    9360
acttagaaaa ggaagaaggc atcataccag attggcagga ttacacctca ggaccaggaa    9420
ttagataccc aaagacattt ggctggctat ggaaattagt ccctgtaaat gtatcagatg    9480
aggcacagga ggatgaggag cattatttaa tgcatccagc tcaaacttcc cagtgggatg    9540 accccttgggg agaggttcta gcatggaagt ttgatccaac tctggcctac acttatgagg    9600
catatgttag atacccagaa gagtttggaa gcaagtcagg cctgtcagag aagaggtta     9660 gaagaaggct aaccgcaaga ggccttctta acatggctga caagaaggaa actcgctgaa    9720
acagcaggga ctttccacaa ggggatgtta cggggaggta ctgggaggga ccggtcgggg    9780
aacgcccact tcttgatgt ataaatatca ctgcatttcg ctctgtattc agtcgctctg     9840
cggagaggct ggcagattga gccctgggag gttctctcca gcactagcag gtagagcctg    9900
ggtgttccct gctagactct caccagcact ggccggtgc tgggcagagt gactccacgc     9960
ttgcttgctt aaagccctct tcaataaagc tgccatttta gaagta                  10006

<210> SEQ ID NO 4
<211> LENGTH: 9609
<212> TYPE: DNA
<213> ORGANISM: HIV (HUMAN)

<400> SEQUENCE: 4
ctcatccagc ctgggtactg aagggctaa ttcactccca acgaagacaa gatatccttg       60
atctgtggat ctaccacaca caaggctact tccctgattg gcagaactac acaccaggac     120
cagggatcag atatccactg acctttggat ggtgctacaa gctagtacca gttgagccag     180
agaagttaga agaagccaac aaaggagaga acaccagctt gttacaccct gtgagcctgc    240
atggaatgga tgacccggag agagaagtgt tagagtggag gtttgacagc cgcctagcat    300
ttcatcacgt ggcccgagag ctgcatccgg agtacttcaa gaactgctga tatcgagctt    360
gctacaaggg actttccgct ggggactttc cagggaggcg tggcctgggc gggactgggg    420
agtggcgagc cctcagatcc tgcatataag cagctgcttt tgcctgtac tgggtctctc     480 tggttagacc agatctgagc ctgggagctc tctggctagc tagggaaccc actgcttaag    540
cctcaataaa gcttgccttg agtgcttcaa gtagtgtgtg cccgtctgtt gtgtgactct    600
ggtaactaga gatccctcag acccttttag tcagtgtgga aaatctctag cagtggcgcc    660
cgaacaggga cctgaaagcg aaagggaaac cagaggagct ctctcgacgc aggactcggc    720
ttgctgaagc gcgcacggca agaggcgagg gcggcgact ggtgagtacg ccaaaaaatt     780
ttgactagcg gaggctagaa ggagagagat gggtgcgaga gcgtcagtat taagcggggg    840
aaaattagat cgatgggaaa aaattcggtt aaggccaggg ggaaagaaaa aatataaaatt   900 aaaacatata gtatgggcaa gcagggagct agaacgattc gcagttaatc ctggcctgtt    960
agaaacatca gaaggctgta gacaaatact gggacagcta caaccatccc ttcagacagg    1020
atcagaagaa tgtagatcat tatataatac agtagcaacc ctctattgtg tgcatcaaag    1080
gatagagata aaagacacca aggaagcttt agacaagata aggaagagc aaaacaaaag     1140 taagaaaaaa gcacagcaag cagcagctga cacaggacac agcagtcagg tcagccaaaa    1200
```

-continued

```
ttaccctata gtgcagaaca tccaggggca aatggtacat caggccatat cacctagaac    1260
tttaaatgca tgggtaaaag tagtagaaga gaaggctttc agcccagaag taatacccat    1320
gttttcagca ttatcagaag gagccacccc acaagattta acaccatgc taaacacagt     1380
gggggacat caagcagcca tgcaaatgtt aaaagagacc atcaatgagg aagctgcaga     1440
atgggataga gtgcatccag tgcatgcagg gcctatcgca ccaggccaga tgagagaacc    1500
aaggggaagt gacatagcag gaactactag tacccttcag gaacaaatag gatggatgac   1560
aaataatcca cctatcccag taggagaaat ttataaaaga tggataatcc tgggattaaa   1620
taagatagta agaatgtata gccctaccag cattctggac ataagacaag gaccaaaaga    1680
acctttttaga gactatgtag accggttcta taaaactcta agagccgagc aagcttcaca   1740
ggaggtaaaa aattggatga cagaaaacctt gttggtccaa aatgcgaacc cagattgtaa   1800
gactattta aaagcattgg gaccagcagc tacactagaa gaaatgatga cagcatgtca    1860
gggagtggga ggacccggcc ataaggcaag gttttggct gaagcaatga gccaagtaac    1920
aaattcagct accataatga tgcagagagg caattttagg aaccaaagaa agattgttaa   1980
gtgtttcaat tgtggcaaag aagggcacat agccagaaat tgcagggccc ctaggaaaaa   2040
gggctgttgg aaatgtggaa aggaaggaca ccaaatgaaa gattgtactg agagacaggc    2100
taattttttta gggaagatct ggccttccta caagggaagg ccaggaatt ttcttcagag     2160
cagaccagag ccaacagccc caccagaaga gagcttcagg tctggggtag agacaacaac   2220
tcccccctcag aagcaggagc cgatagacaa ggaactgtat cctttaactt ccctcagatc   2280
actctttggc aacgacccct cgtcacaata aagataggg ggcaactaaa ggaagctcta    2340
ttagatacag gagcagatga tacagtatta agagaaatga gtttgccagg aagatggaaa    2400
ccaaaaatga tagggggaat tggaggtttt atcaaagtaa gacagtatga tcagatactc   2460
atagaaatct gtggacataa agctataggt acagtattag taggacctac acctgtcaac   2520
ataattggaa gaaatctgtt gactcagatt ggttgcactt taaatttttcc cattagccct   2580
attgagactg taccagtaaa attaaagcca ggaatggatg gcccaaaagt taaacaatgg   2640
ccattgacag aagaaaaaat aaaagcatta gtagaaattt gtacagaaat ggaaaaggaa    2700
gggaaaattt caaaaattgg gcctgaaaat ccatacaata ctccagtatt tgccataaag   2760
aaaaaagaca gtactaaatg gagaaaatta gtagatttca gagaacttaa taagagaact    2820
caagacttct gggaagttca attaggaata ccacatcccg cagggttaaa aaagaaaaaa   2880
tcagtaacag tactggatgt gggtgatgca tatttttcag ttcccttaga tgaagacttc    2940
aggaagtata ctgcatttac catacctagt ataaacaatg agacaccagg gattagatat    3000
cagtacaatg tgcttccaca gggatggaaa ggatcaccag caatattcca agtagcatg    3060
acaaaaatct tagagccttt tagaaaacaa aatccagaca tagttatcta tcaatacatg   3120
gatgatttgt atgtaggatc tgacttagaa atagggcagc atagaacaaa aatagaggag    3180
ctgagacaac atctgttgag gtggggactt accacaccag acaaaaaaca tcagaaagaa    3240
cctccattcc tttggatggg ttatgaactc catcctgata aatggacagt acagcctata   3300
gtgctgccag aaaaagacag ctggactgtc aatgacatac agaagttagt ggggaaattg    3360
aattgggcaa gtcagattta cccagggatt aaagtaaggc aattatgtaa actccttaga    3420
ggaaccaaag cactaacaga agtaatacca ttaacagaag aagcagagct agaactggca    3480
gaaaacagag agattctaaa agaaccagta catggagtgt attatgaccc atcaaaagac    3540
ttaatagcag aaatacagaa gcaggggcaa ggccaatgga catatcaaat ttatcaagag    3600
```

```
ccatttaaaa atctgaaaac aggaaaatat gcaagaatga ggggtaccca cactaatgat    3660
gtaaaacaat taacagaggc agtgcaaaaa ataaccaccg aaagcatagt aatatgggga    3720
aagactccta aatttaaact acccatacaa aaggaaacat gggaaacatg gtggacagag    3780
tattggcaag ccacctggat tcctgagtgg gagtttgtca ataccctcc tttagtgaaa     3840 ttatggtacc agttagagaa agaacccata gtaggagcag aaaccttcta tgtagatggg    3900
gcagctaaca gggagactaa attaggaaaa gcaggatatg ttactaacaa aggaagacaa    3960
aaggttgtcc ccctaactaa cacaacaaat cagaaaactg agttacaagc aatttatcta    4020
gctttgcagg attcaggatt agaagtaaac atagtaacag actcacaata tgcattagga    4080
atcattcaag cacaaccaga taaaagtgaa tcagagttag tcaatcaaat aatagagcag    4140
ttaataaaaa aggaaaaggt ctatctggca tgggtaccag cacacaaagg aattggagga    4200
aatgaacaag tagataaatt agtcagtgct ggaatcagga aaatactatt tttagatgga    4260
atagataagg cccaagatga acatgagaaa tatcacagta attggagagc aatggctagt    4320
gattttaacc tgccacctgt agtagcaaaa gaaatagtag ccagctgtga taaatgtcag    4380
ctaaaaggag aagccatgca tggacaagta gactgtagtc caggaatatg gcaactagat    4440
tgtacacatt tagaaggaaa agttatcctg gtagcagttc atgtagccag tggatatata    4500
gaagcagaag ttattccagc agaaacaggg caggaaacag catattttct tttaaaatta    4560
gcaggaagat ggccagtaaa aacaatacat acagacaatg gcagcaattt caccagtgct    4620
acggttaagg ccgcctgttg gtgggcggga atcaagcagg aatttggaat tccctacaat    4680
ccccaaagtc aaggagtagt agaatctatg aataaagaat aaagaaaat tataggacag    4740 gtaagagatc aggctgaaca tcttaagaca gcagtacaaa tggcagtatt catccacaat    4800
tttaaaagaa aagggggga tgggggtac agtgcagggg aaagaatagt agacataata    4860
gcaacagaca tacaaactaa agaattacaa aaacaaatta caaaaattca aaattttcgg    4920
gtttattaca gggacagcag aaatccactt tggaaaggac cagcaaagct cctctggaaa    4980
ggtgaagggg cagtagtaat acaagataat agtgacataa aagtagtgcc aagaagaaaa    5040
gcaaagatca ttagggatta tggaaaacag atggcaggtg atgattgtgt ggcaagtaga    5100
caggatgagg attagaacat ggaaaagttt agtaaaacac catatgtatg tttcagggaa    5160
agctagggga tggttttata gacatcacta tgaaagccct catccaagaa taagttcaga    5220
agtacacatc ccactagggg atgctagatt ggtaataaca acatattggg gtctgcatac    5280
aggagaaaga gactggcatt tgggtcaggg agtctccata gaatggagga aaaagagata    5340
tagcacacaa gtagaccctg aactagcaga ccaactaatt catctgtatt actttgactg    5400
tttttcagac tctgctataa gaaaggcctt attaggacac atagttagcc ctaggtgaag    5460
accaagggcc acagagggag ccacacaatg aatggacact agagctttta gaggagctta    5520
agaatgaagc tgttagacat tttcctagga tttggctcca tggcttaggg caacatatct    5580
atgaaactta tggggatact tgggcaggag tggaagccat aataagaatt ctgcaacaac    5640
tgctgtttac ccatttcaga attgggtgtc gacatagcag aataggcgtt actcgacaga    5700
ggagagcaag aaatggagcc agtagatcct agactagagc cttggaagca tccaggaagt    5760
cagcctaaaa ctgcttgtac caattgctat tgtaaaaagt gttgctttca ttgccaagtt    5820
tgtttcataa caaaagcctt aggcatctcc tatggcagga agaagcggag acagcgacga    5880
agacctcctc aaagcagtca gactcatcaa gtttctctat caaagcagta agtagtacat    5940
gtaatgcaac ctatacaaat agcaatagta gcattagtag tagcaataat aatagcaata    6000
```

```
gttgtgtggt ccatagtaat catagaatat aggaaaatat aagacaaag aaaaatagac      6060 aggttaattg atagactaat agaaagagca gaagacagtg gcaatgagag tgaaggagaa      6120
atatcagcac ttgcggagat gggggtggag atggggcacc atgctccttg ggatgttgat      6180
gatttgtagt gctacagaaa aattgtgggt cacagtctat tatggggtac ctgtgtggaa      6240
ggaagcaacc accactctat tttgtgcatc agatgctaaa gcatatgata cagaggtaca      6300
taatgtttgg gccacacatg cctgtgtacc cacagacccc aacccacaag aagtagtatt      6360
ggtaaatgtg acagaaaatt ttaacatgtg gaaaaatgat atggtagaac agatgcatga      6420
ggatataatc agtttatggg atcaaagcct aaagccatgt gtaaaattaa ccccactctg      6480
tgttagttta aagtgcactg atttgaagaa tgatactaat accaatagta gtagcggggg      6540
aatgataatg gagaaaggag agataaaaaa ctgctctttc aatatcagca caagcataag      6600
aggtaaggtg cagaaagaat atgcattttt ttataaacat gatataatac caatagataa      6660
tgatactacc agctatacgt tgacaagttg taacacctca gtcattacac aggcctgtcc      6720
aaaggtatcc tttgagccaa ttcccataca ttattgtgcc ccggctggtt ttgcgattct      6780
aaaatgtaat aataagacgt tcaatggaac aggaccatgt acaaatgtca gcacagtaca      6840
atgtacacat ggaattaagc cagtagtatc aactcaactg ctgttaaatg gcagtctagc      6900
agaagaagag gtagtaatta gatctgccaa tctcacagac aatgttaaaa ccataatagt      6960
acagctgaac caatctgtag aaattaattg tacaagaccc aacaacaata caagaaaaag      7020
aatccgtatc cagagaggac cagggagaac atttgttaca ataggaaaaa taggaaatat      7080
gagacaagca cattgtaaca ttagtagagc aaaatggaat aacactttaa aacagatagc      7140
tagcaaatta agagaacaat atggaaataa taaaacaata atctttaagc agtcctcagg      7200
aggggaccta gaaattgtaa cgcacagttt taattgtgga ggggaatttt tctactgtaa      7260
ttcaacacaa ctgtttaata gtacttggtt taatagtact tggagtactg aagggtcaaa      7320
taacactgaa ggaagtgaca caatcacact cccatgcaga ataaaacaaa ttataaacat      7380
gtggcaggaa gtaggaaaag caatgtatgc ccctcccatc agcggacaaa ttagatgttc      7440
atcaaatatt acagggctgc tattaacaag agatggtggt aataacaaca atgggtccga      7500
gatcttcaga cctggaggag gagatatgag ggacaattgg agaagtgaat tatataaata      7560
taaagtagta aaaattgaac cattaggagt agcacccacc aaggcaaaga gaagagtggt      7620
gcagagagaa aaaagagcag tgggaatagg agctttgttc cttgggttct gggagcagc      7680 aggaagcact atgggcgcag cgtcaatgac gctgacggta caggccagac aattattgtc      7740
tggtatagtg cagcagcaga acaatttgct gagggctatt gaggcgcaac agcatctgtt      7800
gcaactcaca gtatgggca tcaagcagct ccaggcaaga atcctggctg tggaaagata      7860
cctaaaggat caacagctcc tggggatttg gggttgctct ggaaaactca tttgcaccac      7920
tgctgtgcct tggaatgcta gttggagtaa taaatctctg gaacagattt ggaatcacac      7980
gacctggatg gagtgggaca gagaaattaa caattacaca agcttaatac actccttaat      8040
tgaagaatcg caaaaccaac aagaaaagaa tgaacaagaa ttattggaat tagataaatg      8100
ggcaagtttg tggaattggt ttaacataac aaattggctg tggtatataa aaatattcat      8160
aatgatagta ggaggcttgg taggtttaag aatagttttt gctgtacttt ctatagtgaa      8220
tagagttagg cagggacatt caccattatc gtttcagacc cacctcccaa ccccggggg      8280 acccgacagg cccgaaggaa tagaagaaga aggtggagag agagacagag acagatccat      8340
tcgattagtg aacggatcct tagcacttat ctgggacgat ctgcgaagcc tgtgcctctt      8400
```

-continued

```
cagctaccac cgcttgagag acttactctt gattgtaacg aggattgtgg aacttctggg      8460 acgcagggggg tgggaagccc tcaaatattg gtggaatctc ctacagtatt ggagtcagga     8520
actaaagaat agtgctgtta gcttgctcaa tgccacagcc atagcagtag ctgaggggac      8580
agatagggtt atagaagtag tacaaggagc ttgtagagct attcgccaca tacctagaag      8640
aataagacag ggcttggaaa ggattttgct ataagatggg tggcaagtgg tcaaaaagta      8700
gtgtgattgg atggcctact gtaagggaaa gaatgagacg agctgagcca gcagcagatg     8760 gggtggggagc agcatctcaa gacctggaaa acatggagc aatcacaagt agcaatacag     8820
cagctaccaa tgctgattgt gcctggctag aagcacaaga ggaggaggag gtgggttttc      8880
cagtcacacc tcaggtacct ttaagaccaa tgacttacaa ggcagctgta gatcttagcc      8940
acttttaaaa agaaaagggg ggactggaag ggctaattca ctcccaacga agacaagata      9000
tccttgatct gtggatctac cacacacaag gctacttccc tgattggcag aactacacac      9060
caggaccagg gatcagatat ccactgacct ttggatggtg ctacaagcta gtaccagttg      9120
agccagagaa gttagaagaa gccaacaaag gagagaacac cagcttgtta caccctgtga      9180
gcctgcatgg aatggatgac ccggagagag aagtgttaga gtggaggttt gacagccgcc      9240
tagcatttca tcacgtggcc cgagagctgc atccggagta cttcaagaac tgctgatatc      9300
gagcttgcta caagggactt tccgctgggg actttccagg gaggcgtggc ctgggcggga      9360
ctggggagtg gcgagccctc agatcctgca tataagcagc tgcttttgc ctgtactggg      9420 tctctctggt tagaccagat ctgagcctgg gagctctctg gctagctagg gaacccactg      9480
cttaagcctc aataaagctt gccttgagtg cttcaagtag tgtgtgcccg tctgttgtgt      9540
gactctggta actagagatc cctcagaccc ttttagtcag tgtggaaaat ctctagcagg      9600
ttgaccaac                                                              9609
```

<210> SEQ ID NO 5
<211> LENGTH: 10274
<212> TYPE: DNA
<213> ORGANISM: HIV (Simian)

<400> SEQUENCE: 5

```
tggaagggat ttattatagt gcaagaagac atagaatctt agacatatac ttagaaaagg        60
aagaaggcat cataccagat tggcaggatt acacctcagg accaggaatt agatacccaa       120
agacatttgg ctggctatgg aaattagtcc ctgtaaatgt atcagatgag gcacaggagg       180
atgaggagca ttatttaatg catccagctc aaacttccca gtgggatgac ccttggggag       240
aggttccagc atggaagttt gacccaactc tggcctacac ttatgaggca tatgttagat       300
acccagaaga gtttggaagc aagtcaggcc tgtcagagga gaggttaga agaaggctaa        360 ccgcaagagg ccttcttaac atggctgaca gaaggaaac tagatgagac agcagggact       420
ttccacaagg ggtgttacgg ggaggtactg ggaggagcc ggtcgggaac acccacttc         480 ttgatgtata aatatcactg cattttgcta tgtagtcagt cgctctgcgg agaggctggc       540
agattgagcc ctgggaggtt ctctccagca ctagcaggta gagcctgggt tttccctgct      600
agactctcac cagcacttgg ccggtgctgg gcagagtgac tccacgcttg cttgcttaaa      660
gccctcttca ataagctgc catttgaaa gtaagctagt gtgtgttccc atctctccta      720
gtcgccgcct ggtcaactcg gtactcggta ataagaagac cctggtctgt taggacccctt     780 tctgctttgg gaaaccgaag caggaaaatc cctagcagat tggcgcccga acagggactt     840
gaaggagagt gagagactcc tgagtacggc tgagtgaagg cagtaagggc ggcaggaacc      900
```

```
aaccacgacg gagtgctcct ataaaggcgc gggtcggtac cagacggcgt gaggagcggg      960
agaggaagag gcctccggtt gcaggtaagt gcaacacaaa aaagaaatag ctgtctttta     1020
tccaggaagg gataataaga tagagtggga gatgggcgcg agaaactccg tcttgtcagg     1080
gaagaaagca gatgaattag aaaaaattag gctacgaccc aacggaaaga aaaagtacat     1140
gttgaagcat gtagtatggg cagcaaatga attagataga tttggattag cagaaagcct     1200
gttggagaac aaagaaggat gtcaaaaaat actttcggtc ttagctccat tagtgccaac     1260
aggctcagaa aatttaaaaa gcctttataa tactgtctgc gtcatctggt gcattcacgc     1320
agaagagaaa gtgaaacaca ctgaggaagc aaaacagata gtacagagac acctagtggt     1380
ggaaacagga acagcagaaa ttatgccaaa acaagcaga ccaactgcac catctagcgg      1440
cagaggagga aattacccag tacaacaaat aggtggtaac tatgtccacc tgccattaag     1500
cccgagaaca ttaaatgcct gggtaaaatt gatagaggaa aagaaatttg gagcagaagt     1560
agtgccagga tttcaggcac tgtcagaagg ttgcaccccc tatgacatta atcagatgtt     1620
aaattgtgtg ggagaccatc aagcggctat gcagattatc agagacatca taaacgagga     1680
ggctgcagat tgggacttgc agcacccaca accagctcca caacaaggac agcttaggga     1740
gccgtcagga tcagatattg caggaacaac tagttcagta gatgaacaaa tccagtggat     1800
gtacagacaa cagaacccca taccagtagg caacatttac aggagatgga tccaactggg     1860
gttgcaaaaa tgtgtcagaa tgtataaccc aacaaacatt ctagatgtaa aacaagggcc     1920
aaaagagcca tttcagagct atgtagacag gttctacaaa agtttaagag cagaacagac     1980
agatgcagca gtaaagaatt ggatgactca aacactgctg attcaaaatg ctaacccaga     2040
ttgcaagcta gtgctgaagg ggctgggtgt gaatcccacc ctagaagaaa tgctgacggc     2100
ttgtcaagga gtaggggggc caggacagaa ggctagatta atggcagaag ccctgaaaga     2160
ggccctcgca ccagtgccaa tccctttgc agcagcccaa cagaggggac caagaaagcc      2220
aattaagtgt tggaattgtg ggaaagaggg acactctgca aggcaatgca gagccccaag     2280
aagacaggga tgctggaaat gtggaaaaat ggaccatgtt atggccaaat gcccagacag     2340
acaggcgggt tttttaggcc ttggtccatg gggaagaag ccccgcaatt tccccatggc      2400
tcaagtgcat cagggctga cgccaactgc tcccccagag gacccagctg tggatctgct     2460
aaagaactac atgcagttgg gcaagcagca gagagaaaaa cagagagaaa gcagagaaa      2520 gccttacaag gagatgacag aggatttgct gcacctcaat tctctctttg gaggagacca     2580
gtagtcactg ctcatattga aggacagcct gtagaagtat tactggatac aggggctgat     2640
gattctattg taacaggaat agagttaggt ccacattata ccccaaaaat agtaggagga     2700
ataggaggtt ttattaatac taaagaatac aaaaatgtag aaatagaagt tttaggcaaa     2760
agaattagag ggacaatcat gacaggggac accccgatta acattttggg tagaaattta     2820
ctaacagctc tggggatgtc tctaaatctt cccatagcta aagtagagcc tgtaaaagtc     2880
gccttaaagc caggaaaagt tggaccaaaa ttgaagcagt ggccattatc aaaagaaaag     2940
atagttgcat taagagaaat ctgtgaaaag atggaaaagg atggtcagtt ggaggaagct     3000
cccccgacca atccatacaa caccccacac tttgctataa agaaaaaaga taagaacaaa     3060
tggagaatgc tgatagattt tagggaacta aataggtca ctcaggactt tacagaagtc      3120
caattaggaa taccacaccc tgcaggacta gcaaaaagga aaaggattac agtactggat     3180
ataggtgacg catatttctc catacctcta gatgaagaat ttaggcagta cactgccttt     3240
actttaccat cagtaaataa tgcagagcca ggaaaacgat acatttataa ggttctgcct     3300
```

| | |
|---|---|
| caaggatgga agggtcacc agccatcttc caatacacta tgagacatgt gctagaaccc | 3360 |
| ttcaggaagg caaatccaga tgtgaccta gtccagtata tggatgacat cttaatagct | 3420 |
| agtgacagga caaacctgga acatgacagg tagttttac agttaaagga actcttaaat | 3480 |
| agcatagggt tttctacccc agaagagaaa ttccaaaaag atcccccatt tcaatggatg | 3540 |
| gggtacgaat tgtggccaac aaaatgaag ttgcaaaaga tagagttgcc acaaagagag | 3600 |
| acctggacag tgaatgatat acagaagtta gtaggagtat taaattgggc agctcaaatt | 3660 |
| tatccaggta taaaaaccaa acatctctgt aggctaatta gaggaaaaat gactctaaca | 3720 |
| gaggaagttc agtggactga gatggcagaa gcagaatatg aggaaaataa ataattctc | 3780 |
| agtcaggaac aagaaggatg ttattaccaa gaaggcaagc cattagaagc cacggtaata | 3840 |
| aagaatcagg acaatcagtg gtcttataaa attcaccaag aagacaaaat actgaaagta | 3900 |
| ggaaaatttg caaagataaa gaatacacat accaatggag ttagactatt agcacatgta | 3960 |
| atacagaaaa taggaaagga agcaatagtg atctggggac aggtcccaaa attccactta | 4020 |
| ccagttgaga aggatgtatg gaacagtgg tggacagact attggcaggt aacctggata | 4080 |
| ccagaatgga attttatctc aacaccacca ctagtgagat tagtcttcaa tctagtgaag | 4140 |
| gaccctatag agggagaaga aacctattat acagatggat catgtaataa acagtcaaaa | 4200 |
| gaagggaaag caggatatat cacagatagg ggcaaagaca aagtaaaagt gttagaacag | 4260 |
| actactaatc aacaggcaga attggaagca ttcctcatgg cattaacaga ctcagggcca | 4320 |
| aaggcaaata ttatagtaga ttcacaatat gttatgggaa taataacagg atgccctaca | 4380 |
| gaatcagaga gcagactagt taaccaaata ataaagaaa tgattaaaaa gtcagaaatt | 4440 |
| tatgtagcat gggtaccagc acacaaaggt ataggaggaa accaagaagt agaccaccta | 4500 |
| gttagtcagg ggattagaca agttctcttc ttggaaaaga tagagccagc caagaagag | 4560 |
| catgataaaat accatagtaa tgtaaaagaa ttggtattca aatttggatt acccagaata | 4620 |
| gtggccagac agatagtaga cacctgtgat aaatgtcatc agaaaggaga agctatacat | 4680 |
| gggcaggtaa attcagatct agggacttgg caaatggatt gtaccatct agagggaaaa | 4740 |
| ataatcatag ttgcagtaca tgtagctagt ggattcatag aagcagaggt aattccacaa | 4800 |
| gagacaggaa gacagacagc actatttctg ttaaaattgg caggcagatg gcctattaca | 4860 |
| catctacaca cagataatgg tgctaacttt gcttcgcaag aagtaaagat ggttgcatgg | 4920 |
| tgggcaggga tagagcacac ctttggggta ccatacaatc cacagagtca gggagtagtg | 4980 |
| gaagcaatga atcaccacct gaaaaatcaa atagatagaa tcaggggaaca agcaaattca | 5040 |
| gtagaaacca tagtattaat ggcagttcat tcgatgaatt ttaaaagaag ggaggaaca | 5100 |
| gggggatatga ctccagcaga aagattaatt aacatgatca ctacagaaca agaaatacaa | 5160 |
| tttcaacaat caaaaaactc aaaatttaaa aattttcggg tctattacag agaaggcaga | 5220 |
| gatcaactgt ggaagggacc cggtgagcta ttgtggaaag ggaaggagc agtcatctta | 5280 |
| aaggtaggga cagacattaa ggtagtaccc agaagaaagg ctaaaattat caaagattat | 5340 |
| ggaggaggaa aagagatgga tagcagttcc cacatggagg ataccggaga ggctagagag | 5400 |
| gtggcatagc ctcataaaat atctgaaata taaaactaaa gatctacaaa aggtttgcta | 5460 |
| tgtgccccat tttaaggtcg gatgggcatg gtggacctgc agcagagtaa tcttcccact | 5520 |
| acaggaagga agccatttag aagtacaagg gtattggcat ttgacaccag aaaaagggtg | 5580 |
| gctcagtact tatgcagtga gggtaacctg gtactcaaag aacttttgga cagatgtaac | 5640 |
| accaaactat gcagacattt tactgcatag cacttatttc ccttgcttta cagcgggaga | 5700 |

```
agtgagaagg gccatcaggg gagaacaact gctgtcttgc tgcaggttcc cgagagctca   5760
taagtaccag gtaccaagcc tacagtactt agcactgaaa gtagtaagcg atgtcagatc   5820
ccagggagag aatcccacct ggaaacagtg gagaagagac aataggagag gccttcgaat   5880
ggctaaacag aacagtagag gagataaaca gagaggcggt aaaccaccta ccaagggagc   5940
taattttcca ggtttggcaa aggtcttggg aatactggca tgatgaacaa gggatgtcac   6000
caagctatgt aaaatacaga tacttgtgtt aatacaaaa ggctttattt atgcattgca    6060
agaaaggctg tagatgtcta ggggaaggac acggggcagg gggatggaga ccaggacctc   6120
ctcctcctcc ccctccagga ctagcataaa tggaagaaag acctccagaa aatgaaggcc   6180
catgaaggga accatgggt gaatgggtag tggaggttct ggaagaactg aaggaaggag    6240 cttaaaaca ttttgatcct cgcttgctaa ctgcacttgg taatcatatc tataatagac     6300
atggagacac ccttgaggga gcaggagaac tcattagaat cctccagcgg gcactcttca   6360
tgcacttcag aggcggctgc atccactcca gaattggcca acctgggga agaaatcctc    6420 tctcagctat accgccctct agaagcatgc tataacacat gctattgtaa aaagtgttgc   6480
taccattgcc agttttgttt tcttaaaaaa ggcttgggga tatgttatga gcagtcacga   6540
aagagaagaa gaactccgaa aaaggctaag gctaatacat cttctgcatc aaacaagtaa   6600
gtatgggatg tcttgggaat cagctgctta tcgccatctt gcttttaagt gtctatggga   6660
tctattgtac tctatatgtc acagtctttt atggtgtacc agcttggagg aatgcgacga   6720
ttcccctctt ctgtgcaacc aagaataggg atacttgggg aacaactcag tgcctaccag   6780
ataatggtga ttattcagaa ttggcccctta atgttacaga aagctttgat gcttgggaga   6840
atacagtcac agaacaggca atagaagatg tatggcaact ctttgagacc tcaataaagc   6900
cttgtgtaaa attaccccca ttatgcatta ctatgagatg caataaaagt gagacagata   6960 gatgggatt gacaaaatca tcaacaacaa ccacagcagc accaaaggca atgtcagaaa    7020
aaataaacat gatcaatgag actagttctt gtatagttca tgataattgc acaggcttgg   7080
aacaagagca aatgataggc tgtaaattca acatgacagg gttaaaaaga dacaagaaaa   7140
aagagtacaa tgaaacttgg tactctgcag atttggtatg tgaacaaggg aatagcactg   7200
gtaatgaaag tagatgttac atgaatcact gtaacacttc tgttatccaa gagtcttgtg   7260
acaaacatta ttgggatgct attagattta ggtattgtgc acctccaggt tatgctttgc   7320
ttagatgtaa tgacacaaat tattcaggct ttatgcctaa atgttctaag gtggtggtct   7380
cttcatgcac aaggatgatg gagacacaga cttctacttg gtttggcttt aatggaacta   7440
gagcagaaaa tagaacttat atttactggc atggtaggga taaagaact ataattagtt     7500 taaataagta ttataatcta acaataaaat gtagaagacc aggaaataag acagttttac   7560
cagtcaccat tatgtctcaa ttggttttcc actcacaacc aatcaatgat aggccaaagc   7620
aggcatggtg ttggtttaga ggaaaatgga aggatgcaat aaaagaggtg aagcagacca   7680
ttgtcaaaca tcccaggtat actggaacta acaatactga taaaatcaat ttgacggctc   7740
ctggaggagg agatccggaa gttaccttca tgtggcaaa ttgcagagga gagtttctct    7800
actgtaaaat gaattggttt ttaaattggg tagaagatag gaatacagct aaccagaagc   7860
caaaggaaca acataaaagg aattacgtgc catgtcatat tagacaaata atcaacactt   7920
ggcataaagt aggcaaaaat gtttatttgc ctccaagaga gggagacctc acgtgtatct   7980
ccacagtgac cagtctcata gcaaacatag attggactga tggaaaccaa actaatatca   8040
ccatgagtgc agaggtggca gaactgtatc gattggaatt gggagattat aaattagtag   8100
```

-continued

```
agatcactcc aattggcttg ccccccacaa atgtgaggag gtacactact ggtggcacct      8160
caagaaataa aagagggtc tttgtgctag ggttcttggg ttttctcgca acggcaggtt       8220
ctgcaatggg cgcggcgtcg ttgacgctga ccgctcagtc ccggacttta ttggctggga     8280
tagtgcagca acagcaactg ctgttggacg tggtcaagac acaacaagaa ttgttgcgac     8340
tgaccgtctg gggaacaaag aacctccaga ctagggtcac tgccatcgag aaatacttaa     8400
aggaccaggc gcagctgaat gcttggggat gtgcgtttag acaagtctgc cacactactg     8460
taccatggcc aaatgcaagt ctaacaccaa agtggaacaa tgagacttgg caagagtggg     8520
agcgaaaggt tgacttcttg gaggaaaata taacagccct cctagaggag cacaaattc       8580
aacaagagaa gaacatgtat gaattacaaa agttaaatag ctgggatgtg tttggcaatt     8640
ggtttgacct tgcttcttgg ataaagtata tacaatatgg agtttatata gttgtaggag     8700
taatactgtt aagaatagta atctatatag tacaaatgct agctaagtta aggcaggggt     8760
ataggccagt gttctcttcc ccaccctctt atttccagta gacccatatc caacaggacc     8820
aggcactgcc aaccagagaa ggcaaagaag gagacggtgg agaaggcggt ggcaacagct     8880
cctggccttg gcagatagaa tatattcatt tcctgatccg ccaactgata cgcctcttga     8940
cttggctatt cagcaactgc agaaccttgc tatcgagagt ataccagatc ctccaaccaa     9000
tactccagag gctctctgcg accctacgaa ggattcgaga agtcctcagg actgaactga     9060
cctacctaca atatgggtgg aactatttcc atgaggcggt ccaggtcgac tggagatctg     9120
cgacagagac tcttgcgggc gcgtggggag acttatgaga ggctcttagg agaggtggaa     9180
gatggatcct cgcaatccct aggagaatta gacaagggct tgagctcact ctcttgtgag     9240
ggacagaaat acaatcagga acagtacatg aatactccat ggagaaaccc agctgaagag     9300
agagaaaaat tagcatacag aaaacaaaat atggatgata tagatgagga agatgatgat     9360
ttggtagggg tatcagtgag gccaaaagtt cccctaagaa caatgagtta caaattggca     9420
atagacatgt ctcattttat aaaagaaaag ggggactgg aagggattta ttatagtgca      9480
agaagacata gaatcttaga catatactta gaaaaggaag aaggcatcat accagattgg     9540
caggattaca cctcaggacc aggaattaga tacccaaaga catttggctg gctatggaaa     9600
ttagtccctg taaatgtatc agatgaggca caggaggatg aggagcatta tttaatgcat     9660
ccagctcaaa cttcccagtg ggatgaccct tggggagagg ttccagcatg gaagtttgac     9720
ccaactctgg cctacactta tgaggcatat gttagatacc cagaagagtt tggaagcaag     9780
tcaggcctgt cagaggaaga ggttagaaga aggctaaccg caagaggcct tcttaacatg     9840
gctgacaaga aggaaactag atgagacagc agggactttc cacaaggggg gttacgggga     9900
ggtactgggg aggagccggt cgggaacacc cactttcttg atgtataaat atcactgcat     9960
tttgctatgt agtcagtcgc tctgcggaga ggctggcaga ttgagccctg ggaggttctc     10020
tccagcacta gcaggtagag cctgggtgtt ccctgctaga ctctcaccag cacttggccg     10080
gtgctgggca gagtgactcc acgcttgctt gcttaaagcc ctcttcaata aagctgccat     10140
tttagaagta agctagtgtg tgttcccatc tctcctagtc gccgcctggt caactcgta     10200
ctcggtaata agaagaccct ggtctgttag gaccctttct gctttgggaa accgaagcag     10260
gaaaatccct agca                                                       10274
```

<210> SEQ ID NO 6
<211> LENGTH: 9413
<212> TYPE: DNA
<213> ORGANISM: HEPATITIS C

<400> SEQUENCE: 6

```
ttgggggcga cactccacca tagatcactc cctgtgagg aactactgtc ttcacgcaga        60
aagcgtctag ccatggcgtt agtatgagtg ttgtgcagcc tccaggaccc ccctcccgg       120
gagagccata gtggtctgcg gaaccggtga gtacaccgga attgccagga cgaccgggtc      180
ctttcttgga tcaacccgct caatgcctgg agatttgggc gtgccccgc gagactgcta       240
gccgagtagt gttgggtcgc gaaaggcctt gtggtactgc ctgatagggt gcttgcgagt      300
gccccgggag gtctcgtaga ccgtgcatca tgagcacaaa tcctaaacct caaagaaaaa      360
ccaaacgtaa caccaaccgc cgcccacagg acgttaagtt cccgggcggt ggtcagatcg      420
ttggtggagt ttacctgttg ccgcgcaggg gccccaggtt gggtgtgcgc gcgactagga      480
agacttccga gcggtcgcaa cctcgtggaa ggcgacaacc tatccccaag gctcgccggc      540
ccgagggtag gacctgggct cagcccgggt acccttggcc cctctatggc aacgagggta      600
tggggtgggc aggatggctc ctgtcacccc gtggctctcg gcctagttgg ggccccacag      660
acccccggcg taggtcgcgt aatttgggta aggtcatcga taccctttaca tgcggcttcg     720
ccgacctcat ggggtacatt ccgcttgtcg gcgcccccct aggggcgct gccagggccc       780
tggcacatgg tgtccgggtt ctggaggacg gcgtgaacta tgcaacaggg aatctgcccg      840
gttgctcttt ctctatcttc ctcttagctt gctgtcttg tttgaccatc ccagcttccg       900
cttacgaggt gcgcaacgtg tccgggatat accatgtcac gaacgactgc tccaactcaa      960
gtattgtgta tgaggcagcg gacatgatca tgcacacccc cggtgcgtg ccctgcgtcc      1020
gggagagtaa tttctcccgt tgctgggtag cgctcactcc cacgctcgcg gccaggaaca     1080
gcagcatccc caccacgaca atacgacgcc acgtcgattt gctcgttggg gcggctgctc     1140
tctgttccgc tatgtacgtt ggggatctct gcggatccgt ttttctcgtc tcccagctgt     1200
tcaccttctc acctcgccgg tatgagacgt acaagattg caattgctca atctatcccg      1260
gccacgtatc aggtcaccgc atggcttggg atatgatgat gaactggtca cctacaacgg     1320
ccctagtggt atcgcagcta ctccggatcc cacaagccgt cgtggacatg gtggcggggg     1380
cccactgggg tgtcctagcg ggccttgcct actattccat ggtggggaac tgggctaagg     1440
tcttgattgt gatgctactc tttgctggcg ttgacgggca cacccacgtg acagggggaa     1500
gggtagcctc cagcacccag agcctcgtgt cctggctctc acaaggccca tctcagaaaa     1560
tccaactcgt gaacaccaac ggcagctggc acatcaacag gaccgctctg aattgcaatg     1620
actccctcca aactgggttc attgctgcgc tgttctacgc acacaggttc aacgcgtccg     1680
ggtgcccaga gcgcatggct agctgccgcc ccatcgatga gttcgctcag ggtgggggtc    1740
ccatcactca tgatatgcct gagagctcgg accagaggcc atattgctgg cactacgcgc    1800
ctcgaccgtg cgggatcgtg cctgcgtcgc aggtgtgtgg tccagtgtat tgcttcactc    1860
cgagccctgt tgtagtgggg acgaccgatc gtttcgcgc tcctacgtat agctgggggg    1920
agaatgagac agacgtgctg ctacttagca acacgcggcc gcctcaaggc aactggtttg    1980
ggtgcacgtg gatgaacagc actgggttca ccaagacgtg cggggccct ccgtgcaaca    2040
tcggggggt cggcaacaac accttggtct gccccacgga ttgcttccgg aagcaccccg    2100
aggccactta cacaaagtgt ggctcgggc cctggttgac acccaggtgc atggttgact    2160
acccatacag gctctggcac tacccctgca ctgttaactt taccgtcttt aaggtcagga    2220
tgtatgtggg gggcgtggag cacaggctca atgctgcatg caattggact cgaggagagc    2280
gctgtgactt ggaggacagg gataggtcag aactcagccc gctgctgctg tctacaacag    2340
```

-continued

```
agtggcagat actgccctgt tccttcacca ccctaccggc cctgtccact ggcttgatcc    2400
atcttcaccg gaacatcgtg gacgtgcaat acctgtacgg tatagggtcg gcagttgtct    2460
cctttgcaat caaatgggag tatatcctgt tgcttttcct tcttctggcg gacgcgcgcg    2520
tctgtgcctg cttgtggatg atgctgctga tagcccaggc tgaggccacc ttagagaacc    2580
tggtggtcct caatgcggcg tctgtggccg gagcgcatgg ccttctctcc ttcctcgtgt    2640
tcttctgcgc cgcctggtac atcaaaggca ggctggtccc tggggcggca tatgctctct    2700
atggcgtatg gccgttgctc ctgctcttgc tggccttacc accacgagct tatgccatgg    2760
accgagagat ggctgcatcg tgcggaggcg cggttttgt aggtctggta ctcttgacct     2820
tgtcaccata ctataaggtg ttcctcgcta ggctcatatg gtggttacaa tattttatca    2880
ccagagccga ggcgcacttg caagtgtggg tccccctct caatgttcgg ggaggccgcg     2940
atgccatcat cctccttaca tgcgcggtcc atccagagct aatctttgac atcaccaaac    3000
tcctgctcgc catactcggt ccgctcatgg tgctccaggc tggcataact agagtgccgt    3060
actttgtacg cgctcagggg ctcatccgtg catgcatgtt agtgcggaag gtcgctggag    3120
gccactatgt ccaaatggcc ttcatgaagc tggccgcgct gacaggtacg tacgtatatg    3180
accatcttac tccactgcgg gattgggccc acgcgggcct acgagacctt gcggtggcag    3240
tagagcccgt cgtcttctct gacatggaga ctaaactcat cacctggggg gcagacaccg    3300
cggcgtgtgg ggacatcatc tcgggtctac cagtctccgc ccgaaggggg aaggagatac    3360
ttctaggacc ggccgatagt tttggagagc aggggtggcg gctccttgcg cctatcacgg    3420
cctattccca caaacgcgg ggcctgcttg gctgtatcat cactagcctc acaggtcggg     3480
acaagaacca ggtcgatggg gaggttcagg tgctctccac cgcaacgcaa tctttcctgg    3540
cgacctgcgt caatggcgtg tgttggaccg tctaccatgg tgccggctcg aagaccctgg    3600
ccggcccgaa gggtccaatc acccaaatgt acaccaatgt agaccaggac ctcgtcggct    3660
ggccggcgcc ccccggggcg cgctccatga caccgtgcac ctgcggcagc tcggacctt    3720
acttggtcac gaggcatgct gatgtcgttc cggtgcgccg gcggggcgac agcaggggga    3780
gcctgctttc ccccaggccc atctcctacc tgaagggctc ctcgggtgga ccactgcttt    3840
gcccttcggg gcacgttgta ggcatcttcc gggctgctgt gtgcacccgg ggggttgcga    3900
aggcggtgga cttcataccc gttgagtcta tggaaactac catgcggtct ccggtcttca    3960
cagacaactc atcccctccg gccgtaccgc aaacattcca agtggcacat ttacacgctc    4020
ccactggcag cggcaagagc accaaagtgc cggctgcata tgcagcccaa gggtacaagg    4080
tgctcgtcct aaacccgtcc gttgccgcca cattgggctt tggagcgtat atgtccaagg    4140
cacatggcat cgagcctaac atcagaactg gggtaaggac catcaccacg gcggccccca    4200
tcacgtactc cacctattgc aagttccttg ccgacggtgg atgctccggg ggcgcctatg    4260
acatcataat atgtgatgaa tgccactcaa ctgactcgac taccatcttg ggcatcggca    4320
cagtcctgga tcaggcagag acggctggag cgcggctcgt cgtgctcgcc accgccacgc    4380
ctccgggatc gatcaccgtg ccacacccca acatcgagga agtggccctg tccaacactg    4440
gagagattcc cttctatggc aaagccatcc ccattgaggc catcaagggg gaaggcatc    4500
tcatcttctg ccattccaag aagaagtgtg acgagctcgc cgcaaagctg acaggcctcg    4560
gactcaatgc tgtagcgtat taccggggtc tcgatgtgtc cgtcataccg actagcggag    4620
acgtcgttgt cgtggcaaca gacgctctaa tgacgggttt taccggcgac tttgactcag    4680
tgatcgactg caacacatgt gtcacccaga cagtcgattt cagcttggat cccaccttca    4740
```

```
ccattgagac gacaacgctg ccccaagacg cggtgtcgcg tgcgcagcgg cgaggtagga    4800
ctggcagggg caggagtggc atctacaggt ttgtgactcc aggagaacgg ccctcaggca    4860
tgttcgactc ctcggtcctg tgtgagtgct atgacgcagg ctgcgcttgg tatgagctca    4920
cgcccgctga gacctcggtt aggttgcggg cttacctaaa tacaccaggg ttgcccgtct    4980
gccaggacca cctagagttc tgggagagcg tcttcacagg cctcacccac atagatgccc    5040
acttcttgtc ccagaccaaa caggcaggag acaacctccc ctacctggta gcataccaag    5100
ccacagtgtg cgccagggct caggctccac ctccatcgtg ggaccaaatg tggaagtgtc    5160
tcatacggct aaagcccaca ctgcatgggc aacgcccct gctgtacagg ctaggagccg    5220
ttcaaaatga ggtcactctc acacaccca taaccaaata catcatggca tgcatgtcgg    5280
ctgacctgga ggtcgtcact agcacctggg tgctagtagg cggagtcctt gcggctctgg    5340
ccgcgtactg cctgacgaca ggcagcgtgg tcattgtggg caggatcatc ttgtccggga    5400
ggccagctgt tattcccgac agggaagtcc tctaccagga gttcgatgag atggaagagt    5460
gtgcttcaca cctcccttac atcgagcaag gaatgcagct cgccgagcaa ttcaaacaga    5520
aggcgctcgg attgctgcaa acagccacca agcaagcgga ggctgctgct cccgtggtgg    5580
agtccaagtg gcgagccctt gaggtcttct gggcgaaaca catgtggaac ttcatcagcg    5640
ggatacagta cttggcaggc ctatccactc tgcctgaaaa ccccgcgata gcatcattga    5700
tggcttttac agcctctatc accagcccgc tcaccaccca aaatacoctc ctgtttaaca    5760 tcttgggggg atgggtggct gcccaactcg ctcccccag cgctgcttcg gctttcgtgg    5820
gcgccggcat tgccggtgcg gccgttggca gcataggtct cgggaaggta cttgtggaca    5880
ttctggcggg ctatggggcg ggggtggctg gcgcactcgt ggcctttaag gtcatgagcg    5940
gcgagatgcc ctccactgag gatctggtta atttactccc tgccatcctt tctcctggcg    6000
ccctggttgt cggggtcgtg tgcgcagcaa tactgcgtcg gcacgtgggc ccggagagg    6060 gggctgtgca gtggatgaac cggctgatag cgttcgcttc gcggggtaac cacgtctccc    6120
ccacgcacta tgtgcccgag agcgacgccg cggcgcgtgt tactcagatc ctctccagcc    6180
ttaccatcac tcagttgctg aagaggcttc atcagtggat taatgaggac tgctccacgc    6240
cttgttccgg ctcgtggcta aaggatgttt gggactggat atgcacggtg ttgagtgact    6300
tcaagacttg gctccagtcc aagctcctgc cgcggttacc gggactccct ttcctgtcat    6360
gccaacgcgg gtacaaggga gtctggcggg gggatggcat catgcaaacc acctgcccat    6420
gtggagcaca gatcaccgga catgtcaaaa atggctccat gaggattgtt gggccaaaaa    6480
cctgcagcaa cacgtggcat ggaacattcc ccatcaacgc atacaccacg ggcccctgca    6540
cgccctcccc agcgccgaac tattccaggg cgctgtggcg ggtggctgct gaggagtacg    6600
tggaggttac gcgggtgggg gatttccact acgtgacggg catgaccact gacaacgtga    6660
aatgcccatg ccaggttcca gcccctgaat tttcacggag ggtggatgga gtacggttgc    6720
acaggtatgc tccagtgtgc aaacctctcc tacgagagga ggtcgtattc caggtcgggc    6780
tcaaccagta cctggtcggg tcacagctcc catgtgagcc cgaaccggat gtggcagtgc    6840
tcacttccat gctcaccgac ccctctcata ttacagcaga cggccaag cgtaggctgg    6900 ccaggggtc tccccctcc ttggccagct cttcagctag ccagttgtct gcgcttctt    6960 tgaaggcgac atgtactacc catcatgact ccccggacgc tgacctcatc gaggccaacc    7020
tcctgtggcg gcaggagatg ggcgggaaca tcacccgtgt ggagtcagaa aataaggtgg    7080
taatcctgga ctcttttcgat ccgattcggg cggtggagga tgagagggaa atatccgtcc    7140
```

```
cggcggagat cctgcgaaaa cccaggaagt tcccccccagc gttgcccata tgggcacgcc    7200
cggattacaa ccctccactg ctagagtcct ggaaggaccc ggactacgtc cccccggtgg    7260
tacacgggtg ccctttgcca tctaccaagg ccccccaat accacctcca cggaggaaga    7320
ggacggttgt cctgacagag tccaccgtgt cttctgcctt ggcggagctc gctactaaga    7380
cctttggcag ctccgggtcg tcggccgttg acagcggcac ggcgactggc cctcccgatc    7440
aggcctccga cgacggcgac aaaggatccg acgttgagtc gtactcctcc atgcccccc     7500 tcgagggaga gccaggggac cccgacctca gcgacgggtc ttggtctacc gtgagcgggg    7560
aagctggtga ggacgtcgtc tgctgctcaa tgtcctatac atggacaggt gccttgatca    7620
cgccatgcgc tgcggaggag agcaagttgc ccatcaatcc gttgagcaac tctttgctgc    7680
gtcaccacag tatggtctac tccacaacat ctcgcagcgc aagtctgcgg cagaagaagg    7740
tcacctttga cagactgcaa gtcctggacg accactaccg ggacgtgctc aaggagatga    7800
aggcgaaggc gtccacagtt aaggctaggc ttctatctat agaggaggcc tgcaaactga    7860 cgccccaca ttcggccaaa tccaaatttg ctacggggc gaaggacgtc cggagcctat      7920
ccagcagggc cgtcaaccac atccgctccg tgtgggagga cttgctggaa gacactgaaa    7980
caccaattga taccaccatc atggcaaaaa atgaggtttt ctgcgtccaa ccagagaaag    8040
gaggccgcaa gccagctcgc cttatcgtat tcccagacct gggggtacgt gtatgcgaga    8100
agatggccct ttacgacgtg gtctccaccc ttcctcaggc cgtgatgggc ccctcatacg    8160
gattccagta ctctcctggg cagcgggtcg agttcctggt gaatacctgg aaatcaaaga    8220
aatgccctat gggcttctca tatgacaccc gctgctttga ctcaacggtc actgagaatg    8280
acatccgtac tgaggaatca atttaccaat gttgtgactt ggccccccgaa gccaggcagg    8340 ccataaggtc gctcacagag cggctttatg tcggggggtcc cctgactaat tcgaagggggc    8400 agaactgcgg ttatcgccgg tgccgcgcaa gtggcgtgct gacgactagc tgcggcaaca    8460
ccctcacatg ttacttgaag gccactgcgg cctgtcgagc tgcaaagctc caggactgca    8520
cgatgctcgt gaacggagac gaccttgtcg ttatctgtga gagtgcggga acccaggagg    8580
atgcggcggc cctacgagcc ttcacggagg ctatgactag gtattccgcc ccccccgggg    8640
acccgcccca accagaatac gacttggagc tgataacgtc atgctcctcc aatgtgtcgg    8700
tcgcgcacga tgcatccggc aaaagggtgt actacctcac ccgtgacccc accaccccc      8760 tcgcacgggc tgcgtgggag acagttagac acactccagt caactcctgg ctaggcaata    8820
tcatcatgta tgcgcccacc ctatgggcga ggatgattct gatgactcat ttcttctcta    8880
tccttctagc tcaggagcaa cttgaaaaag ccctggattg tcagatctac ggggcctgtt    8940
actccattga gccacttgac ctacctcaga tcattgaacg actccatggt cttagcgcat    9000
tttcactcca cagttactct ccaggtgaga tcaatagggt ggcttcatgc ctcaggaaac    9060
ttggggtacc gcctttgcga gtctggagac atcgggccag aagtgtccgc gctaagctac    9120
tgtcccaggg ggggagggct gccacttgcg gcaagtacct cttcaactgg gcagtaaaga    9180
ccaagcttaa actcactcca atcccggctg cgtcccagct agacttgtcc ggctggttcg    9240
ttgctggtta caacggggga gacatatatc acagcctgtc tcgtgcccga ccccgttggt    9300
tcatgttgtg cctactccta ctttctgtag gggtaggcat ctacctgctc cccaaccggt    9360
gaacggggag ctaaccactc caggccaata ggccattccc tttttttttt ttc           9413
```

<210> SEQ ID NO 7
<211> LENGTH: 9365

<212> TYPE: DNA
<213> ORGANISM: HEPATITIS C

<400> SEQUENCE: 7

```
ttggggcga cactccacca tgaatcactc ccctgtgagg aactactgtc ttcacgcaga      60
aagcgtctag ccatggcgtt agtatgagtg tcgtgcagcc tccaggaccc cccctcccgg     120
gagagccata gtggtctgcg gaaccggtga gtacaccgga attgccagga cgaccgggtc     180
ctttcttgga taaacccgct caatgcctgg agatttgggc gtgccccgc aagactgcta      240
gccgagtagt gttgggtcgc gaaaggcctt gtggtactgc ctgatagggt gcttgcgagt     300
gccccgggag gtctcgtaga ccgtgcacca tgagcacgaa tcctaaaccc aaagaaaaa     360
ccaaacgtaa caccaaccgt cgcccacagg acgtcaagtt cccgggtggc ggtcagatcg     420
ttggtggagt ttacttgttg ccgcgcaggg gccctagatt gggtgtgcgc gcgacgagga     480
agacttccga gcggtcgcaa cctcgaggta gacgtcagcc tatccccaag gcacgtcggc     540
ccgagggcag gacctgggct cagcccgggt acccttggcc cctctatggc aatgagggtt     600
gcgggtgggc gggatggctc ctgtctcccc gtggctctcg gcctagctgg ggccccacag     660
accccccggcg taggtcgcgc aatttgggta aggtcatcga taccttacg tgcggcttcg     720
ccgacctcat ggggtacata ccgctcgtcg gcgcccctct tggaggcgct gccagggccc     780
tggcgcatgg cgtccgggtt ctggaagacg gcgtgaacta tgcaacaggg aaccttcctg     840
gttgctcttt ctctatcttc cttctggccc tgctctcttg cctgaccgtg cccgcttcag     900
cctaccaagt gcgcaattcc tcgggctttt accatgtcac caatgattgc cctaattcga     960
gtattgtgta cgaggcggcc gatgccatcc tacacactcc ggggtgtgtc ccttgcgttc    1020
gcgagggtaa cgcctcgagg tgttggtgg cggtgacccc cacggtggcc accagggacg    1080
gcaaactccc cacaacgcag cttcgacgtc atatcgatct gctcgtcggg agcgccaccc    1140
tctgctcggc cctctacgtg ggggacctgt gcggtctgt ctttcttgtt ggtcaactgt     1200
ttaccttctc tcccaggcgc cactggacga cgcaagactg caattgttct atctatcccg    1260
gccatataac gggtcatcgt atggcatggg atatgatgat gaactggtcc cctacgcag     1320
cgttggtggt agctcagctg ctccggatcc cacaagccat cttggacatg atcgctggtg    1380
cccactgggg agtcctggcg ggcatagcgt atttctccat ggtggggaac tgggcgaagg    1440
tcctggtagt gctgctgcta tttgccggcg ttgacgcgga acccacgtc accgggggaa     1500
gtgccggcca caccacggct gggcttgttc gtctcctttc accaggcgcc aagcagaaca    1560
tccaactgat caacaccaac ggcagttggc acatcaatag cacggccttg aactgcaatg    1620
aaagccttaa caccggctgg ttagcaggc tcttctatca ccacaaattc aactcttcag    1680
gttgtcctga gaggttggcc agctgccgac gccttaccga ttttgcccag gcggggtgtc     1740
ctatcagtta cgccaacgga agcggcctcg atgaacgccc ctactgctgg cactaccctc    1800
caagaccttg tggcattgtg cccgcaaaga gcgtgtgtgg cccggtatat tgcttcactc    1860
ccagccccgt ggtggtggga acgaccgaca ggtcggcgc gcctacctac agctggggtg     1920
caaatgatac ggatgtcttt gtccttaaca acaccaggcc accgctgggc aattggttcg    1980
gttgcacctg gatgaactca actgggattca ccaaagtgtg cggagcgccc ccttgtgtca    2040
tcggaggggt gggcaacaac accttgctct gccccactga ttgcttccgc aagcatccgg    2100
aagccacata ctctcggtgc ggctccggtc cctggattac acccaggtgc atggtcgact    2160
acccgtatag gctttggcac tatccttgta ccatcaatta ccatatattc aaagtcagga    2220
```

-continued

```
tgtacgtggg aggggtcgag cacaggctgg aagcggcctg caactggacg cggggcgaac    2280
gctgtgatct ggaagacagg gacaggtccg agctcagccc gttactgctg tccaccacgc    2340
agtggcaggt ccttccgtgt tctttcacga ccctgccagc cttgtccacc ggcctcatcc    2400
acctccacca gaacattgtg gacgtgcagt acttgtacgg ggtagggtca agcatcgcgt    2460
cctgggctat taagtgggag tacgtcgttc tcctgttcct tctgcttgca gacgcgcgcg    2520
tttgctcctg cttgtggatg atgttactca tatcccaagc ggaggcggct ttggagaacc    2580
tcgtaatact caatgcagca tccctggccg ggacgcacgg ttttgtgtcc ttcctcgtgt    2640
tcttctgctt tgcgtggtat ctgaagggta ggtgggtgcc cggagcagcc tacgccctct    2700
acgggatatg gcctctcctc ctgctcctgc tggcgttgcc tcagcgggca tacgcactgg    2760
acacggaggt ggccgcgtcg tgtggcggcg ttgttcttgt cgggttaatg gcgctgactc    2820
tgtcgccata ctacaagcgc tatatcagct ggtgcatgtg gtggcttcag tattttctga    2880
ccagagtaga agcgcaactg cacgtgtggg ttccccccct caacgttcgg ggggggcgcg    2940
atgccgtcat cttactcatg tgtgctgtac acccgactct ggtatttgac atcaccaaac    3000
tactcctggc catcttcgga cccctttgga ttcttcaagc cagtttgctt aaagtccccct    3060
acttcgtgcg cgttcaaggc cttctccgga tctgcgcgct agcgcggaag atagccggag    3120
gtcattacgt gcaaatgatc ttcatcaagt taggggcgct tactggcacc tatgtgtata    3180
accatctcac ccctcttcga gactgggcgc acaacggctt gcgagatctg gccgtggctg    3240
tggaaccagt cgtcttctcc cgaatggaga ccaagctcat cacgtgggg gcagataccg    3300
ccgcgtgcgg tgacatcatc aacggcttgc ccgtctctgc ccgtagggc caggagatac    3360
tgcttggacc agccgacgga atggtctcca aggggtggag gttgctggcg cccatcacgg    3420
cgtacgccca gcagacgaga ggcctcctag ggtgtataat caccagcctg actggccggg    3480
acaagaacca agtggagggt gaggtccaga tcgtgtcaac tgctacccaa accttcctgg    3540
caacgtgcat caatgggta tgctggactg tctaccacgg ggccggaacg aggaccatcg    3600
catcacccaa gggtcctgtc atccagatgt ataccaatgt ggaccaagac cttgtgggct    3660
ggccccgctcc tcaaggttcc cgctcattga caccctgcac ctgcggctcc tcggaccttt    3720
acctggtcac gaggcacgcc gatgtcattc ctgtgcgccg gcaaggtgat agcaggggta    3780
gcctgctttc gccccggccc atttcctact tgaaaggctc ctcgggggt ccgctgttgt    3840
gccccgcggg acacgccgtg ggcctattca gggccgcggt gtgcacccgt ggagtggcta    3900
aggcggtgga ctttatccct gtggagaacc tagagacaac catgagatcc ccggtgttca    3960
cggacaactc ctctccacca gcagtgcccc agagcttcca ggtggcccac ctgcatgctc    4020
ccaccggcag cggtaagagc accaaggtcc cggctgcgta cgcagctcag ggctataagg    4080
tgttggtgct caaccccttct gttgctgcaa cgctgggctt tggcgcttac atgtccaagg    4140
cccatgggt cgatcctaat atcaggaccg gggtgagaac aattaccact ggcagcccta    4200
tcacgtactc cacctacggc aagttccttg ccgacggcgg gtgctcagga ggtgcttatg    4260
acataataat ttgtgacgag tgccactcca cggatgccac atccatcttg gcatcggca    4320
ctgtccttga ccaagcagag actgcgggg cgagattggt tgtgctcgcc actgctaccc    4380
ctccgggctc cgtcactgtg ccccatccta acatcgagga ggttgctctg tccaccaccg    4440
gagagatccc ttttacggc aaggccatcc ctctcgaggt gatcaagggg ggaagacatc    4500
tcatcttctg tcactcaaag aagaagtgcg acgagctcgc cgcgaagctg gtcgcactgg    4560
gcatcaatgc cgtggcctac taccgcggtc ttgacgtgtc tgtcatcccg gccagcggcg    4620
```

```
atgttgtcgt cgtgtcgacc gatgctctca tgactggctt tactggcgac ttcgaccctg    4680
tgatagactg caacacgtgt gtcactcaga cagtcgattt cagccttgac cctaccttta    4740
ccattgagac aaccacgctc ccccaggatg ctgtctccag gactcaacgc cggggcagga    4800
ctggcagggg gaagccaggc atctacagat ttgttgcacc gggggagcgc ccctccggca    4860
tgttcgactc gtccgtcctc tgtgagtgct atgacgcggg ctgtgcttgg tatgagctca    4920
cgcccgccga gactacagtt aggctacgag cgtacatgaa caccccgggg cttcccgtgt    4980
gccaggacca tcttgaattt tgggagggcg tctttacggg cctcactcat atagatgccc    5040
actttctatc ccagacaaag cagagcgggg agaactttcc ttacctggta gcgtaccaag    5100
ccaccgtgtg cgctagggct caagcccctc ccccatcgtg ggaccagatg tggaagtgtt    5160
tgatccgcct taaacccacc ctccatgggc aacacccct gctatacaga ctgggcgctg     5220
ttcagaatga aatcaccctg acgcacccag tcaccaaata catcatgaca tgcatgtcgg    5280
ccaacccgga ggtcgtcacg agcacctggg tgctcgttgg cggcgtcctg gctgctctgg    5340
ccgcgtattg cctgtcaaca ggctgcgtgg tcatagtggg caggattgtc ttgtccggga    5400
agccggcaat tataccctga cagggaggttc tctaccagga gttcgatgag atggaagagt    5460
gctctcagca cttaccgtac atcgaacaag ggatgatgct cgctgagcag ttcaagcagg    5520
aggccctcgg cctcctgcag accgcgtccc gccaagcaga ggttatcacc cctgctgtcc    5580
agaccaactg gcagaaactc gaggccttct gggcgaagca catgtggaat tcatcagtg     5640 ggacacaata cttggcgggc ctgtcaacgc tgcctggtaa ccccgccatt gcttcattga    5700 tggctttac agctgccgtc accagcccac taaccactag ccaaaccctc ctcttcaaca     5760
tattgggggg gtgggtggct gcccagctcg ccgccccgg tgccgctacc gcctttgtgg     5820
gcgctggctt agctggcgcc gccatcggca gcgttggact ggggaaggtc ctcgtggaca    5880
tacttgcggg gtatgcgcg ggcgtggcgg gagcccttgt ggcattcaag atcatgagcg      5940
gtgaggtccc ctccacggag gacctggtca atctgctgcc cgccatcctc tcgcctggag    6000
cccttgtagt cggtgtggtc tgcgcagcaa tactgcgccg gcacgttggc ccgggcgagg    6060
gggcagtgca atggatgaac cggctaatag ccttcgcctc ccgggggaac catgtctccc    6120
ccacgcacta cgtgccggag agcgatgcag ccgcccgcgt cactgccata ctcagcaacc    6180
tcactgtaac ccagctcctg aggcgactgc atcagtggat aggctcggag tgtaccactc    6240
catgctccgg ttcctggcta agggacatct gggactggat atgcgaggtg ctgagcgact    6300
ttaagacctg gctgaaagcc aagctcatgc cacaactgcc tgggattccc tttgtgtcct    6360
gccagcgcgg gtataggggg gtctggcgag gagacggcat tatgcacact cgctgccact    6420
gtggggctga gatcactgga catgtcaaaa acgggacgat gaggatcgtc ggtcctagga    6480
cctgcaggaa catgtggagt gggacgttcc ccattaacgc ctacaccacg ggcccctgta    6540
ctcccctccc tgcgccgaac tataagttcg cgctgtggag ggtgtctgca gaggaatacg    6600
tggagataag gcgggtgggg gacttccact acgtatcggg catgactact gacaatctta    6660 aatgccgtg ccagatccca tcgcccgaat ttttcacaga attggacggg gtgcgcctac      6720
ataggtttgc gcccccctgc aagcccttgc tgcgggagga ggtatcattc agagtaggac    6780
tccacgagta cccggtgggg tcgcaactac cttgcgagcc cgaacggac gtagccgtgt      6840 tgacgtccat gctcactgat ccctcccata taacagcaga ggcggccggg aggaggttgg    6900
cgagagggtc accccttct atggccagct cctcggctag ccagctgtcc gctccatctc      6960
tcaaggcaac ttgcaccacc aaccatgact cccctgacgc cgagctcata gaggctaacc    7020
```

-continued

```
tcctgtggag gcaggagatg ggcggcaaca tcaccagggt tgagtcagag aacaaagtgg   7080
tgattctgga ctccttcgat ccgcttgtgg cagaggagga tgagcgggag gtctccgtac   7140
ccgcagaaat tctgcggaag tctcagagat tcgcccgggc cctgcccgtt tgggcgcggc   7200
cggactacaa ccccccgcta atagagacgt ggaaagagcc tgactacgaa ccacctgtgg   7260
tccatggctg cccgttacca cctccacggt cccctcctgt gcctccgcct cggaaaaagc   7320
gtacggtggt cctcaccgaa tcaaccctat ctactgcctt ggccgagctt gccaccaaaa   7380
gttttggcag ctcctcaact tccggcatta cgggcgacaa tacgacaaca tcctctgagc   7440
ccgccccttc tggctgcccc cccgactccg acgttgagtc ctattcttcc atgcccccc    7500 tggagggga gcctggggac ccggatttca gcgacgggtc atggtcgacg gtcagtagtg   7560
gggccgacac ggaagatgtc gtgtgctgct caatgtctta ttcctggaca ggcgcactcg   7620
tcaccccgtg cgctgcggaa gaacaaaaac tgcccatcaa cgcactgagc aactcgttgc   7680
tacgccatca caatctggtg tattccacca cttcacgcag tgcttgccaa aggcagaaga   7740
aagtcacatt tgacagactg caagttctgg acagccatta ccaggacgtg ctcaaggagg   7800
tcaaagcagc ggcgtcaaga gtgaaggcta acttgctatc cgtagaggaa gcttgcagcc   7860
tgacgccccc acattcagcc aaatctaagt ttggctatgg ggcaaaagac gtccgttgcc   7920
atgccagaaa ggccgtagcc cacatcaact ccgtgtggaa agaccttctg aagacagtg   7980 taacaccaat agacactacc atcatggcca agaacgaggt tttctgcgtt cagcctgaaa   8040 agggggtcg taagccagct cgtctcatcg tgttccccga cctgggcgtg cgcgtgtgcg   8100
agaagatggc cctgtacgac gtggttagca agctccccct ggccgtgatg ggaagctcct   8160
acggattcca atactcacca ggacagcggg ttgaattcct cgtgcaagcg tggaagtcca   8220
agaagacccc gatggggttc tcgtatgata cccgctgttt tgactccaca gtcactgaga   8280
gcgacatccg tacggaggag gcaatttacc aatgttgtga cctggacccc caagcccgcg   8340
tggccataaa gtccctcact gagaggcttt atgttggggg ccctcttacc aattcaaggg   8400
gggaaaactg cggctaccgc aggtgccgcg cgagcggcgt actgacaact agctgtggta   8460
acaccctcac ttgctacatc aaggcccggg cagcctgtcg agccgcaggg ctccaggacc   8520
gcaccatgct cgtgtgtggc gacgacttag tcgttatctg tgaaagtgcg ggggtccagg   8580
aggacgcggc gagcctgaga gccttcacgg aggctatgac caggtactcc gccccccccg   8640
gggacccccc acaaccagaa tacgacttgg agcttataac atcatgctcc tccaacgtgt   8700
cagtcgccca cgacggcgct ggaaagaggg tctactacct tacccgtgac cctacaaccc   8760
ccctcgcaag agccgcgtgg gagacagcaa gacacactcc agtcaattcc tggctaggca   8820
acataatcat gtttgccccc acactgtggg cgaggatgat actgatgacc catttcttta   8880
gcgtcctcat agccagggat cagtttgaac aggctcttaa ctgtgagatc tacggagcct   8940
gctactccta gaaccactg atctacctc aatcattca aagactccat ggcctcagcg   9000
cattttcact ccacagttac tctccaggtg aaatcaatag ggtggccgca tgcctcagaa   9060
aacttggggt tccgcccttg cgagcttgga aacaccgggc ccgagtgtc cgcgctaggc   9120 ttctgtccag gggaggcagg gctgccatat gtggcaagta cctcttcaac tgggcagtaa   9180
gaacaaagcc caaactcact ccaatagcgg ccgctggccg gctggacttg tccggttggt   9240
tcacggctgg ctacagcggg ggagacattt atcacagcgt gtctcatgcc cggccccgct   9300
ggtcctggtt ttgcctactc ctgctcgctg caggggtagg catctacctc ctccccaacc   9360
gatga                                                              9365
```

<210> SEQ ID NO 8
<211> LENGTH: 154746
<212> TYPE: DNA
<213> ORGANISM: HERPESVIRUS 2

<400> SEQUENCE: 8

```
agtccccgtc ctgccgcgcg ggggcgggcg cgggaaaaaa gccgcgcggg ggcgcccgcg      60
ggaaggcagc cccgcggcgc gcggggggag gggcggcgcc cgcggggggag cggccggctc     120
cggggggaggg acggggaagg gggcgcgcgg ggctgccctg ccgcccgccc gccgccgccg     180
cccgccttcg cgcccccccc caaaaaacac cccccccggg ggttgactcc ccggggggaaa     240
agaggcgggg cgggagtccc cgtcctgccg ccgcccctta agagggcccg caacacggcc     300
cgggctgcgc acgccagccg ggacgggtga gttcgctagg caagcacgga ctggcggtta     360
cacgtgcatg cgtgccgagt gaactctccc gccccgacgc gctccggctc cgggcctacg     420
ccgagcccag ccgcccgcca tgtcccgccg ccggggtccc cgccgccggg gtccccggcg     480
ccggccgcgc cccggcgctc cagccgtgcc gcgcccggc gctccagccg tgccgcgccc     540
cggcgcgctc ccaaccgcag actcccaaat ggtccctgcg tacgactcgg gaaccgcggt     600
cgagagcgcg ccggccgcgt cctcgctcct gcggcgctgg ctgctggtgc cccaggcgga     660
cgacagcgac gacgcggact acgccggcaa cgacgacgca gagtgggcga acagcccccc     720
gagcgagggc gggggggaagg cgccggaggc cccgcacgcc gcgcctgccg ccgcctgccc     780
cccgccgccg ccgcgcaagg agcgcgggcc gcagcgcccc cttccgcccc acctggcgct     840
acggctgcgc accacgacgg agtacctggc gcgcctgagc ctgcgccggc ggcggccccc     900
cgcgtccccg cccgcggacg cgccgcgcgg gaaggtacgc ctcccctccg acccctgac       960
gccccctccga ccccctgacg cccctccgac cccctgacgc ccctccgacc ccctgacgcc    1020
cctccgaccc cctgacgccc ctccgacccc ctgacgcccc tccgaccccc gtgtctcccc    1080
gcccgcaggt gtgcttctcg ccgcgcgtgc aggtgcgcca tctggtggcc tgggagacgg    1140
ccgcgcgcct ggcccgacgg gggtcctggg cgcgcgagcg ggccgaccgc gaccggttcc    1200
ggcgccgcgt ggcggcggcc gaggcggtca tcggaccgtg cctggagccc gaggcccgag    1260
ctcgggcccg agcccgagcc cgggcccacg aagacggcgg acccgcggag gaggaggagg    1320
cggcggcggc ggcgcgcggg tcctccgccg ccgcggggcc gggccgtcgg gcggtctagg    1380
gttgaaccgg cgagggcggc ctcggccggc ggagccccgg agctccgaag gtctgcgcga    1440
ggccgctctc cgaagagacg atgggagccc cgcgtatata tccgcgaggg cccggcgccg    1500
cccgccgct ccgcccgccc caggggggcgg cgccggccaa ccgcgcgccg ccgcgcgggc     1560
ccggactccg ccccggcgac cgccccgcgc cggcttcccg gtatggtaat tagaaacttt    1620
taataggcgg tcccggccgc catccccgcg catggtaatt agcaactttt aatgggccgg    1680
cgttcccgct cgcggtaatt agcagctttt aacgggccgc cattcccgct tatggtaatt    1740
aaaaacgttc ggacggcccc tcgctccccg cgtaattact ccctcggggt tccgggttat    1800
gctgattact ttcttggcag aacacgcaga gcctcgcgcg ccgccgggtg ggtgggctga    1860
tcggcccta ttggtcccct gggcttccta gtatgctaat gaattttttcc ccgggggcgg     1920
gcaccactca gggccgcgcc ggcggggcgc cggggggact cccatctgcg tcggcggggg    1980
gcggcgcatg ctaatggggt tcttggagta cacccggttg gtccccgggg acggggccgc    2040
cccgagaggg ggggattccc tccctccgcc ccgccggggg cgcgcggcta ttggggggaat    2100
cgtaaatgcc gccccctttgg gggagtggat aggcgccggg tataaggcag ccccgtgtga    2160
```

-continued

```
cggtcgggcc gcattcgcac cccggcactg cgagcgacgg agcggcggcc cggcgggagg   2220
aggagacccg gagagacaga gactaaaacc cggcaagaga gagaccgcgg gccgccgtct   2280
cgagtctacc ctaccccggc tcatggaacc ccggcccggc acgagctccc gggcggaccc   2340
cggccccgag cggccgccgc ggcagacccc cggcacggtg agagggcgac ccccgggtct   2400
caggcccccc cttttcccg gaccaccgg ctgcgggttg gggtggtcg cgggcggtgg      2460 gctcggggc ggggacgctt gacggggccg acccccggcc cgcttaagcg gtcggggac    2520 ccccgtgggc cgtgcgccgc ccccgaccc tctgggggg cgaggaggc agggaggagc     2580 ccgagagcgg gggacagggg gggagacgag gggtcggaat ccaaaggacg cagaccacct  2640
ttggttacgg accccttcct cccccccttc cgaacaaaaa gcagcgggcg gggggccggg  2700
gtgagggagg gacacggggg acacggcgcg ggggtcccgc ctcacgcccc gcgccctcta  2760 aatcccccccc gttgctttgt caagcagccc gccgccccgc acgcctgggg gatgctcaac 2820
gacatgcagt ggctcgccag cagcgactcg gaggaggaga ccgaggtggg aatctctgac  2880
gacgaccttc accgcgactc cacctccgag gcgggcagca cggacacgga gatgttcgag  2940
gcgggcctga tggacgcggc cacgccccg gcccggcccc cggccgagcg ccagggcagc   3000
cccacgcccg ccgacgcgca gggatcctgt gggggtgggc ccgtgggtga ggaggaagcg  3060
gaagcgggag gggggggcga cgtgtgtgcc gtgtgcacgg acgagatcgc cccgcccctg  3120
cgctgccaga gttttccctg cctgcacccc ttctgcatcc cgtgcatgaa gacctggatt  3180
ccgttgcgca acacgtgtcc cctgtgcaac accccggtgg cgtacctgat agtgggcgtg  3240
accgccagcg ggtcgttcag caccatcccg atagtgaacg acccccggac ccgcgtggag  3300
gccgaggcgg ccgtgcgggc cggcacggcc gtggacttta tctggacggg caacccgcgg  3360
acggccccgc gctccctgtc gctgggggga cacacggtcc gcgccctgtc gcccaccccc  3420
ccgtggcccg gcacggacga cgaggacgat gacctggccg acggtgaggg cgggcggggg  3480
tcgggcgggg ggcgggcggg ggtcgggcgg gggtcgggcg ggggtcgggc ggggtcggg   3540 cggggtcgg gcggggtcg gcggggtc gggcggggt cggcggggg tcggcgggg        3600 gtcgggcact aaccggggc tcccgtctct gtctccctct gcagtggact acgtcccgcc    3660
cgccccccga agagcgcccc ggcgcggggg cggcggtgcg ggggcgaccc gcggaacctc  3720
ccagcccgcc gcgacccgac cggcgccccc tggcgccccg cggagcagca gcagcggcgg  3780
cgccccgttg cgggcggggg tgggatctgg gtctgggggc ggccctgccg tcgcggccgt  3840
cgtgccgaga gtggcctctc ttcccctgc ggccggcgg gggcgcgcgc aggcgcggcg    3900
ggtgggcgaa gacgccgcgg cggcggaggg caggacgccc cccgcgagac agccccgcgc  3960
ggcccaggag ccccccatag tcatcagcga ctctcccccg ccgtctccgc gccgccccgc  4020 gggcccggg ccgtctcct ttgtctcctc ctcctccgca caggtgtcct cgggccccgg   4080
ggggggaggt ctgccacagt cgtcgggcg cgccgcgcgc cccgcgcgg ccgtcgcccc   4140 gcgcgtccgg agtccgcccc gcgccgccgc cgccccgtg gtgtctgcga gcgcggacgc   4200
ggccgggccc gcgccgcccg ccgtgccggt ggacgcgcac cgcgcgcccc ggtcgcgcat  4260
gacccaggct cagaccgaca cccaagcaca gagtctgggc cgggcaggcg cgaccgacgc  4320
gcgcgggtcg ggaggccgg gcgcggaggg aggaccccggg gtcccccgcg gcaccaacac  4380
ccccggtgcc gcccccacg ccgcggaggg ggcggcggcc cgcccccgga agaggcgcgg   4440
gtcggactcg ggcccgcgg cctcgtcctc cgctcttcc tccgccgccc cgcgctcgcc    4500
cctcgccccc caggggggtgg gggccaagag ggcggcgccc cgccgggccc cggactcgga  4560
```

```
ctcgggcgac cgcggccacg ggccgctcgc cccggcgtcc gcgggcgccg cgccccgtc    4620 ggcgtctccg tcgtcccagg ccgcggtcgc cgccgcctcc tcctcctccg cctcctcctc    4680
ctccgcctcc tcctcctccg cctcctcctc ctccgcctcc tcctcctccg cctcctcctc    4740
ctccgcctcc tcctcctccg cctcttcctc tgcgggcggg gctggtggga gcgtcgcgtc    4800
cgcgtccggc gctggggaga gacgagaaac ctccctcggc cccgcgctg ctgcgccgcg     4860 ggggccgagg aagtgtgcca ggaagacgcg ccacgcggag ggcggcccg agcccggggc     4920 ccgcgacccg gcgccggcc tcacgcgcta cctgcccatc gcggggtct cgagcgtcgt     4980 ggccctggcc ccttacgtga caagacggt cacggggac tgcctgcccg tcctggacat     5040
ggagacgggc cacataggg cctacgtggt cctcgtggac cagacgggga acgtggcgga    5100
cctgctgcgg gccgcggccc ccgcgtggag ccgccgcacc ctgctccccg agcacgcgcg    5160
caactgcgtg aggcccccg actacccgac gccccccgcg tcggagtgga cagcctctg     5220 gatgaccccg gtgggcaaca tgctctttga ccagggcacc ctggtgggcg cgctggactt    5280
ccacggcctc cggtcgcgcc acccgtggtc tcgggagcag ggcgcgcccg cccggccgg    5340 cgacgccccc gcgggccacg gggagtaggg ggagctaaca ctcggcttgc tgcccgaagg    5400
aagccgcccc ccaccggacc accggccgag gcgcctcggg ggcaggggga ggtggggggg    5460
gggaaagacg gggaggagac aggaagtggg ggtgggagtg ggggggggg acggacacgg    5520 ccccgaacag caacacacac cagcattttg ttatggactt tctggccttg ttgaaaactt    5580
gaggaaaaaa aaaactttat atttataaaa attttacaat aaagttttgt gatgcttttg    5640
acacactttg ttgttggcct ttgatgcagc tcccccgcgc agggggccg gggatggggg     5700 ggaagggagg aggaggaggg ggggcgggca cgagaagccg ccccccacccc cgaggcctgt    5760 tggtctttat catagaacag agccggggcc cggcctcgtt ctggctccct gtcttggtgg    5820
gtgggcgggc tggctggcgg gtaaaaaaag agtgtgtccg tgttgacagg gagggggcc     5880 cgatcgtgca gagcacgcac gtctggccgg ccagaccctg ggggtggtgg gcaggagtgg    5940
gagggcgcct ggctcgggga gggaggaggg gggggtcag ccgcaccacc ggcgcgaagc     6000
caggggccag ggaactttga tagagagggg ggaaagtggg gcgggggcga gggcggttga    6060
atcacaacgc atgcacgccc tctgccccccg ggacgggtg ggaggaagga ggagggagaa    6120
gagaagaccc gaggcatgca cccgcactta cgcccgtgcc caccccccgcc ccggcgccca   6180 ccccgcccgc acacctgccc gccacgcccc ccctcctca ccctggctgg gagaaaggag     6240
gaggagcagg aagaggagac ccgaggcatg caaccgcact caccccaccccc cgcccgcaca    6300 cctgcccgcc acgcccgccc ctccttaccc tggctgcggg gagactccca tcggggcgag    6360
ggggctcgcg cgttcgcaac accacaccac accacacggc ccaccacaac acggcccacc    6420
acgacacaac acgacacgac gcgttttgcg gggcatgcaa gtcgacacac cgcgcgcgtg    6480 cctaccttc cctagcggcc ccggcccccg gcccgtttcc ttccgccacc actaccacca    6540 ccccccgcc cgcgcccacg cggtagagga aggggacggg cgccacaccc acggctgtgg    6600
ccgggcacgg gcctttgggg ttgttggggg gggtgaccg gcgcgtgggg gcggtgggcg    6660
tacgggcccg acccgcgcct gccccccgg gaacgacgac ggggggggg gaaacggggg     6720 tgggtggaag ggaagaggaa ggagaaaggg ggggtggatc cgaacacgcc ggatccgcga    6780
aaataataac aaaacaaaca aaaacagaaa caaaaacaaa aacacctaga aaaaaggat     6840 acgggttggc tcgcgggcgg tgcggctgac ctgcctgccc tttctgggac ccccgcctcg    6900
tgtttcttga aagggggagg aagaacagtt ctcccccaac ccctgctctc ttctctcttc    6960
```

-continued

| | | | | |
|---|---|---|---|---|
| cgcccgcccc | cccccctct | ccccgccgcc | tcagcagaag | ctcacctgta cgaccctaaa | 7020 |
| cctacctgcg | agaacgcgcg | gcgttcgagg | ggcgcgctct | ctcacacgag acacacgcag | 7080 |
| gcgccccccc | ccccggagc | ctgggtcccc | cggcggacgg | ctcacgcggc gcggcgtctc | 7140 |
| ggtgggacgc | gggcaaaggg | cggcggcggc | gggggggggg | ggggaaatg tgaggagagc | 7200 |
| gagacagaga | gagagaagga | agagggaagg | ggcgcggcgg | gacggggaa gacgaggaga | 7260 |
| aggaaggg | cgagggtcgg | gcccgggagc | ggggcggccc | gggagggaga agaaacggaa | 7320 |
| cgcggaaacg | ccgccggcgc | ggcccggggc | cccggggccc | ccgcgctccg ccggggccc | 7380 |
| gggccggacc | gccgggcggg | ggacgccttc | cgcccgcgc | cgggcggcta cccgggaccc | 7440 |
| ccggccggga | atcgaaaaaa | gcctccgggg | gccccttcg | cgcctttcgc gaacgcgcgg | 7500 |
| cgccggaggg | ggcggccgcc | gaggtgcggg | ggcccctccg | gccggggcgc acctcggcgg | 7560 |
| ccaagccccg | gcccgcccgg | gggtccccga | ggcaagaggc | ggaccctcgg aggcgcggaa | 7620 |
| gaagacggga | ggcgggggaa | aaagggggga | agagagggg | aggtagggag gggagaggag | 7680 |
| aagggcgcgc | cggtgcgcgg | agcagccttc | cttctccgga | gtccctctcg atcggcggcg | 7740 |
| ggcccctgcg | ttcgttgctg | ccgcgcccc | ggttttataa | agacagggat gacgcagcag | 7800 |
| aaatgcccac | agcaacacgc | gggcggggct | cgggctctcc | ggcggcttaa tggatctccg | 7860 |
| ggcacggcgc | ccgcaaccgc | agagcactca | gctggcgcgc | ccccccccaa cgtgggagtg | 7920 |
| tttaatggaa | gggcgtgggg | ccggccgccg | gatgcccgcg | ggggcctaat gcggcgggag | 7980 |
| gcgtgggccc | ctggcgccgc | ggcccgtctg | ctggcccgcg | gcccgtctgc tggcccgcgg | 8040 |
| ccacgtaaac | aatgacacag | gggttctctc | cgccgcggcc | ggcgcggggc gttgccggcc | 8100 |
| cggcccggcc | ccggagcccg | cggcgctgct | cggctgcggc | cgcgggctcc ggggctccg | 8160 |
| cactctgccc | ggctcgcccc | gtcccccctc | ttgctgcttt | tccgcgcgcc tctctttccc | 8220 |
| gttgctttcc | ctctccccccc | ccccccctct | ctctctctct | ctctctctct ccgccatcct | 8280 |
| cccgcccggc | cgcccactcc | ccgctcggcc | tctccggctg | cggtgcttgg gtctccttcg | 8340 |
| tcgggcggcg | gggggggggc | gtcgggactc | gcggagggcc | ggagaatgga aggcgagggg | 8400 |
| atgcaggagg | aggatcggga | ctccccatct | tctgcccttc | catcctccgt ttttccgctt | 8460 |
| tccaccgccg | ccgccaccac | cccccttcc | ttcgcccgcc | cgcctcgccc cggacccctc | 8520 |
| ccccccgtgt | tccccccatc | gttcaccacc | acgccccca | ccgcgccttg gctgtttggg | 8580 |
| gggtggcggc | ggtggtcggc | gtgctgccgg | aggctgcggg | cgcggggtag gtgggtgggc | 8640 |
| gggtggtggg | ggggggcccg | gctgcgtctc | gccgcgatcc | cgccggtggg gcgcggcggc | 8700 |
| ggtcgggggtg | ggggagagt | gtcgtgggtg | tgttttcgtg | tccccacca ccactcccac | 8760 |
| cccgaccgcc | gccgcgcccg | cgtttctgcc | gcccgcgcgc | tcctgtgtgg accccggggt | 8820 |
| gggcggcggg | ggggggtgcc | gtgggtgtgg | cggcggggcg | cggccggggg ccggggctcg | 8880 |
| ctggtccgcc | gaagtaaaga | aaagatcgcc | accgtgtgtt | cgtctgtgtg ttctgcgcgg | 8940 |
| cgccggggcc | cccctgccgg | gcggggcggt | gggcggggt | cgggtcgcg gcggggaagg | 9000 |
| aaggaaagac | cccggaagcg | ccggagggg | gcgccgcgc | gacgcgggcg gccggcgggg | 9060 |
| ggcgcgcggc | ggccgggcgg | gggcgcgcgg | cggccgggcg | gggcgcgcg gcggccgggc | 9120 |
| ggggcgcgc | ggcggccggg | cggggcgcg | cggcggccgg | gcggggcgc gcggcggccg | 9180 |
| ggcgggggcg | cgcttcccc | gcgtcgcccc | tcgggttccc | aagacctatc acgtgtgcgc | 9240 |
| aggggaggg | aggacgcggg | ggaggggagg | acgcggggga | ggggaggacg cggggtatat | 9300 |
| ataaagcggt | agaaagcgcg | ggaatgggca | tattggaccc | gcgtgattcg gttgctcgcg | 9360 |

-continued

```
gttgtcttgt ttggacgttt tttatgcggg aacaagggg cttaccggtt acactgtccg      9420
ctcgctatgg ggttcgtctg tctgtttggg cttgtcgtta tgggagcctg ggggcgtgg      9480
ggtgggtcac aggcaaccga atatgttctt cgtagtgtta ttgccaaaga ggtgggggac     9540
atactaagag tgccttgcat gcggaccccc gcggacgatg tttcttggcg ctacgaggcc     9600
ccgtccgtta ttgactatgc ccgcatagac ggaatatttc ttcgctatca ctgcccgggg     9660
ttggacacgt ttttgtggga taggcacgcc cagagggcgt atctggttaa cccctttctc     9720
tttgcggcgg gattttttgga ggacttgagt cactctgtgt ttccggccga cacccaggaa    9780
acaacgacgc gccgggccct ttataaagag atacgcgatg cgttgggcag tcgaaaacag     9840
gccgtcagcc acgcacccgt cagggccggg tgtgtaaact ttgactactc acgcactcgc     9900
cgctgcgtcg ggcgacgcga tttacggcct gccaacacca cgtcaacgtg ggaaccgcct     9960
gtgtcgtcgg acgatgaagc gagctcgcag tcgaagcccc tcgccaccca gccgcccgtc    10020
ctcgcccttt cgaacgcccc cccacggcgg gtctccccga cgcgaggtcg gcgccggcat    10080
actcgcctcc gacgcaacta gccacgtctg catcgcaagc caccctgggt cgggagcagg    10140
acagccgacc cgtctagcgg ccgggtcggc tgtccagcgt cgtcgcccta gaggctgtcc    10200
gccgggcgtg atgttttccg catctacgac ccccgaacag cccctggggc tgtcgggcga    10260
tgcgacgccg cccctgccga cttccgtgcc cctggactgg gccgcgtttc ggcgcgcgtt    10320
tctgatcgac gacgcctggc ggccctgtt ggagccggag ctcgcgaacc ccctaaccgc     10380
gcgcctcctc gcggagtatg accgtcggtg ccagaccgaa gaggtgctgc cgccgcggga    10440
ggatgtgttc tcctggacgc ggtattgtac ccccgacgac gtgcgcgtgg ttatcatcgg    10500
gcaggacccg taccaccatc ccggccaggc gcacggcctg gcgtttagcg tgcgtgcgga    10560
tgtgccggtg cctccgagtc tacggaacgt gctggcggcg gttaaaaatt gttacccccga   10620
cgcgcgcatg agcggccgcg gctgcctgga aaagtgggct cgcgacgcg tgctgttgtt     10680
gaacacgacc ctgaccgtca agcgcgggc ggcggcgtcc cactccaagc ttggatggga    10740
ccgttttgtg ggcggggtgg tccaacggct ggccgcgcgc cgcccgggcc tggtctttat    10800
gctctgggc gcccatgccc agaacgcgat caggcccgac cctcgccaac actacgtcct    10860
caagttttct cacccgtcgc ccctctccaa ggtcccgttt gggacgtgcc agcatttcct    10920
cgccgcgaat cgctacctcg aaacccggga cattatgccg atcgactggt cggtataaga    10980
tgccgacatc cggggtcttg atttacgagg gggcaattaa taaagactgt tgatggttaa    11040
atctcgggtc tcataccggt ccgtgatgtc gggcgtgggg aaagagaggg tcccctctgc    11100
gtttactatc cttgcctcgt ggggctggac gtttgcaccc cagaaccatg atcctggcgc    11160
gtcgccgaat acgacgccca tagagtcgat tgcggggacc gcaccggacg cgcacgtggg    11220
gcctctcgac ggagagccgg accgggatgc gatctccccg cttacgtcga gcgtggccgg    11280
cgacccgccg ggggcggacg gcccctacgt caccttgat actctgttta tggtatcttc     11340
gatcgacgaa ctgggcgcc gccagctcac ggatacgatc cgtaaggacc tgcggctgtc     11400
gctggccaag ttcagcatcg cgtgtaccaa gacctcgtcg ttttcgggga cggccgcgcg    11460
ccagcgcaag cgcggagcac cgccgcaacg cacatgcgta ccacgcagca acaagagcct    11520
ccagatgttc gttttgtgca agcgcgccaa cgccgcgcag gtgcgcgagc agctgcgggc    11580
ggttattcgg tcgcgcaagc cgcgcaagta ttacacgcgg tcctcggatg ggcggctctg    11640
cccggccgtc cccgtgtttg tacacgagtt tgtttcgtcc gaacccatgc gcctccatcg    11700
agataacgtc atgctgtcta cggaaccaga ctaagcaccc ccgccgtccc ctttcttttc    11760
```

```
cccctaccct tccccgtta ctgatgtgtt gtacgtttca ataaataaca cgtagcttat    11820
tttgttggat gatggattga ttgattttat tgaccgttcg ttcgcccggc ggtgccgtcg    11880
ccgcgcgcag agggaatatg caagcgggcg gggtggggag gaaagaaggt ttcaggttcc    11940
gggggttggg tctgcgtcgt ccaggtggg gctgatctga atttcccgca gaacctcgac    12000
cagtaggtct gttgtgtttg ctgggaactc gcccgccgtt ggggatacgg gggcgggggg    12060
tgtggtcggg cggacgtcca ggggtgcgtt atcgcacccc cgcgccgcct cggggccgt    12120 cccgtagatc gttgcggtga tgtagatggt gtccggggtc cacaccaccg tcaggatgcc    12180
ggccgtcgca ctccggacgc tttcgccgtg cgatgagctg acccaggagt caaagggta    12240 cgcgtacata tgggcgtccc accagcgctc cagcctctgg gtactagcgc gtcctataaa    12300
gcggtatgcg caaaattcgg cacgacagtc gataatcacc agcagcccga tgggggtgtg    12360
ttgtatcacc acgcctccgc ggggcaggcg gtcctggcgc gctcgacccc gcgtcagaac    12420
cgcgcgcgtc cctgactcaa acacgtgcac cacctgtgcc gcgtccggca gcgcgctcgt    12480
tagcgacgcc ctggggtgat gtaggctgta cgcgatggtc gtctgggggt tccccatgtc    12540
tcgggggggt ggggtgaat gtcacccggc ccgggtgcgg tgggaacgcg agggaatgga    12600
gggttaatag acaatgacca cattcggatc gcgtagagca gatagtatgt gctcgctaat    12660
gacgtcatcg cgttcgtggc gctcccggag cgggtttaga ttcatgtgca ggaactcgga    12720
tgaggtggtg cgggacatgg ctacgtacgc gctgtttagg cgcaggtttc cgggcgtgaa    12780
gcatatggcg accttgtcca gactgagccc ctgggagcgc gtgatggtca tcgcgagttt    12840
ggagctgatg ccgtagtcgg cgttgatggc catggccagc tccgtggagt cgatcgactc    12900
gacaaactca ctgatgttgg tattgacgac agacatgaag ccgtgctggt cccgcaggac    12960
gatgtagggc agggggact cctccaagaa ctcggccacg ccggccgtcg cgtgccgccg    13020
ccgcagctcc tccgcgaacg cgaacacccg ggtgtacgtg tacccatca gcgtgtagtt    13080 gtccgtctgc agggccacgg acatcagccc cccgcgcggc gagccggtca gcagctcgca    13140
gccccggaaa atgacattgt ccacgtaggt gctgaagggg gcgctctcaa acacctcccc    13200
gaagagctcc cgtaggataa ggtatcgccc cagaaaggcc ctcttcagga gcccaaactg    13260
ggcgtggacg gccgcggtgg tctcaggctc ttcgagggcg tagtggcagt agaacacgtc    13320
cagctgctgt tcgtccagcc cggcgaagat aacgtcaagg tcgtcgtcgg ggaagtcgtc    13380
cgggcccccg tcccgcgggc ccaggtgctt aaaattgaac gcacgctccc ccggagagcg    13440
gtcgctggtg tcggcggccc tggttgccga tgcgccggcg gcgtcccggc gtagcgacag    13500
gagttctgcc gtcagctccc ctaggcggcc gtaggccagg gtcctctggg tcgcgtccag    13560
gccggggcgc tggagaaagt tgtaaaagtg aatcagcccg ccgaacatga gccgcgcag    13620 gaaccggtag gcgaactcca ccgaggtctc cccctgggtc ttcacgaagc tgtcgtcgcg    13680
cagcacagcc tcgaaggtcc gaaacgtccc gtcgaaccca acaccatct ttcggaggcg    13740 cgcggtcacc gcgacctggc tgttgaggac gtacgtgatg tcgttccggg ccacgactag    13800
ctgttgcttg ctgtgcacct cacagcgcac gtgcccgcg tcctggtcct gactctggga    13860
gtagttggtg atgcgactgg cgttggccgt gatccacttt tccatggtca gcgtgggttg    13920
ctgcgtgagc cgtcgatact cgtcaaactc tttgaccgac acaaacgtga gcacgggag    13980 ggtaaacaca acaaactccc cctcgcgagt cacctttagg taggcgtgga gcttggccat    14040
gtacgcgctg acctccttgt gggacagaaa cagccgcgtc caccccggaa ggttggccgg    14100
gttggtgatg taactttccg ggacgacaaa gcggtccaca aactgcatgt gctcctcggt    14160
```

| | |
|---|---|
| gatgggaagg ccgtactcca gcaccttcat gaggttcccg aactcgtgct ccacacatcg | 14220 |
| cttgttgtta atgaaaatgg cccagctgtg cgagaggcgc gtgtactcgc gtagggtgcg | 14280 |
| gttgcagatg aggtacgtga gcacgttttc gctctgccgg acggagcatc gcagtttttg | 14340 |
| gtgttcgaag gtggactcca gcgaggccgt ctgggtcggc gaccccacgc acaccagcac | 14400 |
| cggccgcagg cggcccgcgt actgggggt gtggtacagg gcgttaatca tccaccagca | 14460 |
| atacaccacg gtcgtgagta ggtgccgccc caggagcccg gcctcgtcga tgacgataat | 14520 |
| gttgctgcgg gtgaaagccg gcagcgcccc gtgtgtgacc gaggccaggc gcgtgagggc | 14580 |
| accctggccc agccccaaag tctgctctag ggcggtgagg gcgtggaact cgtttcgcgc | 14640 |
| gtcttcgccc ccgtgcgccg ccagggcccg cttggtgatg tcgaggatca cctcccagta | 14700 |
| gtacgtcagg tctcgccgct gcaggtcttc cagcgaggcg gggctgctgg ccagggtgta | 14760 |
| cgggtgctgc cccagctggg cctggacgtg attcccgcga aacccgaact cgtgaaagat | 14820 |
| ggtgttgatg ggtcgactca gaaacgcccc cgagagctta acgtacatgt tctgcgccgc | 14880 |
| gattcgcgtg gcgcccgtga ccacgcagtc caggacctcg ttgagggtct gcacgcacgt | 14940 |
| actctttccg gatccggcgt tgccggtgat gagatacgcc gcgaacggaa actcccggag | 15000 |
| cggcaggccg gtcgggacct ccaaggccgc cacgtcccgg aaccactgca ggcgcggcac | 15060 |
| ctgcgtgacg tcgagctgct gctgcgagag ctctcggatg cgtgcgatga ttggttggac | 15120 |
| cccgtgcatg gacgtaaaat ttaaaaacgc ctcgtccctg aaccgcacgg cgggtctggc | 15180 |
| cccgggctgc tgtgggggcg gacctggtgc ccggacgtcc cgcgagccct ccccgccgga | 15240 |
| cgccgccatg gccgcacagc gcgcgcgggc gccggcgatg cggacgcggg gcggcgacgc | 15300 |
| ggcgctatgc gcccccgagg acggctgggt gaaggttcac cccacccccg ggacgatgtt | 15360 |
| gttccgcgag attctcctcg ggcagatggg gtacaccgag ggtcaggggg tgtacaacgt | 15420 |
| cgtccggtcc agcgaggccg ccacccgaca gctgcaggcg gcgatcttcc acgcgctcct | 15480 |
| caacgccacg acgtaccggg acctggagga ggactggcgc cgccacgtgg tggcccgcgg | 15540 |
| cctccagccg cagcggctgg ttcgcaggta ccggaacgcc cgggagggcg atatcgccgg | 15600 |
| ggtggccgag cgggtgttcg acacgtggcg atgcacgctc aggacgacgc tgctggactt | 15660 |
| tgcccacggg gtggtagact gctttgcgcc gggcggccca agcggaccga ccagcttccc | 15720 |
| caaatatatc gactggctga cgtgtctggg gctggttccc atattgcgca agacgcgcga | 15780 |
| ggggagagcg acgcagcgcc tgggggcgtt tctcaggcag cacacgctgc cccggcagct | 15840 |
| ggccacggtc gccggggccg cggagcgcgc cggcccgggg cttctggatc tggccgtcgc | 15900 |
| gttcgactcc acgcgcatgg cggaatacga ccgcgtgcac atctactaca accatcgccg | 15960 |
| gggggagtgg ctggtgcgcg acccggtcag cgggcagcgc ggcgagtgcc tggtgctgtg | 16020 |
| ccccccctg tggaccggcg accgcctggt cttcgattcg cccgttcagc ggctgtgccc | 16080 |
| cgagatcgtc gcgtgccacg ccctccggga acacgcgcac atctgccgtc tgcgcaacac | 16140 |
| cgcgtccgtc aaggtgctgt tggggcgcaa gagcgacagc gagcgcgggg tggctggcgc | 16200 |
| cgcgcgggtc gtcaataagg cgctggggga ggatgacgag acgaaggccg gctcggccgc | 16260 |
| ctcgcgtctc gtgcggctca tcatcaacat gaagggcatg cgccacgtgg gcgacatcaa | 16320 |
| cgacacggta cgcgcctact tggacgaggc gggggggcac ctgatcgaca cccccgccgt | 16380 |
| cgaccacacc ctccctgggt tcggcaaggg cggcaccggc cgcgggtcgc gcccccagga | 16440 |
| cccgggggcg cgaccgcagc agcttcgcca ggcgtttcag acggccgtgg tcaacaacat | 16500 |
| caacggcatg ctggagggct atatcaataa tctctttgga accatagaac gcctgcgaga | 16560 |

```
gacgaacgcg ggtctggcga cccagctgca ggcgcgcgac cgcgagctgc ggcgcgccca   16620
ggcgggggcg ctggagcggg agcagcgcgc ggcggaccgg gcggccgggg gaggcgcggg   16680
ccgcccggcg gaggcggatc ttctccgggc cgactacgac attatcgacg tcagcaagtc   16740
catggacgac gacacgtacg tggccaacag tttccagcac cagtacatcc ccgcgtacgg   16800
ccaggacctc gagcgcctgt cgcgcctctg ggagcacgag ctggtgcgct gcttcaagat   16860
tctgcgccac cgcaacaagc agggccagga aacgtcgatc tcgtactcta gcggggcgat   16920
cgcctccttc gtggccccgt atttcgagta cgtgcttcgc gccccccgag cgggcgcgct   16980
catcaccggc tccgatgtca tcctagggga ggaggagtta tgggaggcgg tctttaagaa   17040
aacccgcctg cagacgtacc tgacagacgt cgcggccctg ttcgtggcgg acgtacagca   17100
cgcggctctg ccccggcccc cctccccaac ccccgccgat ttccgggcga gcgcgtcccc   17160
gcggggcggg tcccggtccc ggacccggac ccgatcccgg tcgcccggga aacgccgag   17220 gggtgcgccg gaccagggct ggggcgtcga acgcagggat ggccgacccc acgcccgccg   17280
atgagggaac ggccgccgcc atcctcaaac aggccatcgc cggggaccgc agtctggtcg   17340
aggtggcgga ggggatcagc aaccaggcgc tgctgcgcat ggcctgcgag gtgcgccagg   17400
tcagcgatcg ccagccgcgg tttaccgcga ccagcgtcct gcgcgttgac gtcaccccca   17460
gggggcggtt gcggttcgtt ctggacggga gttccgacga cgcgtacgtg gcgtcggagg   17520
attactttaa gcgctgcggg gaccagccga cgtatcgcgg ttttgcggtc gtcgtcctca   17580
cggccaacga ggaccacgtg cacagcctgg ccgtgccccc cctcgttctg ctgcaccggc   17640
tctccttgtt tcgccccacg gacctccggg acttcgagct cgtctgcctg ctgatgtacc   17700
tggagaactg tccccggagc cacgccacgc cctcgctgtt cgtcaaggtg tcggcgtggt   17760 tggggtcgt ggcccgccac gcgtctccct tcgagcgcgt ccgctgcctt ctcctccgca   17820
gctgccactg gatcctgaac acgctaatgt gcatggcggg cgtgaagccc ttcgacgacg   17880
agctagtcct gccccactgg tacatggccc actacctgct ggccaacaat ccgcccccg   17940 tcctctcggc cctgttttgc gccacccgc agagctctgc gttgcagttg cccgggcccg   18000
tcccccgcac ggactgtgtg gcctataacc cggccggcgt catgggaagc tgctggaatt   18060
ccaaggacct gcgttcggct ctggtgtatt ggtggctttc ggggagcccc aaacgacgga   18120
cctcgtcgct tttctatcgg ttttgctaac tccggaaaat aaacgtgttt tttatggaac   18180
gttccccacc tgtcgtgtca tctctcgggg gatggtggtg ggcctgtgtg tgtgtcttgt   18240
gcaccgaagg aggaaagtgg gggggtggtg gtgctggtgg tggaaagaca tgatagaggg   18300
aacaaagaaa tagaagaaaa ccacaaccgg cgcgtgccag taaatacgga cgcgcgcaca   18360 cgcgggggt aagttggagc acgggccccc ggtttattga ccaaattcag ggaaacagaa   18420
accgaatctt ttcatcgaaa gggtacacaa agctcccgcc ctcgcccac acgccttcca   18480 gaaccccgt aaacaccagt tgaatctcgc gcaggatctc gcgcaggtga tgggcgcagt   18540
ccacgggggg gagcaccaag ggccgcgggt acagatccac ggggacgccg accgactccc   18600
cgcccccggg acatacgcgc acgacgcgtc tccagtattg ctccgcgtcc agcagggcgc   18660
ctccgcggaa ggccgtttgg ggcaggggt cgtcggcctc gcctgggggg gtcagaacgc   18720
tccagtactc cgcgtccaga cgcctcccga aggcatccag acaaagcgg tcacaggcgt   18780 cctccatgac gccccgggcc gcgcacacgg cctcctccgg cgggccggcg gccggccgcc   18840
ggaggattcg tctcagcgcg tcgcgcataa cctcggccgc cgcggcgtac gcggccccgc   18900
ggagaggaaa tccctgcagg aagtcggtgt catcgcggga gttccagaac cacgcccgg   18960
```

-continued

```
tctggctcca ggtgacgacg tgggtgtaga cgccctctgg cgccaggagg ggggcgaggc   19020
gcgggcgtat gccgttggcc gaaagtacgg cgcgcacgga cgcctcgagg gcccggcggg   19080
cgtcctggat cgcgccgtgc gcggcgtccg cgtccccggg gtccacgttg aacagccccc   19140
agaacgcagc cccggtgccg ccgcagaccg caaacttcac cgagctggcc gtctgctcga   19200
tctgcaggca gacggcggcc atgacccccgc cgagcagctg ccggagcgcg ggcaggcgt   19260
cgcacgcgtc cggcaccagg cgctccagca cggcccgggc ccaggctccc gaggggggcgg   19320
ccgccaccag cgcgtccagc ctttccaggc ccgcccgccc ccgggcttcc ggcagcccgg   19380
cctccccgag gcccgcgagg gcggccagga gctgggcctg gagcccggag aaacaaaacc   19440
gcgccgtcca gaccggcccg acggccgccg ggggtcgag tagttggatg gtggtggccg   19500
tggggtgcca ccgcgcgacc gcttcccgaa aggcgggcag gaggcggccg ccgcctccg   19560
aggccacggc cggccatgcc cgcgggggca ggacgaccct ggcgcccacc gcgggccagg   19620
cccccaggca cgcggcatgg gtggccgcgg cgccccgcac caggtcacgc gccgactcgg   19680
cggcggcggc ggccggcacg gtaaacgtgg ccagcccgg aaatcccagc acggcaaagt   19740
attggacggg ccctccccgg acctcaaacc cgggccccag aaaagcgaag acggggccca   19800
ggctccgggg ggcggcgtgg accgtggtat gccactgccg gaagagggcg accagcgccg   19860
gggcggagaa cccgtcgccg gcgctcacga agtagtcgta ccgcgcggc agcagcaccc   19920
gcgccgtgac ccgctgcggg tgtccgcggg gccgcaggcc gacctcgcac acctcgacca   19980
ggtccgcgaa ggcgccctcc ttcctggtcg gcggaaacgc cagggtggtg tattcgcgcg   20040
caaaacgcgc ggtcctcgtc gtgatggtga cggcgagcga ggcggaggac gcgcactggg   20100
ggctgtcgcg aatggcggcc aggcgcgccc acgccaaccg cgcgccgggg tgctcggcga   20160
cgcgcgcgga cagggccagc gggtcgacgt cgaccttggc ctccacgtcc aggagggcgg   20220
cgcgaggagc ggccggcggg ccccacgacg ccctttcgac cctcacgacc agaccgtct   20280
gcgggtccca gcccaggcgc agcgggacga agagggccca ccggcccgtc tggcgctcca   20340
gggccgccag aacgcacgca tacagcgccc gccacagggt cgggtccccc aggggctcca   20400
gcggggaggc ggccggggcc gtcgcggcgc gggcggccgc gacggcccccg ggggccgaga   20460
cgtcggggga gccgtagaag tcctgcaggt cggacgaacc aacggacacc tccgcgaagc   20520
gcgcgcgcgc ctcccccgcg cgtcgcgac agaccagata cagcagggcg tggaggcagt   20580
cgcgcgtgcg cgggggcagc cataccgcgt ataggggtaat ggcgctgacg ctctcctcca   20640
cccaaacgat gccgggggct tccatgccac gacgcccggg ggttgccgtg tatcgaacga   20700
gcgcggcccc agacttatag ggtgctaaag ttcaccgccc cctgcatcat gggccaggcc   20760
tcggtgggaa gctccgacag agccgcctcg agaatgatgt cagtgttggg ctgggcgccg   20820
gaggcgtgcg tgcgcaagca gcgccccac gcgggcgcgc gcagcttgaa gcgcgcgccc   20880
gcaaactccc gcttatgggc catcagcagc gcgtacagct gtctgtgcgt ccggcaggcg   20940
ctgtggtcga tgcggtgggc gtccagcagc tccacgatgg ctcgcttggt gaggtttttta   21000
acgcgccccc ccccgggaaa cgtctgcgtg ctcttggcca gctgcacccc gaacagttcg   21060
ccccagatga tcttgaacag cgacagcgcg tgctccgtct cgctcacgga cccgcgcggg   21120
gggcagccgc tcaggcgtc ggccacgcgc ttaaccgcgt cctccgacag caaggggccg   21180
tcggtcacgt tacagtggcc cagttcgaac accagctgca tgtagcggtc gtagtggggg   21240
ttcagcagct ccagcacgtc ctcggggcta aaggttcgcc ccgacccccc ggccatcgag   21300
tcccactgca ggcacgcggc catggtgctg cacagacgga acagctccca gacgggggcg   21360
```

```
acgtttaggg tggggtgtag ggccacaagc tccagctctc cggcggcgtt gatcgtgggg    21420
atgacgcccg tggcgtagtg gtcgtaaagc cgccggaaga tggcgctgct atgggcggcc    21480
atggggacgc gaagacaggc ctccagcagc accaggtaga tgaaccgcgt gcggccgacc    21540
aggctgttga ggccgcgcat gagcgcgacc acctcggccg gcgcgacgtc cggccggagg    21600
tacttttcga cgaaaaggcc cacctcctcc gtctcggcgg cctgggccga cagggacgtg    21660
tcgggtcct ggcagcgcag ctcccgcaga tcccgctggg ccctcagggc atcaaaatgt     21720
atcccccgca aaacagaca aaagttcctc ggggtcagcg cggcgtcgtg gccccagaac     21780
cgcacgtgca tgcagttgag ggtcagaagc atgtggagga tgttaagact gtccgcgagg    21840
cacgccagcg tgcacctctc gaagtagtgc ttgtaccgga atttgctgta gatgcgcgac    21900
ccccgcgcct gcgccgcgtc ggcgtgcgac gcgtcgcagc gcccttttgaa ccggcggcac   21960
aacaggttcg tcacctggga aaactgtgcc ggccactgcc cgctggcgct caccacgtgg    22020
ttgagcagca tgggcgtaaa gacgggctcc gagcgcgccc cggacccgtc catgtagatc    22080
agcagctccc ccttgcggag agtccgtacc cgccccagcg actggtacac ggacaccatg    22140
tccgcccgt agttcatggg tttcacgtag gcgaacatgc tgtcaaagtg cggcggatcg     22200
aagctaaggc ccaccgtcac gaccgttgtg tagatgacca cccggtaccg gccccatgtg    22260
gtcacgtcgc cgggcggggt gagcgagtgg agcagcagca cgcggtccgt aaactgccgg    22320
cagaacctgg caacgacctc cgcgaaggag accgtcgacg agaagatgca gacgttatct    22380
ccgccggcca ggcgcgcctc cagctccccg aagaaggtgg cgtccggggg ggcgtccggg    22440
gggggcgccc cgcccgccgg ccccggcgg cgcagggccg cctgcaggac ctcgggcccc     22500
aggcgcggga gaaacagaca acggcgcgcc gaaaatccgg gcatggcgta ctccccgatg    22560
accacgtgaa cgttcttttc gccccggagg ctgcacagaa agtccaccag ctgcgcgttg    22620
gcggtggcgt ccatggcgat gatccgcggg cacgtgcgca gcaggcgcag catcaacgcg    22680
tcgacgcggc ccagctgctg catcgtcggc gagtacagtt ggcccaacgt cgacatgact    22740
tcgtccagga cgagcacgtc gtagttgttc aacaggttcg ggcccacgcg atgaagactt    22800
tccacctgca cgatgagacg gtggaagggg cggtcgttca tgatgtaatt ggtggatgag    22860
aagtaggtga cgaagtcggg caaccctgac tcagcgaacc cgtcgccag ggtctgagta     22920
aaactccgac gacaggagac gaccagcaca ctcgtgtccg gagagtggat cgcttccccc    22980
aaccagcgga tcagcgcggt agttttcccc gagcccattg gcgcgcggac cacagttacg    23040
caccgggccg tcggggcgct cgcgtccggg aaggtgacgg gtccgtgttg ctgccgctcg    23100
atcgttgttt tcgggtggac ccggggaacc cactcggcca aatccccccc gtaaagcatc    23160
cgcgccagcg atacactcga cgtgtactgc tcgcactcgt catccccgat gggacgccgg    23220
gcccccaggg gatcccccga ggccgcgccg ggcgccgacg tcgcgcccgg ggcgcgggcg    23280
gcgtggtggg tctggtgtgt gcaggtggcg acgttcatcg tctcggccat ctgcgtcgtg    23340
gggctcctgg tgctggcctc tgtgttccgg gacaggtttc cctgcctttta cgcccccgcg   23400
acctcttatg cgaaggcgaa cgccacggtc gaggtgcgcg ggggtgtagc cgtccccctc    23460
cggttggaca cgcagagcct gctggccacg tacgcaatta cgtctacgct gttgctggcg    23520
gcggccgtgt acgccgcggt gggcgcggtg acctcgcgct acgagcgcgc gctggatgcg    23580
gcccgtcgcc tggcggcggc ccgtatggcg atgccacacg ccacgctaat cgccggaaac    23640
gtctgcgcgt ggctgttgca gatcacagtc ctgctgctgg cccaccgcat cagccagctg    23700
gcccaccta tctacgtcct gcactttgcg tgcctcgtgt atctcgcggc ccatttttgc     23760
```

-continued

```
accaggggggg tcctgagcgg gacgtacctg cgtcaggttc acggcctgat tgacccggcg    23820
ccgacgcacc atcgtatcgt cggtccggtg cgggcagtaa tgacaaacgc cttattactg    23880
ggcaccctcc tgtgcacggc cgccgccgcg gtctcgttga acacgatcgc cgccctgaac    23940
ttcaactttt ccgccccgag catgctcatc tgcctgacga cgctgttcgc cctgcttgtc    24000
gtgtcgctgt tgttggtggt cgaggggggtg ctgtgtcact acgtgcgcgt gttggtgggc    24060
ccccacctcg gggccatcgc cgccaccggc atcgtcggcc tggcctgcga gcactaccac    24120
accggtggtt actacgtggt ggagcagcag tggccggggg cccagacggg agtccgcgtc    24180
gccctggcgc tcgtcgccgc cttttgccctc gccatggccg tgcttcggtg cacgcgcgcc    24240
tacctgtatc accggcgaca ccacactaaa tttttcgtgc gcatgcgcga cacccggcac    24300
cgcgcccatt cggcgcttcg acgcgtacgc agctccatgc gcggttctag gcgtggcggg    24360
ccgcccggag acccgggcta cgcggaaacc ccctacgcga gcgtgtccca ccacgccgag    24420
atcgaccggt atgggattc cgacggggac ccgatctacg acgaagtggc ccccgaccac    24480
gaggccgagc tctacgcccg agtgcaacgc cccgggcctg tgcccgacgc cgagcccatt    24540
tacgacaccg tggaggggta tgcgccaagg tccgcggggg agccggtgta cagcaccgtt    24600
cggcgatggt agccgtttcg ttcgttttaa taaaccgacg ttgtgcgttt caccatactt    24660
cggcgcgcgt gtgtgtgtgt ttttttttt gtggtgttta ttttccccccc accccttcct    24720
tttctttcgg ccaccacccc cctcctcccc cgtactatac aacaaaaaat accacacata    24780
cgaccaaata cggacaatca tttctgtctt tattcgctat cagagagtgg gggcgtgagc    24840
gtggcaggag ggcgggccac gtcggggtcc cgccgtctgg tgtgacgcga tggggggtcc    24900
gatgcgcgcc ggtactgggg ccccggcgcc cgggtgacca cgcgcacgtc ggggggcacg    24960
tagaagttac cctcttcttc ggactcgatg tccacgacgt caaattcgtg ggcggtcagc    25020
gagacgacct ccccgccgtc ggtggtgatg acgttgtgtc ggcagcagca gggccgcgcc    25080
ccggagaacg cgaggcccat aacttggcga gcgtatcgtc gaaggccagg cggctgtttc    25140
gccggatgtc ccgtagatc cccggctcga cgcggacggg ggtgatgatc agggcgatcg    25200
gaacggcctg gtccgggagg atcgatgcct tggcgggtcc gggggcccccg ccaggcccgg    25260
cgggcgctcc gcggccgtcc tccaggcgga acgtcacgcc ctcctccgcg cccgcgcggt    25320
gcctgccgag gaacgtcacc aggtgcggtt gcaggggggca gtcgggaaag tggctgtcga    25380
ggacgtatcc ctgcaccaag atctgtttga agttcgggtg gcggggggttg gcgaagatgg    25440
gctcgcggcg aaccagctcc ccggagctcc aggcacgggg agagatggtg cgacgctcaa    25500
ggtcggggac gccaaacaga agcacctccg agacaacgcc gctatttaac tccaccagcg    25560
cccgatccgg ggcggagcat cgcctttttt cgccggcggc gcgggaatcg agccagtccc    25620
ggtcttgggt gacgagcgcc tcctccgggc ccggaacgcg cccgggcgcg aagtagcgca    25680
cgccggggtt ggggatggac cggatgaacg cccggaacgc ctccggcgat cgccgcgcca    25740
tcaggtcctc gtacgcggag ccgcgggggg cgccgggtc cgcggggtcg aacgcgtact    25800
tggctcggca cttaacctcg tagaaggcca gggggtctg gggggcgggg gccaggtagc    25860
cgtgagggtc cctggggcac acgaggatgt ccagggacgc ccccaccatg cccgtgtggc    25920
cgtccatgag gaccccgcac gcgtgcacgt tctcctcggc gaggtccccg ggttggtgaa    25980
agacgaagcg cccggcgtcg gcgtcgtcgt tgacgcccgc gtccgcgcgg cccacgcagt    26040
agcgaaacag caggtttcgg gccgtcggct cgttcacccg cccgaacatc accgccgacg    26100
actgggcgtc cagccgcagg ctggcgttgt gggtgagcca ctgggacgag aagcacggac    26160
```

-continued

```
cctgcgcgcc ccaccgcagc gtggaggcgg tcgtcaggcc ccgccgaagc agggcccaga    26220
gctggcagtc ggcctggttt tgcgtcgccg cctcgtaaaa tcccataagc gggcgggggg    26280
cgacggcttc ggcggcggac ggggggggcgc ggcgcgtcag gcgccagagg tgccggccga   26340
gcccgcggtc caccatgccg gccgcctcca gcgacacgac gagggagcac agatagtcca    26400
ggcgagccca caggggcccg atggccagag gggagcggac gccgcgcagc aggccgcgca    26460
ggtggcgctc gaacgtttcc gccaagatat gggggggcag tgcgttgggg atcgccgacg    26520
ccgaccacat cgggtcgggg tccgggggac cggggctgca gtccgggtcg atggcgtgtg    26580
cgcccccccgg cgagaggga atgtcggggg ttggcgggcc ggatgaggcc tcagagaggg    26640
ccggggacgc gggccgggcc ttttcgcccg ggcccccgcc gtcgggttgc ccacgtgggg    26700
ggctctgggg ccaatgggaa cccgggggccc ccggtgacgt ggggcgggggt ggggcggggc   26760
ggggcccaaa gacggtcgcc agatctaggc tgttgggtcg gggccgcttc ggggggactat   26820
cggggtcgcg ggcggggtcc gcggggcgct tggcgccggg tgttgcggcg gccgccattt    26880
ttacgagcag ccgaagagct cgagggcgga agggatcctc acgacagaga gtggcgcgcg    26940
gccgggttgg cgtgacagag gcgggagacc agcaccagca gcggcctcag ctcgggcggc    27000
agcgacaccg acgacaggac ggccttgtgc gtgcgctggt aatttataca ctgctccgtg    27060
aacgcgcgcc gaatcttggg attgcgaagg tggcgccgga tgccctccgg cacgtcatac    27120
gccaggccgt gggtgttggt ctcggccgag ttgacaaaga gggcggggtg cagaacgcag    27180
cgataggcga ggagggccac ggcaaagtcc ggcgagagct ggttgttaaa gtactggtag    27240
cccgggacgc gggtcacggg gacgcccagg ctcggggcca cgtacacgct aaccagcagc    27300
tccagcagcg tctgccccag ggcgtagaga tcgaccgcca gcccgacgtc gtgcttcagg    27360
gggcggttgt taaactcggc ccgctcgttg ttgaggtact ttaccgagag ctccggtggc    27420
tggttgtacc cgtgccccac cagagtgtga aagttggccg tggtcagggc ggcgggcatc    27480
ccaaaccccc gggggactc gaggtccggc tcctggaggc aaaactggcc ccgggatatc     27540
gtggagttgg agttcagggt caccaggcta aagtcggcca ggacggccgg ccggagcgac    27600
accgcgtccg atcgcagcat cacgaggacg ttggcgcact tgatgtccag gtggctgatc    27660
ccgcacctgg tgttcaggaa caccacggcg cgcgccaggt ctgtgaagca gtggtggagg    27720
gccgtcgcga cggaggggggt ggtcgcgcgc agggacgcca gctggccgat gtacttgccg    27780
aggtccatgt cgtacgcggg gaacacgatc tggcgctgct gcagcgagaa cccgagcggg    27840
gtgataaagc cgcggatgtc gtgggtgcgg ccgccgcgaa gagcgcactc ccccacgagc    27900
agggtcgcga cgagctccac ggcaaaccac tctttttccc ggatggtctt cacggcgagc    27960
ttgtgttcgc gaatcaactg cacctcgccg tacccccccg agcccccgaa gctgcgggcc    28020
ccggggatct ccagggtcgt gtagcggagg gcggggttga cggcgaatac ggggatgcat    28080
agcttgtgga tgcgcgcgag ggacaggatg tgcgagggggg cgacggggg cgaggtcatg    28140
gccgtctcgg acctgcgcag gggcgggcgc cttagcttgg ccgcagggcc ggggggcctcg   28200
ggggacgagc ggcgacgaga cgagcggctc actcgccatc gggacagtcc cgcgcgaagc    28260
cgctcccgga agctggatcg gcggcggggac ccggggcggg ctccggagac ggcgccgtct    28320
cggggggagg ggccgcttgg gcgtccggac gcccggcggc tgagggagtg tatgtaggac    28380
gcgagccagg ccttgaagga gcgtcggtgt gcaccttggg ggctgatgtc agctgccaca    28440
tgactagcag gtcgctgtcg cccggactca tccatccgtc cgccaggtcg ccgtcccccc    28500
acagagacgc gttcgccgcg gcctcttcga gctgctcctc ctggtccgca agacgatcgt    28560
```

```
ccgccgcgtc caggcgctcg ctaagcgcgg gatcgaggta ccgtcggtgt gcggttagaa    28620
aatcacgtcg cgccgcttgc tcttccacgc gaattttaac acaggtcgct cgctgtcgca    28680
tcatctctaa gcgcgcgcgg gactttagcc gcgcctccaa ttccaagtgg gccgccttgg    28740
cggccataaa ggcgccaaca aacctaggat cttgtgtact cacgccctcc cggtgtagct    28800
gcagggtctg gtccctgtac acctcggccc ggaggtgcgt ctcggccaaa cgtcggcgca    28860
gggccgcgtg gctggcgtct cggctcatct cgccgcccc gcgcgcgccc gacgtcggac     28920
tccttcgccc cgaccccct gacctcagcc gccccgcct cgcccgcgat gtttggccag      28980
cagctggcgt ccgacgtgca gcagtacctg gagcgcctgg agaaacagag caacagaag     29040 gtgggcgtcg acgaggcgtc ggcgggcctg acgctcggcg gcgatgcgct gcgcgtccct    29100
tttttggatt ttgccaccgc gacgcccaag cgccaccaga ccgtggtccc gggcgtcggg    29160
acgctccacg actgctgcga gcactcgccg ctcttctcgg ccgtcgcgcg gcggttgctg    29220
tttaatagcc tggtgccggc gcaactcagg gggcgtgact tgggggcga ccacacggcc     29280 aagctggagt tcctggcccc cgagctggtg cgggcggtgg cgcgcctgcg gtttcgggag    29340
tgcgcgccgg aggacgccgt gccccaacgc aacgcctact acagcgtcct gaacacgttt    29400
caggccctgc accgctccga agcctttcgg cagttggttc acttcgtgcg ggacttcgcc    29460
cagttgttga aaacctcgtt ccgggcctct agtctcgcgg agactacggg ccccccgaag    29520
aaacgggcca aggtggacgt ggccacccac gggcagacgt acggcacctt ggagctcttc    29580
cagaaaatga tactaatgca cgcgacctac tttctggccg ccgtgctgct cggggaccac    29640
gcggagcagg tcaacacgtt cctgcggctc gtgttcgaga tcccctgtt tagcgacacg     29700 gccgtgcggc acttccgcca gcgcgccacc gtgtttctag tccccaggcg ccacggaaag    29760
acctggtttt tggtgcccct catcgcgctg tcgctcgcgt ccttcgggg gatcaagata    29820 ggctacacgg cccacatccg caaggcgacc gagcccgtgt ttgatgagat cgacgcctgc    29880
ctgcggggct ggtttggctc gtcccgggtg gaccacgtca gggggaaac catctcgttc      29940 tcgttcccgg acggctcgcg cagcacgatc gtgtttgcct ccagccacaa cacgaacgta    30000
agtacgcctt cctcccgcgg tgcctgtttc cccggtgccg ccctccccga gatcgaccga    30060
cagacaaaca cagccagacg cgagtgtggg acgacacgcc cgcagccccc ccccgccat     30120 ggcgggggg aagccttact gtttatttgt aatcggacga tgaggctctg gccacggccc      30180
gcgcgaccgc ggggcagctc gttgcaaaca ggcggctggt atacgatgac agaacgcaga    30240
ggcgccaccc ggcgctggtc gggcggatga cgctttccgc gccgtccgg cccacgacga     30300 cctcgtgcag gtgggccgtg atgcgcgggc ggcgggtcgc ctgccgcagg ataaccgcgt    30360
ccacggggtg cccgaagagg agctgacaca ggctcgcgtc ccccggacg gccagggtgc     30420 gctgggccat attggaccac atgcacgggg cgacgcaggg acaggcctcc gccacggcgg    30480
gggcgcgcca cagcgcgttg gcggaatcga tgtgggccgt cggggcgcag gcgccgcctc    30540
ctcccggggg gtcggtaatc ctggatagca gccatcctaa atggcgggcc cggctgcccg    30600
ggggacagag cgaccccagg tcatcatcca tggcccagca gtatatgcgg ccgcggggga    30660
ggtgccacca ggccccggga cccagggcac agcacgcccc ggattcgggg gccgtgtccg    30720
tgggtaccag gtaggcgccg tcgagctcgt gggccacggg ctcgtccgcg agctgttcgg    30780
cggcggggtc gggggttttcc tccgggggg aggcagcttc caggtggccg aaggctaggg    30840
tgcacagcag cggggtccgg gggtgcgtta cgctgcggag gtggacggtg gcgcagtagc    30900
ggcgctcgcg gttaaagaag aaaatggcaa agaacgtgtt cgaaggcagg cgcagcgcct    30960
```

-continued

```
tgggccgcgt caggtacagg aagatctcgc agaaaagggc acgctcgggg tcggggtccg    31020
gaagggccac ctggcacagc ggctcggtga ggaccgtgag gcaccgaaaa atcttaagcc    31080
gctcgtcccc ccgaacgacg cgccacacga agacagagtt ggcgatgcgc gcgacgaggt    31140
cggcttcggg ccccgggtcg ggggcgcgcg cgtcggggg ggcgcccgg tgacccggcg    31200
gggccgcgc tcccgggggg cctggcgtcg cctggggacg ccagagtgcc cgctgtgcca    31260
ggttggtggt ggggaaggga ccggagacg accaaaagca gaggggccag cgcgtgtatg    31320
agttggggg gggtggtg agcggtggaa caaaagcacg cgtcagcgga caaggccggg    31380
tcccgtagcc gccccgcgac agaaccggag tccgacggca cgcgcgacgg ggtctgcgag    31440
gctgaggtac ccgcgggtgt taatggtaaa cgcaaagcct cccggaaaga ccactagccc    31500
gcagaggcgg cgattgaacc caaggcagag gtacgcgtag ctctctcccg gaaggtattg    31560
ctcgcagacc ctgtgtgggg cagtggaggg gctgccctcc atgaagcgac atttactctg    31620
ctcgcgtcca ttgacgtcac cgtcaatcac cactgcgatt ggacggttgg tgaggcgcag    31680
cgtgtctccg ctggtgctgt agtagtcaaa cgcgtagtgg gcgtcggagt cggcgaagcg    31740
ggcggggatg tcgtcgctga gagggacgag ccgccgccgc cgcccccgac cgccctggcc    31800
gcccagatgc gccagcacgg ccagggcgta cgcggtgtga aagaacgcgt cggggggcggt    31860
cccctcgagg gcgcgcatca ggttctccag gagcacgggg aagcgccgcg tcacctcccc    31920
tagccactcg ctctggtggg ggccaaagtc gtagcgcagg cgctggaaga tgcgcgggcc    31980
gccttggagc gcggcccgga tagagtggcc cagggcccgc agacacgcga tctggatgcg    32040
cgcgacgaag gccacctcgg ccgcgatgtc aaagggctgc agcacggggc gcgggtggcg    32100
caggggtccc tcgagcgcgg gaaagcgacg cagcagcgcc gtctgggccg cgggggacag    32160
ctggtggggg cgcacgacgc gctcggcggc acaggcctcc gtcagggccg tggccagctc    32220
ggaggacagc cgcggggggc gggcgcgtcg cccgccccac gccaccgaat tctcgtagga    32280
gacgacgacg aagcgctgct tggtcccgta gtgatggcgc aggaccacgg agatggagcg    32340
acggctccac agccagtcgg gccggtcgcc gccggccaga gcttcccacc cgcggtccag    32400
ccactcgacc agcgatcgcg gcttggcggt ccccggcacg agggtgagca cgtcgttgag    32460
gacgtcctcg cccgcggccc ggggggccccc ccggctggca aagcgccccc cgccgggcgg    32520
ctccaggccc gccagcaccg cctccgcgtc cgacgcgccc agggctcccc cgctgacggc    32580
ctggtggacc agggcgccct ggcggagccc cgaggcgacg ccggaggccg cgtgcttggg    32640
gcgcgcgcgg accgggtggc ggcgggtgac gtcctgcacg gcccgctgga ccagcgcgag    32700
gatctcctcg ttctcttgcg tgatggacac gtcctccgcg gtggccgtgt cgcctcccgg    32760
ggccgtgagc tgctcctccg gggagatggg ggggtctggg gtgccgacaa cggccggccc    32820
ggccccgccc gagaccgagg acgcctgggg agtgggggtg ccgctttccc ccatccccag    32880
ggacaggtgg gccgccgcct ccgtcgcggc ggcgggagcc gcggccccca gccgcgcgac    32940
gtagcgacaa aagtggcgac agaggcgcat gaggcgcgcg ccgtcggccg cgtatcgcgt    33000
gtttggcggg acgagctcgt cgtaactgaa caggagcacg cgggcacagg tcgcccacgg    33060
gccccacgcc aggcgcagcg ccgcgaccgt gtacgggtcg tacacgcctt gggcgtcgca    33120
cgcgaccggc agggagacga acagcccgcc cgcgctgggg acgcgcggca ggaggtccgg    33180
gtgcgccggg atgacggggg ctaggatcgc ccccaccgca tccgccggca cgtaggcggc    33240
aaacgccgaa cgccacgggg tgcagtcgcc ggtcgcgtgg gccgggtct gggtttcgac    33300
ccggaagttc gcggccgccc caccgtcggg gcggccgcgc acgagggcgg acagcgggac    33360
```

```
ccccgccgcc gccaggcact cgctggagat gatgacgtga atcagcgagg cggggctgct   33420
cgggtcccgg gtgagatcgt attggacctc gttggcaaag tgcgcgttca tggcccggcc   33480
ggcggtgcga gcccttcccg gtgccggaag gggcgtgggt gggggtgcg tgtgcgcgtc    33540
ctcggggccc gcgggcgcac gtgcgcttat acgctgtgtg tttcgtctgt ccccagggaa   33600
tccggggcca ggactttaac ctgcttttcg tcgacgaggc caactttatt cgcccgatg    33660
cggtccagac gattatgggc tttctcaatc aggccaactg caagatcatc ttcgtctcgt   33720
cgaccaacac cgggaaggcc agcacgagct ttttgtacaa cctccgcggg gccgccgacg   33780
agctgctcaa cgtggtcacc tatatatcg acgaccacat gccgcgggtg gtgacgcaca    33840
ccaacgccac ggcctgttcc tgctatatcc tgaacaaacc cgtgtttatc acgatggacg   33900
gcgccgttcg ccgacggcc gatctgtttc tgcccgactc cttcatgcag gagatcatcg    33960
gggggcaggc ccgcgagacc ggcgacgacc ggcccgtcct aacaaagtcg gcggggagc    34020
ggtttctgct gtaccgcccc tccaccacca ccaacagcgg cctgatggcc cccgagctgt   34080
acgtgtacgt ggacccggcg ttcacggcca acacgcgcgc ctccggcacc ggcatcgcgg   34140
tcgtcgggag gtaccgcgac gatttcatta tcttcgccct ggagcacttt ttcctccgcg   34200
cgctcacggg atcggccccc gcggacatcg cccgctgcgt cgtgcacagc ctcgcccagg   34260
tgctggcgct gcaccccggg gcgtttcgca gcgttcgcgt ggcggtcgag ggcaacagca   34320
gccaggactc ggccgtggcc atcgccacac acgtgcatac cgagatgcac cgcatcctgg   34380
cctcggcggg ggccaacggc ccggggcccg agctcctctt ctatcactgc gagccgcccg   34440
gcggcgcggt attgtacccc ttctttctgc tcaacaaaca gaagacgccc gccttcgaat   34500
actttatcaa aaagttcaac tccggggggcg tcatggcgtc ccaggagctc gtctccgtga   34560
cggtgcgcct gcagaccgac ccggtcgagt atctgtccga gcagctcaac aacctcatcg   34620
aaaccgtctc tcccaacacc gacgtccgca tgtactccgg aaaacgcaac ggtgccgcgg   34680
acgacctcat ggtcgcggtc atcatggcca tttacctggc ggccccgacc gggatccccc   34740
cggccttttt tccgatcacg cgcacgtctt gagtctttct tgccgtttct tttgtttctc   34800
tttctttccc ccctctctc cgcaataaac gccttcccgg aactgtgttt cccccctac    34860
aacagtgttg tccgttggtt gggtggttgg ggtgcggggg tgggcggggg aagcaagaaa   34920
acggtcggcg aacacaacat cgggaaaacg gattcccgca cgtgcgtctt cccagattcg   34980
acacacacac ccccccttctc cttaaataaa cacaaaccac acgctcgttg gttggttaat   35040
gccagcgctt tatttacgtc ttgttttttt tgcgtttcct ccgcgggtcc cttcccaaca   35100
cgcctgcccc cgcctcaggg gtagcggata accggggcca tgtcgccgga ttgcacaacg   35160
gcggcgccgt cgaacgtaca cacccgaacc gccggggcca gggccaggat gtccccgagt   35220
tggcccgcgt gcgccagcca ggcgaccagc gcctcgtaaa gcggcagcct gcgttcgccg   35280
tcctgcatca gcatgggggc ttcggggtgg atgagctggg cggcttctcg cgtgacgctc   35340
tgcatctgca ggagcgcgtt cacgtatccg tcctgggcgc tcagcgcgag cagccggggg   35400
atgagcgtga ggatgagggt ggttccttcg gttatggagt agaccatgtt gaggacgagc   35460
gaccgcagct cggtgtttac ggaggcgagt tgctggacgt cggccacgag cgagagacgg   35520
gccccgttgt aatacagcac gttgaggtcg gggagctccc cggcgtccg ggggtcgggg    35580
ttgaggtccc ggatgccccg ggcgaccagc cgcgcgacta tctcgcgggc caggggcgtt   35640
gggagcggga ccggaaaccg cagcgtgagg tccagcgact ccaggcgcac gtccgtcgcc   35700
tggccctcga agacgggcgg gacgaggctg acgggatccc cgttgcagag gtcgacgggg   35760
```

-continued

```
gaggtgttgc ggagattgac ggtgccggcg tgcgtgagcc ccaggtccac ggggcaggcg    35820
acgattcgcg tgggcagcac ccgcgtgatt accgcgggga agcgcctgcg gtacgccagc    35880
aacaacccca acgtgtcggg actaactcct ccggagacga acgattcgtg cgccacgtcc    35940
gcgagcgcca gctggcggcg gatggtcggc agaaagacca ctcgaccctc gcaccgctgc    36000
agcgccgcgg catcgggcgc cgagataccc gaggggatcg cgatgtctgc ttcgaaacaa    36060
tccgtgatca tggcgccggg ccgcgagaca ccggaacgcg ggggtgcggg agggccggaa    36120
agcgcaacgc aaccgggacg atgatgaaac agagatgggg ggcaccgacc gtgtgggaga    36180
gggggcgggg cagggctcag cagcacgcac ggggaggtct gtcgtgcgca ggagccccag    36240
gtgagaatca gtcccccgga gctcgggtct gggttttatt gggacctgcc ctcggaatcg    36300
cggctcccag tccaagcccc cctggggggg cggggacag ggggtgtgtg tgggtaaaag     36360
caacgtcgga aaatcaaacc caatgcccca acaggaaaa aaaagacgg gcgggtggag      36420 ggaaagctgg ggaagaagaa gccaatttta cagagacagg ccctttagcg gggaggcgtc    36480
gtagatgaga tactgcgtaa agtgggtctc tcgcgcgtgg gcctccccat cgcgggcgct    36540
gcgtagcagg gcggggtcgc tggcgcaggt gatcgggtag gcttcctgaa acaggccgca    36600
cgggtcttcc acgagctcgc ggcaccccgg cgggcgctta aactgcacgt cgctggcagc    36660
ggtggccgtg gataccgccg atcccgtttc cacgatgaga cgctccaggc agcgatgttt    36720
ggccgtgatg tcggccgcgg tgaagaactt gaagcagggg ctgaggacgg gcgaggcccc    36780
gttgaggtga taggccccgt tgtacagcag gtccccgtac gagaaccgct gcgacgccca    36840
cgggttggcc gtggccgcga agggccgcgc cgggtcgctc tggccgtggt cgtacatgag    36900
ggctatgacg tccccctcct tgtcccccgc gtacacgccg ccggccgcgc gtccccgcgg    36960
gttgcagggc cggcgaaagt agttgatgtc cgtggccacg ggggtggcga tgaactcaca    37020
cacggcatcc tgcccgtggt ccatgccggc gcgccgcggc acctgggcgc agccaaagac    37080
cgggaggggc tgggccggcc ccagccggtt tcccgccacg accgcgttgc gcaggtacac    37140
ggcggccgcg ttgtctagca gcgggggggc cccgcggccg aggtaaaagt tttgggggag    37200
gttgcccatg tccgtaacgg ggttgcggac ggtgcccgtg gccgcgacgg cggtgtagcc    37260
cacacccagg tccacgtttc cgcgcggctg ggtgagcgtg aagttgaccc ccccgcccgt    37320
ttcgtggcgg gccacctgga gctggcccag aaagtacgcc tccgacgcgc gctcggaaaa    37380
cagcacgttc tcggtcacga agcggtcctg ccgcacgacg gtgaacccga acccggggtg    37440
gaggcccgtc ttgagctggt gatacagggc cacgggctc atcttgaagt accccgccat     37500
gagcgcgtag gtcagcgcgt tctcccccgc cgcgctctcg cgggcgtgct gcaccacggg    37560
ctggcggatg gaggagaagt agttggcccc cagggccggg gggaccaggg ggacgtcgcg    37620
cgccaggtcg cgcagggccg gggggaagtt gggcgcgttg ccacgtggt cggcgcccgc     37680 aaacagcgcg tggacgggca ggacgtagaa gtattcgcca ttttggatgg tgtggtccag    37740 gtgctgggg gccatgagca gcacgccggc gtgcagcgcc ccgtcgaaga tgcgcatgtt     37800
ggccgtcgac gcgtgttgg cgcccgcgtc gggcgccgcg gagcacagca gcgccgtcgt     37860
gcgctcggcc atgttgtgcg ccagcacctg cagcgtgagc atggcgggcc cgtcgacgac    37920
gacgcgcccg ttgtggaaca tgcgcttgac cgtgttggcc accagattgg cgggatgcag    37980
cgggtgggcg gggtcggtca cgggatcgct cgggcactcc tcaccggggg cgatctccgg    38040
gaccaccatg ttctgcagcg tggcgtacac gcggtcgaag cggacccccg cggtgcagca    38100
gcgcccccgc gagaaggccg gcaccagcac gtaatagtag attttgtggt ggacggtcca    38160
```

-continued

| | | | | |
|---|---|---|---|---|
| gtcggccggc | cggtgcggcc | ggtcgtcggc | ggcgtcggcc | gcgcgggcct gggtgttgtg | 38220 |
| cagcagccgg | ccgtcgttgc | ggttaaagtc | ggccgtcgcc | acgttgcacg ccgccgcgta | 38280 |
| gacgggctcg | tgccccccg | cgtcaatccg | gcagtctcgg | tggcggtcca gggccgcgtg | 38340 |
| tcgcataagg | ccgtcgcagt | cccacacgag | gggcggcagc | agcgccgggt cgcgcatcag | 38400 |
| gtgattcagc | tcggcctgag | cctgcccgcc | cagctccggg | cccggcaggg taaagtcgtc | 38460 |
| caccagctgg | gccagggcct | cgacgtgggc | caccaggtcc | cgatacacgg ccatgcactc | 38520 |
| ctcggggagg | tcgcccccga | ggtaggtcac | gatgtacgag | accagcgagt agtcgttcac | 38580 |
| gaacgccgcg | catcgcgtgt | tgttccagta | gctggtgatg | cactgagtca cgagccgcgc | 38640 |
| cagggcgcag | aacacgtgct | cgttgccgtg | aatcgcggct | tgcagcaggt aaaacaccgc | 38700 |
| cgggtagctg | cggtcctcga | acgccccgcg | gacggcggct | atggtagccg gcgccatggc | 38760 |
| gtggcggcca | acgccgagct | ccaggccccg | ggcgtcacga | aacgccaccg gacacagcgc | 38820 |
| cagggggcagg | ttgccgttga | ccacgcgcca | ggtggcctgg | atcgccccg gaccggccgg | 38880 |
| ggggacttcg | ccgccgggaa | gctcgacgtc | ggccacgccc | gcgaagaagt cgaacgcggg | 38940 |
| gtgcagctcc | agagccaggt | tggcgttgtc | gggctgcatg | aactgctccg cggtcatctg | 39000 |
| gcactcggcg | acccaccgga | cccggccgtg | ggcgaggcgc | tgccgccagg cgttcagaaa | 39060 |
| acgctgctgc | atgtccgcgc | cggggccggc | cggggccgcg | acgtacgccc cgtacggatt | 39120 |
| cgcggcctcg | acggggtcgt | ggttcacgcc | cccgacggcc | gcgtcgatgt tcatgagcga | 39180 |
| aggatgacac | acgtcccga | ccgcgttctc | catggacagc | cgcagaacct ggtggtcctt | 39240 |
| tccccaaaaa | aacagctgcc | ggggagggaa | cgcgcgggc | tccgggtggc cggggcggg | 39300 |
| caccaggtcc | ccgcgtgcg | cggcgaagcg | ctccatggcc | gggttgaaca gccccagggg | 39360 |
| caggacgaac | gtcaggtcca | tggcgcccac | caggggggtag | ggcacgttgg tggcggcgta | 39420 |
| gatgcgtctc | tccagggcct | ccaggaagac | cagcctgtcg | cctatggcca ccagatccgc | 39480 |
| gcgcacgcgc | gttgtctggg | gggcgctttc | gagttcatcc | agcgtctccc ggttcgcctc | 39540 |
| gagttgctcc | tcctgcatat | ccagcaggtg | gcggcccacg | tcgtccaggc tccgcacggc | 39600 |
| cttgcccatc | accagcgccg | tgacgaggtt | ggccccgttc | aagaccatct cgccgtaggt | 39660 |
| caccggcacg | tcggcctcgg | tgtcctccac | cttcaggaag | gactgcagga ggcgctgttt | 39720 |
| gatggcggcg | gtggtgacca | gcaccccgtc | gaccggccgc | ccgcgcgtgt cggcgtgcgt | 39780 |
| caggcgggc | acggccacgg | acggctgcgt | cgccgtggtc | aggtccacga gccaggcctc | 39840 |
| gatggcctcg | cggcgatggc | ccgccttgcc | caggaagaag | ctcgtgtcgc aaaagctccg | 39900 |
| cttcagctcg | gcgaccaggg | tcgcccgggc | aaccctggtc | gccaggcgcc cgttgtcgag | 39960 |
| atatcgttgc | atgggcaaca | gcagggccag | gggaggcgcg | ttctccaaca gcacgtgcag | 40020 |
| catctggtcg | gccgtgccgc | gctcaaacgc | ccccaggacg | gcctggacgt tgcgcgcgag | 40080 |
| ctgctggatg | gcgcgcagct | ggcgatgcag | gctaatgccc | gtcccgtcca gggcctcccc | 40140 |
| cgtgagcagg | gcaatggcct | cggtggccag | gctgaaggcg | gcgttcaggg cccggcggtc | 40200 |
| gatgaccttc | gtcatgtaat | tatgcacggg | ctgctcgacg | gggtgcgggc cgtcgcgggc | 40260 |
| gatgagggc | tggtggacct | cgaactgcac | acgcccttcg | ttcatgtaag ccagctccgg | 40320 |
| gaacttggtg | cacacgcacg | ccacggacag | gccgagctcc | agaaagcgca cgagcgacag | 40380 |
| ggtgttgcag | taggacccca | gcagggcgtc | aaactctacg | tcatacaggc tgttttcgtc | 40440 |
| ggagcgcacg | gcgcgaaaa | aatcaaagag | tctgcggtgg | gacgccacct cgatcgtact | 40500 |
| caggatggag | ccggtgggca | ggatggccgc | ggcgtaccgg | taacccgggg ggtcgcgggc | 40560 |

-continued

```
aggagcggcc attgggttcc ttgggggatt cgcaggctcc atcaagccga gctcgggaag    40620
gccaagcccc tcccgcacaa cgcctcaccg ccggcggacg cgactaacaa cccacgggcc    40680
gccaaaaccc caaggggcaa cccgaccaac aacaggcgag gggaggaaag gcgtaaaggg    40740
ggcgttggga ggcaaaaaga aagaaaacac ccagacgtag gcccgaggac cggccggcgt    40800
cctctgtccc cgagcaccca ctgtgcccaa caggcacggg ggcgagctgc ccctgcctta    40860
tataccccc cgccacaccc ccgttagaac gcgacgggtg ccttcaagat ggccctggtc     40920
caaaagcgtg ctagaaaaaa gttggtaaag gcggcaaagc agtccgccgc cgccacccac    40980
atggcggcgc cggccgcgca ggcgattccc agagaacggg cgcggagggg atccgtgcgg    41040
ggcagcagct ggctggcggt gatccaatgg aaaagcccgt cgggactgaa cgtctcatgg    41100
gcggccgcca ccaggcgcca cagggccgcg ccgcccatga tcacgcacaa ccccaaaac    41160
acgggtggcg acaacggcag gcgatcccgt ttgatgttca cgtacaggag gagcgcccgt    41220
gccagccacg tgacatagta ggcgaggacg gcggctataa tacatgccgg cgccaccgcc    41280
cgtccggtcc acccgtaata catgcccgcg gccaccagct ccagcggctt gaggaccagg    41340
aacgaccaag caaacatcac cacccgcttg aaaagaccg gctgggtgtg gggcggaaga    41400
cgcgagtagg ccgaactgac aaaaaaatca gacgtgccgt acgaggacag cgaaaactgt    41460
tcatcgagcg gcagttctcc gtcctccccg ccacacgcgg cctcgtctac cagctcgcga    41520
tccaacaaag gaacatcatc ccgcattgtc atggtcggtg cggggagccg gcgaggcagc    41580
aaaaccgaaa gtagtgctgg cggcgcgggc ccgggtccgg acccaagctt cagggatggg    41640
gggcggaggc caaaatcaaa caagcaccgc gcgggttcta cacacaaccc ccacccgggt    41700
agtatccgcg gatgcgagtg cctggcgaag tcacgtccca gcaggatata aacctcggcc    41760
gttgggcccg gaaccccga aattcacacc cacgccctga cgcccaaatc atgggtggat    41820
gtggttcgcg agccgcacat ccgtgcgtcc gccctccccc gcgggctgat gacgtggcgg    41880
ttagtcagtg ggaaggcagg gggaaagatg ggttggggga ggaaacgaag aaaacaccca    41940
gagggccacg tcgggaatgc gcccggagtt gtccttaaaa ggccggccgt gcgtgacgga    42000
agccgtcgtt tgcccaagca ccgacgccgc gatccacagt ggggggagtt cctccgtccg    42060
gccacaaccc tacgcgcggg cggcacgcgc gagagcaacc cacgggtccc gttcgcgcca    42120
ccgccagccc ttgctcccac caccctcctc ccaccacccc actattcccc ccccccaagtc   42180
cgccccgtgg ctcgccggcc atggagctca gctatgccac caccctgcac caccgggacg    42240
ttgtgtttta cgtcacggca gacagaaacc gcgcctactt tgtgtgcggg gggtccgttt    42300
attccgtagg gcggcctcgg gattctcagc cggggaaat tgccaagttt ggcctggtgg     42360
tccgggggac aggcccaaa gaccgcatgg tcgccaacta cgtacgaagc gagctccgcc     42420
agcgcggcct gcgggacgtg cggcccgtgg gggaggacga ggtgttcctg gacagcgtgt    42480
gtctgctaaa cccgaacgtg agctccgagc gagacgtgat taataccaac gacgttgaag    42540
tgctggacga atgcctggcc gaatactgca cctcgctgcg aaccagcccg ggggtgctgg    42600
tgaccggggt gcgcgtgcgc gcgcgagaca gggtcatcga gctatttgag cacccggcga    42660
tcgtcaacat ttcctcgcgc ttcgcgtaca cccctcccc ctacgtattc gccctggccc     42720
aggcgcacct ccccggctc ccgagctcgc tggagcccct ggtgagcggc ctgtttgacg     42780
gcattcccgc cccgcgccag cccctggacg cccgcgaccg gcgcacggat gtcgtgatca    42840
cgggcacccg cgcccccaga ccgatggccg ggaccggggc cggggcgcg ggggccaagc     42900
gggccaccgt cagcgagttc gtgcaagtga agcacatcga ccgtgttgtg tccccgagcg    42960
```

-continued

```
tctcttccgc cccccgccg agcgccccg acgcgagtct gccgccccg gggctccagg    43020 aggccgcccc gccgggcccc ccgctcaggg agctgtggtg ggtgttctac gccggcgacc   43080
gggcgctgga ggagcccac gccgagtcgg gattgacgcg cgaggaggtc cgcgccgtgc    43140
atgggttccg ggagcaggcg tggaagctgt ttgggtcggt gggggctccg cgggcgtttc   43200
tcggggccgc gctggccctg agcccgaccc aaaagctcgc cgtctactac tatctcatcc   43260
accgggagcg gcgcatgtcc cccttccccg cgctcgtgcg gctcgtcggt cggtacatcc   43320
agcgccacgg cctgtacgtt cccgcgcccg acgaaccgac gttggccgat gccatgaacg   43380
ggctgttccg cgacgcgctg gcggccggga ccgtggccga gcagctcctc atgttcgacc   43440
tcctcccgcc caaggacgtg ccggtgggga gcgacgcgcg ggccgacagc gccgccctgc   43500
tgcgctttgt ggactcgcaa cgcctgaccc cgggggggtc cgtctcgccc gagcacgtca   43560
tgtacctcgg cgcgttcctg ggcgtgttgt acgccggcca cggacgcctg ccgcgcggcca   43620 cgcataccgc gcgcctgacg ggcgtgacgt ccctggtcct gaccgtgggg gacgtcgacc   43680
ggatgtccgc gtttgaccgc gggccggcgg gggcggctgg ccgcacgcga accgccgggt   43740
acctggacgg gctgcttacc gtttgcctgg ctcgcgccca gcacggccag tctgtgtgag   43800
atatcccaat aaagtgcagt cgttttctaa cccacggatg ccgttgtatg cctatacggg   43860
ggactatggg gggggaaagg aaaggaaaca ggaatggaga agggaaagga acagaggcgg   43920
tagcggacgc acggcggaca caataacaaa cagaccgcgg acacggaggg agtcggttgg   43980
gttgggcgtg gacgccgctg cgtccacaca cccgtttatt cgcgtctcca caaaaatggg   44040
acgcacgttc ggaccaccct aaggatgccc gccagggccg cggtaatcat aacgaccccc   44100
agcgcggacg cggccagaaa cccgggggcg atggtggcga tgggcagcgt gtcaaaggcc   44160
agcagatgaa tcacagttcc gttggggaac aacaacaggg ccacggacgg cacgtcgctg   44220
gaaaacacgt tcggggtgcc cgccaccggc ccctgggcca gctgctgttg ggtggcatcc   44280
gtgtccacca gcagcaccga catgacctcc ccggccgggg tgtagcgcag aaacacggcc   44340
cccacgaggc cgaggtcgcg ccggttttcg gtgcgcacca gccgcttcgg ctcaatctcc   44400
cgcgcgtgcc cttcgcaggt ggcggtgaga taggtgataa acagcgggcg gcggacgtca   44460
acgcccgtaa gcttgtatcc gatcccgcgg ggcaagggg tgtgggtgac gacgtagctg    44520
gcgttgtggg tgatgggcac gaggatccgg ggctccgcgt tgtgcgacgg gccgctacac   44580
tggtgggtgg cctccgggac gaaggcgcg atcagggcgt tgtagtgcgc ccagcgcgtg    44640
agaacggagg ccacgccgcg ggtctgttgt gccatgacgt ccgccgggat gtcggatcgg   44700
gtggccatgg ccagcgcgtc caggatgaac ccgcccctcgg cgagatcgaa gcgcagggaa    44760
gctgcgcatg gggaaaagtg gtccgggagc cagaagaggt ttttctggtg gtcggtcctg   44820
gctagcgcgg cccggagatc ggcgtgggtc gccgcggcga cgtcggacgt acacagggcc   44880
gtggttatga ggaggccccg gcgggcgcgt tcccgctgct cggccgaggg cgcgcccgcc   44940
aggaacggcg cccggaggac ggccgtggcg taaaacagcg ctcggcggac catcggggcg   45000
gttagcgcgc ggccgccgag aaactcggcg tacagggcgt cgatcaggcg ggccgcgctc   45060
ggggccaccg cgccataggc gcggggctg tccaacacga acgccagctg atagcccagc    45120
gcgtgcgcca ccaggctctg ctctcgctcg aggatcgcgg ccaccagatg cccgaggcgc   45180
gcctccagcc gcaggcgggc gcccgggtcc aacacggaca cgttcaggaa caccgagtcg   45240
gccgcgcagc ccgctgctcc ccgggcggcc aggccggcca gcacgcgcga gtgggccaaa   45300
aagcccagca ggtcggagag gcgaatcgcg tcgtgggcgt gggccgcgtt gacgaacgca   45360
```

```
aaccccgacg aggcgagcag ccccgcgagg cgccagaaca gggacggacg cgcgtccgtg    45420
ccggagcccg ggtcctcccc caaaaactcc gcataggccc gcgacatata ctgggcgtag    45480
ttcgtgctct cctcggggta gccggccacc cgccggaggg cgtccagcgc cgagccgttg    45540
tcggcgggcg tcggggcccc caggacaaag acgcgatacc tggggccggc cggaggcccg    45600
gggagcaccg cggggggcgtt ttcgtcggtc ggatttccga cccgagcgag ggtcttgtcc   45660
gcaggcacca ctatgatctc ggccggaggg ctgtcccgca tcgatatcac gagccccatg    45720
aagcccttcc cgtatcgcgc gcgcacgagc gcggcgtcgc acccgaacgc cagcccgccc    45780
gtcgtccaga cgcccacggg ccacgtcgag gccgacgggg agaggtacac gtaccgaccc    45840
ggagtccgta gcaggcccct ggcggccagc caggtcacgg atgcgttgtg cagatgcgcg    45900
atgctcaggt tcgtcgtcgg atgcctcggt gtccccgcgg gcggcccggg gggcggcgcg    45960
ttgcgtcggc cgtccgggtg cctctcggtc gccccgtcgt ctcccgcgg gaacgtaagc     46020 ccctcgcggt ccggcgcggc cgcgaatgtt acccaggccc gggaccgcaa cagcgcggag    46080
gcgccggggt tgtgcgacag tcccttgagc tgggtcacct cggcgggggg acgggacgtg    46140 ggcccccgcct cggggagctc gggcaggctc gcgttccgag gccggccgag cagataggtc   46200
tttgggatgt aaagcagctg cccggggtcc cgaggaaact cggccgtggt gaccaacacg    46260
aaacaaaagc gctcggcgta ccaccgaagc atgggcacgg atgccgtagt caggttgagt    46320
tcgcccgggg gcgccaagcg tccgcgctgg gggtcgctgg cgtcggggt gttgggcaac     46380 cacagacgcc cggtgtttgt gtcgcgccag tacgtgcggg ccaaccccag accgtgcaaa    46440
aaccacgggt cgatttgctc cgtccagtac gtgtcatggc cccggcaac gcccaccagg     46500 acccccatca ccacccacag accggggccc atggtcgtcg tcccggctgc cagtccgcag    46560
atgggggggg gtgtccgtac ccacggccca aagaggctcc gcacctcgga ggctatcgga    46620 ggcccctttgt tgccgtaagc gcgggccaaa ggatggggtg gggtgagggt aaaagcacaa    46680
agggagtacc agaccgaaaa caaggacgga tcggcccgct ccgttttttcg gtggggtgct   46740 gatacggtgc cagcccctggc cccgaacccc gcgcgcttatg gacacaccac acgacaacaa   46800
tgccttttat tctgttcttt tattgccgtc atcgccggga ggccttccgt tcgggcttcc    46860
gtgtttgaac taaactcccc ccacctcgcg ggcaaacgtg cgcgccaggt cgcgtatctc    46920
ggcgatggac ccggcggttg tgacgcgggt tgggatcatc ccggcggtga ggcgcaacag    46980
ggcgtctcga cacccgacgg gcgactgatc gtaatccagg acaaatagat gcatcggaag    47040
gaggcggtcg gccaagacgt ccaagaccca ggcaaaaatg tggtacaagt ccccgttggg    47100
ggccagcagc tcgggaacgc ggaacagggc aaacagcgtg tcctcgatgc ggggcagaga    47160
ccccgcgccg tcctcggggt cggggcgcgg ggtcgccgcg gcgaccccg tcagccggcc     47220 ccagtcctcc cgccacctcc cgccgcgctg caggtaccgc accgtgttgg cgagtagatc    47280
gtagacacgg cgaatggcgg acagcatggc caggtcaagc cgctcgcccg ggcgttggcg    47340
tctggccagg cggtcggcgt gttcggcctc cggaaggaca cccaggacca ggttcgtgcc    47400
gggcgcggtc gggggcatga gggccacgaa cgccaacacg gcctgggggg tcatgcttcc    47460
catgaggtac cgcgcggccg ggtagcacag cagggaggcg ataggtgcc ggtcgaaaac     47520 aagggtgagg gccgggggcg gggcttgcgg gcccacagcc tcccccccga tatgaggagc    47580
caaaacggcg tccgtcgccg cataaggcgt gctcattgtt atctgggcgc tggtcattac    47640
caccgccgcc tccccggccg atatctcgcc gcggtccaga cggtgctgcg tgttgtagat    47700
gttcgtcagg gtctcggagg cccccagcac ctgccagtaa gtcatcggct cggggacgta    47760
```

```
gacgatattg tcgcgcggcc ccagggcctc catcagctgc gcggaggtgg tggtcttccc    47820
caccccgtgg ggtccgtcta tataaacccg cagcagcgtg ggcagctccg gatccccgcg    47880
ggctccggag gccccctggc gatggctagg acgggacgcc gcgcggccgt cggtaggccc    47940
gctcgcacga gcagcctgac cgaacgcagg cgcgtgctgt tggccggcgt gagaagccat    48000
acccgcttct acaaggcgtt cgcccgagag gtgcgggagt tcaacgccac caggatttgt    48060
ggaacgctgc tgacgctgat gagcgggtcg ctgcagggtc gctcgctgtt cgaggccacg    48120
cgcgtcacct taatatgcga agtggacctc gggccgcgcc gcccagactg catctgcgtg    48180
ttcgaattcg ccaatgacaa aacgttggga ggtgtgtgcg tcatcctgga gctaaagaca    48240
tgcaaatcga tttcttccgg ggacacggcc agcaaacgcg aacagcggac cacgggcatg    48300
aagcagctgc gccactccct gaagctgctg cagtcgctcg cgcctccggg ggacaaggtc    48360
gtctacctgt gtcctatttt ggtgtttgtc gcgcagcgta cgctgcgcgt cagccgcgtg    48420
acccggctcg tcccgcaaaa gatctccggc aacatcaccg cggccgtgcg gatgctccaa    48480
agcctgtcca cgtatgccgt gccgccggaa ccgcagaccc ggcggtcgcg gcgccgggtc    48540
gccgcgaccg ccagaccgca aaggcccccc tccccgacac gtgacccgga aggcacggcg    48600
ggtcatccgg ccccaccaga gagcgacccc ccctcccag gggtcgtagg cgtcgctgcg    48660
gagggtgggg gtgtgcttca gaaaatcgcg gcgcttttt gcgtgccggt ggccgccaag    48720
agcagacccc ggaccaaaac cgagtgaggt tctgtgtgtt gtttttttt ttttttttcc    48780
tcgttttgtt ttctcttctt tcccccccc ctccccgct tctggccaag catcctcacc    48840
tgcttaagcg gaacccgcgg gcgcgcgggg actcatttgt cgccggcgac acccacccga    48900
caacagcccc tgggtgtcga ccgctgtcgc ccccgtctgt cgcctctccc ttttttcccc    48960
ccctcaaaga acgtggtgtt gggcgccggc caattcttcc cggagcgccg tcgtcgcccg    49020
cccgccgccc tcgaacatgg acccgtacta cccttttcgac gcgctggacg tttgggaaca    49080
caggcgcttc atcgtcgccg actccaggag cttcatcacc cccgagttcc cccgggactt    49140
ctggatgttg cccgtgttca acatcccccg ggagacggcg gcggagcggg cggcagtgct    49200
gcaggcccag cgcaccgcgg ccgcggcggc cctggagaac gccgccctcc aggccgccga    49260
gctgcccgtc gacatcgagc gccggatacg cccgatcgag cagcaggtgc atcacatcgc    49320
cgacgccctg gaggcgctgg agaccgcggc ggccgcggcc gaagaggcgg atgccgcgcg    49380
ggacgccgag gcgaggggg agggcgctgc ggacgggca gcgccgtcgc ccaccgcggg    49440
ccccgccgcc gcggagatgg aggttcagat cgtacgcaac gacccgccgc tacgatacga    49500
taccaacctc cccgtggatc tgctacacat ggtgtacgcg ggccgcgggg ccgcgggttc    49560
gtcgggagtc gtctttggta cctggtaccg cacgatccag gaacgcacca tcgcggactt    49620
ccccctgacc acccgcagcg ccgactttcg agacgggcgc atgtccaaga ccttcatgac    49680
cgcgctggtc ctgtctctgc agtcgtgcgg ccggctgtac gtgggccagc gccactattc    49740
cgccttcgag tgcgccgtgc tgtgtctgta tctgctgtac cgaaccaccc acgagtcctc    49800
ccccgatcgc gatcgcgctc ccgttgcgtt cggggacctg ctggcccgcc tgccgcgcta    49860
cctggcgcgt ctggccgcgg taatcggcga cgagagcgga cgcccgcagt accgctaccg    49920
cgacgacaag ctgcccaaag cgcagttcgc ggcggccggc ggccgctacg agcacggggc    49980
cctggccacc cacgtcgtga tcgccacgtt ggtgcgccac ggggtgctac cggcggcccc    50040
gggcgacgtt ccccgagaca ccagcacccg cgtgaacccc gacgacgtgg cccaccgcga    50100
cgacgtcaac cgcgccgccg ccgcgttttt ggcacgcggc cacaacctct tcctgtggga    50160
```

-continued

| | | | | |
|---|---|---|---|---|
| ggaccagacg | ctgctgcggg | cgaccgccaa | caccattacg | gccctggccg tgcttcggcg | 50220 |
| gctcctcgcg | aacggcaacg | tgtacgcgga | ccgcctcgac | aaccgcctgc agctgggcat | 50280 |
| gctgatcccg | ggagccgtcc | cggcggaggc | catcgctcgg | ggggcgtccg gattggactc | 50340 |
| gggcgccata | aaaagcggcg | acaacaacct | ggaggcgctg | tgcgttaact atgtacttcc | 50400 |
| gctgtatcag | gcagacccca | cggtcgagct | gacccagttg | tttccggggc tggccgccct | 50460 |
| gtgcctggac | gcccaggcgg | ggcggccact | ggcgtcgacg | aggcgcgtgg tggatatgtc | 50520 |
| gtcgggcgcc | cgccaggcgg | cgctcgtgcg | cctcaccgcg | ctggagctca tcaaccgcac | 50580 |
| ccgcacaaac | accacccctg | tggggagat | tattaacgcc | cacgatgcct tgggataca | 50640 |
| atacgaacag | gggcctgggc | tgctcgccca | gcaggcacgc | atcggcttgg cgtcaaacac | 50700 |
| caagcgattc | gccacgttca | acgtgggcag | cgactacgac | ctgttgtact ttttgtgtct | 50760 |
| cgggttcatt | ccccagtacc | tgtccgtggc | ctagggaagg | gtgggggtgg tggtggtggg | 50820 |
| gtgtttttct | gttgttgttt | ctggtccgcc | tggtcacaaa | aggcacggcg ccccgaaacg | 50880 |
| cgggctttag | tcccggcccg | gacgtcggcg | gacacgcaac | aacggcgggc ccgtggggtg | 50940 |
| ggtaagttgg | ttcgggggca | tcgctgtatt | cccttgcccg | cttccacccc ccccccccctt | 51000 |
| cccgttttgt | ttgtttgtgc | gggtgcccat | ggcgtcggcg | gaaatgcgcg agcggttgga | 51060 |
| ggcgcctctg | cccgaccggg | cggtgcccat | ctacgtggcc | gggtttttgg ccctgtacga | 51120 |
| cagcggggac | ccgggcgagc | tggccctgga | cccagacacg | gtgcgtgcgg ccctgcctcc | 51180 |
| ggagaacccc | ctgccgatca | acgtagacca | ccgcgctcgg | tgcgaggtgg gccgggtgct | 51240 |
| cgccgtggtc | aacgaccctc | ggggggccgtt | ttttgtgggg | ctgatcgcgt gcgtgcagct | 51300 |
| ggagcgcgtc | ctcgagacgg | ccgccagcgc | cgctattttt | gagcgccgcg gacccgcgct | 51360 |
| ctcccgggag | gagcgtctgc | tgtacctgat | caccaactac | ctgccatcgg tctcgctgtc | 51420 |
| cacaaaacgc | cggggggacg | aggttccgcc | cgaccgcacc | ctgtttgcgc acgtggccct | 51480 |
| gtgcgccatc | gggcggcgcc | ttggaaccat | cgtcacctac | gacaccagcc tagacgcggc | 51540 |
| catcgctccg | tttcgccacc | tggacccggc | gacgcgcgag | ggggtgcgac gcgaggccgc | 51600 |
| cgaggccgag | ctcgcgctgg | ccgggcgcac | ctgggccccc | ggcgtggagg cgctcacaca | 51660 |
| cacgctgctc | tccaccgccg | tcaacaacat | gatgctgcgt | gaccgctgga gccttgtggc | 51720 |
| cgagcggcgg | cggcaggccg | ggatcgccgg | acacacgtac | cttcaggcga gcgaaaaatt | 51780 |
| taaaatatgg | ggggcggagt | ctgcccctgc | gccggagcgc | gggtataaaa ccggcgcccc | 51840 |
| gggtgccatg | gacacatccc | ccgccgcgag | cgttcccgcg | ccgcaggtcg ccgtccgtgc | 51900 |
| gcgtcaagtc | gcgtcgtcgt | cttcttcttc | ttcttttccg | gcaccggccg atatgaaccc | 51960 |
| cgtttcggca | tcgggcgccc | cggcccctcc | gccgcccggc | gacgggagtt atttgtggat | 52020 |
| ccccgcctct | cattacaatc | agctcgtcac | cgggcaatcc | gcgccccgcc acccgccgct | 52080 |
| gaccgcgtgc | ggcctgccgg | ccgcggggac | ggtggcctac | ggacaccccg cgccggcc | 52140 |
| gtccccgcac | tacccgcctc | ctcccgccca | cccgtacccg | ggtatgctgt tcgcgggccc | 52200 |
| cagtcccctg | gaggcccaga | tcgccgcgct | ggtgggggcc | atccgccgcg accgccaggc | 52260 |
| gggtgggctt | ccggcggccg | ccggagacca | cggatccgg | gggtcggcga agcgccgccg | 52320 |
| acacgaggtg | gagcagccgg | agtacgactg | cggccgtgac | gagccggacc gggacttccc | 52380 |
| gtattacccg | ggcgaggccc | gcccgagcc | gcgcccggtc | gactccggc gcgccgcgcg | 52440 |
| ccaggcttcc | gggccccacg | aaaccatcac | ggcgctggtg | ggggcggtga cgtccctgca | 52500 |
| gcaggaactg | gcgcacatgc | gcgcgcgtac | ccacgccccc | tacgggccgt atccgccggt | 52560 |

```
ggggccctac caccaccccc acgcagacac ggagaccccc gcccaaccac cccgctaccc    52620
cgccaaggcc gtctatctgc cgccgccgca catcgccccc ccggggcctc ctctatccgg    52680
ggcggtcccc ccaccctcgt atcccccagt tgcggttacc cccggtcccg ctcccccgct    52740
acatcagccc tccccgcac acgcccaccc ccctccgccg ccgccgggac ccacgcctcc     52800
ccccgccgcg agcttacccc aacccgaggc gcccggcgcg gaggccggcg ccttagttaa    52860
cgccagcagc gcggcccacg tgaacgtgga cacggcccgg gccgcgatc tgtttgtgtc     52920 acagatgatg gggtcccgct aactcgcctc caggatccgg acttgggggg ggtgtgtgtt    52980
ttcatatatt ttaaataaac aaacaaccgg acaaaagtat acccacttcg tgtgcttgtg    53040
tttttgtttg agagggggggg gtggagtggg ggggaaagtg ggccgaatga cacaaaaatt   53100
aggtcggagg ggtgagggggg gggggctagg agccgaaccg atggccccca cacgcgacgg   53160
aaggcccgga agactaccac ggggaggggg tgtggaaagc gaccggtcgc agggagacgg    53220
ggttggtttg gggttggttt ggggttggtt ttcccgttag cacatgtctg catttgtttt    53280
tctagtcaca cgcccccccc ccccaaata aaaaccaagg caaaacaata ccagaagtca     53340
tgtgtatttt tgaacatcgg tgtcttttta tttatacaca agcccagctc ccctcccctc    53400
ccttagagct cgtcttcgtc tccggcctcg tcctcgttgt ggagcggaga gtacctggct    53460
ttgttgcgct tgcgcagaac catgttggtg accttggagc tgagcagggc gctcgtgccc    53520
ttctttctgg ccttgtgttc cgtgcgctcc atggccgaca ccaaagccat atatcggatc    53580
atttctcggg cctcggccaa cttggcctcg tcaaacccgc cccctccgc gccttcctcc     53640 ccctccccgc ccacgccccc ggggtcggaa gtcttgagtt ccttggtggt gagcggatac    53700
agggccttca tgggattgcg ttgcagttgc aggacgtagc ggaaggcgaa gaaggccgcg    53760
accaggccgg ccaggaccag cagccccacg gcaagcgccc cgaagggggtt ggacataaag   53820 gaggacacgc ccgagacggc cgacaccacg cccccacta ctcccatgac taccttgccg     53880
accgcgcgcc ccaagtcccc catcccctcg aagaacgcgc acagccccgc gaacatggcg    53940
gcgttggcgt cggcgcggat gaccgtgtcg atgtcggcaa agcgcaggtc gtgcagctgg    54000
ttgcggcgct ggacctccgt gtagtccagc aggccgctgt ccttgatctc gtggcgcgtg    54060
tagacctcca ggggcacaaa ctcgtggtcc tccagcatgg tgatgttcag gtcgatgaag    54120
gtgctgacgg tggtgacgtc ggcgcgactc agctggtgag agtacgcgta ctcctcgaag    54180
tacacgtagc ccccgccgaa gatgaagtag cgccggtggc ccacggtgca cggctcgagc    54240
gcgtcgcggg tgaggcgcag ctcgttgttc tcgcccagct gccctcgat cagcgggccc     54300 tggtcttcgt accgaaagct gaccagggggg cggctgtagc acgtcccggg ccgcgagctg    54360
acgcgcatcg agttctgcac gatcacgttg tccggggcga cgggcacgca cgtggagacg    54420
gccatgacgt ctccgagcat gcgcgcgctc acccgccggc cgacggtggc ggaggcgatg    54480 gcgttgggggt tgagcttgcg ggcctcgttc cagagagtca gctcgtggtt ctgcagctcg    54540
caccacgcga cggcgatgcg ccccagcatg tcattcacgt ggcgctgtat gtggttatac    54600
gtaaactgca gccgggcgaa ctcgatcgag gaggtggtct tgatgcgctc cacggacgcg    54660
ttggcgctgg gcgcctcccg cagtggcgcg ggcgtggcat tccggggctt gcggtcctgc    54720
tcccgcatgt actcccgcac gtacagctcg gcgagcgtgt tgctgaggag gggctggtac    54780
gcgatgagga agccccccgt ggccaggtag tactgcggct ggcccaccct gatgtgcgtg    54840
gcgttgtact tgcgcgcaaa catgcggtcg atggcctcgc gggcatcccg gccgatgcag    54900
tcgcccaggt cgacgcgcga gagcgagtac tcggtcaggt tggtggtgaa ggtggtcgag    54960
```

-continued

```
atggcgtcgg aggagaagcg gaaggagccg ccgtactcgg cgcggagcat ctcgtccacc    55020
tcctgccact tggtcatggt gcagaccgcc ggtcgcttcg gcacccagtc ccaggccacg    55080
gtaaacttgg gggtcgtcag caagttgcgg gtcgtcggcg acgtggcccg ggccttcgtg    55140
gtgaggtcgc gcgcgtagaa gccgtcgacc tgcttgaagc ggtcggcggc gtagctggtg    55200
tgctcggtgt gcgaccccte ccggtagccg taaaacgggg acatgtacac aaagtcgccc    55260
gtcgccagca caaactcatc gtacgggtac accgaccgcg cgtccacctc ctcgacgatg    55320
cagttgaccg tcgtgccgta ccgatggaac gcctccaccc gcgaggggtt gtacttgagg    55380
tcggtggtgt gccacccccg gctcgtgcgc gtggcgacct tcgccggctt gagctccatg    55440
tcggtctcgt ggtcgtcccg gtgaaacgcg gtggtctcca tgttgttccg cacgtacttg    55500
gccgtggagc ggcagacccc cttggtgtta atcttgtcga tcacctcctc gaagggaacg    55560
ggggcgcggt cctcgaatat ccccataaac tgggagtagc ggtggccgaa ccacacctgc    55620
gacacggtca cgtctttgta gtacatggtg gccttgaatt tgtacggggc gatgttctcc    55680
ttgaagacca ccgcgatgcc ctccgtgtag ttctgccccct ccgggcgcgt cgggcagcgg    55740
cgcggctgct caaactgcac caccgtggcg cccgtcgggg gcgggcacac gtaaaactgg    55800
gcatcggcgt tctcgacctt gatttcccgc aggtgcgcgc gcagcgtggc gtggccggcg    55860
gcgacggtcg cgttggcgtc gggggcggg gtcgcctcgg gccgcttggg cggcttttg    55920
gttttccgct tccgggcctt ggtggtcgcg gggctcggga cgggggggcgg ccgggaggcg    55980
ggacccccgt tcgccgcgac ggtcgcggcc acgccgcccg aggcgcgggg ggccgccggg    56040
gccgccgggg ccgccgacgc caccgcggcc accagcgccc ccacgaccag cgcgcaaatc    56100
aagcccccc cgcgcatggc gggcctacgg gggcgcgtcg ctcccgccgc ccgctagtct    56160
gggggcgagg tgctgcagga ccgagtagag gatggaaaaa acgtctcggt cgtaaaccac    56220
gaccgagcgg ggtccgatgc agccgtcggg gccgctctcg acgatggcca ccagcggaca    56280
gtcggagttg tacgtgaggt acacgcccgg cgggtagcgg tacagacctt cggaggtcgg    56340
gcggctgcag tcggggcggc gcaactcaag ctccccgcac cggtagaccg acgcaaagag    56400
tgtggtggcg ataatgagct cgcgaatata tcgccaggcg gcgcgctggg tgggcgtgat    56460
tccggaaaca ccgtcaaaac agtagaactt ttgaaactcg ctgacggccc aatcagcgcc    56520
cgaaccccc gcgcccatga tgaagcgggc gagttcctcc ttgaggtgcg gcaggagccc    56580
cacgttctcg acgctgtagt acagcgcggt gttgggggc tgggcgaagc tgtgggtgga    56640
gtggtcgaac aggggcccgt tgacgagctc gaagaagcga tgggtgatgc tggggagcag    56700
ggccgggtcc acctggtggc gcagcagcga cgctcgcatg aaccggtgcg cgtcaaacac    56760
gcccggggcg gcgcggttgt cgatgaccgt gcccgcgccc gccgtcaggg cgcagaagcg    56820
cgcgcgcgcc gcgaagccgt tggcgaccgc ggcgaaggtc gcgggcagca cctcgccgtg    56880
gacgctgacc cgcagcatct tctcgagctc ccgcgctgc tcgcgcacgc agcgcccgag    56940
gctggccagc gaccgcttgg tcaggcggtc cgcgtacagc cgccggcgct cccgcacgtc    57000
cgcggcggcc cgcgtcgcga tgtcgcccca gctctccggc cctgcgccc ctggctcggg    57060
gccgcgctcc ccgtcctcgc tcgcgggcgt cccgcgcca cgcctccgcc ccccctcctc    57120
cgcggcggcc cggggctctt cctcctcggc ccccccggtc gcgccgccgg ccccagccg    57180
cgccagcacg cggcgcagcg cctcctcgtc gcactgctcg gggctgacga ccgccgcag    57240
cagcggcgtc gtcaggtggt ggtcgtagca cgcgcgtatc agcgcctcga tctgatcgtc    57300
gggcgacgtc gcctggccgc cgatgatcag ggcgtccacc atgtccagcg ccgccaggtg    57360
```

```
gcccccgaac gcgcgatcga agtgctccgc ccgccgcccg aacagcgcca gctccacggc   57420
caccgcggcg gtctcctgct gcagctcgcg ctgcgccagc gcgttcaggt tgtcggcgaa   57480
ggcgtccatg gtggagtggc gggcgcgatc gccggacgcc agccagaagc gcagctcgct   57540 gatgcgtac aggccgggcg tagtggcctg aaacacgtca tgcgcctcca gcagggcgtc    57600
ggcctcctcg cggacagaag agctatcggg gggcggcggg ccggccctgg ccccgccgcc   57660
cgccgcggtc cgcgccagcg cctggtccag cacacagagc gctcgcgcgc gggcggcgtc   57720
cgacagcccg gcggcgtggg gcaggtaccg tcgcagctcg ttggcgtcca gccgcacctg   57780
ggcctgttgg gtgacgtggt tacagatgcg gtccgccagg cggcgggcga tggtcgcccc   57840
ttggttcgcg gtgacgcaca gctcctcgaa acagaccgcg cacgggtggg acgggtcgct   57900
cagctccggg ggcacgatga ggcccgaccc caccgccgcc accataaact cccggacgcg   57960
ctccagcgcg gccgtggcgc cgctcggggg ggtgatgagg tggcagtagt tcagctgctt   58020
gagaaaattc tcgacatcat gcaggaagca cagctccatg cggacgtccc cgccgtacgt   58080
ctgcagccgg atctgctggt ggtacggaca gggtcgggcc agacccatgg tctcggtgaa   58140
aaaggcagag acgtcacccg tggtcgcgaa cgtttccagg tggcccagga gccgctcccc   58200
ctcgcgccac gcgtactcca ggagcaactc caggggtgacc gacagcgggg tgagaaaggc   58260
ggcggcctga gcctccagcc ccggccgcag gtgccgccgc agcacgcgca cctggagcgc   58320
gttgagtttt agctgggcga gcttccccag gccgatctgg gggtcgcatc gtcgaagcag   58380
ctctagctga aaaacgtacg tctgtacctg cccgagcagg gccaacagtt tctgtcgggc   58440
cgcagtgggc tcggaaaccg cggccggggg cgcggccgcc atggcgagtc acccggccgt   58500
gctgtggttt agttaaggtt tgggggggggg tgggtcagag gcgcgccccg cgcggactga   58560
tgcggcggcg ggcccctgac atcccctctt tatgcccgtc gcccgcccgc ccgccccgcc   58620
ggtgtgccgt gattcgcgga gtcgggggcct tgtgtttctt tctttccccc ccgaatccgt   58680
tctttcttcc tcacccccccc ctccccacac acccacccag gactcgccac acaaggagg   58740 cgagagcccg tcgctaaccc aaagacacag tcacgagaca cgatatcgac tgtagttgcg   58800
atcgtttatt ttatacacaa caccaacctt tccttcgacc ccccccaccc ccgcccctag   58860
agcatatcca acgtcaggtc cttttttctcc ggtggtccct ccccaaacgg atcgtcgccg   58920
tgaaacgccc gctttcgggc gacgccggcc gcccccgccg ccgccgccaa accgccgaac   58980
gacgccgcgt ggtcatcctc gtcgccgaaa tccccaaagt taaacacctc cccggcggcg   59040
ccgagctggc tgaccagggc ctccgcctcg tgggccacct ccaggccgc gtcggtcgac    59100 cactcgccat gcccgcgctc cagggcgcgg gtggtaaact ccatcatttc ctcgctcagg   59160
tactcgtcct ccagcagcgc cagccagtcc tcgatctgca gctgctgggt gcgggggccc    59220
aggctcttga cggtcgccac aaacacgctg ctggcgaccg ccgccccgcc ctccgcaatg   59280
atgccccgga gctgctcgca cagcgaatgc tcgtgggccc cgcccccgag actcgacgcc   59340
gcgcacacaa acccggccct ggggcaggcc aggacaaact tgcgggtgcg gtcaaagatc   59400
agcagcgggc acgcgttttt gccgcccagc aggctggccc agttcccggc ctgaaacacg   59460
cggtcgttgc cggccatgcc gtagtatttg ctgatgctga ggcccagcac gaccatcggg   59520
cgcgcggcca tcacgggccg cagcaggttg cagctcgcga acatggacgt ccaggcgccg   59580
gggtgcgcgt cgagggagtc catcagcgcg cgggccccgg cctccaggcc cgcgccgccc   59640
tgcggggccc aggcggccgc cgcctgcacg ctggggggac ggcgggaccc ggcgatgacg   59700
gccgtgaggg tgtttatgaa gtacgtcgag tggtcgcagt acctcaagat ctggttggcc   59760
```

```
atgtagtaca tggccagttc gctcacgtta ttgggggcca ggttgataaa gttaatcgcg   59820
ccgtagtcca gggagaacct cttaatgaac gcgatggtct ctatgtcctc gcgcgacaag   59880
agccgggcgg ggagctggtt gcgctggagg gcggtccaga accactgcgg gttcggctgg   59940
ttcgaccccg ggggcttgcc gttgggaaag atgaccgcgt ggaactgctt cagcaggaag   60000
cccagcggtc cgaggaggat gtccacgcgc ttgtcgggct tctggtaggc gctctggagg   60060
ctggcgaccc gcgccttggc ggcctcggac gcgttggcgc tcgcgcccgc gaacaacacg   60120
cggctcttga cgcgcagttc cttgggaaac ccaagggtca cgcgggcaac gtcgccctcg   60180
aagctgctct cggcggggc cgtctggccg gccgttaggc tgggggcgca gatagccgcc    60240
ccctccgaga gcgcgaccgt cagcgtcttc gccgacagga acccgttgtt gaacaggtcc   60300
atgacgcgcc gccgcagcac cggttggaat tgattgcgaa agttgcgccc ctcgaccgac   60360
tgcccggcga acacccegtg gcactggctc agggccaggt cctggtacac ggcgaggttg   60420
gaccgccgcg cgaggagctg cagcagggg cacggcccgc aggtgtacgg gtccagcgac    60480
agcgacatgg cgtggttggc ctcggccaga ccgtcgcgga acttaaagtt gcgcccctcg   60540
atcaggttgc gcatcagctg ttccacctcg cgatccacca gctgcttgat gttgttcacc   60600
accgtgtgca gggcctcgcg gttgccgata tcgtctcca gcctccccag ggccgtgggc    60660
accgcctggt ccacgtactg cagggcctcg agctcggcca tgacgcgctc ggtggccgcg   60720
cggtacgtct cctgcatgat ggtccgggtg ttctcggacc cgtccgcgcg cttcagggcc   60780
gagaaggcgg cgtagttccc cagcacgtcg cagtcgctgt acgcgctgtt catcgttccg   60840
aagaccccaa tggccccccg ggcggcgctc gcgaacttgg ggtggcgggc ccgcagccgc   60900
atcagcgtcg tgtgcgcgca ggcgtggcgg gtctcgaagg tacacaggtt gcagggcacg   60960
tcggtctggc ccgagtccgc gacgtagcga aacacgtcca tctcctggcg cccgacgatg   61020
actccgccgt cgcagcgctc caggtaaaac agcatcttgg ccagcagggc cggagagaac   61080
ccgcacagca tggccaggtg ctcgccggcg aactcctggg ttccgccgac gagggcgcc    61140
gtggggcgcc cctcgtaccc gggcaccacg tggccctcgc ggtccagctg cgggttggcc   61200
gccacgtgcg tgccgggcac gagaaagaag cggtaaaagg agggcttgct gtggtccttg   61260
gggtccgccg gccccggcgtc gtccacctcg gtcaggtgga gggccgaatt ggtgctgaac   61320
accatggcgc ccacgaggcc cgcggcgcgc gccaggtacg ccccgacggc gccggcgcgg   61380
gccgcgggcg tttcctggcc ctcaagcagg ggccacgtgg tgatgtcggg gggcggctcg   61440
tcaaagaccg ccatcgacac gatggactcc agggccaggg cggcgtcgcc cgccatcacc   61500
gaggccaggc gctgctcaaa cccgcccgcc gggcccttgt tccggcgtc gcgcgcgccc    61560
cgctgggct acctggct ggcctcgaag gccgtgaacg taatgtcggc ggggagggcc      61620
gcgccctcgt ggttttcgtc gaacgccagg tgggcggccg cgcgggccac ggcgtccacg   61680
ttccgggcac gcagggccac ggcggcgggc ccgacgaccg cctcgaacag caggcggcg    61740
aggggcggt tgaaaacgg aagggggtag ttgaaattct ccccgatcga tcggtggttg     61800
cagttaaacg gatcggcgat gacccggcta aaatccggca taaacatctg cagcggatac   61860
acggggatgc ggtgaacctc cgcgtccccg atggttacct tgtccatccc gcccagatgc   61920
aggaaggtgt tgctgatgca cacggcctcc cggaagccct ccgtgatcac cagatacagc   61980
aaggcccggt ccgggtccag tccgagccgc tcgcacagcg cgtccccgt cgtctcgtgc    62040
tttaggtcgc agggccgggg cgcgtagtcc gcgaagccaa aatgcgggcg cgcccgctcg   62100
cagagccgcg tcaggttggg ggcctgggtg ctgggggcca ggtggcggcc gccgtgaaag   62160
```

-continued

```
acgtaaacgg acgggctgta gtgcgagggc ataagcttga gggacaccgc ggtccccca    62220
aggcccgtcg tgcgggaccc gacgaccgcg gccacgttgg cctcaaaccc gctctccacg   62280
gtcaggccga cgatgagggg cgcgacggcg acgtccgcgt cgccgctgcg cgccgacagt   62340
agcgacagca gctccaggcc ttcggccgga caggcgcgga catacacgta ccccatcggc   62400
cccggaggaa ccttgacggt ggtcgtcgtt ttgggcttgg tgtccatggc tttcggagaa   62460
tcggcgaccg gcaggaacgg gggcccggca agacgaccgg gggcagacgg ggaggccgc    62520
gcgtggtcga cggctgctgc ccgccgtcgt ctctccgatg gggtcgaatg ccggcgctgg   62580
gggtggggtc tacacccgcc cgttcgccga gcggcccctg gtgggggtgg gatgggtggg   62640
atgggtggg cgagaatggc ccgccaccgg atcgcgccgg acgggggggc ccggggttgg    62700
gcaaggtttg ggcgcaaggc tccagcggcg attcgagagg cctgcggatg gcggcccaga   62760
gctgggtatg ctcggccggg gcggccggta tatgtacggc gtgctgggag gggcggcgtc   62820
gggccccgcc cacggtccgc cacgccccgc gcgtcatcgg caggggcgt ggccgcccctt   62880
ctaaaaaag tgagaacgcg aagcgttcgc actttgtcct aataatatat atactattag    62940
gacaaagtgc gaacgcttcg cgttctcact ttttttagaa gggcggccac gccccctttg   63000
acgtcacgct cacccgggcg gccggccgcc cataagcgcg gcctgccggg ccgataaaaa   63060
gaaaccgcgg cgccccgcg gacaccacac actggctctc gaaccccgga cgcgcagaag    63120
ggacccgggc gcgggtccgc cggtaagagc cgggggaac atcggcaccg ccatcccacc    63180
ccgagctgtt gggtgggcgg gtgggggggc tggtgaggcg gtggtgggag gggcggcgt    63240
atagcaggac aacgaccggc ggcgatgttt tgtgccgcgg gcggcccggc ttcccccggg   63300
gggaagccgg cggctcgggc ggcgtctggg ttttttgccc cccacaaccc ccggggagcc   63360
acccagacgg caccgccgcc ttgccgccgg cagaacttct acaaccccca cctcgctcag   63420
accgaaacgc agccaaaggc cctcgggccg gctcagcgcc atacgtacta cagcgagtgc   63480
gacgaattc gatttatcgc cccgcgttcg ctggacgagg acgcccccgc ggagcagcgc    63540
accgggtcc acgacggccg cctccggcgc gcccctaagg tgtactgcgg ggggacgag    63600
cgcgacgtcc tccgcgtggg cccggagggc ttctggccgc gtcgcttgcg cctgtgggc    63660
ggtgcggacc atgccccga gggttcgac cccaccgtca ccgtcttcca cgtgtacgac    63720
atcctggagc acgtggaaca cgcgtacagc atgcgcgccg cccagctcca cgagcgattt   63780
atggacgcca tcacgcccgc cgggaccgtc atcacgcttc tgggtctgac ccccgaaggc   63840
catcgcgtcg ccgttcacgt ctacggcacg cggcagtact tttacatgaa caaggcgag    63900
gtggatcggc acctgcagtg ccgtgccccg cgcgatctct gcgagcgcct ggcggcggcc   63960
ctgcgcgagt cgccggggc gtcgttccgc ggcatctccg cggaccactt cgaggcgag    64020
gtggtggagc gcgccgacgt gtactattac gaaacgcgcc cgaccctgta ctaccgcgtc   64080
ttcgtgcgaa gcgggcgcgc gctggcctac ctgtgcgaca acttttgccc cgcgatcagg   64140
aagtacgagg ggggcgtcga cgccaccacc cggtttatcc tggacaaccc ggggtttgtc   64200
accttcggct ggtaccgcct caagcccggc cgcgggaacg cgccggccca accgcgcccc   64260
ccgacggcgt tcggaaccctc gagcgacgtc gagtttaact gcacggcgga caacctggcc   64320
gtcgaggggg ccatgtgtga cctgccggcc tacaagctca tgtgcttcga tatcgaatgc   64380
aaggccgggg gggaggacga gctggccttt ccggtcgcgg aacgcccgga agacctcgtc   64440
atccagatct cctgtctgct ctacgacctg tccaccaccg ccctcgagca catcctcctg   64500
ttttcgctcg gatcctgcga cctccccgag tcccacctca gcgatctcgc ctccaggggc   64560
```

```
ctgccggccc ccgtcgtcct ggagtttgac agcgaattcg agatgctgct ggccttcatg   64620
accttcgtca agcagtacgg ccccgagttc gtgaccgggt acaacatcat caacttcgac   64680
tggcccttcg tcctgaccaa gctgacgag  atctacaagg tcccgctcga cgggtacggg   64740
cgcatgaacg gccggggtgt gttccgcgtg tgggacatcg ccagagcca  ctttcagaag   64800 cgcagcaaga tcaaggtgaa cgggatggtg aacatcgaca tgtacggcat catcaccgac   64860
aaggtcaaac tctccagcta caagctgaac gccgtcgccg aggccgtctt gaaggacaag   64920
aagaaggatc tgagctaccg cgacatcccc gcctactacg cctccgggcc cgcgcagcgc   64980
ggggtgatcg gcgagtattg tgtgcaggac tcgctgctgg tcgggcagct gttcttcaag   65040
tttctgccgc acctggagct ttccgccgtc gcgcgcctgg cgggcatcaa catcacccgc   65100
accatctacg acgccagca  gatccgcgtc ttcacgtgcc tcctgcgcct tgcgggccaa   65160
aagggcttca tcctgccgga cacccagggg cggtttcggg gcctcgacaa ggaggcgccc   65220 aagcgccccgg ccgtgcctcg ggggaaggg gagcggccgg gggacgggaa cggggacgag   65280
gataaggacg acgacgagga cggggacgag gacggggacg agcgcgagga ggtcgcgcgc   65340
gagaccgggg gccggcacgt tgggtaccag ggggcccggg tcctcgaccc cacctccggg   65400
tttcacgtcg accccgtggt ggtgtttgac tttgccagcc tgtacccag  catcatccag   65460 gcccacaacc tgtgcttcag tacgctctcc ctgcggcccg aggccgtcgc gcacctggag   65520
gcggaccggg actacctgga gatcgaggtg gggggccgac ggctgttctt cgtgaaggcc   65580
cacgtacgcg agagcctgct gagcatcctg ctgcgcgact ggctggccat gcgaaagcag   65640
atccgctcgc ggatccccca gagcaccccc gaggaggccg tcctcctcga caagcaacag   65700
gccgccatca aggtggtgtg caactcggtg tacgggttca ccggggtgca gcacggtctt   65760
ctgccctgcc tgcacgtggc cgccaccgtg acgaccatcg gccgcgagat gctcctcgcg   65820
acgcgcgcgt acgtgcacgc gcgctgggcg gagttcgatc agctgctggc cgactttccg   65880
gaggcggccg gcatgcgcgc ccccggtccg tactccatgc gcatcatcta cggggacacg   65940
gactccattt tcgttttgtg ccgcggcctc acggccgcgg gcctggtggc catgggcgac   66000
aagatggcga gccacatctc gcgcgcgctg ttcctccccc cgatcaagct cgagtgcgaa   66060
aaaacgttca ccaagctgct gctcatcgcc aagaaaaagt acatcggcgt catctgcggg   66120
ggcaagatgc tcatcaaggg cgtggatctg gtgcgcaaaa acaactgcgc gtttatcaac   66180
cgcacctcca gggccctggt cgacctgctg ttttacgacg ataccgtatc cggagcggcc   66240
gccgcgttag ccgagcgccc cgcagaggag tggctggcgc gacccctgcc cgagggactg   66300
caggcgttcg gggccgtcct cgtagacgcc catcggcgca tcaccgaccc ggagagggac   66360
atccaggact ttgtcctcac cgccgaactg agcagacacc cgcgcgcgta caccaacaag   66420
cgcctggccc acctgacggt gtattacag  ctcatggccc gccgcgcgca ggtcccgtcc   66480
atcaaggacc ggatcccgta cgtgatcgtg cccagaccc  gcgaggtaga ggagacggtc   66540
gcgcggctgg ccgccctccg cgagctagac gccgccgccc caggggacga gcccgccccc   66600
ccagcggccc tgccctcccc ggccaagcgc ccccgggaga cgccgtcgca tgccgacccc   66660
ccgggaggcg cgtccaagcc ccgcaagctg ctggtgtccg agctggcgga ggatcccggg   66720
tacgccatcg cccggggcgt tccgctcaac acggactatt acttctctgca cctgctgggg   66780 gcggcctgcg tgacgttcaa ggccctgttt ggaaataacg ccaagatcac cgagagtctg   66840
ttaaagaggt ttattcccga gacgtggcac ccccgacg  acgtgccgc  gcggctcagg   66900 gccgcggggt tcgggccggc ggggccggc  gctacggcgg aggaaactcg tcgaatgttg   66960
```

```
catagagcct tgatactct agcatgagcc ccccgtcgaa gctgatgtcc cgcatcttgc    67020
aataaatgtc tgcggccgac acggtcggaa tttccgcgtc cgctggtttc tctgcgttgc    67080
gtctgaccac gagcacaaac gtgctctgcc acacgtgggc ggcgaaccgg tagccggggc    67140
acgcggtcag catccgatcg atgagccggt agtgcaggtg ggccgacgtg ccggggaaga    67200
tgacgtacag catgtggccc ccgtacgtgg ggtccgggta aaaagaaac cggggtcgc      67260
acgccccccc tccgcgcagg atcgtgtgca cgaaaaagag ctcgggctgg ccgagcgtat    67320
cggccaggag gtcctggagg ggggtgctgt ggcggtcggc cagcacgacc agggaggcca    67380
gaaaggtgcg gtgctcaaag atcgtattga tctgctgcac gaaggccagg atgagggcct    67440
cgcggctgac ggtggccagc cgcccgtcgc ccgcgctgca cgcggggcag cagcccccga    67500
tccccaggta gtagcccatg cccgagaggg tcaggcagtt gtcggccacg gtctggtcca    67560
ggctgaaggg gagcgacacg ggggtcgtct tcaccagggg cacggagagc gagcgcacga    67620
tggcgatctc ctcggagggc gtctgggcga gggcggcgaa gaagccgcgg tagcgacggc    67680
gctcgtgcag gcagagctcc agcctgcgcg cgtgcgacgg caggctcttg cgggaggccc    67740
ggcgctccac gccggggttc ccggcggcgg aaaagcgcga ccgccgccgg gtcttgtcgc    67800
ggccgggccc gggccgggag ccggagcgac gggggggcgat gtcatacata ggtacagagg    67860
gtgtgctcca gggacaggag agagatcgag tgtcgtctga gcagcgcgcc ggcctcgcgg    67920
acaaatgtgg ccagcgcggt gggcttcggc acaaataacct ggtacgtctt gaaggtgtag    67980
atgagggccc gcagggctat acagacccgc ccctcgaact cgttgccgca ggccaacttg    68040
gccttgtgaa gctgcagctc gtcgcgatgg tcggcgcggg ggtggccaaa caggacccag    68100
gggtcgactt ccatctccgt gatggcgcac atcggatcgc agaacatgtg cttgaagatg    68160
gcctcggggc ccgcggcccg aagcaggctc acgaaccggc ccccgtcccc gggctgcgcc    68220
tcggggtccg cctcgagctg gtccacgacc ggcactatgc agtcgaagag ctggtgttg     68280
ttctccgagt agcggacgac ggacgccctc aggcgtcgca tggccagcca gtaggcccgc    68340
accagcaaca gattgcacag caggcattcc ccgccggtgc gcccgcgccc ccggccgtgc    68400
ttcagcacgg tggccatcag cgggcccagg tccaggtcgg gctggggctg gggctcggcg    68460
aactgcgcaa aacgcgggc cgcgtcgcgc atgcgcgccc cgcggtgcgc ttcccaggac    68520
tcgctgaccg cggcgcggcg ggcgtccgcg gcggcgcgca gccggggccc cgactcccag    68580
acggcggggg tgccggcgag cagcagcagg atcaggtcgg cgtacgccca cgtctccggc    68640
tcacccccct gcgccagcgc cccggcggcg gcctcgaact cccgttgcg ggcggcggcg    68700
cgcgtgcagc agctgtctcc gccccgcgcg ttgccctcgg tgcagtcgag caggcgggcg    68760
cagtccttcc agttcatcag gcggtggtg agggagggtt gcgttcccga gccccgccc    68820
gccccgccc ccgcccgtc atcgccccg gaggccaggg tcccgatgag ggcccgggtt     68880
gcggactgcg cgaggaagga atagttggag tactgcacct tggcggcgcc cggggagggc    68940
gtcggcctgg gttgcttctg ggcgtggcgc ccgggcaccc cgccgtcggt ccggaagcag    69000
cagtggagaa agaaatgccg gtggatgtcg ttgatggtca gggcgaagcg cgcgaaggag    69060
ccgacaaggg tcgccttctt ggtgcgcagg aagtggtggt ccatgacgta gacgaactcg    69120
aaggcggcca cgaagatgct cgcggcgcag tgggcgcgc caggcacttt ggcgcagagg    69180
aacgcgtaat cggccaccca ctggggcgag aggcggtagg cctgcttgta cagctcgatg    69240
gtgcggcaga ccagacaggg gcggtccagc gcgaaggtgt cgacgacgc cgcggcgaag    69300
ggccccgtgt ccaagagtcc ctctgccgtg gggtctgcgg gcgggccgcg ggcggacccc    69360
```

```
ggcccccgcc ccccccgaagc ctcgcgcgcg gcccgcgcgg gccgcggggg ggcgggcgcg    69420
acgtcgctct ccacgtcctc gtcgagcgcg ctcgcgggcc gcacgcctac cacgtgacag    69480
gccgccagga gctcggcgca cagggcctcg ttaagagcca gaaggtcggg atcgaaggcc    69540
acatacggac gctcgaacgc gccctccttc cagctgctgc ccggcgactc ttcgcgcacg    69600
gcggcgctcg acggcacccc cggggcggac gtcgccatgg ccggtcgagc ggggcgcacg    69660
cgtccgcgaa cgttacggga cgcgatcccc gactgcgcgc tgcggtccca gaccctggaa    69720
agtctagacg cgcgctacgt ctcgcgagac ggcgcggggg acgcggccgt ctggttcgag    69780
gacatgaccc ccgccgaact agaggttata ttcccgacca cggacgccaa gctgaactac    69840
ctctcgcgga cgcagcggct ggcctccctc ctgacgtacg ccgggcctat aaaagcgccc    69900
gacggccccg ccgccccaca tacgcaggac accgcgtgcg tgcacggcga gctgctcgcg    69960
cgaaagcgcg aacggttcgc ggcggtcatt aaccggttcc tggacctgca ccagatcctg    70020
cggggctgac gcgcgcttcg gcggggcacc ggcaccggga ccgacttgtt ttacataaca    70080
gtaggggtg ggggaacgcg cacccttgcc cggtcgcgat ggcggggatg gggaagccct    70140
acggcggccg cccgggggac gcgttcgagg gtctcgttca gcgcatcagg ctcattgttc    70200
ccgccacgct gcgcggcggg ggtggggagt cgggccccta ctcgccatcc aacccgccct    70260
cgagatgtgc cttccagttc cacggccagg atgggtccga cgaggccttc ccgatcgagt    70320
acgtcctgcg gctcatgaac gactgggccg atgtgccctg caaccctac ctgcgcgtgc    70380
agaacaccg cgtttcggtg ctgtttcagg gttttttaa ccggcccac ggcgccccgg    70440
ggggcgcgat cacggcggag cagaccaacg tgattctgca ctccaccgag acgacgggac    70500
tgtccctcgg agacctggac gacgtcaagg gcgcctcgg cctggacgcc cggccgatga    70560
tggccagcat gtggatcagc tgctttgtgc gcatgccccg ggtgcagctc gcgtttcggt    70620
tcatgggccc cgaggacgcc gttcgcacgc ggcggatcct tgtcgcgcc gccgagcagg    70680
ccctcgcccg tcgccgccgg tccaggcggt cccaggatga ctacggggcg gtggtggtgg    70740
cggcggcgca ccactcttcc ggagcgcccg ggcgggggt cgccgcctcg ggcccgccag    70800
cgccgcccgg acggggaccg gcccgtccgt ggcatcaggc cgtgcagttg ttccgggccc    70860
cgcgtccggg ccccccggcg cttctgttgc tggcggcggg gctgtttctg ggggccgcta    70920
tctggtgggc ggttggcgcg cgcctatgaa aggggcgag ccaccgtccc gcccgccagt    70980
gcatcccaga cgcccgcgag ccgcacatcc cctccgctcc cgcctccggc ccgattctta    71040
cggcgcgacc caaggtcccg atggccgccc cgcagtttca ccgccccagc accattaccg    71100
ccgacaacgt ccgggcgctc ggcatgcgcg ggctcgtgtt ggccaccaac aacgctcagt    71160
tcatcatgga taacagctac ccgcatccgc acggaacgca gggtgcggtg cgagagtttc    71220
ttcgcgggca ggccgcggcg ctgacggacc tcggggtgac ccacgccaac aacacgttcg    71280
ccccgcagcc tatgttcgcg ggcgacgccg cggccgaatg gctgcggccc tcgttcggtc    71340
ttaagcgcac gtattccccc tttgtcgttc gcgaccccaa gaccccagc accccgtgag    71400
tcctcggcgg gtccctccgc ggccgtctct cgttgccccc cttccccct tcccgggtgg    71460
ttcaataaaa aacaccaaca tacgatattc gcgtttgata cgtttattgg gggggtgta    71520
gggcccaacg atcggcgatt aacaacacca aacaatcgag cgcgtctaac ccagtaacat    71580
gcgcacgtga tgtaggctgg tcagcacggc gttgctgcgc tgaaacagcg ccctgcgggt    71640
ccgctgcagc tgttgttgta tgcggcggca tgcgcggatc aaaaccgcca gggcgctacg    71700
accggtgctt cgtacgtagc gtcgcgacaa gacggcattt gcctgtacgg gcaaggggcc    71760
```

```
aaattgcgag tgtggtgact ggaggtggtc ggcggccaat gggccgggtg gttcgtcggc    71820
ggggggcaag tgcggttccg gtgggagggg gtcgagcgcc tcggtatcat ccgagtccga    71880
gaaacgcagg gagtctgcgt cggagtgttc atcatcggag gagatgtgca gcgtctgaag    71940
cagcgatgcg ggtgggggcg cggagtcgac gtgaagcgcg agagaggaag cccacgaagt    72000
cacagcggac actgggaggt gggtgtttgt atgtgtggga gactcgggcg tcgggaccga    72060
gtctcggctc tggggtgtaa gcgtccgagt tacgggcggc aggggcggct ggggcagggg    72120
cggctggggc aggggcggct ggggcagggg cggctggggc aggggcggct ggggcagggg    72180
cggctggggc aggggcggct ggggcagggg cggctggggc aggggcggct ggggcagggg    72240
cggctggggc aggggcggct gggcaccga gcgcgcgcgg atgcgcgtcc gcgcggcggg    72300
tttggtcgcg ggtgactggg gtgggggggcg cgggcaacc gggcctccgg gcacgaccca    72360
accgcacaaa ggctcgctcg gggcaaccgg gcctgggcc aaaggcgggg ggctggtctg    72420
gacggcggag gtcggggggg caaggcccgg agaaggcggc actgccgccg ctgcggcgga    72480
aaccgcggcc gcgtggtcgg ctgggtcccg gggagagggg agggagttca acgaggccga    72540
gagcgaggcg accgcggggc gcgtgaggcg ccggggtggg ccggccgcgg gccccgggg    72600 gggtgtcggc gagggacccg ctgttgtctg gcggcggccg cggcggcggt cgcccccggg    72660
gacgaccgct ccttcggcgg gcggaggcgg gatgggcgcg agcgtggggg cgggaaaggc    72720
cccgcgagcc gaggcggggc cgggcggaag gggcaaagca gaaacccaag ccggggggcgc    72780 ggactccggg gtgggcggct ggtcgggagg acgcgcggaa gcggcgaccg gggcgaccgg    72840
ggcggggagt gccggcggac gccacccctc ggggggggcg gaggcccggg gcgcgcgcga    72900
tttggcacgc gtccggcggg acctgcgcac gcgcggcacg gcggcggaga aagcggcggc    72960
agagccggaa aaggccgggg gaggaagcgc ggcatccgcg gggggactcg gtgtgggtgg    73020
cgagggccgt gggtcgtcgc gagggggccac gggcacgcgc cccgtgtttt gttgaggcgg    73080
gacactcggt cgtgtttcgc gagccgtagc tgccggcccg atgggccgcg gtgcgtactg    73140
ggacgtgggg acggactgat cggtggcggg ggggggaaga aagggccgggg ccggattggg    73200 cgtgggccg ccggcgtcgt cggacgccag ctcctccagg ccgtggatcc aggcccacat    73260 gcgaggggg acgggctcgc cggtggtggc gtcggtgagg agagtgggggg cgaggacccc    73320 cgggtccgcc tgccgtgcgg ggggggcagc ggggtcctcg ggacccgatc cgccatcccc    73380
ccccgcaagg tcccgcgggt cgcgggcggc ggtcggggca gagggacctg cctcgtcggc    73440
gagggggcgc tggtaaaccg ggtgtcccgg gaacagctcc cccgtcagga gggaggcgtc    73500
gaagggccgc ccgaggatgg cccgcgcgaa aagggtcc gcgtcggcgg cgctcgccgc    73560
gagaacgtcc cccgcggtag ccacaaacgg aagctcctcg gtggcctcgc tgcccacaaa    73620
ccgcacgtca gggggccgg ggggctccgg ggcttcccac aagaccgcga ccggggtcat    73680
ggagatgtcc acgaggacca ggcacggggg cccgtcggcg agagggcgct cggcgatgag    73740
cgccgacagg cgcgggagct gcgccgccag acacgcgttt tcgatcgggt tgagatcggt    73800
gtggaggagg ccgacggccc acgtctcgat gtcggacgac acgacgtcgc gcagggcggc    73860
gtccggcccg ccggggcgcg agtcgaagag cgtcaggcac agttccagtt ccgactcgcg    73920
ggagaaggcc gtggtgttgc ggagcgccac cacgacgggc gcgccgagga gcaccgcggc    73980
cagaaccagg tccatggccg taacgcgcgc ggcgggggtg cggtgggtcg cggcggccag    74040 cacgccacg tgctgcccg tgggtcggta gaggggcgtgg ggggcctcgg ggagggacgc    74100
ctcgcgcccc cccgccgggc cgagcgtctg gccagactcc aggcgtgcgg ccaggagggc    74160
```

-continued

```
gtcgaagctg tcgtactcgg tgtagtcgtc gggaaacatg caggtccaca gcgcggccaa    74220
agcggcgctc ggcagacaca tgcgcccgag gacgctcacc gccgccaggg cctgggccgg    74280
actgagcttc ccgagcgccg ggacgtcccg gcgctgggtc ccgagctcca aggccgagcg    74340
ccagggcgcc agcgggtcgg tttcggacag cttgccccgg cgccagtcgg ccagccgcgt    74400
gccgaacagg aggccccggg tcgggggggcc tccgtccaaa aacgtcggca acacgcggat    74460
gcgggcgtcg ggatgcgggg tcaggcgctg gacgaacagc atggactccg ctgcgtcctc    74520
gaacgcgcgt tcgagggtga ggtgcatgta ctcgtgctgg cgaacgaggt ccaggcgcca    74580
gaagttgtag atgtgttccg gaacgccggc caccagcgcg accagcacgt cgttctcgtt    74640
gaaggcgacg cagtggcgct gggacccccg ggggcccggc ggcggacgcg cgccgccgc    74700 tccgacgcc cagcccagct gggcccagcg cacccaaac tcgcgcgtga gggtggtggc     74760
gacgagggcg acgtacagct cggccgccgc gtccatcgag gcgccccacg tcgcctggcg    74820
atggcgcaca aagcgaccga acagctgaaa gttggcggcc tgggcgtcgc tgagggccag    74880
ctggagccgg ttcacgacgg tcagcacgta catggccgtg accgtcgggg ccgattcgag    74940
gacgtccgtc ggaagcgggg gccgcacgca ggccgcctcg ggacgcatca gcagcgcgcc    75000
gagtttgtcg gtgacggccg ggaagcatag cgcgtactgc agcggcgttc cgtccggggc    75060 caaaagctg gtggcgaacg gcagatccag agcgctgacg gcctcacgca gcaccagggg    75120
ccccgggtct ccgccggcgc gcagatacgc ctcgccccgg cggcgcagca gctgcgggtc    75180
gacctcgtgg ccctcggggg aagaagaggc ccgggcgcgg gcgtcgaggg cgcgaagatc    75240
aacgagcagg ggcgcgggcg cggactccgc gcccgcgccc gtctggccgc cggccctggc    75300
gtacgcgcta tataagccca tgcggtattg gatgagttcc cgcgcgcccc ggaactcctc    75360
caccgcccac ggggccaggt ccgcggccgc cgcgtcgaac tccgccagca ggcccccag    75420 ggcgtcaaag ttcatctccc agggcaccct gcgcaccacc tcatcccgca gccgggcgca    75480
cagggcggtg tgcttggtga cgcgcgcgcc cagctcctcc acggcctccg cgcgctcggc    75540
gcccttggcg cccaggacgc cctggtacct ggcggaaagg cgctcgtagg ccggctgggc    75600
ccgcagcccc gacaccgtgt tggtggtgtc ctgcagggcg cgcagctgct cgtgcatggc    75660
gcggaacccc tcgggggact tccaggcgcc ccccggacg cggccaaagc gaccccagac     75720
ctcgtcccac tccgcctcgg cctcctccag ggacctccgc agggcgtcga cgcggcgccg    75780
agtatcaaag agcgccccca ggcggccggc gtgccgcgcc aggggccgg ggccgtcgcc     75840 gcgggcggcg cttagcgggt gcgtctcgaa ggtgcgctgg gcgtgctcta gccagataac    75900
cgcgggcacg tcgagctcgc gcgttttctc ggtctgatcc aacagaacct cgacctggtc    75960
ggcgatctcc gccaccgagc gcgcctggtc gagcgtcttg gccacggtcg ccgggacggc    76020
gaccaccttc agcatggtct tgaggttggc caggccctcg gcctcgatct gggcccggcg    76080
ctcgcgcgcg gccagcgcct cccgcaggcc cgccatgacc cgctcggtgg cctccgcgcg    76140
ctgctgtttg gcgcgcacca ctgcgtcctt ggtctcggcc gtgtcctgcc gggtcacgaa    76200
ggcgacatac tcgcgtacg ccgtgttctt cacgggctc tggtccacgc gctccaacgc      76260
cgccgcgcac gcgaccagcg cgtcctcgct gggacacggc agggtgaccc cggtccggac    76320
cagctccgcg gtggcctccg ggtcattccg ggccgcggat atctgctccg cggcggccgc    76380
caggtccagg ggcacgccgc cgagcgcccg gtgcacgtcg gcccggatgg cgtccaggcg    76440
atcgcggagc tccacgtagt cggcgtagcc atgttggaag aacggcacgt accgcgcag    76500 gccgggcacg ctcgtcatgt cgtccgccag gcgccccacg gcctcgtggt agtcgataaa    76560
```

```
cccgtcgccc gcctgggcca tttccaggag cccctccgcg atgcgcagca gccgcgccag   76620
gggctcggcg tcgacccgaa acatgtcggc gtaggtttcg gcggcggcgt ggaacgccgc   76680
gctccagccg aggcggtgga tggcggcgag cggggggagc atgggtggc gctggttctc    76740 gggggtgtag gggttaaacg cgaaggccgt atccagggcg agggtgaccg cctcggcgtt   76800
ggccgcgagc gcctgctcgg cgcgcttgcg gaagtcccgg gggttgtagc cgtgcgtgcc   76860
cgccagcgcc tgcaggcggc gcagctcgac cacgtcgaac tcggcgcggt tctcgacgcg   76920
gtccagcgcc gcctcgacgc cggcggccca gcgctcgctg ctgccccggg cgcgctgggc   76980
cgccatcttc gccgtcaggt cggcgacggc ggcctcaagt tcgtcggcgc ggcgtcgcgt   77040
ggcgccgatg accttgccca gctcctgcag ggcgcgcccg ctgggggaat ggtccccggc   77100
cgtcccttcg gcgtgcagca ggcccccgaa cccagcctcg tgccccgcga ggctttcccg   77160
agcagcggtc gtcgcgcggg ccgcggcatc gatgagggcg gcatggtccc cctccggctg   77220
ggcgcaggcc cggcgcgcct ggactaccag gtcggcggcc gccgacccca gggtcgtgag   77280
ctcgtcgatg gccccccgcg cctccagggc cagccgagtc gcctttacat accccgcggc   77340
gctatcggcc agcaccgcga ggaaggacag gggcgaggcc gggtcgcggg cggccgcgcc   77400
cagggccgac accgcgtccg ccagggcgcc atgcgcccgc acggccgcgt ccaccgtcgc   77460
cgcgggactt gccgtcgcga cggcggcgct cccggcgttg atggcgtttg cacggctttt   77520
ggcgattgtg ggggcgtgat cggaaaagaa ctgcacgagg accggcgtct cggggggcgtc  77580 ggcgaacagg gtcttcagca ccaccacgaa ggcgggatgc aggccggcca gagccgtcgc   77640
ggtatccggg gtcgggtgtt ccagggcctc ccggtactgc cccagcagcc cccacaggtc   77700
cgcccgcagc gccgccgtga cttcggggg ggggccccgg acggcatcgg ccaggtcggt    77760
ccaccccgcg ggcagggagg cccgcagggt cgccagcacg gccggacacg cctttagccc   77820
cacaaagtcc gggaggggcc gcaggacccc ttggagtttg tgcaggaact tctcccgggc   77880
gtcgtgggcc accttggcgc gctcccgcgc gtcgttgagc atcgcctcca gggcgtgggc   77940
gcgctcccga agccgggagc gcgcctccgg agcgagctcc gccgtcatct tggccgcctc   78000
catggccctc gcctgccgca gcgcgtcttc ggccatgcgc gtggcctcgg gggacagccc   78060 gccccgtcg acgtacgcg cgggccggt cgccgggacg aaggccgcgt cgctgtccag      78120
ctgctgcgcg agcgccgcgt cgaggcgtc gaagcgctgc agttcggcca gccccgagct   78180
gcgccgcgcc tgctggtcgt tgatgccgtg gatgctgcgc gccagctctt ccagggcctt   78240
gcgttcgatg agccctggg tcgcggcgtc ggtcaggacc gagagccagg ccgccaggtc    78300
ctcgggggca tctagggct ggccccgctg gagcaggtcc cgcagcagga tggcctgggg    78360
gctggtggcg aggggggcg gggggggag gcgcggcgcg tgagcgacgt cccgcgtgtg     78420
ttggtcaaag gccggtagcg attccagcaa ctggaccatg gcacgaccg cggccgaggc    78480 cacgtgaaac cgacagtcgt ggctgtcgct ggcctgcagg gccttcgcgc tgtatacggc   78540
tccccggtgg aagtactcct tgaccgcgct ctcgatcgcc cggcgggcct ggatccgcac   78600
gtcctccagc cgcgcctgga tggcctcggg gccagggcg ggcgggcacg gggccctgcc    78660
gccggcgccc ggggcggcgg gcacgggcat cacggtcagg ggcccggcgc gctgcgagac   78720
cgagtcgacc ccgcgggcga gggcgtctaa ggcctcgcgc atctcgcggg cctccgcctc   78780
gacccgcatc tcttcgcccc gggcaaactg ggccagcgcc tggatccgat ggagaagcgg   78840
ctccgggtgc gtcggggtgg cggggcgaa caggtgtc gggtgggcgc gcgagcgctc      78900
caggagccac tctccgaggc gtgcgtacag attggccggc ggggcggcgc gcagctgcag   78960
```

```
atccaggtcc gcgaggtccc cgtaaaaggc gtccgtctcc cgaataacgt ccctggcgac   79020
caggaccagc ttagcgaggg ccaggcgccc gatctgcgaa ttttcgtcca gcacgtgctg   79080
gatgagggc cggtgggcgg ccacgtccgc caggctcatg cgcgtggacg ccaggaagtc    79140
cccgacggcc gttttgcggg gcagcatgcg cagggtgaag tccagcaggg ccgcggccgg   79200
gccggccacc ccggcctgcg tatgcgtgcg ggccccgttc tcgatcaaaa aggcgaggac   79260
gcgctcaaag aagaagatga cgcagagctc caacagcccc gggtgcgccg ggtacggcga   79320
ccgcagggcg ttgatggtga gctgcgaaca cgcggccacc tcgcgggcca gggcggcatc   79380
gcgcgccgcg agccggaccg ccgtggcggc cacattgggg tggacctcga acagctgcgc   79440
caggtcggcg ccgggggct ccggggggcg gcgggccccc agcgtctcga gcacggacgg    79500
cgacgacggg ctcgcgggcc cgtcgtcgcc gccgccctgc ccggactgcg gggggtatc    79560
cggtgcggga gggaccgtgg cggctatggg cgtcggggag gaggcgggga cctcggcggc   79620
gacggggcc ttcttcttgg gcgcggactt cttcttggcc ttggcgggcg gggccttggg    79680
ggcgggcctc tcgcccgagg tcagatcctc cacgctggac ggtgggtcc aggtgggccg    79740
gcggcgcttg ggcaagccgg tagaatagcg cgcccggtgg cgacccaccg gcactgcccc   79800
cacctccagg acccgcaggt cctcggcttc ttcggccgcg tccccggcgg gtgtctgcgg   79860
gggcggggcg gcgtgcggtg gacccgaggc gcggcgtcc ggggccgagg gcttcgcggg    79920
cggggtcccc tccagggctg ctgcccacac atcatcgggg gggcggtttg ggtgccccgc   79980
ctgcggtgtg tcggtgggc ccgaggcccc ccggggggcc tcgggggcc ggtcggcccc     80040
aggggtctgg acgtgggtgg gcgcggggag cgcggggacg accgggcccg agccttctcc   80100
gtcccccctg gggaccacac cgacaaagag cgccccgagc ccccgatct cgccccgcag    80160
ggggtgggtg atggccacgc gccgctcgac gaacggttcg tcctgcaggt aagtctcgct   80220
ggccccgtag aggtgcaggg ccgcggcggt caggtccgcc ggcgccacgg ccccggggcc   80280
ggagggcaca aaaacacca tggcgcccgc ccaccgcacc ttggggcggt cgtgggcgta    80340
atacgtcagg tacgggtaca cgtcgcccgc ccgcaccttg gcgataaacg cgggcgttcc   80400
cgcgggcagg ccgtgcgggt caaacagata ggccgtgtcg ccgtcccggt agagcccat    80460
gcccagggg ccgatggtca ggagcgtgta ggacagcggc cgcatggccc agggccggc     80520
gaagaacgtg tgcgcgggc attgcgtctc cagcagcccc gccgtgggct ccccgaagaa   80580
gcccacctcg ccgtacaccc gcgaaaacac gcaacgcagg ccgccgcgcg ccgccgggta   80640
ctccaggaag ttggggagct cgataatgga acacatgcgc ggcggcccgg agcccgcggc   80700
cgcgcgcgtc cactcgcccc cctccaccag acatccctcg atggcctccg cggacagcac   80760
gtcgcgggc cccacgtcga aagaagact gagaaacgac agggacgagc gcatgacga     80820
taccgacccc cccggctcca gatcggtcgc gaactggttc cgaacaccgg tgaccacgat   80880
atcgcgatcc ccctggcgct tcatcgtggg gtgaggtagc gcggccggaa tcatgtgtgc   80940
cgcgcccgcc acgagcgggg cctgtttatg ggccgggcgt cccgatgagt actgttgttt   81000
ccgccgcccg aaccccccg cccatcaacc gcctgttcgt cccctaacc acacacccgg     81060
tatcgcgtgt gtgtggtttc ccgggaagac acatcccacc ccatgaagtt tgccctttt   81120
tttccgtccc gcactacgcc acctttccac ccccccccaa aaaacaaca accaactccc    81180
agatggatgg gtgcgataat aaagcttat tattgtttaa ccaaaggcga gtcctacggg    81240
tgtaccggtg gtgtctcctg cggcgtcatc tcgtcgtcct ccacgggggt gttgggccaa   81300
gggaccgtct cgcggcccgc cgggcgcgtc gacggcgcgc gggcctgcgt gtcctgtggg   81360
```

-continued

| | |
|---|---|
| ccgggtgtcg tgggttcggg ggtgctaccg ccggcatctt gggcctccag gtccccgggg | 81420 |
| gcccccgggc cggcggaagg ccgaaacgcc gaggcgcgaa acacgccgtc ggtgacctgc | 81480 |
| aggagctcgt ttattaatag ccagtccatg ctcagcgtag cggccagccc ctggggagac | 81540 |
| aggtccacgg agtccggaac caccgtcggc tgacccaggg gccccaggct gtagtccccc | 81600 |
| caggccccca ggtcatgacg gttcgtgagc acgacgaggt ctgcggccgg gctgggggc | 81660 |
| gcgtcctcgg tcgcgtgggc catcacctcc tgaatggctg cggtgcgctg atcggccgag | 81720 |
| ctggcgaagc gcgccacgac cagcgcgcgc tccgtctgca ggcccttcca cgtgtcgtgg | 81780 |
| agttcctgaa cgaactcggc cacccgctcg ggcccgtgg ccgcgcgtgc ggcctgatag | 81840 |
| ccggccgaga ggcgccgcca gcgcgccagg aactgactca tgtaacagaa cccggggacc | 81900 |
| tggtcccccg acatcaactt tgacgccctg gcgtggatgc ccgacacgat ggccaggaac | 81960 |
| ccgtggattt cccgccgcac gacggccagc acgttaccct cgtgcgagac ctgggccgcc | 82020 |
| agctcgtcgc ataccccgag gtgcgccgtc gtctcggtga cgacgaccg cagccccgcg | 82080 |
| agggacgcga ccagcgcgcg cttggcgtcg tgatacatgc cgcagtactg gctcaccgcg | 82140 |
| tcgcccatgg cctcggggcg ccagggcccc aggcgctcgt gggcgtctgc gaccacggcg | 82200 |
| tacaggcggt gcccgtcgct ctcgaaccgg cactcaaaga aggcggcgag cgtgcgcatg | 82260 |
| tgcagccgca gcagcacgat cgcgtcctcc agctggcgga ccaggggtc ggcgcgctcg | 82320 |
| gcgagctcct gcagcacccc ccgggccgcc agggcgtaca tgctgatcag cagcaggctg | 82380 |
| ctgcccacct cgggaggctg ggggggaggc agctggaccg cgggccgcag ctgctcgacg | 82440 |
| gcccccctgg cgatcacgta cagctcgcgc agcagctgct cgatgttgtc ggccatctgc | 82500 |
| atcgtgggcc cgacgccggc ccgggtggcc ggttcgagga gggtgatcag cgcgcccaat | 82560 |
| tttgtgcggt gcccctcgac ggtggggaga tagcccaggc cgaagtcgcg cgcccaggcc | 82620 |
| agcacccgca gggcaaactc gatgggggcgg ggcaggtagg cagcgttgca cgtggccctc | 82680 |
| agcgcgtccc cgaccaccag ggccagcacg taagggacga accccgggtc ggcgaggacg | 82740 |
| ttggggtgga tgcccctccag ggccgggaag cggatcttgg tggccgcggc caggtgaacc | 82800 |
| gaggggggcgt ggctaggcgg cccgacgggg agcagcgcgg acagcggcgt ggccggggtg | 82860 |
| gtggggtca ggtcccagtg ggtctggccg tacacgtcga gccagatgag cgccgtctcg | 82920 |
| cgcaggaggc tgggctggcc ggcgctgaag cggcgctcgg ccgtctcaaa ctcccccacg | 82980 |
| agcgtgcgcc gcaggctcgc caggtgttcc gtcggcacgg ccgggcccat gatgcgcgcc | 83040 |
| agcgtctggc tgaggacgcc gcccgacagg ccgaccgcct cacagagccg cccgtgcgtg | 83100 |
| tgctcgctgg cgccctggat ccgccggaac gttttcacgt agccggcgta gtgcccgtac | 83160 |
| tcccgcgcga gcccgaacac gttcgccccc gcaagggcaa tgcacccaaa gagctgctgg | 83220 |
| atctcgctga gcccgtgcc gggggcgtc cgcgcgggca ccccgccac caaaaccccc | 83280 |
| tccagggccg atatgtactg ggtgcagtgc gcggcgtga accccgcgtc ggtaagcgtg | 83340 |
| ttgatcacca cggagggcga gttgctgttc tggaccaaag cccacgtctg ctgcagcagc | 83400 |
| gcgaggagcc gttgctgggc cccggcgag ggcggctccc ctagctgcag caggccggtg | 83460 |
| acggccggac ggaagatggc cagcgccgac gcactcagaa acggcacgtc ggggtcgaag | 83520 |
| acggccgcgt ccgtccgcac gcgcgccatc agcgtcccg ggggcgcgca cgccgaccgc | 83580 |
| gggctgacgc ggcttagggc ggtcgacacg cgcacctcct cgcgactgcg aaccattttg | 83640 |
| gtggcctcga ggggcgggat catgatagcc gggtcgatct cccgcaccgt gtgctgaaac | 83700 |
| tgggccagca gcggcggcgg gaccaccgcg ccccgatcgg gggtcgtcag gtagtcgtcc | 83760 |

```
accagcgcca gcgtaaacag ggcccgcgtg agggggggtca gggcggcgtc gtcgatgcgc    83820
tgtaggtgcg ccgagaacag cgtcacccaa ttgctgacca gggccaagaa ccggagaccc    83880
tcttgcacga tcggggacgg gaagagcagg ctgtacgccg gggtggtcag gttggcgccg    83940
ggttgcccca ggggaaccgg ggacatctta agcgacatct ccccgagggc ctccagggag    84000
gtccgcgggt tcatggccag gcagctctgg gtgacggtcc gccagcggtc gatccactcc    84060
acggcacact ggcggacgcg caccggcccc agggccgccg tggtgcgcag cccggcggcc    84120
tccagcgcgt gggtcgtgtc ggagccggtg atcgccagga ccgtgtcctt gatgacgtcc    84180
atctcccgga aggccgcctc gggggtctcg ggagccgcca ccgccatgcg gtgcaccagc    84240
agcccgggga ggttctcggc caagagcgcc gtctccggaa gcccgtgggc ccggtgcaag    84300
gcgcacagtt gctccaggag cgggtgccag cacgcccgcg cctccgccgg ccgaccgcc    84360
gcgcccgaca acagaaacgc cgccgtggcg gcgtgcagtt tggccgcgga cagaaacgcc    84420
ggctcgtccg cgctgcccgc cggctcgctc gagggggagg gcggccggcg gaggttggtc    84480
aggctcccca acaggacctg caacggtccg tttggggggtg gagcggacgg ggggtcatg    84540
ccggcgggcg ccgggacctg gagcgcgctg tccgacatgg cgaccggcgt gcgcgctcgg    84600
cgacgcggcg cggagaccgc gggcccaaac gggaatgact gccgccgccc tatacggagg    84660
ggctaagtat cgcccgggga cccttcgaaa ccccgggcgt gtcgcaagta cgccgcgaag    84720
gcgcggcgtg ttatacggcg cgttatgtcc cggcattccg ttcgtgggtt cgggcccggg    84780
tgctgtcggg tgggagtgtg tgtggggggg ggcggcgcga cggcggcccg gaccaagtgt    84840
atcgcggccg ttccgtgggg cggcccaaca ggcccttttaa acatttgcgt atgcaccggc    84900
ccagccagtc ggacaccgga acccaccaga ggcggaagcc gccttcgccc gtgagggtgc    84960
gtgtgttttc tggtggcgtg tttttccttt ccgccctcct ccctcccac ctccaccacc    85020
ccccccacaa actcgcccgt tggcgatcgg cgggaaaacc atgaaaacca agccactccc    85080
gacagccccg atggcgtggg ccgagagtgc cgtggaaacc accaccagcc cgcgcgagct    85140
cgcgggccac gccccgctcc ggcgcgtcct cgcgcccgcc atcgctcgcc gcgacggccc    85200
ggtgcttttg ggggacaggg ccccccaggag gacggccagt acgatgtggc tgctggggat    85260
cgaccccgcg gagtcgtctc cgggaacgcg cgctacccga gacgataccg agcaggccgt    85320
ggacaagatc ctcagggggag cccggcgcgc gggagggctg accgtccccg gcgccccccg    85380
ctatcacctg acccgccagg taaccctgac ggatctctgc caaccaaacg cggagccggc    85440
cggggcgctc cttttggccc tgcggcaccc caccgacctc ccccacctgg cccgccatcg    85500
ggctccgccc ggccggcaga ccgagcgact ggccgaggcc tggggccagc tcctggaggc    85560
ctccgccctg gggtccgggc gggccgagag cggctgcgcg cgcgcgggcc ttgtgtcgtt    85620
taactttctg gtggccgcgt gcgccgccgc ctacgatgcg cgcgacgccg ccgaggcggt    85680
ccgggcccac atcacgacca actacggcgg gacgcgggcc ggggcgcggc tggaccggtt    85740
ttccgaatgc ctgcgcgcca tggtccacac gcacgtgttt ccccacgagg tcatgcggtt    85800
tttcgggggg ctagtgtcgt gggtcacaca ggacgagctg gctagcgtca ccgccgtctg    85860
cagcggaccc caggaggcca cacacaccgg ccacccgggc aggccccgtt cggccgttac    85920
catcccggcc tgcgccttcg tggacctgga cgccgagctg tgcctggggg gcccctgggg    85980
ggcgttcctg tacttggtct tcacctaccg acagtgccgg gaccaagagc tctgttgcgt    86040
gtacgtggtc aagagccagc tcccccgcg cggactggag cgggccctcg agcggctgtt    86100
cgggcgcctc cggataacca acacgattca cggggccgag gacatgacgc cccctccccc    86160
```

```
gaaccgaaac gttgactttc cgctcgccgt cccggccgcg agctcgcaat ccccgcggtg   86220
ctcggcgagc caagtcacga accccccagtt tgtcgacagg ctgtaccgct ggcagccgga  86280
tctgcggggg cgccctaccg cacgcacctg cacatacgcc gccttcgcag agctgggtgt   86340
catgccagac gacagccccc gctgtctgca ccgcaccgag cggtttgggg cggtcggcgt   86400
tccggttgtc atcctggagg gcgtggtgtg gcgcgcggcg gggtggcggg cctgcgcgtg   86460
atcgtctatt gacgacggcc gcccaacccg agcgaccttc ccctcccact tccccccccc   86520
tacacaccaa ctccgccctc gccgtcttgg ccgtgcgcgg ccccgtgcgt ccgtctcaat   86580
aaagccaggt taaatccgtg acgtggtgtg tttggcgtgt gtctctgaaa tggcggaaac   86640
cgacatgcaa atgggattca tggacatgtt acacccccct gactcaggag ataggcatat   86700
cctccttaga ttgactcagc acgatcgc accccacccc tgtgtgccgg ggataaaagc     86760
caacgcgggc ggtctgggtt accacaacag gtgggtgctt cggggacttg acggtcgcca   86820
ctctcctgcg agccctcacg tcttcgccca ccgattcctg ttgcgttcct gtcggccggt   86880
gctgtcctgt cgacagattg ttggcgactg cccgggtgat tcgtcggccg gtgcgtcctt   86940
tcggtcgtac cgcccacccc gcctcccacg ggcccgccgc tgtttccgtt catcgcgtcc   87000
gagccaccgt caccttggtt ccaatggcca accgccctgc cgcatccgcc ctcgccggag   87060
cgcggtctcc gtccgaacga caggaacccc gggagcccga ggtcgccccc cctgcggcg    87120 accacgtgtt ttgcaggaaa gtcagcggcg tgatggtgct ttccagcgat ccccccggcc   87180
ccgcggccta ccgcattagc gacagcagct ttgttcaatg cggctccaac tgcagtatga   87240
taatcgacgg agacgtggcg cgcggtcatt tgcgtgacct cgagggcgct acgtccaccg   87300
gcgccttcgt cgcgatctca aacgtcgcag ccggcgggga tggccgaacc gccgtcgtgg   87360
cgctcggcgg aacctcgggc ccgtccgcga ctacatccgt ggggacccag acgtccgggg   87420
agttcctcca cgggaaccca aggaccccg aaccccaagg accccaggct gtcccccgc     87480 cccctcctcc ccccttccca tggggccacg agtgctgcgc ccgtcgcgat gccaggggcg   87540
gcgccgagaa ggacgtcggg gccgcggagt catggtcaga cggcccgtcg tccgactccg   87600
aaacggagga ctcggactcc tcggacgagg atacgggttc ggagacgctg tctcgatcct   87660
cttcgatctg ggccgcaggg gcgactgacg acgatgacag cgactccgac tcgcggtcgg   87720
acgactccgt gcagcccgac gttgtcgttc gtcgcagatg gagcgacggc cccgcccccg   87780
tggcctttcc caagccccgg cgccccggcg actcccccgg aaaccccggc ctgggcgccg   87840
gcaccgggcc gggctccgcg acggaccgc gcgcgtcggc cgactccgat tccgcggccc    87900
acgccgccgc accccaggcg gacgtggcgc cggttctgga cagccagccc actgtgggaa   87960 cggacccccgg ctacccagtc cccctagaac tcacgcccga gaacgcggag gcggtggcgc  88020
ggtttctggg ggacgccgtc gaccgcgagc ccgcgctcat gctggagtac ttctgtcggt   88080
gcgcccgcga ggagagcaag cgcgtgcccc cacgaaccft cggcagcgcc cccgcctca    88140 cggaggacga ctttgggctc ctgaactacg cgctcgctga gatgcgacgc ctgtgcctgg   88200
accttccccc ggtccccccc aacgcataca cgccctatca tctgagggag tatgcgacgc   88260
ggctggttaa cgggttcaaa cccctggtgc ggcggtccgc ccgcctgtat cgcatcctgg   88320
gggttctggt ccacctgcgc atccgtaccc gggaggcctc cttgaggaa tggatgcgct    88380 ccaaggaggt ggacctggac ttcgggctga cggaaaggct tcgcgaacac gaggcccagc   88440
taatgatcct ggcccaggcc ctgaacccct acgactgtct gatccacagc accccgaaca   88500
cgctcgtcga gcgggggctg cagtcggcgc tgaagtacga agagttttac ctcaagcgct   88560
```

```
tcggcgggca ctacatggag tccgtcttcc agatgtacac ccgcatcgcc gggtttctgg    88620
cgtgccgggc gacccgcggc atgcgccaca tcgccctggg gcgacagggg tcgtggtggg    88680
aaatgttcaa gttctttttc caccgcctct acgaccacca gatcgtgccg tccaccccg     88740 ccatgctgaa cctcggaacc cgcaactact acacgtccag ctgctacctg gtaaaccccc    88800
aggccaccac taaccaggcc accctccggg ccatcaccgg caacgtgagc gccatcctcg    88860
cccgcaacgg gggcatcggg ctgtgcatgc aggcgttcaa cgacgccagc cccggcaccg    88920
ccagcatcat gccggccctg aaggtcctcg actccctggt ggcggcgcac aacaaacaga    88980
gcacgcgccc caccggggcg tgcgtgtacc tggaaccctg gcacagcgac gttcgggccg    89040
tgctcagaat gaagggcgtc ctcgccggcg aggagcccca gcgctgcgac aacatcttca    89100
gcgccctctg gatgccggac ctgttcttca gcgcctgat ccgccacctc gacggcgaga    89160
aaaacgtcac ctggtccctg ttcgaccggg acaccagcat gtcgctcgcc gactttcacg    89220
gcgaggagtt cgagaagctg tacgagcacc tcgaggccat ggggttcggc gaaacgatcc    89280
ccatccagga cctggcgtac gccatcgtgc gcagcgcggc caccaccgga agccccttca    89340
tcatgtttaa ggacgcggta aaccgccact acatctacga cacgcaaggg gcggccatcg    89400
ccggctccaa cctctgcacc gagatcgtcc acccggcctc caagcgatcc agtgggtct    89460 gcaacctggg aagcgtgaat ctggcccgat gcgtctccag gcagacgttt gactttgggc    89520
ggctccgcga cgccgtgcag gcgtgcgtgc tgatggtgaa catcatgatc gacagcacgc    89580
tacaacccac gccccagtgc acccgcggca acgacaacct gcggtccatg ggcattggca    89640
tgcagggcct gcacacggcg tgcctcaaga tgggcctgga tctggagtcg gccgagttcc    89700
gggacctgaa cacacacatc gccgaggtga tgctgctcgc ggccatgaag accagtaacg    89760
cgctgtgcgt tcgcggggcg cgtcccttca gccactttaa gcgcagcatg taccgggccg    89820
gccgctttca ctgggagcgc ttttcgaacg ccagcccgcg gtacgagggc gagtgggaga    89880
tgctacgcca gagcatgatg aaacacggcc tgcgcaacag ccagttcatc gcgctcatgc    89940
ccaccgccgc ctcggcccag atctcggacg tcagcgaggg cttttgcccc ctgttcacca    90000
acctgttcag caaggtgacc agggacggcg agacgctgcg ccccaacacg ctcttgctga    90060
aggaactcga gcgcacgttc ggcgggaagc ggctcctgga cgcgatggac gggctcgagg    90120
ccaagcagtg gtctgtggcc caggccctgc cttgcctgga ccccgcccac ccctccggc     90180 ggttcaagac ggccttcgac tacgaccagg aactgctgat cgacctgtgt gcagaccgcg    90240 cccccctatgt tgatcacagc caatccatga ctctgtatgt cacagagaag gcggacggga    90300
cgctccccgc ctccaccctg gtccgccttc tcgtccacgc atataagcgc ggcctgaaga    90360
cggggatgta ctactgcaag gttcgcaagg cgaccaacag cggggtgttc gccggcgacg    90420
acaacatcgt ctgcacaagc tgcgcgctgt aagcaacagc gctccgatcg gggtcaggcg    90480
tcgctctcgg tcccgcatat cgccatggat cccgccgtct cccccgcgag caccgacccc    90540 ctagatacccc acgcgtcggg ggccggggcg gccccgattc cggtgtgccc cacccccgag    90600
cggtacttct acacctccca gtgccccgac atcaaccacc ttcgctccct cagcatcctg    90660
aaccgctggc tggagaccga gctcgtgttc gtggggacg aggaggacgt ctccaagctc     90720
tccgagggcg agctcggctt ctaccgcttt ctgtttgcct tcctgtcggc cgcggacgac    90780
ctggtgacgg aaaacctggg cggcctctcc ggcctcttcg aacagaagga cattcttcac    90840
tactacgtgg agcaggaatg catcgaggtc gtccactcgc gcgtctacaa catcatccag    90900
ctggtgctct ttcacaacaa cgaccaggcg cgccgcgcct atgtggcccg caccatcaac    90960
```

```
cacccggcca ttcgcgtcaa ggtggactgg ctggaggcgc gggtgcggga atgcgactcg   91020
atcccggaga agttcatcct catgatcctc atcgagggcg tcttttttgc cgcctcgttc   91080
gccgccatcg cgtacctgcg caccaacaac ctcctgcggg tcacctgcca gtcgaacgac   91140
ctcatcagcc gcgacgaggc cgtgcatacg acagcctcgt gctacatcta caacaactac   91200
ctcgggggcc acgccaagcc cgaggcggcg cgcgtgtacc ggctgtttcg ggaggcggtg   91260
gatatcgaga tcgggttcat ccgatcccag gccccgacgg acagctctat cctgagtccg   91320 ggggcccctgg cggccatcga gaactacgtg cgattcagcg cggatcgcct gctgggcctg   91380
atccatatgc agcccctgta ttccgccccc gccccgacg ccagctttcc cctcagcctc   91440
atgtccaccg acaaacacac caacttcttc gagtgccgca gcacctcgta cgccggggcc   91500
gtcgtcaacg atctgtgagg gtctgggcgc ccttgtagca atgtctaacc gaaataaagg   91560
ggtcgaaacg gactgttggg tctccggtgt gattattacg caggggaggg gggtggcggc   91620
tggggaaagg gaaggaacgc ccgaaaccag agaaaaggac caaagggaa acgcgtccaa   91680 ccgataaatc aagcgccgac cagaaccccg agatgcataa taacgatttt attactctta   91740
ttattaacag gtcgggcatc gggaggggat ggggcgcgc gtttcctccg ttccggctac   91800
tcgtcccaga atttagccag gacgtccttg taaaacgcgg gcggggcgc gtgggcccac   91860 agctgcgcca gaaaccggtc ggcgatgtcc ggggcggtga tatgccgagt cacgatggag   91920
cgcgctaaat cttcgtcgcg gaggtcctga tagatgggca gtcttttag aagagtccag   91980 ggtccccgct ccttgggggct gataagcgat atgacgtact tgacgtatct gtgctccacc   92040
agctcggcga tggtcatcgg atcgggcagc cagtccaggg cctccggggc gtcgtggatg   92100
acgtggcggc gacgtccggc gacatagccg cggtgttccg cgacccgctg cgcgttgggg   92160
acctgcacga gctcgggcgg ggtgagtatc tccgaggagg acgaccgggc gccgtcgcgc   92220
ggcccaccgg cgacgtccgg gggctggagg gggggtctt cttcgtagtc gtcctcgccc   92280
gcgatctgtt gggccagaat tcggtccac gagatgcgcg tctcgaggcc gaccggggcc   92340
gcggtcagcg taggcatgct ctccagggag cgcgagttgg cgcgctcccg ccgggccgcc   92400
cggcgggcct gggatcggct cggggcggtc cagtgacact cgcgcagcac gtcctcgacg   92460
gacgcgtagg tgttattggg gtgcaggtct gtgtggcagc ggacgaacag cgccaggaac   92520
tgcgggtaac tcatcttgaa gtactgcagc aggtcgcggc agtgaatcgt cggaatgtag   92580
ccggtgctga tgtccaacac gatatcgcag cccatcagca ggagatcggt atccgtggta   92640
tgcacgtacg cgaccgtgtt ggtatgatag aggttcgcgc aggcgtcgtc ggcctccagc   92700
tgacccgagt tgatgtaggc gtaccccagc gcccgcagaa cgcggataca gaacaggtga   92760
gccaggcgca gggccggctt cgaggcgcg cccgaggggg ccgccgggcc tgggccggcg   92820
gcccgcgttc cccggtcccc cggggcgaag gcgtgcccgc ggcggcgcat gttggaaaag   92880
gcgaaactgg gcctggagtc ggtgatgggg gaaggcggcg gcgaggcgtc tacgtcactg   92940
gcctcctcgt ccgtgcggca ctgggccgtc gtgcgggcca ggatcgcctt ggccccgaac   93000
acaaccggct cggtacactc gaccccgcga tcggtcacga agatggggaa caggggacttt   93060 tgggtaaaca cccgtaacat actacagaga cagtgtagcg tgattgcctc gcggtcgtaa   93120
cttgggtagc ggcgctgata tttaaccacc agggtataca tgcattcca caggtccacg   93180 gcgatggggg taaagtagcc ctccggggcc cggaggcccc ggcgcttcac cagatggtga   93240
gtctgggcaa acttcatcat gccaaacaga cccattccgg cacgattgta ggtgcggata   93300
ggtctctcta cagagctgta taggtgtgac ggtccgggac acccaagccc gccgcccctg   93360
```

-continued

```
tgtacagtgg ctgcggcgac gaccccgctc aacaagacg ctatcccggg aaaggcacgc    93420
tctttataat tcttttttat ttcccatcta cgtgcggatt ggtgcaaccg ccggcgcgcg    93480
ccggtgcagg ccgaccatct ctctcttccc cccctccccc tccccgagc cctcaaagag    93540
ggtgtggcct aactagcgga aggcgtattt aaccagacta gggcggcggg tccgccgtag    93600
tccttggctc gggtagccac tgctctgtgg ctcgggtccc ccggcccccc taaccccat    93660
ccggtccgcg tcatccgccc cctccgcctg cgacacaaac ggccgcgcct ccgggcccgg    93720
tgacacgacg cgcctcgtct ctgcggattg tcccgggagc gtcgcggcat ggctcatctt    93780
cccggcggtg cggccgccgc cccctttcg gaggacgcga tcccgtcgcc gcgcgagcgg     93840
acggaagact ggccgccctg ccagatagtg ctgcaggcg ccgagctgaa cgggatcctg     93900
caggcctttg cgccgcttcg cacgagcctt ttggactcgc tcctggtcgt gggcgaccga    93960
ggcatccttg tacataacgc gattttcggc gagcaggtgt ttctgcccct cgaccattcg    94020
cagttcagtc gctatcgatg gggcggaccc accgcggcgt tcctgtctct cgtggaccag    94080
aagcgatccc tgctgagcgt gtttcgcgcc aaccagtacc ctgacctgcg gcgggtggag    94140
ctgacggtca cgggccaggc cccgtttcgc acgctggtgc agcgcatatg gacgaccgcg    94200
tccgacggag aggccgtgga gcttgccagc gagacgctca tgaaacgcga gttgacgagc    94260
ttcgcggtac tactccccca gggcgacccc gacgtccagc tgcgcctcac gaagcccag    94320
ctcacgaagg tggtgaacgc cgtcggggac gagaccgcca acccaccac gttcgagctc    94380
ggccccaacg gcaagttttc cgtgtttaac gcgcgcacct gcgtcacctt tgccgcccgc    94440
gaggagggcg cgtcgtccag caccagcgcc caggtccaga ttctgaccag cgcgctgaag    94500
aaggcgggcc aagcggccgc caacgccaag acggtctacg gggaaaacac acaccgcaca    94560
ttctcggtgg tcgtcgacga ctgcagcatg cgggcggtcc tccggcggct ccaggtcggc    94620
gggggaccc tcaagttctt cctcacggcc gacgtcccca gcgtgtgtgt caccgccacc    94680
ggccccaacg cggtgtcggc ggtgtttctt ttaaaacccc agcgggtctg cctgaactgg    94740
ctcggccgga gccggggttc ctcgaccggg agcttggcgt cccaggactc tcgggccggc    94800
ccgaccgaca gccaggactc ctcctccgag ccggacgcgg gcgaccgcgg cgccccagaa    94860
gaagaaggcc tcgagggcca ggcccgggta ccgcccgcgt tcccggaacc gccgggaacc    94920
aagcggaggc accccggggc cgaagttgtc cccgcggacg acgccaccaa gcgcccgaag    94980
acgggcgtgc ccgccgcccc cacgcgagcc gagtcgcccc ccctctccgc gagatacgga    95040
cccgaggcgg cggagggtgg tggggacggc ggccgctacg cgtgctactt tcgcgacctc    95100
cagaccggcg acgcgagccc cagccccctc tccgccttcc ggggtcccca aagacccca    95160
tacggctttg ggttgccctg acggcaacgg gtggtggccg aacgcctcac cgcgcccggg    95220
cacgcggggt gcgttgtgtt aaaaaaataa ataaatgggg tagtgtgtcc cccccccctc    95280
caaccaatat ggctgtcgtg tgtggttccg ggttgcgcct ccgtccttc cacccccctt     95340
cccctcctt ttttgttttg cgtgcgctta taagagcggg cccggggccc ttcgcagctt     95400
caccgagagc gccgtcgggc cccgggtgcg ggatgtgtcg cggggacagc cccggggtcg    95460
cgggcgggag cggcgaacac tgcctcggag gggatgatgg ggacgacggg cgccccccgcc   95520
tcgcctgcgt gggtgccatc gctcgggggt tcgcgcatct ctggctccag gccgccacgc    95580
tgggcttcgt ggggtctgtc gttctgtcgc gcggcccgta tgcggacgcc atgtcggggg    95640
cgttcgtgat cgggagcacc ggcctggggt tcctccgcgc ccccccgcg ttcgcccggc     95700
cgccgacgcg tgtgtgcgcg tggctgaggc tggtcggcgg gggagcggcc gtggccctgt    95760
```

-continued

```
ggagcctcgg ggaggccggc gcgcctccgg gggttccggg cccggcgacc cagtgcctgg      95820
cgctcggggc cgcctacgcg gcgctgctgg tgctggccga cgacgtccat cccctttcc       95880
tcctcgcccc gcggcccctg tttgtcggca ccctgggggt tgtcgtcggc gggctgacga      95940
taggcggcag tgcgcgctac tggtggatcg accccccgcg cgccgcggcc ctgacggcgg      96000
cggtggtggc gggcctcggg acaaccgccg ccggggacag cttttccaag gcctgtcccc      96060
gccaccgccg cttttgcgtc gtctccgcgg tcgagtctcc cccgcccga tacgcccgg       96120
aggacgccga gcggccaaca gaccacggac ccctgttacc gtcgacgcac caccagcgat      96180
ctccgcgggt ctgcggcgac ggggccgcac ggcccgaaaa catctgggtt cccgtggtga      96240
cctttgcggg cgcgctcgcg ctggccgcct gcgccgcgcg agggtctgac gcggctccgt      96300
caggcccggt cctgccgctg tggccccagg tgtttgtcgg gggccacgcg gcggcgggcc      96360
tgacggagct gtgtcagacc ctcgcgcccc gggacctcac ggacccgctg ctgtttgcgt      96420
acgtcggatt ccaggtcgtg aaccacgggc tgatgtttgt ggtccccgac atcgccgtat      96480
acgcgatgct gggggggcgcc gtgtggatct cgctgacgca ggtgcttggg ctccggcgcc      96540
gccttcacaa ggacccagac gccgggccct gggcggccgc gaccctgcgg ggcctctttt      96600
tctccgtcta cgcattgggg tttgcggcgg gggtgctggt gcggccgcgg atggcggcga      96660
gccggcggtc gggtgatcg ccatttcaaa taaaaggcac gagttccccg aataccaccg       96720
gcgtgtgatg atttcgccct accgctccga tccccggggg gagggggaa ggaaatgggg       96780
gcggggggtgc cgtggacggg tataaaggcc aggggggcag gcgggcccat cactgttagg      96840
gtgttaggtt gggaggtggc acaaaaagcg acactcccgt gttgtagttg tccgcgggag      96900
gcggtggttt ccggcaaccc tcctcgctgc gccgggcgcg cccaccggtc cttcgcgggg      96960
gccggggctc ttctggtcat ggcccttgga cgggtgggcc tagccgtggg cctgtggggc      97020
ctgctgtggg tgggtgtggt cgtggtgctg gccaatgcct cccccggacg cacgataacg      97080
gtgggcccgc gggggaacgc gagcaatgcc gccccctccg cgtcccgcg gaacgcatcc       97140
gcccccccgaa ccacacccac gccccccaa ccccgcaagg cgacgaaaag taaggcctcc      97200
accgccaaac cggccccgcc ccccaagacc gggccccga agacatcctc ggagcccgtg       97260
cgatgcaacc gccacgaccc gctggcccgg tacggctcgc gggtgcaaat ccgatgccgg      97320
tttcccaact ccacccgcac ggagttccgc ctccagatct ggcgttatgc cacggcgacg      97380
gacgccgaga tcggaacggc gcctagctta gaggaggtga tggtaaacgt gtcggccccg      97440
cccggggcc aactggtgta tgacagcgcc cccaaccgaa cggacccgca cgtgatctgg       97500
gcggagggcg ccggcccggg cgccagcccg cggctgtact cggtcgtcgg gccgctgggt      97560
cggcagcggc tcatcatcga agagctgacc ctggagaccc agggcatgta ctactgggtg      97620
tggggccgga cggaccgccc gtccgcgtac gggacctggg tgcgcgttcg cgtgttccgc      97680
cctccgtcgc tgaccatcca cccccacgcg gtgctgaggg ccagccgtt taaggcgacg       97740
tgcacggccg ccacctacta cccgggcaac cgcgcggagt tcgtctggtt cgaggacggt      97800
cgccgggtgt tcgatccggc ccagatacac acgcagacgc aggagaaccc cgacggcttt      97860
tccaccgtct ccaccgtgac ctccgcggcc gtcggcggcc agggccccc gcgcaccttc       97920
acctgccagc tgacgtggca ccgcgactcc gtgtcgttct ctcggcgcaa cgccagcggc      97980
acggcatcgg tgctgccgcg gccaaccatc accatggagt ttacgggcga ccatgcggtc      98040
tgcacggccg gctgtgtgcc cgagggggtg acgtttgcct ggttcctggg ggacgactcc      98100
tcgccggcgg agaaggtggc cgtcgcgtcc cagacatcgt gcgggcgccc cggcaccgcc      98160
```

-continued

| | |
|---|---|
| acgatccgct ccaccctgcc ggtctcgtac gagcagaccg agtacatctg ccggctggcg | 98220 |
| ggatacccgg acggaattcc ggtcctagag caccacggca gccaccagcc cccgccgcgg | 98280 |
| gaccccaccg agcggcaggt gatccgggcg gtggaggggg cggggatcgg agtggctgtc | 98340 |
| cttgtcgcgg tggttctggc cgggaccgcg gtagtgtacc tcacccacgc ctcctcggtg | 98400 |
| cgctatcgtc ggctgcggta actccggggc cgggcccggc cgccggttgt cttcttttcc | 98460 |
| accccttccg tcccccgtac ccaccacacc ccaccccacc ccccgccgt ccccggggcg | 98520 |
| ttataagccg ccgcactcgc ttttcccacc ggaaaatcct cggcccgatc cgaacggcgc | 98580 |
| acgccgcgtg ggctccaaac gcctccggaa gagagcgccc cgcccgata ttcaagcccg | 98640 |
| cggtggtgct atggctttcc gtgcttcggg acccgcctac cagcccctcg ccccgcggc | 98700 |
| ctccccggcg cgggctcgtg ttccggccgt ggcctggatc ggcgtcggag cgatcgtcgg | 98760 |
| ggcctttgcg ctcgtcgccg cgttggttct cgtaccccct cggtcctcgt ggggactctc | 98820 |
| gccgtgcgac agcggctggc aggaattcaa cgcgggatgc gtcgcgtggg accccacccc | 98880 |
| cgtcgagcac gagcaggcgg tcggcggctg cagcgcgccg gccacccta tccccgtgc | 98940 |
| ggccgccaag cacctggccg ctctgacacg cgtccaggcg gagagatcgt cgggttactg | 99000 |
| gtgggtgaac ggagacggca tccggacctg tctgagactc gtcgacagcg tcagtggcat | 99060 |
| cgacgagttt ttcgaggagc tcgcgatccg catatgctac tacccacgaa gccccggcgg | 99120 |
| gtttgtccgc ttcgtaactt cgatacgtaa cgccctgggg ttgccgtgag gcgcgcgtcc | 99180 |
| gacggtcccg cttctcgcct ctcttcttcc cccaccccac ccaccgacca acgacggcgt | 99240 |
| ttggccaata ccctcctttt ttctttttct cttcccccc cccaaaaaa aacaataaac | 99300 |
| agctaattgc gtacgacaaa ccatgcggaa ctcgctgttt tttttctctg tttgttactt | 99360 |
| tttattgaaa cagacatacg gggaaagggg ccggaaaccg agacggtggg gccggcggtc | 99420 |
| gcattttttt aatggctctg gtgtcggccg cgtttgagct tcgtcaacag ggcgctgagg | 99480 |
| gcggcgacgt tcgtcgggcc gtcgttggcc agcgcgttgg tccggggggcg ggcgggcatg | 99540 |
| ggcgacaggc ttagtcccgg gtccggggcg cgtgtggccc gccgagggga gaagagggca | 99600 |
| gacccgcccc agtcgtacag gggattttcc gcctcgatgt acggggagtc cggggcgtct | 99660 |
| cccggcaggg cggcccccgcc ggcaagacgc cggcgagggc agatgttttc gtataccccga | 99720 |
| acccagggga tctcctcgta gacgcgcccc ccatcctcgc ccaccgactc gtaaatggaa | 99780 |
| tctgcgtcct cggaggggggc gcggggggcg tggctttcgg ccggccaggc ggcggcggcg | 99840 |
| gtggtgtcgc cggcggggggt ggcgccaagc ccgacgcccg cgggcatggc ggcgtcatcg | 99900 |
| tcgggcagca gatacgtgtt ttccatctgg tccggttcgg cctccgcgtc cggccccag | 99960 |
| gtccgcaccg cgtcgtagac cccggcgcc tcgcgctgag ccgcgagcgg gcgcgccgcg | 100020 |
| gctgccggcc gctgctcggg gggcgcgggg ttgcggggcg ggaggcgcgg gggcgccccg | 100080 |
| gccatatgcg tgtaatacgt ggccggccgg ccggcgcagg gctcgggacc ccgtcggcc | 100140 |
| gcgtcgacgt gcgggggctc ggggaggtcc tcgcggtggc gcctgcacct ccgagggggcc | 100200 |
| gcgggggtcg agtgggggcg agcccggggg agcggcgggg gtgcgttgtc gcgccgggtc | 100260 |
| cgttgtatct tgtcccggca gctcccgccg accgcgccgc ggcccccgg tgggccggac | 100320 |
| gccgcgaggc gcaggatgga ctcgtagtgg ggcgacgggg ttccgctccg aagcaggtcc | 100380 |
| ggggccaggg cggccccgaa ccaggacttg atgctgagtt ccatccgggc ccagctcggg | 100440 |
| gcggtcatcg tggggaacag gggggcggcg gtcctgcaga agcgctcctg gctgtccacc | 100500 |
| gccgccgtaa ggtactcgtt gttcaggctg tcggaggccc agacgacata cccggtaagc | 100560 |

```
gtcgcgttaa ttatatactg ggcgtggtgg tggactatgg atagaacctc gacggtcgag    100620
acgatggcgt ccacgatccc gtacgtgccg ccgctgcgct tgccggtctc ccacaggtgg    100680
gccaggcgcg tcaggtggcc caggacgtcg ctgaccgccg cccgcagggc catgcactgc    100740
atcgagcccg tggtgccgct gggcccgcgg tccagtggc gcgcaaacgt ctccgcgggc     100800
gcctccagac tcccgctgag cgccacgaac cggcgatcgg cggggcccag gcggcgacac    100860
acgtacttgt ccgccgtcca cagcatccac gaggcccaat ggtacaacac ggagacgtag    100920
gccaggagct cgctcagccg cagtgcggtg tccgtgctcg gccggctcgg gtctgcgggg    100980
cgcataaaga acatgtactg ctggagcctg tgggccgcgt cgcgcaaccc cgccaccgcg    101040
gcggcgtact tggccgcggc ggccccgctc ttgaacgggg cgcgcaccag cagcttcggg    101100
agcagggtgg gccgcagcag cacgtgcagg ctggggtcgc agtcgcccgc cgggtcgtcg    101160
gggatgtcca ggccgctggg cacgaccgtc tggaggtact tccagtactg cgctaggatg    101220
gcgcggctca gctggccgcc cgacagctcc acctcgccga gcgcctgctt ggcggccgac    101280
gcgtagtgcc ggatgtagtc gtagtgcggg tcgctggcga gccgtctac gatcaggctc     101340
tcggggacgg tgttatggtg ccgcgccgcc agccggacgc tgcgatcggc gccggtcaga    101400
aacgccggct gcaggtcgtc ggcgcgctgc cgcaggacgc ccacggccgc gctgaggagc    101460
ccctccgggg tggggagcag acacccggcg aagatgcgcc gctcggggac gcccgcgttg    101520
gcgccgcgga tgaggttggc cggcgtcagg caccgcgcca gccgcaggga gctcgcgccg    101580
cgcgcccggc gttgcatggc ggagaccgtt cggtcggggg ccccgccggt cggaggtatg    101640
ccgcgtcccg ggatataggg ttgcttttta tggggaggcg cctatgggcg tggcgggccg    101700
cccagcccgg tcgcgcgcct cccggacacg tgcgcccgga gggcggcggt ctcctcgtcg    101760
cccatgagca gtttccgaaa ctgcgccatg atgtccacga cgcggacccg cggccccagc    101820
acggactcgc tattcagggg ggcggggggg aaggccgcca ggtcttcgag caggaaggcg    101880
gggtctgccg tcccgctcac gggcgcccgg ggcgccgagg acgcggggcg aaggtccacg    101940
tgttccgcgg cggcgcgcac gtccgcccaa aatttggcgg gggtggtccg cgcgtacagg    102000
ggctgggtcg cgcggaggac gcacgcgtag cgcagggggg tgtacgtgcc cacctcgggg    102060
gccgtcgacc cgccgtcaaa cgcggccagg gccacgcacg cgaccaccgt gtcggccagg    102120
cccagcagcc gctgcaggat gagccccgtc gccagcacgg cgcgcgcggc cgccgcgtcg    102180
tccctgcgcc ggcgcgcgtc cccgcaggcc agggcgtatt tcagggtaac ggtcgccagg    102240
gccgtgtgca gcgcgtacac ggccgcgccc agcacggcgt tcagcccgct ggtggcgagc    102300
aggcggcgcg ccgcggtgtc gcccagcgcc tcgtgctcgg ccgccacgac cccggggctg    102360
cccagggcgca gggcgcgaaa cagcgcctcc tgctccacgt ccgcaaacgc ggggtgggcg    102420
gagtgcgggt gcaggcgcgc ccccacgacc accgagagcc actggaccgt ctgctccgcc    102480
aggaccgcca gcacgtccag gacgcgcccc gcaaacgcgg cctcccgcgg gagcacgcat    102540
ttgacggcgc cggggttgaa gcgggcgagc agagccccgg tggcgatgta cgtcatgcgc    102600
cccgcgtagc gggcggccac gcgacagtcg cgccccagga gcgcgcgcac cccgggccag    102660
tacagcaggg accccagcga actgcgaaag accgcggcgt cggggccggg gtgggggggc    102720
gcggcccctc ccgcgctgag cagcggcacg gcggcggccc ccacgggccg caacgccgtg    102780
aggctcgcga actgccgtcg gagctcggcc gccctgtcgt cgagctccga gccgcgcccc    102840
tccgtgtgca ggcgcgtccc gcagaccac ccgttgatcg ccaccgcac gatgcgtcg      102900
accagaaaac ccatcgcgcg ggaggggctg gttttgccc gccgatccgt caggtcgagg    102960
```

-continued

```
atcgcgtcgc ccgtgacgta ccaggccagc gcctcgccct gctgcagcgt ctggcggaaa   103020
aacacctttg ggtcggccgg ggaggcaaag tgcatgaccc ccacgcgcga cagcccgaac   103080
gcgctatccg gacacgggta gaacccggcc ggatgtccca gggccagggc cgagcgcacg   103140
gactcgtccc acgcggcgac tcgggggggtc aggcggtcca gggggaatgc cgcctgcagc   103200
tccgggcccg acacgcggcc cgcgagaatc tcgaccgtcg cggaaggccg cccccgggg    103260
ccgtcatcgt gcgcgacggc ggcggggtag tcgtcctcct cgtagttgag ctcgtccagg   103320
aacagcggcg agggcaccac ccgcgaaccg cccacccgcc ccaaaacgtc gcgtgggtcc   103380
atcgggccca ggtagcctcc ccgcggggcc cgcgtgatgg cgctgtcccg cgtccgcga    103440
acggactggc tcctggccgt aacggacctg gggcgcggaa aggacgcccg gcggggggc    103500
gccgccgccc gggcctcgga cgcgcgtcgg gacccggggt gaccgcgggc ctccggcga    103560
cggcgcgggg gcggctcttc gctcgccatc tcccccgcgg cctcgacctc gctgtcgtcg   103620
tccacgttaa acaccgcccg caggtacccc attaacccga ctccaccgcc ctcgggctcg   103680
tcctccacgg gcgagtcggc gcgatgcgcg gacgggcat gggaccgggt ggaggcgcgc   103740
ctccggcgta cggcatgccc gcgcacggac atggtggccg gaggcccgat tttttacaca   103800
cgccctcccc gcagacggac gaggaaaggg gtggtgcgag gggggaggcc caaacgggga   103860
ggtgggggt aggggcggt cccagggagc gggggtagg aaccggcacg acggaacag      103920
agaaaacgcg accgctccaa caagggtggg ggggtgggcc tcgtccccac gcagacccgc   103980
gggcaaatgc gagaacggga cccgcgcgcc tgcctttata cgcggacccc agcaccacga   104040
gccgttctgt gacgcgaatc tacacgaccg cgggctcgta ggcgcgacta acgcccaacc   104100
caacggcaca caccccccac cccgcgcgta acccccatttc tttcatggtc ccgtaataaa   104160
cagccaacgc acgccgcgta tgatgagttg cttgccaatg tttattgctg tggttgcgaa   104220
ccctctatcg cgatacagac ggaggtgagg cggggcggtg gtgggggggg ggcgcgccgc   104280
ccggtcgcac atcctacccc ccaaagtcgt caatgcccat ggcatcggta acatctgtt    104340
caaactcaaa atcgtccacg tccaaagccc catacgagac ggggtcgtgg gtcattcccg   104400
gggaggggga ctccacgtcc cccagcatct ccaagtcgaa gtcgtccagg gcgtcggcgg   104460
gcgtcatatc cacctcctcg ccgtccaggc ggagttcgtc tcccaggctg acgtcggtaa   104520
tgggggcggt ggtggacagt ctgcggggc gttgtcccgc ggagagaaac gacatgcgcg   104580
gcgccaccag cccggcctcc gcaggagcgt catcgtcgtc cgggaggtcg agcaggccct   104640
cgattgtcga tccgtaattg tttctggtcc gcccgcggct atacgcgtgc tcccgcatga   104700
cggactcgcc ctccgaggtc gcgacgctgg agtacgagtc caacttggcc cggatcagca   104760
gcataaagta cccagaggag cgggcctggt tgccctgcag gacgggcggg gtcgtgaggg   104820
gcgccccggg ttcctccgcc gccgcacttc gcaccagcgg gaggttcagg tgctcgcgaa   104880
tgtggtttag ctcccgcagt cgccgggcct ccacgggaac tccccgcacg gtgagcgatc   104940
cgttgataaa catcaggggc tgaaacagac acgccaactg gcgccagctc tccaggtcgc   105000
agcagaggcc gtcgaacaga tcgggccgca tcatctgctc ggcgtacgcg gcccatagga   105060
tctcgcggct cagaaagagg tatagatgca gaaacaggac gcgcgccagg cgcgcggtct   105120
cgcggtagta cctgtccgcg atcgtggtgc gcagcatctc ccgcaggtcg cggttgcggc   105180
cccgcatgtg tgcctggcgg tgtagctgcc gaacgctggc gcgcaggtac cggtacaggg   105240
ccgagcaaaa atttgccaac acggtccggt agctctcctc ccgcgcccgc agctcaccgc   105300
ggaaaaactg cgccatggcc tcgtagtacg aaggcagctc gtcgcgggtg gcgggcaggg   105360
```

-continued

```
tggggaacgc cacgtcgccg tgggcgcgaa tgtcgatcgg ggagcgctcg gggacgtgcg  105420
catccccca  gtcgatcacg tcgctgggca gcgtcgacag aaacttgcac tcccggtaca  105480
tgtcggcgtt ggtcgggaac ccagagaaca ggtcctcgtt ccaggtatct agcatggtac  105540
acagcgcggg acccgcgctg aagcccagat cgtcgaggag acggttaaac agggccgcgg  105600
gggggacggg catgggcggc gagggcatca gctgggcctg actcagccga ccggtggcgt  105660
acagcggagg ggcggctggg gtgttcttgg accccggc   tggcctgggg ggcggtggcg  105720
aaacccgtc  cgcgtccgca aacagatcgt cgaccaacag gtccatgggg gcggttgggt  105780
ccgggaataa cgatctcgag aggcgaatga gacgtgcccg agcgcccggc ggcggagagg  105840
ggggagggga tccgggaccc gcgacagaaa aaggccgggg ccctcgcgaa gggaatcgcc  105900
ggggggtgccg tgcgtccccg aggactgaca tctcgcgtcc accacccgc  atttaagtat  105960
caccccagtg ccgccccaaa cctcgtgact tccccaccgc tccgggcggc ccgtcccccg  106020
cgctcggaag ggaggcgtgt ccttcctccc gcccctcccg cccctcccgc ccctcccgcc  106080
cctcccgccc ctcccgcccc tcccgcccct cccgcccctc cgcccctccc  106140
gcccctcccg cccctcccgc ccctcgcac  aaacgcgtgc tgacagcgaa gtggttaaat  106200
cgaccgtgat gctttattgt ctgtcgtctg aacgcggtcg gggtcgctac tcgagggggc  106260
ggcggggacg ggaagccgag cgggcggggg ccgtgcggt  cgcggcggca cgccccgcgg  106320
ggcggccccg ggcggccgcg gtcgcgtcga cgtcctgcgc cgcgtcggga ttcaccaact  106380
cgttcgcgcg ctgcaggagg ttcttgccct cgcagaccgt cacgcgaatg gtggtgaggt  106440
cgaggagctc gttgaggtct cgtcggtgt  gcggccgcga catgtcccac agctgtaccg  106500
ccgccagccg ggcgtgcgtg gccgccaggc gcccgaccgc ggcgcagaag acgcgcttgt  106560
tgaacccggc caccgggggg gtccacggcg ccgtgggggct cggtggggcg gtgctgaagt  106620
gcagcttctt ggccagtccc tgggcgggtg tcttggttct tcccgaggcc gtgggagcgg  106680
gggcgtctag gagcacggcg gagtcggcct gggcgggtcg cctgccgcgg gcggggtcgg  106740
tcgccggggt cgcggaggcc ttaggcgccc cgcgcgtcat tttgggggtc cgcgcgggag  106800
gggcgtgcga gcgcccgccg gcgcccacgg ggcccccggg gggtggagga gcgcgcgcgg  106860
ggccggggcc gtgagagccc gcgacggacg ccgaacgacg cggtcgcgcg gtatcccggg  106920
actcgtcgtc gtccgaagac gagtcccggt agagggcata cccagcctcg tcataatgga  106980
gaaagcgaac ctcgcccctc gggcgcgcgc gcatcgggcc agcgccgcgg cggaagtcgt  107040
cgcgcggact ctctgggtcc gccggggaga ccggccata  gtacagctcc tcgtgggtcc  107100
cgcgcggcgc ttcccgcgga cacgacttga cggagcggcg agaggtcatg gtctatcgga  107160
gacaccgggg acgcccgtgc ggatcacagg gaaggcgtcg gcgaaggagg cagagagcgt  107220
cggaaggcgg cgagggaggg aaagagggag accggcgggg tacgggagag cagcgagggc  107280
ctgcgtaacc cacgggggcc gcgggagtgg ctccctgcgg gttgcggggg agagtttata  107340
ggaagtggat ataaccgcag gcgacgggac taaccaatcc ccgggggggc aacggacaga  107400
cacgccccga acaggcccga cttccgcgag gaagcaaagg ccgggggccg cccaacgaca  107460
cgcccacccc ttcccaacag ggcgggctca ggctgacccg cgccagtg   cccgctgaca  107520
tatctgatac acgtgcgcga tcatacatac gcccatcgag gtcatgccta gataaagggg  107580
caccaggacc cccgggacgg acaccacacc ggcgctgtcg ccccggcatt gcgcgtcccc  107640
gataacgccg cgtgcgcctg ccgcgttcgg cggctccccg ggcacgcccg cgacgagcgc  107700
gacgaacaac agcaccaccc agcggcccag tcttgcgggt ttccccgtca tcgcggcgat  107760
```

```
gagtcagtgg gggcccaggg cgatccttgt ccagacggac agcaccaacc ggaatgccga   107820
tggggactgg caagcggccg tagctattcg cgggggcgga gtcgttcaac tgaacatggt   107880
caacaaacgc gccgtggatt ttaccccggc agaatgcggg gactccgaat gggccgtggg   107940
ccgcgtctct ctgggcctgc gaatggcaat gccgcgggac ttctgcgcga ttattcacgc   108000
ccccgcggta tccggccccg ggccccacgt gatgctcggt tcgtcgact  cgggctaccg   108060 cggaaccgtc ctggccgtgg tcgtagcccc gaacgggacg cgcgggtttg ccccggggc    108120 cctccgggtc gacgtgacgt ttctggacat ccgggccacc ccccgaccc  tcaccgagcc   108180 gagctccctg caccggtttc cgcagttggc gccgtccccg ctgcagggt  tacgagaaga   108240 tccttggttg gacggggcgc tcgcgaccgc cgggggggcg gtggccctgc cggccagacg   108300
gcgcggggga tcgctggtct acgcgggcga gctaacgcag gtgaccaccg agcacgcgca   108360
ctgcgtgcac gaggcgcccg cctttctgcc aaagcgcgag gaggacgcag gctttgacat   108420
tctcatccac cgagccgtga ccgtcccggc caacggcgcc acggtcatac agccgtccct   108480
ccgcgtattg cgcgcggccg acggaccaga ggcctgctat gtgctggggc ggtcgtcgct   108540
caatgccagg ggcctcctgg tcatgcctac gcgctggccc tccgggcacg cctgtgcgtt   108600
tgttgtatgt aacctgaccg gagtcccggt gaccctacaa gccgggtcca aggtcgccca   108660
gctgctcgtc gcggggaccc acgccctccc ctggatcccc cccgacaaca tccacgagga   108720
cggcgcattc cgggcctacc ccagagggt  tccggacgcg accgccaccc cccgagaccc   108780
gccgattttg tgtttacga  acgagtttga cgcggacgcc  ccccaagca agcgggggc    108840 cgggggtttt ggctccactg gcatctagac cgcgcctcgc gtcgggccag atgggcccc    108900 ggtcaataaa gagctctgtt tcgcatatgc cctggtgttg gcggttttttt tttgttgtct  108960 gtctgcccgg cgctcggttg tccgttctgt cgtcgctatc acatacgcac aaacacacgg   109020
gtagagtgga accgaaaccg gtcgacgttt attcaccaca cagaaacaca agctaagcga   109080
gaaggagggg ggcctcggtc gacgaggcct ggcgtttggg ggcggacgtg cgatgacgtg   109140
ggtccggtgt agggtccgcg gggggcacgg gcccggggcg aacgggggat ctgtcgccgg   109200
cgtgggtgac tgggaccgac gcaacctccg gggcttgtgc cctcgtaggc ccggggggg    109260 cctcggtcgc tccaagcccc gcggtgcggg tccctccggc cagagccgag gtggagagac   109320
caagggcccg ctccgcgatc gccacgtcct ccatgaccac gtcgctctcg gccatgctcc   109380
gaatggcctg ggagacgagc acgtccgccg acttgtccgc ggcccccacc gacatgtaca   109440
tctgcaggat ggtggccatg cacgtgtccg ccaggcggcg catcttgtcc cgatgcgccg   109500
caacggcccc gtcgatggtg gagccctcga gtcccgggtg gtggcgcgcc agcctctcga   109560
ggttgaccat gcaggcgtgg tatgtgcggg ccagggcgcg cgccttcacg aggcgccggg   109620
tgtcgtccag cgactctagg gcgtcgtcga gcgtgatggg ggcgggcaaa agcgcattga   109680
ccaccgccag ggcctcctgc agccgcgcct ccgcctccga gggcggagcc gcggcccgaa   109740
tcatctcata ttgttgttcc tcgggcgcg  ttccccaacc gcacagcacc ccgagcaggg   109800
acgccatccc ggaacacgcg cgcggctctg cgccggcttt ccccaccccc accccctccg   109860
ggttcgcagg ggcgatgggg acggaagact gcgatcacga agggcggtcg gttgcggctc   109920
ccgtggaggt tacggcgctg tatgcgaccg acggtgcgt  tatcacctcc tcgctcgccc   109980
tcctcacaaa ctgcctgctg ggggccgagc cgttgtatat attcagctac gacgcgtacc   110040
ggtccgatgc gcccaatggc cccacggcg  cgcccaccga acaggagagg ttcgagggga   110100
gccgggcgct ctaccgggat gcgggggggc taaatggcga ttcatttcgg gtgaccttt    110160
```

-continued

```
gtttattggg gacggaagtg ggcgtgaccc accacccgaa agggcgcacc cggcccatgt    110220
ttgtgtgccg cttcgagcga gcggacgacg tcgccgtgct ccaagacgcc ctgggccgcg    110280
ggacccgatt gctcccggcc cacgtcacag caactctgga cttggaggcg acgtttgcgc    110340
tccacgctaa catcatcatg gctctcaccg tggccatcgt ccacaacgcc cccgcccgca    110400
tcggcagcgg cagcaccgcc ccctgtatg agcccggcga atcgatgcgc tcggtcgtcg    110460
ggcgcatgtc cctgggcag cgcggcctca ccacgctgtt cgtgcaccac gaggcgcgcg    110520
tgctggggc gtaccgccgg gcgtattatg ggagcgccca agcccctttt tggtttctga    110580
gcaaattcgg cccggacgaa agagcctgg tgctggccgc taggtactac ctactccagg    110640
ctccgcgctt ggggggcgcc ggagccacgt acgatctgca ggccgtgaaa gacatctgcg    110700
cgacctacgc aatcccccac gacccacgcc ccgacaccct cagtgccgcg tccttgacct    110760
cgttcgccgc catcactcgg ttctgttgca cgagccagta ctcccgcggg gccgcggccg    110820
ctgggtttcc gctgtatgtg gagcgccgca tcgccgccga cgtacgcgag accggcgcgc    110880
tggagaagtt catcgcccac gatcgcagct gcctgcgcgt gtccgaccgg gaattcatta    110940
cgtacatcta cctggcccac tttgagtgct tcagcccccc gcgcctggcc acgcatctcc    111000
gggccgtgac cacccacgac cccagccccg cggccagcac ggagcagccc tcgcccctgg    111060
gtcgggaggc ggtggaacag ttcttccggc acgtgcgcgc ccagctgaac atccgcgagt    111120
acgtaaagca aaacgtcacc cccagggaaa ccgccctggc gggagacgcg ccgccgcct    111180
acctgcgcgc cgcacgtat gccccggcgg ccctcacgcc cgcccccgcg tactgcgggg    111240
tcgcagactc gtccaccaaa atgatgggac gtctggcgga agcagaaagg ctcctagtcc    111300
cccacggctg gccgcgttc gcaccaacaa ccccgggga cgacgcgggg ggcggcactg    111360
ccgcccccca gacctgcgga atcgtcaagc gcctcctcaa gctggccgcc acggagcagc    111420
agggcacgac gccccggcg atcgcggctc tcatgcagga cgcgtcggtc caaacccccc    111480
tgcccgtgta caggattacc atgtccccga ccggccaggc gtttgccgcg gcggcgcggg    111540
acgactgggc ccgcgtgacg cgggacgcgc gcccgccgga agcgaccgtg gtcgcggacg    111600
cggcggcggc gcccgagccc ggcgcgctcg gccggcggct cacgcgccgc atttgcgccc    111660
ggggcccccgc gctcccccccg gcggcctgg ccgtcggggg ccagatgtac gtgaaccgca    111720
acgagatctt caacgccgcg ctggccgtta cgaacatcat cctggatctg gacatcgccc    111780
tgaaggagcc cgtcccctttt ccccggctcc acgaggccct gggtcacttt aggcgcgggg    111840
cgctggcgg ggttcagctg ttgtttcccg cggcccgcgt agaccccgac gcctatccct    111900
gttattttt caaaagcgcc tgtcggcccc gcgcgccgcc cgtctgtgcg ggcgacgggc    111960
cctcggccgt tggcgacgac ggcgacgggg actggttccc cgacgccggt ggtcccggcg    112020
acgaggagtg ggaggaggac acggaccccca tggacacgac ccacggcccc ctcccggacg    112080
acgaggccgc gtacctcgac ctgctacacg aacagatacc agcggcgacg cccagcgaac    112140
cggactccgt cgtgtgttcc tgcgccgaca agatcgggct gcgcgtgtgc ctaccggtcc    112200
ccgcccgta cgttgtgcac ggctccctga cgatgcgtgg ggtggcgagg gtgatccagc    112260
aggcggtgct gttggaccgc gacttcgtgg aggccgtagg gagccacgta aagaactttt    112320
tgctgatcga tacgggcgtg tacgcccacg gccacagcct gcgcttgccg tatttcgcca    112380
agatcggccc cgacggctcc gcgtgcggcc ggttattgcc cgtcttcgtg atccccccg    112440
cgtgcgagga cgttccggcg ttcgtcgccg cgcacgccga cccgcggcgc ttccactttc    112500
acgccccgcc catgtttccc gcggccccgc gggagatccg cgtcctccac agcctgggcg    112560
```

-continued

```
gggactatgt cagcttttc gagaagaagg cgtcgcgcaa cgccctggag cactttgggc    112620
gacgcgagac cctgacggag gttctgggcc gctacgatgt gcggcccgac gccggggaga    112680
ccgtggaggg gttcgcgtca gaactgctgg ggcgaatagt cgcgtgcatc gaggctcact    112740
ttcccgagca cgcgcgggaa tatcaggccg tgtccgttcg ccgggccgtc attaaggacg    112800
actgggtcct gctgcagctg atccccggcc gcggcgccct gaaccaaagc ctctcgtgtc    112860
tgcgcttcaa gcacggcagg gcaagtcgcg cgacggcccg gacctttctc gcgctgagcg    112920
tcgggaccaa caaccgccta tgcgcgtccc tgtgtcagca gtgctttgcc actaaatgcg    112980
ataacaaccg cctgcacacg ctgtttaccg tcgatgcggg cacgccatgc tcgcggtccg    113040
ctccctccag cacctcacga ccgtcatctt cataacggcc tacggcctcg tgctcgcgtg    113100
gtacatcgtc tttggtgcca gtccgctcca ccgatgtatt tacgcggtgc gccccgccgg    113160
ggcgcacaac gataccgccc tcgtgtggat gaagataaac cagacgctgt tgtttctggg    113220
cccgccgacc gccccccccg gcggggcatg gacccccac gcccgcgtct gctacgccaa    113280
tatcatcgaa ggtcgggccg tgtccctccc ggccatcccc ggcgccatga gccgccgggt    113340
catgaacgtg cacgaggccg taaactgctt ggaggccctc tgggacaccc agatgcgcct    113400
ggtggtcgtc ggttggtttc tgtatctagc gttcgtcgcc cttcaccaac gacgatgcat    113460
gttcggcgtc gtgagtcccg cgcacagcat ggtggcccg cgacctatc ttttgaacta    113520
cgccggccgc atagtgtcga gcgtgttctt gcaataccc tacacgaaaa tcacccgcct    113580
cctctgcgag ctatccgttc aacgccagac cctggtgcag ctgttcgagg cggatccggt    113640
caccttcttg taccaccgcc cggccattgg cgtcatcgtg ggctgcgagc tgctgctccg    113700
cttcgtggcc ctcggtctca tcgtcggcac cgctctcatc tcccggggcg cctgcgcgat    113760
cacacacccc ctgtttctaa caatcaccac ctggtgtttc gtgtccatca tcgccctgac    113820
ggagctgtat ttcatcctgc ggcgggctc ggcccccaaa aacgcggaac cagcggcccc    113880
caggggcgc tccaaagggt ggtcgggcgt ctgcgggcgc tgctgttcca tcatcctctc    113940
cggtatcgcc gtgcgcctgt gctatatcgc cgtcgtggcc ggggtggtgc tcgtggcgct    114000
tcgctacgaa caggagattc agcggcgcct gtttgatctg tgacgtaacg cctcttccgt    114060
tggaagaggc ggacccagtc gcccatacaa attaaataca cgacccgcct cgggcctacg    114120
caccctcgca cgtcgcatgc aaattaaaat cgtgcacaga gccgatccgg cctcgggtct    114180
gcttgcccct cccccggccc agcacaggca ggctcgtccg acttccgcat acaccccacc    114240
ctaccgcgtg cttccgcacc cccgcctacg cgtgtacgcg aaggcggacc cagacctgcc    114300
gtatgctaat taaatacata aaacccaccc tcggtgtccg attggtttct ggggacggcg    114360
ggggcggggg cggtgacgcc cgacggggag ggacaaggag gagtttcgga aagcggcccc    114420
cggtcgtgcg ggtataaggg cagccaccgg cccactgggc gctgtgtgct gccgtgtgcc    114480
gaccccggtt gcgcgtcggt gccgctcctc gattcggacc cggccactct cttccgacac    114540
gcgccccctc ggaggacacc cgccatccca gccccggcga cctacaacat ggctaccgac    114600
attgatatgc taatcgacct aggattggac ctgtccgaca gcgagctcga ggaggacgct    114660
ctggagcggg acgaggaggg ccgccgcgac gaccccgagt ccgacagcag cggggagtgt    114720
tcctcgtcgg acgaggacat ggaagacccc tgcgagacg gagggcggca ggccatcgac    114780
gcggcgattc ccaaaggtcc cccggcccgc cccgaggacg ccggcacccc cgaagcctcg    114840
acgcctcgcc cggcagcgcg gcggggagcc gacgatccgc cacccgcgac caccggcgtg    114900
tggtcgcgcc tcgggaccag gcggtcggct tccccccggg aaccgcacgg ggggaaggtg    114960
```

```
gcccgcatcc aaccccgtc gaccaaggca ccgcatcccc gaggcgggcg gcgaggtcgc    115020
cgccggggcc ggggtcgata cggccccggc ggcgccgact ccacaccaaa accccgccgg   115080
cgcgtctcca gaaacgccca caaccaaggg ggtcgccacc ccgcgtcggc gcggacggac    115140
ggccccggcg ccacccacgg cgaggcgcgg cgcggagggg agcagctcga cgtctccggg    115200
ggcccgcggc cacgaggcac gcgccaggcc cccctccgc tgatggcgct gtccctgacc    115260
cccccgcacg cggacggccg cgccccggtc ccggagcgaa aggcgccctc tgccgacacc    115320
atcgaccccg ccgttcgggc ggttctgcga tccatatccg agcgcgcggc ggtcgagcgc    115380
atcagcgaaa gctttggacg cagtgccctg gtcatgcaag acccctttgg cgggatgccg    115440
tttcccgccg cgaacagccc ctgggctccc gtgctggcca cccaagcggg ggggtttgac    115500
gccgagaccc gtcgggtttc ctgggaaacc ctggtcgctc acggcccgag cctctaccgg    115560
acattcgcag ccaacccgcg ggccgcgtcg acagccaagg ccatgcgcga ctgcgtgctg    115620
cgccaggaaa atctcatcga ggccctggcg tccgcggatg agacgctggc gtggtgcaag    115680
atgtgcattc accacaatct gccgctccgc ccccaggacc ctatcatcgg aacggcggcc    115740
gccgtgctgg aaaacctcgc cacgcgcctg cgcccctttc tgcagtgcta cctgaaggcc    115800
cgaggcctgt gcgggctgga cgacctgtgc tcgcggcgac gcctgtcgga cattaaggat    115860
attgcctcct ttgtgttggt catcctggcc cgcctcgcca accgcgtcga gcgcggcgtg    115920
tcggagatcg actacacgac cgtgggggtt ggggccggcg agacgatgca cttttacatc    115980
ccgggggcct gcatggcggg tctcattgaa atactggaca cgcaccgcca ggagtgttcc    116040
agtcgcgtgt gcgagctgac ggccagtcac actatcgccc ccttatatgt gcacggcaaa    116100
tacttctact gcaactccct attttaggca agaataaaca tattgacgtc aacccaagtg    116160
gttccgtgtg atgttcttgg cgcgcgcggc gggtggggcg gagactccgg ggcgatgccg    116220
gcgtgcgcgt gggaggaggg cgatgaccca ccggataaat gtggggcccc ggcccggccc    116280
gcttcatagc gcgtccagga actcacggca gacgcgtatt caccgacccc cccctcgcaa    116340
catgacaacg acgcccctct cgaacctgtt tttacgggcc ccggacatca cccacgtcgc    116400
cccccgtac tgtctgaatg ccacgtggca ggccgaaaac gccctgcaca cgaccaaaac    116460
ggaccccgcg tgcctggccg cgcggagtta tttagtccgc gcctcctgct cgaccagcgg   116520
ccccatccac tgtttttct ttgcggtgta caaggactcg cagcactccc ttccgctggt    116580
taccgagctc cgcaacttcg cggacctggt caaccacccg cccgtcttgc gcgaactaga    116640
ggataagcgt gggggcggc tgcggtgcac gggcccattc agctgcggaa ccatcaagga    116700
cgtctccggt gcatccccg cggggaata cacgataaac ggtatcgtgt accactgtca    116760
ctgtcggtat ccgttctcca aaacctgctg gctcgggcca tccgcggccc tacaacacct    116820
tcgctctata agctcaagcg gcacggccgc tcgcgcggca gaacagcgac gccacaaaat    116880
caaaatcaaa atcaaggtat aacccacccc cttccctccg agtccgtatg caacctcatt    116940
aataaagagt gagaaccaac caaaacagac gcggtgtgag tttgtgggtt ataggaaccc    117000
ggtaaatacc acgcgacgaa ccagcatgtg tgttaacgca actttattc gttgtatcgc    117060
gggagggggg aagcttaccg ccaaaggaag gccaagatga taacgacgac caccgcgacc    117120
accccaaaaa ccgcatgacg acacgtcccg ccacaccacc ctggggcttg gggcgtgtcg    117180
gagctcgacg cacagcgggc cgcgcgttgg gcccggtaca gctctcgcga attgacaagc    117240
ggggggtcgcc acgtgcgcga gctttgcacg cggggttggt cggccggccc cacgacccg    117300
cccggtggct cggtcggaca tgcggccatg accatggcgt aggtgggggg gcgatccgag    117360
```

```
gtcgcctctg cgtaagtagg gaggcccgac gggaggtcgc ctcccacgcc agggtgggcc    117420
ccaatcatag tttccggtag aaacaggggg gtctccacaa acaacccccc tgggccaaag    117480
ctccggcgcc gcgcccgtcg ttcggcgcgc cgcctggcgc gccgagcggc ccgccaggcg    117540
gcgcggcgcg agcggccacg ctcacacacc tcgccgtcac cggaagaagc cggtgaaaca    117600
agcccaaccg gcgacgtccc tgcagagtac ggtggaggcg agtccgtggg ggtgtcgata    117660
tcaataacga caaactggcc cgcgctcgcg ccggccacac tctcgtatgg gggcggggcg    117720
tcaatcacgc tatcatctcc gtcatccctg catgcgtggg catgcccagc ccccaacgcc    117780
atggtgggga ttcgcggctc agaagcctgc atgtcgtgtg gtcggtcgta gtccaacgtg    117840
cctcccccac ccaccacaca gccggtcccc acgccgacca ctagaccgca gacgtcgccc    117900
aaccgaggtc cccgtgcaca gaccgcgcct tttatagccc caggggttgc taattaacgc    117960
acgcatgcag acgcaattta ttttgctccc ccgcgtcctc ccctcccctg cgcacacgtg    118020
ataggtcttg ggaacccgag gggcgacgcg gggaaagcgc gcccccgccc ggccgccgcg    118080 cgccccgcc cggccgccgc gcgccccgc ccggccgccg cgcgccccg cccggccgcc     118140 gcgcgccccc gccggccgc cgcgcgcccc gcccggccg ccgcgcgccc ccgcccggcc     118200
gcccgcgtcg cgccggcgcc ccctccggc gcttccgggg tctttccttc cttccccgcc    118260
gcgaccccga ccccgcccca ccgccccgcc cggcaggggg gccccggcgc cgcgcagaac    118320
acacagacga acacacggtg gcgatctttt ctttacttcg gcggaccagc gagccccggc    118380
cccggcccgc gccccgccgc cacacccacg gcacccccc ccgccgccca ccccgggtc     118440 cacacaggag cgcgcgggcg gcagaaacgc gggcgcggcg gcggtcgggg tgggagtggt    118500
ggtgggggac acgaaaacac acccacgaca ctctccccc accccgaccg ccgccgcgc     118560 ccaccggcgg gatcgcggcg agacgcagcc gggccccccc ccaccacccg cccacccacc    118620
taccccgcgc ccgcagcctc cggcagcacg ccgaccaccg ccgccacccc ccaaacagcc    118680
aaggcgcggt gggggcgtg gtggtgaacg atgggggga cacggggggg agggtccgg     118740 ggcgaggcgg gcgggcgaag gaagggggg tggtggcggc ggcggtggaa agcggaaaaa    118800
cggaggatgg aagggcagaa gatggggagt cccgatcctc ctcctgcatc ccctcgcctt    118860
ccattctccg gccctccgcg agtcccgacg cccccccccc gccgcccgac gaaggagacc    118920
caagcaccgc agccggagag gccgagcggg gagtgggcgg ccgggcggga ggatggcgga    118980
gagagagaga gagagagaga gaggggggg ggggagagg gaaagcaacg ggaaagagag     119040
gcgcgcggaa aagcagcaag aggggggacg gggcgagccg gcagagtgc ggagcccccg     119100 gagcccgcgg ccgcagccga gcagcgccg gggctccggg gccgggccgg ccggcaacg     119160 ccccgcgccg ccgcggcgg agagaacccc tgtgtcattg tttacgtggc cgcgggccag    119220
cagacgggcc gcgggccagc agacgggccg cggcgccagc ggccacgcc tcccgccgca    119280 ttaggccccc gcgggcatcc ggcggccggc cccacgccct tccattaaac actcccacgt    119340 tgggggggg cgcgccagct gagtgctctg cggttgcggg cgccgtgccc ggagatccat    119400
taagccgccg gagagcccga gccccgcccg cgtgttgctg tgggcatttc tgctgcgtca    119460
tccctgtctt tataaaaccg ggggcgcggc agcaacgaac gcaggggccc gccgccgatc    119520
gagagggact ccggagaagg aaggctgctc cgcgcaccgg cgcgcccttc tcctctcccc    119580
tccctacctc cccctctctt cccctttttt tcccccgcct ccgtcttct tccgcgcctc     119640 cgagggtccg cctcttgcct cggggacccc cgggcggggcc ggggcttggc cgccgaggtg    119700
cgccccggcc ggaggggccc ccgcacctcg gcggccgccc cctccggcgc cgcgcgttcg    119760
```

-continued

```
cgaaaggcgc gaaagggcc cccggaggct tttttcgatt cccggccggg ggtcccgggt    119820
agccgcccgg cgccgggcgg aaggcgtccc ccgcccggcg gtccggcccg ggcccccggc    119880
ggagcgcggg ggccccgggg ccccgggccg cgccggcggc gttccgcgt tccgtttctt    119940 ctccctcccg ggccgccccg ctcccgggcc cgaccctcgc cccttcccttc tcctcgtct    120000 tcccccgtcc cgccgcgccc cttccctctt ccttctctct ctctgtctcg ctctcctcac    120060 atttccccc ccccccccg ccgccgccgc cctttgcccg cgtcccaccg agacgccgcg    120120
ccgcgtgagc cgtccgccgg gggacccagg ctccggggg ggggggcgcc tgcgtgtgtc    120180
tcgtgtgaga gagcgcgccc ctcgaacgcc gcgcgttctc gcaggtaggt ttagggtcgt    120240
acaggtgagc ttctgctgag gcggcgggga gaggggggg gggcgggcgg aagagagaag    120300
agagcagggg ttgggggaga actgttcttc ctccccttt caagaaacac gaggcggggg    120360
tcccagaaag ggcaggcagg tcagccgcac cgcccgcgag ccaacccgta tccttttttt    120420
ctaggtgttt ttgtttttgt ttctgttttt gtttgttttg ttattatttt cgcggatccg    120480
gcgtgttcgg atccaccccc ccttctcct tcctcttccc ttccacccac ccccgtttcc    120540
cccccccccg tcgtcgttcc cgggggggca ggcgcgggtc gggcccgtac gcccaccgcc    120600
cccacgcgcc ggtcaccccc ccccaacaac cccaaaggcg cgtgcccggc cacagccgtg    120660
ggtgtggcgc ccgtcccctt cctctaccgc gtgggcgcgg gcggggggt ggtggtagtg    120720 gtggcggaag gaaacgggcc gggggccggg gccgctaggg aaaggtaggc acgcgcgcgg    120780
tgtgtcgact tgcatgcccc gcaaaacgcg tcgtgtcgtg ttgtgtcgtg gtgggccgtg    120840
ttgtggtggg ccgtgtggtg tggtgtggtg ttgcgaacgc gcgagccccc tcgcccgat    120900 gggagtctcc ccgcagccag ggtaaggagg ggcgggcgtg gcgggcaggt gtgcgggcgg    120960
ggtggggtga gtgcggttgc atgcctcggg tctcctcttc ctgctcctcc tcctttctcc    121020
cagccagggt gaggaggggc gggcgtggcg ggcaggtgtg cgggcggggt gggcgccggg    121080 gcggggggtgg gcacgggcgt aagtgcgggt gcatgcctcg ggtcttctct tctccctcct    121140
ccttcctccc acccgtcccc gggggcagag ggcgtgcatg cgttgtgatt caaccgccct    121200 cgccccccgcc ccactttccc ccctctctat caaagttccc tggcccctgg cttcgcgccg    121260
gtggtgcggc tgaccccccc cctcctccct ccccgagcca ggcgccctcc cactcctgcc    121320
caccaccccc agggtctggc cggccagacg tgcgtgctct gcacgatcgg gccccctcc    121380 ctgtcaacac ggacacactc ttttttacc cgccagccag cccgcccacc caccaagaca    121440
gggagccaga acgaggccgg gccccggctc tgttctatga taaagaccaa caggcctcgg    121500
gggtgggggc ggcttctcgt gcccgccccc cctcctcctc ctcccttccc cccatccccc    121560
ggcccccctg cgcggggag ctgcatcaaa ggccaacaac aaagtgtgtc aaaagcatca    121620
caaaacttta ttgtaaaatt tttataaata taaagttttt ttttttcctca agttttcaac    121680 aaggccagaa agtccataac aaaatgctgg tgtgtgttgc tgttcgggc cgtgtccgtc    121740 cccccccccc actcccaccc ccacttcctg tctcctcccc gtctttcccc cccccaccct    121800 cccctgccc ccgaggcgcc tcggccggtg gtccggtggg gggcggcttc cttcgggcag    121860
caagccgagt gttagctccc cctactcccc gtggcccgcg gggcgtcgc cggccggcgc    121920 gggcgcgccc tgctcccgag accacgggtg gcgcgaccgg aggccgtgga agtccagcgc    121980
gcccaccagg gtgccctggt caaagagcat gttgcccacc gggtcatcc agaggctgtt    122040 ccactccgac gcgggggggcg tcgggtagtc ggggggcctc acgcagttgc gcgcgtgctc    122100
ggggagcagg gtgcggcggc tccacgcggg ggccgcggcc cgcagcaggt ccgccacgtt    122160
```

-continued

```
ccccgtctgg tccacgagga ccacgtaggc ccctatgtgg cccgtctcca tgtccaggac  122220
gggcaggcag tcccccgtga ccgtcttgtt cacgtaaggc gccagggcca cgacgctcga  122280
gaccccgcg atgggcaggt agcgcgtgag gccgggcgcc gggtcgcggg ccccgggctc  122340
ggggccgccc tccgcgtggc gcgtcttcct ggcacacttc ctcggccccc gcggcgcagc  122400
agcgcggggg ccgagggagg tttctcgtct ctccccagcg ccggacgcgg acgcgacgct  122460
cccaccagcc ccgcccgcag aggaagaggc ggaggaggag gaggcggagg aggaggaggc  122520
ggaggaggag gaggcggagg aggaggaggc ggaggaggag gaggcggagg aggaggaggc  122580
ggaggaggag gaggcggcgg cgaccgcggc ctgggacgac ggagacgccg acgggggcgc  122640
ggcgcccgcg gacgccgggg cgagcggccc gtggccgcgg tcgcccgagt ccgagtccgg  122700
ggcccggcgc ggcgccgccc tcttggcccc cacccctgg ggggcgaggg gcgagcgcgg  122760
ggcggcggag gaagaggcgg aggacgaggc cgcggggccc gagtccgacc cgcgcctctt  122820
ccggggggcgg gccgccgccc cctccgcggc gtggggggcg gcaccggggg tgttggtgcc  122880
gcggggggacc ccgggtcctc cctccgcgcc cggccctccc gacccgcgcg cgtcggtcgc  122940
gcctgcccgg cccagactct gtgcttgggt gtcggtctga gcctgggtca tgcgcgaccg  123000
gggcgcgcgg tgcgcgtcca ccggcacggc gggcggcgcg ggcccggccg cgtccgcgct  123060
cgcagacacc acggggggcgg cggcggcgcg ggcggactc cggacgcgcg gggcgacggc  123120
cgcgcggggg cgcgcggcgc gccccgacga ctgtggcaga cctccccccc cggggcccga  123180
ggacacctgt gcggaggagg aggagacaaa ggagagcggc ccggggcccg cggggcggcg  123240
cggagacggc gggggagagt cgctgatgac tatggggggc tcctgggccg cgcggggctg  123300
tctcgcgggg ggcgtcctgc cctccgccgc cgcggcgtct tcgcccaccc gccgcgcctg  123360
cgcgcgcccc ccgccggccg caggggggaag agaggccact ctcggcacga cggccgcgac  123420
ggcagggccg cccccagacc cagatcccac ccccgcccgc aacggggcgc cgccgctgct  123480
gctgctccgc ggggcgccag ggggcgccgg tcgggtcgcg gcgggctggg aggttccgcg  123540
ggtcgccccc gcaccgccgc ccccgcgccg gggcgctctt cgggggggcgg gcgggacgta  123600
gtccactgca gagggagaca gagacgggag ccccgggtta gtgcccgacc cccgcccgac  123660
ccccgcccga cccccgcccg accccgccc gaccccgcc cgaccccgc ccgacccccg  123720
cccgacccc gcccgacccc cgcccgaccc ccgcccgccc ccgcccgac cccgcccgc  123780
cctcaccgtc ggccaggtca tcgtcctcgt cgtccgtgcc gggccacggg ggggtgggcg  123840
acagggcgcg gaccgtgtgt ccccccagcg acagggagcg cggggccgtc cgcgggttgc  123900
ccgtccagat aaagtccacg gccgtgccgg cccgcacggc cgcctcggcc tccacgcggg  123960
tccgggggtc gttcactatc gggatggtgc tgaacgaccc gctggcggtc acgcccacta  124020
tcaggtacgc caccggggtg ttgcacaggg gacacgtgtt gcgcaacgga atccaggtct  124080
tcatgcacgg gatgcagaag gggtgcaggc agggaaaact ctggcagcgc aggggcgggg  124140
cgatctcgtc cgtgcacacg gcacacacgt cgccccccc tcccgcttcc gcttcctcct  124200
cacccacggg cccaccccca caggatccct gcgcgtcggc gggcgtgggg ctgccctggc  124260
gctcggccgg gggccgggcc ggggggcgtgg ccgcgtccat caggcccgcc tcgaacatct  124320
ccgtgtccgt gctgccgcc tcggaggtgg agtcgcggtg aagtcgtcg tcagagattc  124380
ccacctcggt ctcctcctcc gagtcgctgc tggcgagcca ctgcatgtcg ttgagcatcc  124440
cccaggcgtg cggggcggcg ggctgcttga caaagcaacg ggggggattt agagggcgcg  124500
gggcgtgagg cgggacccc gcgccgtgtc ccccgtgtcc ctccctcacc ccggcccccc  124560
```

```
gcccgctgct ttttgttcgg aaggggggga gaaagggggtc cgtaaccaaa ggtggtctgc   124620
gtcctttgga ttccgacccc tcgtctcccc ccctgtcccc cgctctcggg ctcctccctg   124680
cctccctcgc ccccccagag ggtcgggggg cggcgcacgg cccacggggg tcccccgacc   124740
gcttaagcgg gccggggggtc ggccccgtca agcgtccccg ccccccgagcc caccgcccgc  124800
gaccacccccc aacccgcagc cgggtggtcc ggggaaaagg gggggcctga gacccggggg  124860
tcgccctctc accgtgccgg gggtctgccg cggcggccgc tcggggccgg ggtccgcccg   124920
ggagctcgtg ccgggccggg gttccatgag ccggggtagg gtagactcga gacggcggcc  124980
cgcggtctct ctcttgccgg gttttagtct ctgtctctcc gggtctcctc ctcccgccgg  125040
gccgccgctc cgtcgctcgc agtgccgggg tgcgaatgcg gcccgaccgt cacacggggc  125100
tgccttatac ccggcgccta tccactcccc caaaggggcg gcatttacga ttcccccaat  125160
agccgcgcgc cccggcgggg gcggagggag ggaatccccc cctctcgggg cggccccgtc  125220
cccgggggacc aaccgggtgt actccaagaa ccccattagc atgcgccgcc ccccgccgac  125280
gcagatggga gtcccccccgg cgccccgccg gcgcggccct gagtggtgcc cgccccccggg  125340
gaaaaattca ttagcatact aggaagccca ggggaccaat aggggccgat cagcccaccc  125400
acccggcggc gcgcgaggct ctgcgtgttc tgccaagaaa gtaatcagca taacccggaa  125460
ccccgaggga gtaattacgc ggggagcgag gggccgtccg aacgttttta attaccataa  125520
gcgggaatgg cggccccgtta aaagctgcta attaccgcga gcgggaacgc cggcccatta  125580
aaagttgcta attaccatgc gcggggatgg cggccgggac cgcctattaa aagtttctaa  125640
ttaccatacc gggaagccgg cgcggggcgg tcgccggggc ggagtccggg cccgcgcggc  125700
ggcgcgcggt tggccggcgc cgccccctgg ggcgggcgga gcggcggggc ggcgccgggc  125760
cctcgcggat atatacgcgg ggctcccatc gtctcttcgg agagcggcct cgcgcagacc  125820
ttcggagctc cggggctccg ccggccgagg ccgcccctcgc cggttcaacc ctagaccgcc  125880
cgacggcccg ggcccgcggc ggcggaggac ccgcgcgccg ccgccgccgc ctcctcctcc  125940
tccgcgggtc cgccgtcttc gtgggcccgg gctcgggctc gggcccgagc tcgggcctcg  126000
ggctccaggc acggtccgat gaccgcctcg gccgccgcca cgcggcgccg gaaccggtcg  126060
cggtcggccc gctcgcgcgc ccaggacccc cgtcggccca ggcgcgcggc cgtctcccag  126120
gccaccagat ggcgcacctg cacgcgcggc gagaagcaca cctgcgggcg gggagacacg  126180
gggggtcggag gggcgtcagg gggtcggagg ggcgtcaggg ggtcggaggg gcgtcagggg  126240
gtcggagggg cgtcaggggg tcggaggggc gtcagggggt cggagggggcg tcaggggtc  126300
ggaggggagg cgtaccttcc cgcgcggcgc gtccgcgggc ggggacgcgg ggggccgccg  126360
ccggcgcagg ctcaggcgcg ccaggtactc cgtcgtggtg cgcagccgta cgccaggtg   126420
gggcggaagg gggcgctgcg gcccgcgctc cttgcgcggc ggcggcgggg ggcaggcggc   126480
ggcaggcgcg gcgtgcgggg cctccggcgc cttccccccg ccctcgctcg ggggggctgtt  126540
cgcccactct gcgtcgtcgt tgccggcgta gtccgcgtcg tcgctgtcgt ccgcctgggg  126600
caccagcagc cagcgccgca ggagcgagga gcgggccggc gcgctctcga ccgcggttcc   126660
cgagtcgtac gcagggacca tttgggagtc tgcggttggg agcgcgccgg ggcgcggcac   126720
ggctggagcg ccggggcgcg gcacggctgg agcgccgggg gcggccggcc gccgggggacc   126780
ccggcggcgg ggaccccggc ggcgggacat ggcgggcggc tgggctcggc gtaggcccgg   126840
agccggagcg cgtcggggcg ggagagttca ctcggcacgc atgcacgtgt aaccgccagt   126900
ccgtgcttgc ctagcgaact cacccgtccc ggctggcgtg cgcagcccgg gccgtgttgc   126960
```

```
gggccctctt aagggqcqqc ggcaggacgg ggactcccgc cccgcctctt ttccccgggg   127020
gagtcaaccc ccgggggggg tgtttttgg gggggggcg gaaggcgggc ggcggcggc     127080 ggcgggcggc agggcagccc cgcgcgcccc cttcccgtc cctccccgg agccggccgc   127140 tccccgcgg gcgccgcccc tccccccgcg cgccgcgggg ctgccttccc gcgggcgccc   127200
ccgcgcggct tttttcccgc gcccgccccc gcgcggcagg acggggacta gcaggctgtg   127260
ccgcagacca ccacacactc ccaagctccc cgccccccg aagacgccag tcgcaccacc    127320
gctcgccctc gcagaccaga cagttgcacc aagcacccgc ccgcccgcac acggttcccc   127380
gccaccccct ccctcccctc catcccgccg agctcgcggc agcccctccc ccccgcgcgc   127440
cacggggctg cggtcccgcg gccgcctccc ccgcggccgc ctccccgcg ccccgccccg    127500 ggggcttccc ccgcccctcc ccccgcgccc gcggccccga gctcgcagca gcccctccct   127560
cccgcgcccc gtgccttccc tcccgctcct gcgggggggc tcgggccacc tgaccttcgt   127620
aacctgcact caggtcagag ccccagaccc ccgcgggcg cgggagacgt gccgcccgcc    127680 cgaccccccgc ccgcccgacc ccgcccgcc cgaccccccgc ccgcccgacc cccgcccgcc   127740 cgaccccccgc ccgcccgacc cccgcccgcc cgaccccccgc ccgcccgacc cccgcccgcc   127800 cgaccccccgc ccgcccgacc cccgcccgcc cgaccccccgc ccgcccgacc cccgcccgcc   127860 cgaccccccgc ccgcccgacc cccgcccgcc cgaccccccgc ccgcccgacc cccgaataaa   127920
ccacacaagg cggtacgttt tcgtctgtct cgttctttat ttctcacaca cgcgcgcggc   127980
catcgccgcg tctgtcttaa aggcgcacag acgcccgatt ccttcccct ctccccatct     128040 cccccctccc ccgctcccgg aagtttcccc ccccgtcact cccaaacag tccgtcgtcg    128100 tcgtcctcca gctccgcgtc catgtccacg ggctcgcgcc tcggcggcgt ggccagcccc   128160
gcggcggtcc ccaccacctc cacgccgccg cccgccgcgg ccagcaccgt ccccgcgcgg   128220
cccgcggccg acgcccagcg tatctgcggg ggcgggcccg cgtccgcgtc gtcgcgcagc   128280
accagcgggg gcgcgtcgcc gtcgggctcg agcagcgccc gcgcgcagaa ctcccgccgc   128340
ggcccgcgca gctccgccgg gccgccgcgc acggcgtcgc gccccagcgc cacgtagacg   128400
ggccgcagcg gcgcgcccag gccccagcgc gcgcaggcgc ggtgcgagtg cgcctcgtcc   128460
tcgcagaagt ccggcgcgcc gggcgccatg gcgtcgcccg cgcccgaggc ggcggcccgg   128520
ccgtccagcg ccgggagcac ggcgcggcgg tactcgcgcg gggacatggg caccagcgtg   128580
tcggggccga agcgcgtgcg cacgcggtac cgcacgttgg ccccgcggca gaggcgcagc   128640
ggcggcgcgt cggggtacag gcgcgcgtgc gcggcctcca cgcgcgcgaa gacccccggc   128700
ccgaacacgc ggccggaggc cagcacggtg cggcgcaggt cccgcgccgc cggccagcgc   128760
acggcgcact gcacgcgggg cagcacctcg caggccaggt aggcgtgctg ccgcgagacc   128820
acgggcccgt cggcgggcca gtccgcggcg cgcacggcgt tgacgacgat gaggcggcgg   128880
tcgcaggcgc cggccagcag ccccaggaac tccacgcgc cggcgaaggc caggtcccgc   128940
gtggacagca gcagcacgcc ctgcgcgccc agcgccgaga cgtcggggc gccggtccag   129000 ttgcccgccc aggcggccgt ggcgggcccg cagagccggt tgcccagggc cgccagcagg   129060
caggacagcc cgccgcgctc ggcggaccac tccggggggg gccgcccccc ggcgcggccc   129120
gcggccaggt cctcgcccgg cagcggcgag tagaggatca ccacgcgcac gtcctccggg   129180
tcgggcacct ggcgcatcca ggccgccgcg cggcgcagcg ggcccgaggc gcgcagcggg   129240
ccgaaggcgg cgggcgcgcc gccggggggc ggggcggcgc agcgcgcggc cagcgaggcc   129300
agcgcgcgcg ggtcgaacat gagggccggg cgccacggcg cggggaagag cgggtggtcc   129360
```

-continued

```
gtgagctcgg ccacggcccg cggggcgcag taggcctcca gggcggcggc cgagggcgcc    129420
ggcgtgtggc tgggccccgg cggctggcgg cgccagccgc cctgcgggtc ggggccctcg    129480
gcgggccggc gggtcagcgc cgcggggcgc ggcggccgcg gcggcggcgt cggcggggcg    129540
gggggcgcgg cccccgcggg agggggcggcc gcggggcggg gggcgtccgc gcggctcttc    129600
ttcggggggc gcggggcgcc gcccggcggc gccctggccg gggcggggct cttgcgcttg    129660
cgcgcctccc gcggcgcgga ggcgggcgcg gcgagcgagt cggccgcggc gacggtgtcg    129720
gccagcaggg ggcgcaggct ctggttctgg aagagcaggt ccgcggcggc ggcggcggcg    129780
gagctcagca ggcgcgggct ccgcggcagc gccgggccca gggccccggc gaccaggctc    129840
acggcgcgca cggcggccac ggcggcctcg ctgccgccgg ccacgcgcag gtccccgcgc    129900
aggcgcatca gcaccagcgc gtcgcgcacg aaccgcagct cgcgcagcca ggcgcgcagg    129960
cggggcgcgt cggcgtgcgg cggggcggcc gcgcccgcgg gccccgggcg cggggcgcg    130020 gcgggccggg ctccgccag ccccggcacg gccgccaggt cgccgtcgaa gccctccgcc    130080
agcgcctcca ggatcccgcg gcaggcggcc aggcactcca cggccacgcg gcccgcctcc    130140
gcgcgccggc cgccgccacc accgccgcgg ccgtcgtcgt cgtcgtcgtc gtcggccccg    130200
gccggcgcgg aggcgggcgc ggcgctcagg cgccccaggg cggcgagcac ccccgcggcg    130260
ccgtagccgg cgggcaccgc gcgctcgtcg gccggcgacg ccgccgccga cggcaacggg    130320
gcggcggcgg cggcgggctt cccgcgggcg tcgtcgccgt cgtggcggtt ggcgtcgccg    130380
ccgtcgtcgg gggttcgcgc cccggtcagc gccgcgttct cgcgcgccag cagggcgcg    130440 taggcgcggc gcaggctggt cagcaggaag cccttctgcg cgcggtcgta gcggcggctc    130500
atggccacgg cggccgccac gtgcgccagg ccccagccga agcggcccgc cgccatggcg    130560
taccccaggt ggggcacggc ccgcgccacg ctgccggaga tgaaggagct gctgttgcgc    130620
gccgcgcccg agatccggaa gcaggcctgg tccagcgcca cgtccccggg cgccacgcgc    130680
gggttctgga gccaccccat cgcctccgcg tccggcgtgt acagcagccg cgtgatcagg    130740
gcgtactgct gcgccgcgtc gcccagctcg ggcgcccaca cgggcgccgg ggcgcccgag    130800
gcctcgaacc gggcccgcgc ctcctccgcc tcgggcgccc cccagaggcc ggggcggctg    130860
tcgcccagcc cgccgtacag cacgcgcccc ggggcggggg ggccggcccc gggccacggg    130920
tccccgctga cgtacccgtc gcggtagcgc gcgtagaagg cgccggaggc cgcgtcggcg    130980
tccagctcga cccgcggggg ccgccggcc gtgaagcggc ccgtggcgtc gcggccggcc    131040
accgccgcgc gggcccggcg gcgctccagg cggcccgcgc tcgccgcggg ggtccgggcc    131100
ggggcgggct cggccctggg cgggctcggc cggggcgccg ccccgggggc cctcgcgggc    131160 accccgcct cctcgtcgtc cgcgccgagg gtcccgcccg cggcgtggtc tgcggcgctg    131220 gcggggcgc gggcggcgtc gtcgtcgtcg tcgtcgtcag acgaggaggc ggatgcagac    131280
gaggaggagg aggcggagga ggaggcggag gacgccgacg acgaggatcc ggattttgat    131340
gagtcagagg cggccgagcg ccggcggggg gcgcgccggc ggcggtggtg gtggtggtgg    131400
tggtgtcggc ggggcgccgg gggtcgcggc gacaggctgg ccatgggggtc cgggtacgcc    131460 ccgcggaccg cggacgtcgt ctccggtccg cggacccagc ggcccgcgtc gcggtcgtcg    131520
tcatcgtcgt cgtcgtcgtc gtcgtcgttc tcctcgccat aatcggcgcg catggaggg    131580 gtccgcggcg gagaaggcga gcgggccgct tcttcttgcg cgccgtcgcg ctccgggggg    131640
ggcgacggga tcgtgcgaac ggcctcgtcc accatcgagg ccagcagggc cagctgccgc    131700
ggcgagacga cgccgtccgc ggcaggctcg tcgacggcct ccccggacgc cggggccgcc    131760
```

-continued

```
tcgtcggcat cggcatcggc ggcggcgtcg tcggcctcgt cttcgttctc ctccggccca   131820
ccgtgccacc cgaacccggg ccgcgcgcg gggcgacggt ccgggttcgg ggtgggcggc    131880
ggtccgtcgg ctggatccgg agatccgggg ccgccggtcg tctccgccgc ggcccggaga   131940
cgtccccgt cctcgtccgc catcgcgacc tcggccccgc ggccctgcgt cgtcgtcgtc    132000
gtcttcttct tcttccgctg ctccgccgac atcgcctccg accggggtgt gcggggggg    132060
ggtcttcttc ttcttcttca ggggcggcag tgggggggg tggttggcag tctctctccc    132120
ccccgtgcgg tgcgtgcgtg tgcctgtgtc ttttcgcctc tccgcgccga tcgggtagat   132180
cctggcggcc gcgtcggtag ccgcgctccg tgtggacgat cgccccgtcg cctggctgat   132240
atagtcctcg gggcgcgcgg ggcgggggga aaggaggagg acgcggagga ggagcgatcg   132300
acgccgccgc gccccggctc gccggggttc cgcccccagg tggaaccgca ttatgcgcgg   132360
ccccgccccg acgcccgcgc gtccgcgtcc gtggcggcgg cccgttggtc gcgccgccgc   132420
cgctccgccc gcgcggcatc tcattagcgc ccggcgcggg cggcttccgc ttccgcccgc   132480
gatgctaatg agaccctcgt cgcgggcggg ctcgctcccc tgcccttccg ggttcgtggt   132540
aatgagatgc cggccccgcg ctcccgttgg ccccgccgg ccccaaaggg gccggcgagg    132600
tcgccccgtt ggtccgcggg cggctccgcc ccaaagggg cggggccgca gggtaaaaga    132660
agtgagaacg cgaagcgttc gcacttcgtc ctaatagtat atatattatt agggcaaagt   132720
gcgagcgctg gcgccctgcc cggggcccgc gtcatcccgc gctccgcccc aaaggggcg    132780
gggccgcagg gtaaaagaag tgagaacgcg aagcgttcgc acttcgtcct aatagtatat   132840
atattattag ggcaaagtgc gagcactggc gccctgcccg gggcccgcgt catcccgcgg   132900
gctccgcccc gaggcgggcc cggacggggg gcgggccgtt cctcgcgcac ataaagggcc   132960
ggcgtcccgg tcgccgccgc accaggggca caccggctgc gcggcggaga ccgggacggc   133020
agcggcggca tcgcgaaggg ggccacagcg agacagagac gccggcggcg agcggggcac   133080
cgacgcaccc ggatcggatc ggatacagag acgcggcgc atcggttcct tttcgttctg    133140
cctttccctc ccccccccc cccccaccc tgtacgtacc gcgaggaccc atccacccac     133200
tgcagcctta tcgcaggtac ggtgacccgg ggggccggcc gggggggacgg gcgggggacg   133260
gggggacggg ccgggggggac gggcggggg dacgggccgg ggggacgggc cggggggacg    133320
ggccggggggg acggccgggg gggacgggcc ggggggacgg gccgggggga cgggccgggg   133380
ggccgggggg ccggggggcc ggggggccgg gggacgggg ggacggggg acggggggac     133440
ggggggacgg ggggacgggg ggacggggg acggggggac gggggacgg gggacgggg      133500
ggacggggg acggggggac gggggacggg ggacggggcg ggggacggg                133560
gggacgggcc ggggggacgg gggacgggc cgggggggacg ggggacggg ccgggggggac    133620
gggggacgg gccggggggga cggggcccg atcccaacat ccgcgctttc tcgcaggccg    133680
ggcgccgcct tcgtggacgg gacaccggtg tggtaactgg cgacaaggcg ttgccactat   133740
ggcagacatc cccccggacc cgcccgcgct caacacgacg cctgcgaatc atgctccccc   133800
atccccaccc ccgggttcac ggaagcgcag acgccccgtc ctccccagct cgtcggaatc   133860
tgagggtaag cccgacacag aatcggaatc ctcctcgacc gagtcgtccg aggatgaggc   133920
gggagaccta cgcggcgggc gccgtcgctc ccgcgggag ctcggggga ggtattttt     133980
ggatctgtcg gcagaatcga ccacggggac ggaatcggag ggaacggggc cgtcggacga   134040
cgatgatgat gatgcgtcag acggctggtt ggttgacaca ccccccgca aatccaagcg    134100
accccgaatc aacctgcgat taacgagctc ccccgaccgg cgtgcgggtg tggttttccc    134160
```

```
cgaggtgtgg agaagcgaca gacctatccg cgcggcgcaa ccccaggccc cggccagtct 134220 tccgggatc gcgcacgcgc accggcgctc tgctcgccag gcccagatgc ggagcggagc 134280
cgcctggacg cttgatctgc attacatacg ccagtgcgtc aaccagctct ttcggatcct 134340
gcgtgccgcc ccgaacccgc ccggcagcgc caaccgcctg cgccacctgg tgcgagactg 134400
ctacctcatg ggctactgcc ggacccgcct ggggccgcgc acgtggggcc gcctgctgca 134460
gatctcgggc ggaacctggg acgtgcgcct gcgaaacgca atccgggagg tcgaggcgca 134520
ttttgaaccc gccgccgagc ccgtgtgcga gctgccctgt ctgaacgcca ggcgttacgg 134580
ccccgagtgt gatgttggca atctcgagac caacggcggc tcgacgagcg atgatgagat 134640
atcggatgcg acggactcgg acgataccct cgcgtcccat tccgacacgg agggggggcc 134700
ctccccggcc ggccgggaga acccggaatc cgcgtccggc ggggctatcg cggctcggct 134760
ggagtgtgag tttgggacgt tgactggac gtccgaggag ggctcccagc cctggctgtc 134820
cgcggtggtc gccgatacca gctccgccga acgctctggc ctaccgccc cgggcgcgtg 134880 tcgcgcaacg gaagcccag aacgcgagga cgggtgccga aaaatgcgct tccccgccgc 134940
ctgcccctat ccctgcggcc acacatttct ccggccatga gcgcgggacc cccagcccgg 135000
tgtgtttgcc aaacgaaaaa taaacgccct acaagaaagc ttttgtgtct gagtgtctgg 135060 ttttttctggg ggtggaggaa ggaacgacaa aaaaaagaaa caaacgcgac accgctcgta 135120
cgtgtaatgg ggccgcagtg tttttatta gcatcggggg gggttagagg ttggtgattg 135180
gatagcaaac gtgggatgac ggaggccact cgtcgccaac ggccagcggg ggcccggggt 135240
tctgggggtc atcgtccccc gtctgccagg agggctcatc gggaatctcg ggtcgcccca 135300
tgcacgtaaa acacgggcgc tgcgtggggt gggtcgccgg atgcgggcgg gatgatgcgg 135360
ggcggggttt gttgtgagga gccacgaggg accgtagcca gcgaagacag ctgcgttccc 135420
ggtcgccggg caccaccacg ccgtattggt attcgtatcg gctaaggaga ttttccaggg 135480
ggtgattagg cgctgcgggg aacggggtcc acgacacggt ccgctcgggc aaaaaccgat 135540
cgggcagggg ccacggttcc cccacccacg cgtcgttggt cttcgtggcg atgaagcgaa 135600
accccagccg ggttttttgt gcgtactcga aaaacggcac acacaggtcc gccgccccga 135660
ccacccacag gtggtatagc cggtgggggc cggggcgctc ttgatgcagg agccgaaaac 135720
acgcaggggc atccagaatc tcgatgcttt ccaggggtc gtcctccgca aacaggcccg 135780
tcgtggtgtt tgggggacag cgacaggagc gggttcgcac gatcggtcgg gtgaatttgg 135840
gcaagtccat cagaggctcg gccagcctgc gaaggttcgc cgggcgaacc accacgggg 135900 ttcccagagg ctcggaggcc aggatccggc attgccgaag cagaaaactc cacagagccg 135960
ggcttgcgtc agcggaagtc cgcggcaggg cgtttcgttg gtctaggagg gtaaccacac 136020
ttacaacaac aacgcccatg tcggtatatt aggcccgtgg tccgatcttc actcactcgc 136080
ctgtctgcgc acctatgcac ggcggacg cgcgcggacc cgggggggct gcttgctatc 136140
acacggcccg ttcgcacgtt cgatttttc agccttgttt ggttggctag gtatcccgga 136200
taatctgacg ttccggatat aggggcggg gggtagtggg gggtgtgtcg acaaactgcc 136260
gcttcttaaa acaccggggc ccgtcgctcg gggtgctcgt tggttggcac gcgcgacgcg 136320
gcaaatggcc tgtcgtaagt tctgtgggt ctaccgtaga cccgacaaga gacaggaggc 136380
gtccgtcccg ccggagacaa acacggcccc ggccttcccg gcgagcacct tttataccc 136440 cgcggaggat gcgtacctgg cccccggcc ccggaaaacc atccaccctt cccgcccacc 136500
gtcccccggc gaggctgcgc gcctgtgtca gctgcaggag atcttggccc agatgcacag 136560
```

-continued

```
cgacgaggac tacccccatcg tggacgccgc gggtgcggag gaggaagacg aggccgacga  136620
tgacgcccccg gatgacgtgg cctacccgga ggactacgcg gagggcgtt  ttctgtccat  136680
ggtttcggcc gcccccctgc ccggagccag cggccatcct cctgttccgg gccgcgcagc  136740
ccccccccgac gtccggacct gcgacacggg taaggtgggg gccacggggt tcaccccgga  136800
agagctcgac accatggacc gggaggcact tcgggccatc agccgcgggt gcaagccccc  136860
ttcgaccctg gcaaaactgg tgaccgggct gggattcgcg atccacggag cgctcatccc  136920
ggggtcggag gggtgtgtct ttgatagcag ccacccgaac taccctcatc gggtaatcgt  136980
caaggcgggg tggtacgcca gcacgagcca cgaggcgcgg ctgctgagac gcctgaacca  137040
cccccgcgatc ctacccctcc tggacctgca cgtcgtttct ggggtcacgt gtctggtcct  137100
ccccaagtat cactgcgacc tgtataccta tctgagcaag cgcccgtctc cgttgggcca  137160
cctacagata accgcggtct cccggcagct cttgagcgcc atcgactacg tccactgcaa  137220
aggcatcatc caccgcgata ttaagaccga gaacatcttc atcaacaccc ccgagaacat  137280
ctgtctgggg gactttgggg cggcgtgctt tgtgcgcggg tgtcgatcga gccccttcca  137340
ttacgggatc gcaggcacca tcgatacaaa cgccccccgag gtcctggccg gggatccgta  137400
cacccaggta atcgacatct ggagcgccgg cctggtgatc tttgagaccg ccgtccacac  137460
cgcgtccttg ttctcggccc cgcgcgaccc cgaaaggcgg ccgtgcgaca accagatcgc  137520
gcgcatcatc cgacaggccc aggtacacgt cgacgagttt ccgacgcacg cggaatcgcg  137580
cctcaccgcg cactaccgct cgcgggcggc cgggaacaat cgtccggcgt ggacccgacc  137640
ggcgtggacc cgctactaca agatccacac agacgtcgaa tatctcatat gcaaagccct  137700
taccctttgac gcggcgctcc gcccaagcgc cgcggagttg ctgcgcctgc cgctatttca  137760
ccctaagtga cccccgctccc cccgggggggc gtggaggggg gggctggttg atgttttttg  137820
cacaaaaaga cgcggccctc gggctttggt gttttttggca ccttgccgcc cggcgtcatg  137880
cacgccatcg ctcccaggtt gcttcttctt tttgttcttt ctggtcttcc ggggacacgc  137940
ggcgggtcgg gtgtccccgg accaattaat ccccccaaca gcgatgttgt tttcccggga  138000
ggttccccccg tggctcaata ttgttatgcc tatcccccggt tggacgatcc cgggcccttg  138060
ggttccgcgg acgccgggcg gcaagacctg ccccggcgcg tcgtccgtca cgagcccctg  138120
ggccgctcgt tcctcacggg ggggctggtt ttgctggcgc cgccggtacg cggatttggc  138180
gcacccaacg caacgtatgc ggcccgtgtg acgtactacc ggctcacccg cgcctgccgt  138240
cagcccatcc tccttcggca gtatggaggg tgtcgcggcg gcgagccgcc gtccccaaag  138300
acgtgcgggt cgtacacgta cacgtaccag ggcggcgggc ctccgacccg gtacgctctc  138360
gtaaatgctt ccctgctggt gccgatctgg gaccgcgccg cggagacatt cgagtaccag  138420
atcgaactcg gcggcgagct gcacgtgggt ctgttgtggg tagaggtggg cggggagggc  138480
cccgccccca ccgccccccc acaggcggcg cgtgcggagg gcggcccgtg cgtcccccccg  138540
gtccccgcgg gccgcccgtg gcgctcggtg cccccggtat ggtattccgc ccccaacccc  138600
gggtttcgtg gcctgcgttt ccgggagcgc tgtctgcccc cacagacgcc cgccgccccc  138660
agcgacctac cacgcgtcgc ttttgctccc cagagcctgc tggtggggat tacgggccgc  138720
acgtttattc ggatggcacg acccacggaa gacgtcgggg tcctgccgcc ccattgggcc  138780
ccccggggccc tagatgacgg tccgtacgcc cccttcccac cccgcccgcg gtttcgacgc  138840
gccctgcgga cagaccccga gggggtcgac cccgacgttc gggccccccg aaccggcggg  138900
cgcctcatgg ccttgaccga ggacacgtcc tccgattcgc ctacgtccgc tccggagaag  138960
```

```
acgcccctcc ctgtgtcggc caccgccatg gcaccctcag tcgacccaag cgcggaaccg  139020
accgcccccg caaccactac tccccccgac gagatggcca cacaagccgc aacggtcgcc  139080
gttacgccgg aggaaacggc agtcgcctcc ccgcccgcga ctgcatccgt ggagtcgtcg  139140
ccactccccg ccgcggcggc ggcaacgccc ggggccgggc acacgaacac cagcagcgcc  139200
tccgcagcga aaacgccccc caccacacca gccccacga cccccccgcc cacgtctacc    139260
cacgcgaccc cccgcccac gactccgggg ccccaaacaa ccctcccggg acccgcaacc    139320
ccgggtccgg tgggcgcctc cgccgcgccc acggccgatt ccccctcac cgcctcgccc    139380 cccgctaccg cgccggggcc ctcggccgcc aacgtttcgg tcgccgcgac caccgccacg    139440
cccggaaccc ggggcaccgc ccgtaccccc ccaacggacc caaagacgca cccacacgga    139500
cccgcggacg ctcccccgg ctcgccagcc ccccaccccc cgaacatcg cggcggaccc     139560 gaggagtttg agggcgccgg ggacggcgaa ccccccgagg acgacgacag cgccaccggc    139620
ctcgccttcc gaactccgaa ccccaacaaa ccaccccccg cgcgcccgg gcccatccgc     139680 cccacgctcc cgccaggaat tcttgggccg ctcgccccca acacgcctcg ccccccgcc    139740 caagctcccg ctaaggacat gccctcgggc cccacacccc aacacatccc cctgttctgg    139800
ttcctaacgg cctcccctgc tctagatatc ctctttatca tcagcaccac catccacacg    139860
gcggcgttcg tttgtctggt cgccttggca gcacaacttt ggcgcggccg ggcggggcgc    139920
aggcgatacg cgcacccgag cgtgcgttac gtatgtctgc caccgagcg ggattagggg     139980 gtgggggtgg gggcgagaa acgatgaagg acgggaaagg gaacagcgac caaatgtcac    140040
gataagaaca ataaacctgt gacgtcaatc agatatgtga gtttggttgt gttttgtggg    140100 actggggcg ggggtggga ggtatcagtg ggtgacagag tcttttaaaa gacgtgtccc       140160
ggggccctcg agatgcgcaa cttttggcca cacagagaaa ggcccccaga cgaagtcacc    140220
cgggtccccg aacaaaaaca aaaaccttga ccgccgccgg ggggcgtgcc tgttgttttg    140280
gtctcaatgg atcggtatgc cgttcggacc tgggggattg tgggaatcct cgggtgtgct    140340
gctgttgggg ccgcacccac cggccccgcg tccgatacaa caaacgcgac cgcacgcctc    140400
cccacgcacc ccccactcat ccgttccggg ggctttgccg tcccctcat cgtgggggg     140460 ctgtgtctca tgattctggg gatggcgtgt ctactcgagg tcctgcgtcg cctgggtcgc    140520
gagttggcga ggtgctgccc ccacgcgggc caatttgccc catgatttt cgcctttctg     140580 gccttgcccc cacccatcg ccccgattgt gtgtcgggtg cccggggtac agcagctatg     140640
gagcggtcgg taatataact ttggttgtcg ccacacgccc cgtgccgggc atgggttgtg    140700
cgggaaggac gaaataatcc ggcgatcccc aagcgtacca actgggggg gggggggg      140760 ggaaaagaaa ctaaaaacac atcaagccca caacccatcc cacaatgggg gttatggcgg    140820
acccaccgca ccaccatact ccgattcgac cacatatgca accaaatcac ccccagaggg    140880
gaggttccat ttttacgagg aggaggagta taatagagtc tttgtgttta aaacccgggg    140940
tcggtgtggt gttcggtcat aagctgcatt gcgaacgact agtcgccgtt tttcgtgtgc    141000
atcgcgtatc acggcatggg gcgtttgacc tccggcgtcg ggacggcggc cctgctagtt    141060
gtcgcggtgg gactccgcgt cgtctgcgcc aaatacgcct tagcagaccc ctcgcttaag    141120
atggccgatc ccaatcgatt tcgcgggaag aaccttccgg ttttggacca gctgaccgac    141180
ccccccgggg tgaagcgtgt ttaccacatt cagccgagcc tggaggaccc gttccagccc    141240
cccagcatcc cgatcactgt gtactacgca gtgctggaac gtgcctgccg cagcgtgctc    141300
ctacatgccc catcggaggc cccccagatc gtgcgcgggg cttcggacga ggcccgaaag    141360
```

-continued

```
cacacgtaca acctgaccat cgcctggtat cgcatgggag acaattgcgc tatcccatc   141420
acggttatgg aatacaccga gtgccctac aacaagtcgt tgggggtctg ccccatccga   141480
acgcagcccc gctggagcta ctatgacagc tttagcgccg tcagcgagga taacctggga  141540
ttcctgatgc acgccccgc cttcgagacc gcgggtacgt acctgcggct agtgaagata   141600
aacgactgga cggagatcac acaatttatc ctggagcacc gggcccgcgc ctcctgcaag  141660
tacgctctcc ccctgcgcat cccccggca gcgtgcctca cctcgaaggc ctaccaacag   141720
ggcgtgacgg tcgacagcat cgggatgcta ccccgcttta tccccgaaaa ccagcgcacc  141780
gtcgccctat acagcttaaa aatcgccggg tggcacggcc caagcccccc gtacaccagc  141840
accctgctgc cgccggagct gtccgacacc accaacgcca cgcaacccga actcgttccg   141900
gaagaccccg aggactcggc cctcttagag gatcccgccg ggacggtgtc ttcgcagatc   141960
cccccaaact ggcacatccc gtcgatccag gacgtcgcgc cgcaccacgc ccccgccgcc  142020
cccagcaacc cgggcctgat catcggcgcg ctggccggca gtaccctggc ggtgctggtc  142080
atcggcggta ttgcgttttg ggtacgccgc cgcgctcaga tggccccaa gcgcctacgt   142140
ctcccccaca tccgggatga cgacgcgccc ccctcgcacc agccattgtt ttactagagg  142200
agtttccccg ctcccgtgta cctctgggcc cgtgtgggag ggtggctggg gtatttgggt  142260
gggacttgga ctccgcataa agggagtctc gaaggaggga aactaggaca gttcataggc  142320
cgggagcgtg gggcgcgcac cgctgtcccg acgattagcc accgcgccca cagccacctc  142380
gacccgtccg atcccggtat gcccggccgc tcgctgcagg gcctggcgat cctgggcctg  142440
tgggtctgcg ccaccggcct ggtcgtccgc ggccccacgg tcagtctggt ctcagactca   142500
ctcgtggatg ccggggccgt ggggcccag ggcttcgtgg aagaggacct gcgtgttttc   142560
ggggagcttc attttgtggg ggcccaggtc ccccatacaa actactacga cggcatcatc   142620
gagctgtttc actacccct ggggaaccac tgccccgcg ttgtacacgt ggtcacactg    142680
accgcatgcc cccgccgccc cgccgtggcg ttcaccttgt gtcgctcgac gcaccacgcc  142740
cacagccccg cctatccgac cctggagctg ggtctggcgc ggcagccgct tctgcgggtt  142800
cgaacggcaa cgcgcgacta tgccggtctg tatgtcctgc gcgtatgggt cggcagcgcg  142860
acgaacgcca gccggtttgt tttgggggtg gcgctctctg ccaacgggac gtttgtgtat  142920
aacggctcgg actacggctc ctgcgatccg gcgcagcttc ccttttcggc cccgcgcctg  142980
ggaccctcga gcgtatacac ccccggagcc tcccgaccca cccctccacg gacaacgaca  143040
cccccgtcct cccccgaga cccgacccc gccccgggg acacagggac gcccgcgccc    143100
gcgagcggcg agatagcccc gcccaattcc acgcgatcgg ccagcgaatc gagacacagg  143160
ctaaccgtag cccaggtaat ccagatcgcc ataccggcgt ccatcatcgc ctttgtgttt   143220
ctgggcagct gtatctgctt catccataga tgccagcgcc gatacaggcg ccccgcggc   143280
cagatttaca accccggggg cgtttcctgc gcggtcaacg aggcggccat ggcccgcctc  143340
ggagccgagc tgcgatccca cccaaacacc cccccaaac cccgacgccg ttcgtcgtcg   143400
tccacgacca tgccttccct aacgtcgata gctgaggaat cggagccagg tccagtcgtg  143460
ctgctgtccg tcagtcctcg gccccgcagt ggcccgacgg ccccccaaga ggtctaggtc   143520
caagcgggcc gttcggcagg cccgccccac cgccccatc gtggttattt ccccccccc    143580
cccccaata aaccgatgtt atttgcctat atgcgtgtgt tggatcccctt tgtgatcgtt   143640
cgtcattccc cggatggcat gggaggcggg taatggatgg gcgggcccg ggggaggaa    143700
aaagaataaa gggggtagtg tcggagaggc ccgccgcgca tttaaggagt cgccgccccg   143760
```

```
actctgtgtc ttcgggtgac ttggtgcgcc gccgtcagct agtctccgat ctgccccgac 143820
cgacggctcc tgccacccga acatggctcg cggggccggg ttggtgtttt tgttggagt  143880
ttggtcgta  tcgtgcctgg cggcagcacc cagaacgtcc tggaaacggg taacctcggg 143940
cgaggacgtg gtgttgcttc cggcgcccgc ggaacgcacc cgggcccaca aactactgtg 144000
ggccgcggaa cccctggatg cctgcggtcc cctgcgcccg tcgtgggtgg cgctgtggcc 144060
cccccgacgg gtgctcgaga cggtcgtgga tgcggcgtgc atgcgcgccc cggaaccgct 144120
cgccatagca tacagtcccc cgttccccgc gggcgacgag ggactgtatt cggagttggc 144180
gtggcgcgat cgcgtagccg tggtcaacga gagtctggtc atctacgggg ccctggagac 144240
ggacagcggt ctgtacaccc tgtccgtggt cggcctaagc gacgaggcgc gccaagtggc 144300
gtcggtggtt ctggtcgtgg agcccgcccc tgtgccgacc ccgaccccg  acgactacga 144360
cgaagaagac gacgcgggcg tgacgaacgc acgccggtca gcgttccccc cccaaccccc 144420
cccccgtcgt cccccgtcg  cccccccgac gcaccctcgt gttatcccg  aggtgtccca 144480
cgtgcgcggg gtaacggtcc atatggagac cctggaggcc attctgtttg ccccggga   144540
gacgtttggg acgaacgtct ccatccacgc cattgcccac gacgacgtc  cgtacgccat 144600
ggacgtcgtc tggatgcggt ttgacgtgcc gtcctcgtgc gccgatatgc ggatctacga 144660
agcttgtctg tatcacccgc agcttccaga gtgtctatct ccggccgacg cgccgtgcgc 144720
cgtaagttcc tgggcgtacc gcctggcggt ccgcagctac gccggctgtt ccaggactac 144780
gcccccgccg cgatgttttg ccgaggctcg catggaaccg gtcccggggt tggcgtggct 144840
ggcctccacc gtcaatctgg aattccagca cgcctccccc cagcacgccg gcctctacct 144900
gtgcgtggtg tacgtggacg atcatatcca cgcctgggc  cacatgacca tcagcaccgc 144960
ggcgcagtac cggaacgcgg tggtggaaca gcacctcccc cagcgccagc ccgagcccgt 145020
cgagcccacc cgcccgcacg tgagagcccc ccatcccgcg ccctccgcgc gcggcccgct 145080
gcgcctcggg gcggtgctgg gggcggccct gttgctggcc gccctcgggc tgtccgcgtg 145140
ggcgtgcatg acctgctggc gcaggcgctc ctggcgggcg gttaaaagcc gggcctcggc 145200
gacgggcccc acttacattc gcgtggcgga cagcgagctg tacgcggact ggagttcgga 145260
cagcgagggg gagcgcgacg ggtccctgtg gcaggaccct ccggagagac ccgactctcc 145320
ctccacaaat ggatccggct ttgagatctt atcaccaacg gctccgtctg tatacccca  145380
tagcgagggg cgtaaatctc gccgcccgct caccacttt  ggttcgggaa gcccgggccg 145440
tcgtcactcc caggcctcct atccgtccgt cctctggtaa ggcgtcttcc gacgacgcgg 145500
acgtcggcga tgaactgatt gccatcgcgg acgcacgcgg ggacccgcca gagaccctgc 145560
cccccggcgc gggcggcgcc gcgcccgcgt gccgcagacc acctcgcggc ggctcccccg 145620
cggcctttcc cgtggccctc cacgccgtgg acgcccctc  ccaattcgtc acctggctcg 145680
ccgtgcgctg gctgcggggg gcggtgggtc tcggggccgt cctgtgcggg attgcgtttt 145740
acgtgacgtc aatcgcccga ggcgcataaa ggtccggcgg ccaccccgcc gcagctcata 145800
aaaatcgtga gtcacggcaa ccccaccttc gcctccgccc tccgcagcg  ccttccgcg  145860
tccgcgatga cctcccggcc cgccgaccaa gactcggtgc gttccagcgc gtcggtgccg 145920
ctttaccccg cggcctcgcc cgtcccgca  gaagcctact actcggaaag cgaagacgag 145980
gccgccaacg acttcctcgt gcgcatgggc cgccagcagt cggtcctaag gcgccgacgg 146040
cggcgcacgc ggtgcgtcgg gctggttatc gcctgtctcg tcgtggccct cctatctgga 146100
gggttcgggg cacttttggt gtggctgctc cgctaaatga cgcctcgatg tatggcgcct 146160
```

-continued

```
tcttcgcccc cacccctcgc cgcgacccac gtccgtatgt taattgcaat aaagtggttg 146220
attgtcatta cggtctacta ggttgtcttt ttttttggg gggggggag gaaatgcaga 146280
aaagggtaag aaattctcgg aatttcaccc ccggggggg gcaagtgcag taacccagtt 146340
cctcagtgtt tgggaaatct attgaactct cccggctcct ccgtgttagg gaagtctctt 146400
ggggaaatct attgacctct cgcccccccc ccccaggag gggggcagtg cagtacccca 146460
gttcctccgt gctggggaaa tctctctgcc gggtacgggc tccagacgaa ggacccatac 146520
atttccccat ccgcaccca catctggcgt tctagagtca cgacgcattt gcccccgtcc 146580
ccgcagcaac acacaaagcg atttcaattt tcacgatttt attattaatt acaccaacca 146640
ccctgtcccc gggacgtggt caggaccggg ggtccgcacc caaacgcacg aaacaaatgc 146700
tggcagtgtg ccgaatataa ccccgcgtag gaacacgtcg acgcgtgcgc caaacagcac 146760
cagaaggcgc atgccatcag caggtcgtgc atatggcgat gtgtttggac gcagggcgca 146820
gccgcggcga taaaattcat ggcggccgtc cgccagggcc acagcggcga ggactccctg 146880
ttggcccgaa gccattgggt atgaaccagc tgcgcctcct gtccgaccct ggctccgcc 146940
agcgggggcg gtgggtcgtg ggtgttgaga gcacacaggc gggacacctc gatcaccgtc 147000
cgaaaaaagg cccggtggtc cgcgggcagc atctgcaggt gcgccagggc ctggcgttg 147060
agagggtaca actcggagcc gggggactcc ggggccggt ccgcgcggtg ccgcgagttg 147120
gcacgctttg gggcccgggt gtcggacgcg ggcgcgttat ggatcccgac gcggggcaga 147180
acgtacgtgc gttggcgcgg cgatgagggg tccgggctgc cgagggggc gtaggggacc 147240
gggctaggca agcccgcggg ttgcgcgggg ttcccgtggg ggtctaggct ccctgggcac 147300
ccgtgggggt cgtgggggtc gcgggtccct gggtatgcgc gggaccctgg gttctctggg 147360
agatcgtgga actcgcggtt ccctgggctc tcggggaacc cggggctccc tggggacacg 147420
tggtgccctg ggaattcttg atggtcggac ggcttcagat ggcttcggga tcgagagggc 147480
cgcacagact cgtagtagac ccgaatctcc acgtttcccc gccgccggat catggtcgcc 147540
gccccggtgc gggggcccgt cggtcggaag cgagtgccct tcaagcgtgt ccgtcctct 147600
gggctgcatg ccgtcggatg gggtgccttt taaggaaagg tctcggctgc ccgccccaac 147660
cggggtttgg gggtgggccg gggaaacccc ggatgccatg gggggtcac accctaagcg 147720
ccggcgcgct ggttgggtgg gggtagaggg gagtccccgg tcgacgagat cgtatcaagg 147780
ggccagcacg cgatcctgcc gctcgttcga tctagcacac ccacgggtct gctgtgtggg 147840
atttcgactc gcgggatccg atcgcacgtc cggaggacac agcagcggga gctccgggtc 147900
ggtcaccgca gttctggccg cctctcggtc ctcccgttcc cttttatgga tctccgcgca 147960
gacatcgcca tacgtccggt gtgtgcaccg cgaagaatcc agaaacatgt ccgtcgtttt 148020
cagggcccaa gacatggtgt ccgtccacg aaggcggcgc ccggcctgcg agaaagcgcg 148080
gatgttggga tcggggcccc gtcccccgg cccgtccccc cgtccccccg gcccgtcccc 148140
ccgtcccccc ggcccgtccc cccgtccccc cggcccgtcc cccgtcccc cggccgtc 148200
cccccgtccc cccgtccccc cgtcccccg tccccgtc cccgtccc cccgtccccc 148260
cgtccccccg tccccgtc cccgtccc cgtccccg tccccgtc ccccgtc 148320
cccgtccc cccggccccc cggccccg gccccggc cccggccc gtccccgg 148380
ccgtccccc cggccgtcc cccggcccg tccccgg ccgtccccc ggccgtccc 148440
ccggcccgt ccccgg ccgtcccccg gccgtccccc cgtccccg cccgtccccc 148500
cggccggccc cccgggtcac cgtacctgcg ataaggctgc agtgggtgga tgggtcctcg 148560
```

```
cggtacgtac agggtggggg ggggggggggg ggagggaaag gcagaacgaa aaggaaccga 148620
tgcgcccgcg tctctgtatc cgatccgatc cgggtgcgtc ggtgcccgc tcgccgccgg 148680
cgtctctgtc tcgctgtggc cccttcgcg atgccgccgc tgccgtcccg gtctccgccg 148740
cgcagccggt gtgcccctgg tgcggcggcg accgggacgc cggcccttta tgtgcgcgag 148800
gaacggcccg ccccccgtcc ggggccgcct cggggcggag cccgcgggat gacgcgggcc 148860
ccgggcaggg cgccagtgct cgcactttgc cctaataata tatatactat taggacgaag 148920
tgcgaacgct tcgcgttctc acttcttttta ccctgcggcc ccgcccctt tggggcggag 148980
cgcgggatga cgcgggcccc gggcagggcg ccagcgctcg cactttgccc taataatata 149040
tatactatta ggacgaagtg cgaacgcttc gcgttctcac ttcttttacc ctgcggcccc 149100
gccccctttg gggcggagcc gcccgcgac caacggggcg acctcgccgg ccccttggg 149160
gccggcgggg gccaacggga gcgcgggccc ggcatctcat taccacgaac ccggaagggc 149220
aggggagcga gcccgcccgc gacgagggtc tcattagcat cgcgggcgga agcggaagcc 149280
gcccgcgccg ggcgctaatg agatgccgcg cgggcggagc ggcggcggcg cgaccaacgg 149340
gccgccgcca cggacgcgga cgcgcgggcg tcgggcgggg gccgcgcata atgcggttcc 149400
acctggggc ggaaccccgg cgagccgggg cgcggcggcg tcgatcgctc ctcctccgcg 149460
tcctcctcct ttccccccgc cccgcgcgcc ccgaggacta tatcagccag gcgacggggc 149520
gatcgtccac acggagcgcg gctaccgacg cggccgccag gatctacccg atcggcgcgg 149580
agaggcgaaa agacacaggc acacgcacgc accgcacggg ggggagagag actgccaacc 149640
accccccccc actgccgccc ctgaagaaga agaagaagac cccccccccg cacacccgg 149700
tcggaggcga tgtcggcgga gcagcggaag aagaagaaga cgacgacgac gacgcagggc 149760
cgcggggccg aggtcgcgat ggcggacgag gacggggac gtctccgggc cgcggcggag 149820
acgaccggcg gccccggatc tccggatcca gccgacggac cgccgcccac cccgaacccg 149880
gaccgtcgcc ccgccgcgcg gcccgggttc gggtggcacg gtgggccgga ggagaacgaa 149940
gacgaggccg acgacgccgc cgccgatgcc gatgccgacg aggcggcccc ggcgtccggg 150000
gaggccgtcg acgagcctgc cgcggacggc gtcgtctcgc cgcggcagct ggccctgctg 150060
gcctcgatgg tggacgaggc cgttcgcacg atcccgtcgc ccccccggga gcgcgacggc 150120
gcgcaagaag aagcggcccg ctcgccttct ccgccgcgga cccctccat gcgcgccgat 150180
tatggcgagg agaacgacga cgacgacgac gacgacgatg acgacgaccg cgacgcgggc 150240
cgctgggtcc gcggaccgga gacgacgtcc gcggtccgcg gggcgtaccc ggaccccatg 150300
gccagcctgt cgccgcgacc cccgcgcgcc cgccgacacc accaccacca ccaccaccg 150360
cgccggcgcg cccccccgcg gcgctcggcc gcctctgact catcaaaatc cggatcctcg 150420
tcgtcggcgt cctccgcctc ctcctccgcc tcctcctcct cgtctgcatc cgcctcctcg 150480
tctgacgacg acgacgacga cgacgccgcc gcgcccccg ccagccgcgc agaccacgcc 150540
gcgggcggga ccctcggcgc ggacgacgag gaggcgggg tgcccgcgag ggccccgggg 150600
gcggcgcccc ggccgagccc gcccaggccc gagcccgccc cggcccggac cccgcgcgcg 150660
accgcgggcc gcctggagcg ccgccgggcc cgcgcggcgg tggccggccg cgacgccacg 150720
ggccgcttca cggccgggcg gccccggcgg gtcgagctgg acgccgacgc ggcctccggc 150780
gccttctacg cgcgctaccg cgacgggtac gtcagcgggg agcgtggcc cggggccggc 150840
ccccgcccc cggggcgcgt gctgtacggc gggctgggcg acagccgccc cggcctctgg 150900
ggggcgcccg aggcggagga ggcgcgggcc cggttcgagg cctcgggcgc cccggcgccc 150960
```

```
gtgtgggcgc ccgagctggg cgacgcggcg cagcagtacg ccctgatcac gcggctgctg 151020
tacacgccgg acgcggaggc gatggggtgg ctccagaacc cgcgcgtggc gcccggggac 151080
gtggcgctgg accaggcctg cttccggatc tcgggcgcgg cgcgcaacag cagctccttc 151140
atctccggca gcgtggcgcg ggccgtgccc cacctggggt acgccatggc ggcgggccgc 151200
ttcggctggg gcctggcgca cgtggcggcc gccgtggcca tgagccgccg ctacgaccgc 151260
gcgcagaagg gcttcctgct gaccagcctg cgccgcgcct acgcgcccct gctggcgcgc 151320
gagaacgcgg cgctgaccgg ggcgcgaacc cccgacgacg cggcgacgc caaccgccac 151380 gacggcgacg acgcccgcgg gaagcccgcc gccgccgccg ccccgttgcc gtcggcggcc 151440
gcgtcgccgg ccgacgagcg cgcggtgccc gccggctacg gcgccgcggg ggtgctcgcc 151500
gccctggggc gcctgagcgc cgcgcccgcc tccgcgccgg ccggggccga cgacgacgac 151560
gacgacgacg gcgccggcgg tggtggcggc ggccggcgcg cggaggcggg ccgcgtggcc 151620
gtggagtgcc tggccgcctg ccgcgggatc ctggaggcgc tggcggaggg cttcgacggg 151680
gacctggcgg ccgtgccggg gctggccgga gcccggcccg ccgcgccccc gcgcccgggg 151740 cccgcggggcg cggccgcccc gccgcacgcc gacgcgcccc gctgcgcgc ctggctgcgc 151800 gagctgcggt tcgtgcgcga cgcgctggtg ctgatgcgcc tgcgcgggga cctgcgcgtg 151860
gccggcggca gcgaggccgc cgtggccgcc gtgcgcgccg tgagcctggt cgccggggcc 151920
ctgggcccgg cgctgccgcg gagcccgcgc ctgctgagct ccgccgccgc cgccgccgcg 151980
gacctgctct tccagaacca gagcctgcgc ccctgctgg ccgacaccgt cgccgcggcc 152040
gactcgctcg ccgcgcccgc ctccgcgccg cgggaggcgc gcaagcgcaa gagccccgcc 152100
ccggccaggg cgccgccggg cggcgcccccg cgccccccga agaagagccg cgcggacgcc 152160
ccccgccccg cggccgcccc tccgcgggg gccgcgcccc ccgccccgcc gacgccgccg 152220
ccgcggccgc cgcgccccgc ggcgctgacc cgccggcccg ccgagggccc cgacccgcag 152280
ggcggctggc gccgccagcc gccggggccc agccacacgc cggcgccctc ggccgccgcc 152340
ctggaggcct actgcgcccc gcgggccgtg gccgagctca cggaccaccc gctcttcccc 152400
gcgccgtggc gcccggccct catgttcgac ccgcgcgcgc tggcctcgct ggccgcgcgc 152460
tgcgccgccc cgcccccgg cggcgcgccc gccgccttcg gcccgctgcg cgcctcgggc 152520
ccgctgcgcc gcgcggcggc ctggatgcgc caggtgcccg accggagga cgtgcgcgtg 152580 gtgatcctct actcgccgct gccgggcgag gacctggccg cgggccgcgc cggggcggg 152640 ccccccccgg agtggtccgc cgagcgcggc gggctgtcct gcctgctggc ggccctgggc 152700
aaccggctct gcgggcccgc cacggccgcc tgggcgggca actggaccgg cgccccgac 152760 gtctcggcgc tgggcgcgca gggcgtgctg ctgctgtcca cgcgggacct ggccttcgcc 152820
ggcgccgtgg agttcctggg gctgctggcc ggcgcctgcg accgccgcct catcgtcgtc 152880
aacgccgtgc gcgccgcgga ctgggccgcc gacgggcccc tggtctcgcg gcagcacgcc 152940
tacctggcct gcgaggtgct gcccgccgtg cagtgcgccg tgcgctggcc ggcggcgcgg 153000
gacctgcgcc gcaccgtgct ggcctccggc cgcgtgttcg gccgggggt cttcgcgcgc 153060 gtggaggccg cgcacgcgcg cctgtacccc gacgcgccgc cgctgcgcct ctgccgcggg 153120
gccaacgtgc ggtaccgcgt gcgcacgcgc ttcggcccg acacgctggt gcccatgtcc 153180
ccgcgcgagt accgccgcgc cgtgctcccg gcgctggacg gccgggccgc gcctcgggc 153240 gcgggcgacg ccatggcgcc cggcgcgccg gacttctgcg aggacgaggc gcactcgcac 153300
cgcgcctgcg cgcgctgggg cctgggcgcg ccgctgcggc ccgtctacgt ggcgctgggg 153360
```

-continued

```
cgcgacgccg tgcgcggcgg cccggcggag ctgcgcgggc cgcggcggga gttctgcgcg     153420
cgggcgctgc tcgagcccga cggcgacgcg ccccgctgg tgctgcgcga cgacgcggac     153480
gcgggcccgc ccccgcagat acgctgggcg tcggccgcgg gccgcgcggg gacggtgctg    153540
gccgcggcgg gcggcggcgt ggaggtggtg gggaccgccg cggggctggc cacgccgccg    153600
aggcgcgagc ccgtggacat ggacgcggag ctggaggacg acgacgacgg actgtttggg    153660
gagtgacggg gggggaaact tccgggagcg ggggagggg gagatgggga gaggggggaag    153720
gaatcgggcg tctgtgcgcc tttaagacag acgcggcgat ggccgcgcgc gtgtgtgaga    153780
aataaagaac gagacagacg aaaacgtacc gccttgtgtg gtttattcgg gggtcgggcg    153840
ggcgggggtc gggcgggcgg gggtcgggcg ggcgggggtc gggcgggcgg gggtcgggcg    153900
ggcgggggtc gggcgggcgg gggtcgggcg ggcgggggtc gggcgggcgg gggtcgggcg    153960
ggcgggggtc gggcgggcgg gggtcgggcg ggcgggggtc gggcgggcgg gggtcgggcg    154020
ggcgggggtc gggcgggcgg gggtcgggcg ggcgggggtc gggcgggcgg cacgtctccc    154080
gcgcccgcgg ggggtctggg gctctgacct gagtgcaggt tacgaaggtc aggtggcccg    154140
agcccccccg caggagcggg agggaaggca cggggcgcgg gagggagggg ctgctgcgag    154200
ctcggggccg cgggcgcggg gggaggggcg ggggaagccc ccggggcggg gcgcggggga    154260
ggcggccgcg gggggaggcgg ccgcgggacc gcagccccgt ggcgcgcggg ggggaggggc    154320
tgccgcgagc tcggcgggat ggagggggagg gagggggtgg cggggaaccg tgtgcgggcg    154380
ggcggtgct tggtgcaact gtctggtctg cgagggcgag cggtggtgcg actggcgtct     154440
tcgggggggc ggggagcttg ggagtgtgtg gtggtctgcg gcacagcctg ctagtccccg    154500
tcctgccgcg cggggggggg cgcgggaaaa aagccgcgcg ggggcgcccg cgggaaggca    154560
gccccgcggc gcgcgggggg aggggcggcg cccgcggggg agcggccggc tccgggggag    154620
ggacggggaa gggggcgcgc ggggctgccc tgccgcccgc ccgccgccgc cgcccgcctt    154680
cgcgccccc cccaaaaaac acccccccg ggggttgact ccccgggggga aagagggcgg     154740
ggcggg                                                              154746
```

<210> SEQ ID NO 9
<211> LENGTH: 15
<212> TYPE: PRT
<213> ORGANISM: HIV p18

<400> SEQUENCE: 9

Arg Ile Gln Arg Gly Pro Gly Arg Ala Phe Val Thr Ile Gly Lys
1               5                   10                  15

<210> SEQ ID NO 10
<211> LENGTH: 15225
<212> TYPE: DNA
<213> ORGANISM: RSV

<400> SEQUENCE: 10

```
acgcgaaaaa atgcgtacta caaacttgca cattcggaaa aaatgggggca aataagaatt      60
tgataagtgc tatttaagtc taacctttc aatcagaaat ggggtgcaat tcactgagca       120
tgataaaggt tagattacaa aatttatttg acaatgacga agtagcattg ttaaaaataa      180
catgttatac tgacaaatta attcttctga ccaatgcatt agccaaagca gcaatacata      240
caattaaatt aaacggtata gtttttatac atgttataac aagcagtgaa gtgtgccctg     300
ataacaacat tgtagtaaaa tctaacttta caacaatgcc aatattacaa aacgaggat      360
```

```
acatatggga attgattgag ttgacacact gctctcaatt aaacggtcta atggatgata    420
attgtgaaat caaattttct aaaagactaa gtgactcagt aatgactaat tatatgaatc    480
aaatatctga tttacttggg cttgatctca attcatgaat tatgtttagt ctaactcaat    540
agacatgtgt ttattaccat tttagttaat ataaaaactc atcaaaggga aatggggcaa    600
ataaactcac ctaatcaatc aaactatgag cactacaaat gacaacacta ctatgcaaag    660
attaatgatc acggacatga gaccccctgtc gatggattca ataataacat ctctcaccaa    720
agaaatcatc acacacaaat tcatatactt gataaacaat gaatgtattg taagaaaact    780
tgatgaaaga caagctacat ttacattctt agtcaattat gagatgaagc tactgcacaa    840
agtagggagt accaaataca agaaatacac tgaatataat acaaaatatg gcactttccc    900
catgcctata tttatcaatc atggcgggtt tctagaatgt attggcatta agcctacaaa    960
acacactcct ataatataca aatatgacct caacccgtaa attccaacaa aaaaaaccaa   1020
cccaaccaaa ccaagctatt cctcaaacaa caatgctcaa tagttaagaa ggagctaatc   1080
cgttttagta attaaaaata aaagtaaagc caataacata aattggggca aatacaaaga   1140
tggctcttag caaagtcaag ttaaatgata cattaaataa ggatcagctg ctgtcatcca   1200
gcaaatacac tattcaacgt agtacaggag ataatattga cactcccaat tatgatgtgc   1260
aaaaacacct aaacaaacta tgtggtatgc tattaatcac tgaagatgca aatcataaat   1320
tcacaggatt aataggtatg ttatatgcta tgtccaggtt aggaagggaa gacactataa   1380
agatacttaa agatgctgga tatcatgtta aagctaatgg agtagatata acaacatatc   1440
gtcaagatat aaatggaaag gaaatgaaat tcgaagtatt aacattatca agcttgacat   1500
cagaaataca agtcaatatt gagatagaat ctagaaaatc ctacaaaaaa atgctaaaag   1560
agatgggaga agtggctcca gaatataggc atgattctcc agactgtggg atgataatac   1620
tgtgtatagc agcacttgta ataaccaaat tagcagcagg agacagatca ggtcttacag   1680
cagtaattag gagggcaaac aatgtcttaa aaaatgaaat aaaacgctac aagggtctca   1740
taccaaggga tatagctaac agtttttatg aagtgtttga aaaacaccct catcttatag   1800
atgttttgt gcactttggc attgcacaat catcaacaag agggggtagt agagttgaag   1860
gaatctttgc aggattgttt atgaatgcct atggttcagg gcaagtaatg ctaagatggg   1920
gagttttagc caaatctgta aaaaatatca tgctaggtca tgctagtgtc caggcagaaa   1980
tggagcaagt tgtggaagtc tatgagtatg cacagaagtt gggaggagaa gctggattct   2040
accatatatt gaacaatcca aaagcatcat tgctgtcatt aactcaattt cctaacttct   2100
caagtgtggt cctaggcaat gcagcaggtc taggcataat gggagagtat agaggtacgc   2160
caagaaacca ggatctttat gatgcagcca agcatatgc agagcaactc aaagaaaatg   2220
gagtaataaa ctacagtgta ttagacttaa cagcagaaga attggaagcc ataaagaatc   2280
aactcaaccc taaagaagat gatgtagagc tttaagttaa caaaaaatac ggggcaaata   2340
agtcaacatg gagaagtttg cacctgaatt tcatggagaa gatgcaaata caaagctac   2400
caaattccta gaatcaataa agggcaagtt cgcatcatcc aaagatccta agaagaaga   2460
tagcataata tctgttaact caatagatat agaagtaacc aaagagagcc cgataacatc   2520
tggcaccaac atcatcaatc aacaagtga agccgacagt accccagaaa ccaaagccaa   2580
ctacccaaga aaaccctag taagcttcaa agaagatctc accccaagtg caacccttt   2640
ttctaagttg tacaaagaaa caatagaaac atttgataac aatgaagaag aatctagcta   2700
ctcatatgaa gagataaatg atcaaacaaa tgacaacatt acagcaagac tagatagaat   2760
```

```
tgatgaaaaa ttaagtgaaa tattaggaat gctccataca ttagtagttg caagtgcagg    2820
acccacttca gctcgcgatg gaataagaga tgctatggtt ggtctgagag aagaaatgat    2880
agaaaaaata agagcggaag cattaatgac caatgatagg ttagaggcta tggcaagact    2940
taggaatgag gaaagcgaaa aaatggcaaa agacacctca gatgaagtgc ctcttaatcc    3000
aacttccaaa aaattgagtg acttgttgga agacaacgat agtgacaatg atctgtcact    3060
tgatgatttt tgatcagtga tcaactcact cagcaatcaa caacatcaat aaaacagaca    3120
tcaatccatt gaatcaactg ccagaccgaa caaacaaatg tccgtcagcg gaaccaccaa    3180
ccaatcaatc aaccaactga tccatcagca acctgacgaa attaacaata tagtaacaaa    3240
aaaagaacaa gatggggcaa atatggaaac atacgtgaac aagcttcacg aaggctccac    3300
atacacagca gctgttcagt acaatgttct agaaaaagat gatgatcctg catcactaac    3360
aatatgggtg cctatgttcc agtcatctgt accagcagac ttgctcataa agaacttgc     3420 aagcatcaac atactagtga agcagatctc tacgcccaaa ggaccttcac tacgagtcac    3480
gattaactca agaagtgctg tgctggctca aatgcctagt aatttcatca taagcgcaaa    3540
tgtatcatta gatgaaagaa gcaaattagc atatgatgta actacaccct tgtgaaatcaa   3600 agcatgcagt ctaacatgct taaaagtgaa aagtatgtta actacagtca agatcttac    3660 catgaagaca ttcaaccca ctcatgagat cattgctcta tgtgaatttg aaaatattat     3720
gacatcaaaa agagtaataa taccaaccta tctaagacca attagtgtca aaacaagga    3780 tctgaactca ctagaaaaca tagcaaccac cgaattcaaa aatgctatca ccaatgcgaa   3840
aattattccc tatgctggat tagtattagt tatcacagtt actgacaata aggagcatt    3900 caaatatatc aagccacaga gtcaatttat agtagatctt ggtgcctacc tagaaaaaga   3960
gagcatatat tatgtgacta ctaattggaa gcatacagct acacgttttt caatcaaacc    4020
actagaggat taaatttaat tatcaacact gaatgacagg tccacatata tcctcaaact    4080
acacactata tccaaacatc atgaacatct acactacaca cttcatcaca caaaccaatc    4140
ccactcaaaa tccaaaatca ctaccagcca ctatctgcta gacctagagt gcgaataggt    4200
aaataaaacc aaaatatggg gtaaatagac attagtaga gttcaatcaa tctcaacaac    4260
catttatacc gccaattcaa tacatatact ataaatctta aaatgggaaa tacatccatc    4320
acaatagaat tcacaagcaa atttgggccc tattttacac taatacatat gatcttaact    4380
ctaatctctt tactaattat aatcactatt atgattgcaa tactaaataa gctaagtgaa    4440
cataaaacat tctgtaacaa tactcttgaa ctaggacaga tgcatcaaat caacacatag    4500
tgctctacca tcatgctgtg tcaaattata atcctgtata tataaacaaa caatccaat    4560 cttctcacag agtcatggtg tcgcaaaacc acgccaacta tcatggtagc atagagtagt    4620
tatttaaaaa ttaacataat gatgaattat tagtatggga tcaaaacaa cattggggca    4680 aatgcaacca tgtccaaaca caagaatcaa cgcactgcca ggactctaga aaagacctgg    4740
gatactctca atcatctaat tgtaatatcc tcttgtttat acagattaaa tttaaaatct    4800
atagcacaaa tagcactatc agttctggca atgataatct caacctctct cataattgca    4860
gccataatat tcatcatctc tgccaatcac aaagttacac taacaacggt cacagttcaa    4920
acaataaaaa accacactga aaaaacatc accacctacc ttactcaagt cccaccagaa    4980
agggttagct catccaaaca acctacaacc acatcaccaa tccacacaaa ttcagccaca    5040
acatcaccca acacaaagtc agaaacacac cacacaacag cacaaaccaa aggcagaacc    5100
accacctcaa cacagaccaa caagccgagc acaaaaccac gcctaaaaaa tccaccaaaa    5160
```

-continued

```
aaaccaaaag atgattacca tttttgaagtg ttcaacttcg ttccctgtag tatatgtggc    5220
aacaatcaac tttgcaaatc catctgtaaa acaataccag caacaaaacc aaagaagaaa    5280
ccaaccatca aacccacaaa caaaccaacc accaaaacca caaacaaaag agacccaaaa    5340
acaccagcca aaacgacgaa aaaagaaact accaccaacc caacaaaaaa accaaccctc    5400
acgaccacag aaagagacac cagcacctca caatccactg tgctcgacac aaccacatta    5460
gaacacacaa tccaacagca atccctccac tcaaccaccc ccgaaaacac acccaactcc    5520
acacaaacac ccacagcatc cgagccctct acatcaaatt ccacccaaaa tacccaatca    5580
catgcttagt tattcaaaaa ctacatctta gcagaaaacc gtgacctatc aagcaagaac    5640
gaaattaaac ctggggcaaa taaccatgga gctgctgatc cacaggttaa gtgcaatctt    5700
cctaactctt gctattaatg cattgtacct cacctcaagt cagaacataa ctgaggagtt    5760
ttaccaatcg acatgtagtg cagttagcag aggttatttt agtgctttaa gaacaggttg    5820
gtataccagt gtcataacaa tagaattaag taatataaaa gaaaccaaat gcaatggaac    5880
tgacactaaa gtaaaactta taaaacaaga attagataag tataagaatg cagtgacaga    5940
attacagcta cttatgcaaa acacaccagc tgccaacaac cgggccagaa gagaagcacc    6000
acagtatatg aactatacaa tcaataccac taaaaaccta aatgtatcaa taagcaagaa    6060
gaggaaacga agatttctgg gcttcttgtt aggtgtagga tctgcaatag caagtggtat    6120
agctgtatcc aaagttctac accttgaagg agaagtgaac aagatcaaaa atgctttgtt    6180
atctacaaac aaagctgtag tcagtctatc aaatgggggtc agtgttttaa ccagcaaagt    6240
gttagatctc aagaattaca taaataacca attattaccc atagtaaatc aacagagctg    6300
tcgcatctcc aacattgaaa cagttataga attccagcag aagaacagca gattgttgga    6360
aatcaacaga gaattcagtg tcaatgcagg tgtaacaaca cctttaagca cttacatgtt    6420
aacaaacagt gagttactat cattgatcaa tgatatgcct ataacaaatg atcagaaaaa    6480
attaatgtca agcaatgttc agatagtaag gcaacaaagt tattctatca tgtctataat    6540
aaaggaagaa gtccttgcat atgttgtaca gctacctatc tatggtgtaa tagatacacc    6600
ttgctggaaa ttacacacat cacctctatg caccaccaac atcaaagaag gatcaaatat    6660
ttgtttaaca aggactgata gaggatggta ttgtgataat gcaggatcag tatccttctt    6720
tccacaggct gacacttgta aagtacagtc caatcgagta ttttgtgaca ctatgaacag    6780
tttgacatta ccaagtgaag tcagccttg taacactgac atattcaatt ccaagtatga    6840
ctgcaaaatt atgacatcaa aaacagacat aagcagctca gtaattactt ctcttggagc    6900
tatagtgtca tgctatggta aaactaaatg cactgcatcc aacaaaaatc gtgggattat    6960
aaagacattt tctaatggtt gtgactatgt gtcaaacaaa ggagtagata ctgtgtcagt    7020
gggcaacact ttatactatg taaacaagct ggaaggcaag aacctttatg taaaggggga    7080
acctataata aattactatg accctctagt gtttccttct gatgagtttg atgcatcaat    7140
atctcaagtc aatgaaaaaa tcaatcaaag tttagctttt attcgtagat ctgatgaatt    7200
actacataat gtaaatactg gcaaatctac tacaaatatt atgataacta caattattat    7260
agtaatcatt gtagtattgt tatcattaat agctattggt ttgctgttgt attgcaaagc    7320
caaaaacaca ccagtacac taagcaaaga ccaactaagt ggaatcaata atattgcatt    7380
cagcaaatag acaaaaaacc acctgatcat gtttcaacaa cagtctgctg atcaccaatc    7440
ccaaatcaac cctaacaaa cacttcaaca tcacagtaca ggctgaatca tttcttcaca    7500
tcatgctacc cacacaacta agctagatcc ttaactcata gttacataaa aacctcaagt    7560
```

-continued

| | |
|---|---|
| atcacaatca aacactaaat caacacatca ttcacaaaat taacagctgg ggcaaatatg | 7620 |
| tcgcgaagaa atccttgtaa atttgagatt agaggtcatt gcttgaatgg tagaagatgt | 7680 |
| cactacagtc ataattactt tgaatggcct cctcatgcct tactagtgag caaaacttc | 7740 |
| atgttaaaca agatactcaa gtcaatggac aaaagcatag acactttgtc tgaaataagt | 7800 |
| ggagctgctg aactggacag aacagaagaa tatgctcttg gtatagttgg agtgctagag | 7860 |
| agttacatag gatctataaa caacataaca aaacaatcag catgtgttgc tatgagtaaa | 7920 |
| cttcttattg agatcaatag tgatgacatt aaaaagctga gagataatga agaacccaat | 7980 |
| tcacctaaga taagagtgta caatactgtt atatcataca ttgagagcaa tagaaaaaac | 8040 |
| aacaagcaaa caatccatct gctcaaaaga ctaccagcag acgtgctgaa gaagacaata | 8100 |
| aaaaacacat tagatatcca caaaagcata atcataagca acccaaaaga gtcaaccgtg | 8160 |
| aatgatcaaa atgaccaaac caaaaataat gatattaccg gataaatatc cttgtagtat | 8220 |
| atcatccata ttgatttcaa gtgaaagcat gattgctaca ttcaatcata aaaacatatt | 8280 |
| acaatttaac cataaccatt tggataacca ccagcgttta ttaaataata tatttgatga | 8340 |
| aattcattgg acacctaaaa acttattaga tgccactcaa caatttctcc aacatcttaa | 8400 |
| catccctgaa gatatatata caatatatat attagtgtca taatgcttgg ccataacgat | 8460 |
| tctatatcat ccaaccataa aactatctta ataaggttat gggacaaaat ggatcccatt | 8520 |
| attaatggaa actctgctaa tgtgtatcta actgatagtt atttaaaagg tgttatctct | 8580 |
| ttttcagaat gtaatgcttt agggagttac cttttttaacg gcccttatct caaaaatgat | 8640 |
| tacaccaact taattagtag acaaagtcca ctactagagc atatgaatct taaaaaacta | 8700 |
| actataacac agtcattaat atctagatat cataaaggtg aactgaaatt agaagaacca | 8760 |
| acttatttcc agtcattact tatgacatat aaaagcatgt cctcgtctga acaaattgct | 8820 |
| acaactaact tacttaaaaa aataatacga agagctatag aaataagtga tgtaaaggtg | 8880 |
| tacgccatct tgaataaact aggactaaag gaaaaggaca gagttaagcc caacaataat | 8940 |
| tcaggtgatg aaaactcagt acttacaact ataattaaag atgatatact ttcggctgtg | 9000 |
| gaaagcaatc aatcatatac aaattcagac aaaaatcact cagtaaatca aaatatcact | 9060 |
| atcaaaacaa cactcttgaa aaattgatg tgttcaatgc aacatcctcc atcatggtta | 9120 |
| atacactggt tcaatttata tacaaaatta ataacatat taacacaata tcgatcaaat | 9180 |
| gaggtaaaaa gtcatggggtt tatattaata gataatcaaa cttttaagtgg ttttcagttt | 9240 |
| attttaaatc aaatatggttg tatcgtttat cataaaggac tcaaaaaaat cacaactact | 9300 |
| acttacaatc aattttaac atggaaagac atcagcctta gcagattaaa tgtttgctta | 9360 |
| attacttgga taagtaattg tttgaataca ttaaataaaa gcttagggct gagatgtgga | 9420 |
| ttcaataatg ttgtgttatc acaattattt ctttatggag attgtatact gaaattattt | 9480 |
| cataatgaag gcttctacat aataaaagaa gtagagggat ttattatgtc tttaattcta | 9540 |
| aacataacag aagaagatca atttaggaaa cgattttata atagcatgct aaataacatc | 9600 |
| acagatgcag ctattaaggc tcaaagaac ctactatcaa gggtatgtca cactttatta | 9660 |
| gacaagacag tgtctgataa tatcataaat ggtaaatgga taatcctatt aagtaaattt | 9720 |
| cttaaattga ttaagcttgc aggtgataat aatctcaata atttgagtga gctatatttt | 9780 |
| ctcttcagaa tctttggaca tccaatggtt gatgaaagac aagcaatgga tgctgtaaga | 9840 |
| attaactgta atgaaactaa gttctactta ttaagtagtc taagtacgtt aagaggtgct | 9900 |
| ttcattttata gaatcataaa agggtttgta aataccatca acagatggcc cactttaagg | 9960 |

-continued

```
aatgctattg tcctacctct aagatggtta aactattata aacttaatac ttatccatct  10020
ctacttgaaa tcacagaaaa tgatttgatt attttatcag gattgcggtt ctatcgtgaa  10080
tttcatctgc ctaaaaaagt ggatcttgaa atgataataa atgacaaagc catttcacct  10140
ccaaaagatc taatatggac tagttttcct agaaattaca tgccatcaca tatacaaaat  10200
tatatagaac atgaaaagtt gaagttctct gaaagcgaca gatcaagaag agtactagag  10260
tattacttga gagataataa attcaatgaa tgcgatctat acaattgtgt agtcaatcaa  10320
agctatctca acaactctaa tcacgtggta tcactaactg gtaaagaaag agagctcagt  10380
gtaggtagaa tgtttgctat gcaaccaggt atgtttaggc aaatccaaat cttagcagag  10440
aaaatgatag ccgaaaatat tttacaattc ttccctgaga gtttgacaag atatggtgat  10500
ctagagcttc aaaagatatt agaattaaaa gcaggaataa gcaacaagtc aaatcgttat  10560
aatgataact acaacaatta tatcagtaaa tgttctatca ttacagatct tagcaaattc  10620
aatcaagcat ttagatatga acatcatgt atctgcagtg atgtattaga tgaactgcat  10680
ggagtacaat ctctgttctc ttggttgcat ttaacaatac ctcttgtcac aataatatgt  10740
acatatagac atgcacctcc tttcataaag gatcatgttg ttaatcttaa tgaagttgat  10800
gaacaaagtg gattatacag atatcatatg ggtggtattg agggctggtg tcaaaaactg  10860
tggaccattg aagctatatc attattagat ctaaatctc tcaaagggaa attctctatc  10920
acagctctga taaatggtga taatcagtca attgatataa gtaaaccagt tagacttata  10980
gagggtcaga cccatgctca agcagattat ttgttagcat taaatagcct taaattgcta  11040
tataaagagt atgcaggtat aggccataag cttaagggaa cagagaccta tatatcccga  11100
gatatgcagt tcatgagcaa aacaatccag cacaatggag tgtactatcc agccagtatc  11160
aaaaaagtcc tgagagtagg tccatggata aatacaatac ttgatgattt taaagttagt  11220
ttagaatcta taggtagctt aacacaggag ttagaataca gagggaaag cttattatgc  11280 agtttaatat ttaggaacat ttggttatac aatcaaattg ctttgcaact ccgaaatcat  11340
gcattatgta acaataagct atatttagat atattgaaag tattaaaaca cttaaaaact  11400
ttttttaatc ttgatagtat cgatatggcg ttatcattgt atatgaattt gcctatgctg  11460
tttggtggtg gtgatcctaa tttgttatat cgaagctttt ataggagaac tccagacttc  11520
cttacagaag ctatagtaca ttcagtgttt gtgttgagct attatactgg tcacgattta  11580
caagataagc tccaggatct tccagatgat agactgaaca aattcttgac atgtgtcatc  11640
acattcgata aaaatcccaa tgccgagttt gtaacattga tgagggatcc acaggcgtta  11700
gggtctgaaa ggcaagctaa aattactagt gagattaata gattagcagt aacagaagtc  11760
ttaagtatag ctccaaacaa aatattttct aaaagtgcac aacattatac taccactgag  11820
attgatctaa atgacattat gcaaaatata gaaccaactt accctcatgg attaagagtt  11880
gtttatgaaa gtctaccttt ttataaagca gaaaaaatag ttaatcttat atcaggaaca  11940
aaatccataa ctaatatact tgaaaaaaca tcagcaatag atacaactga tattaatagg  12000
gctactgata tgatgaggaa aaatataact ttacttataa ggatacttcc actagattgt  12060
aacaaagaca aaagagagtt attaagttta gaaaatctta gtataactga attaagcaag  12120
tatgtaagag aaagatcttg gtcattatcc aatatagtag gagtaacatc gccaagtatt  12180
atgttcacaa tggacattaa atatacaact agcactatag ccagtggtat aattatagaa  12240
aaatataatg ttaatagttt aactcgtggt gaaagaggac ctactaagcc atgggtaggt  12300
tcatctacgc aggagaaaaa aacaatgcca gtgtacaata gacaagtttt aaccaaaaag  12360
```

```
caaagagacc aaatagattt attagcaaaa ttagactggg tatatgcatc catagacaac    12420
aaagatgaat tcatggaaga actgagtact ggaacacttg gactgtcata tgaaaaagcc    12480
aaaaagttgt ttccacaata tctaagtgtc aattatttac accgtttaac agtcagtagt    12540
agaccatgtg aattccctgc atcaatacca gcttatagaa caacaaatta tcatttcgat    12600
actagtccta tcaatcatgt attaacagaa agtatggag atgaagatat cgacattgtg     12660
tttcaaaatt gcataagttt tggtcttagc ctgatgtcgg ttgtggaaca attcacaaac    12720
atatgtccta atagaattat tctcataccg aagctgaatg agatacattt gatgaaacct    12780
cctatattta caggagatgt tgatatcatc aagttgaagc aagtgataca aaaacagcat    12840
atgttcctac cagataaaat aagtttaacc caatatgtag aattattcct aagtaacaaa    12900
gcacttaaat ctggatctaa catcaattct aatttaatat tagtacataa aatgtctgat    12960
tattttcata atgcttatat tttaagtact aatttagctg acattggat tctaattatt     13020 caacttatga aagattcaaa aggtattttt gaaaagatt ggggagaggg gtacataact     13080
gatcatatgt tcattaattt gaatgttttc tttaatgctt ataagactta tttgctatgt    13140
tttcataaag gttatggtaa agcaaaatta gaatgtgata tgaacacttc agatcttctt    13200
tgtgttttgg agttaataga cagtagctac tggaaatcta tgtctaaagt tttcctagaa    13260
caaaaagtca taaatacat agtcaatcaa gacacaagtt tgcatagaat aaaaggctgt     13320
cacagtttta agttgtggtt tttaaaacgc cttaataatg ctaaatttac cgtatgccct    13380
tgggttgtta acatagatta tcacccaaca catatgaaag ctatattatc ttacatagat    13440
ttagttagaa tggggttaat aaatgtagat aaattaacca ttaaaaataa aaacaaattc    13500
aatgatgaat tttacacatc aaatctcttt tacattagtt ataacttttc agacaacact    13560
catttgctaa caaaacaaat aagaattgct aattcagaat tagaagataa ttataacaaa    13620
ctatatcacc caaccccaga aactttagaa aatatatcat taattcctgt taaaagtaat    13680
aatagtaaca aacctaaatt ttgtataagt ggaaataccg aatctataat gatgtcaaca    13740
ttctctaata aaatgcatat taaatcttcc actgttacca caagattcaa ttatagcaaa    13800
caagacttgt acaatttatt tccaaatgtt gtgatagaca ggattataga tcattcaggt    13860
aatacagcaa aatctaacca actttacatc accacttcac atcagacatc tttagtaagg    13920
aatagtgcat cactttattg catgcttcct tggcatcatg tcaatagatt taactttgta    13980
tttagttcca caggatgcaa gatcagtata gagtatattt taaagatct taagattaag    14040 gaccccagtt gtatagcatt cataggtgaa ggagctggta acttattatt acgtacggta    14100
gtagaacttc atccagacat aagatacatt tacagaagtt taaagattg caatgatcat    14160 agtttaccta ttgaatttct aagattatac aacgggcata taaacataga ttatggtgag    14220
aatttaacca ttcctgctac agatgcaact aataacattc attggtctta tttacatata    14280
aaatttgcag aacctattag catctttgtc tgcgatgctc aattacctgt tacagccaat    14340
tggagtaaaa ttataattga atggagtaag catgtaagaa agtgcaagta ctgttcttct    14400
gtaaatagat gcattttaat cgcaaaatat catgctcaag atgatattga tttcaaatta    14460
gataacatta ctatattaaa aacttacgtg tgcctaggta gcaagttaaa aggatctgaa    14520
gtttacttag tccttacaat aggccctgca aatatacttc ctgttttga tgttgtgcaa    14580 aatgctaaat tgattttttc aagaactaaa aatttcatta tgcctaaaaa aactgacaag    14640
gaatctatcg atgcaaatat taaaagctta atacctttcc tttgttaccc tataacaaaa    14700
aaaggaatta agacttcatt gtcaaaattg aagagtgtag ttaatgggga tatattatca    14760
```

-continued

| | |
|---|---|
| tattctatag ctggacgtaa tgaagtattc agcaacaagc ttataaacca caagcatatg | 14820 |
| aatatcctaa aatggctaga tcatgtttta aattttagat cagctgaact taattacaat | 14880 |
| catttataca tgatagagtc cacatatcct tacttaagtg aattgttaaa tagtttaaca | 14940 |
| accaatgagc tcaagaaact gattaaaata acaggtagtg tactatacaa ccttcccaac | 15000 |
| gaacagtaac ttaaaatatc attaacaagt ttggtcaaat ttagatgcta acacatcatt | 15060 |
| atattatagt tattaaaaaa tatgcaaact tttcaataat ttagcttact gattccaaaa | 15120 |
| ttatcatttt attttaagg ggttgaataa aagtctaaaa ctaacaatga tacatgtgca | 15180 |
| tttacaacac aacgagacat tagttttga cactttttt ctcgt | 15225 |

<210> SEQ ID NO 11
<211> LENGTH: 9913
<212> TYPE: DNA
<213> ORGANISM: HIV (Human)

<400> SEQUENCE: 11

| | |
|---|---|
| tggaagggtt aatttactct aagaaaaggc aagagatcct tgatttgtgg gtctatcaca | 60 |
| cacaagaata cttccctgac tggcaaaact acacaccggg accagggatc agatacccac | 120 |
| tgacctttgg atggccattc aagctagtgc cagttgaccc aagggaagta gaagaggcca | 180 |
| acaatggaga gaacaactgt ttgctacatc ctatgagcca gcatggaatg gatgatgagg | 240 |
| aaagagaagt attaacatgg aagtttgaca gtcagcctag tacacagaca catggcccgc | 300 |
| gagctacatc cggagtatta caaagactgc tgacacagaa gggactttcc gctgggactt | 360 |
| tccactgggg cggttcagga ggtgtggtct gggcgggacg gggagtggtc aaccctcaga | 420 |
| tgctgcatat aagcagctgc ttttcgcctg tactgggtct ctctaggtag gccagatctg | 480 |
| agcccgggag ctctctggct atatggggaa cccactgctt aagcctcaat aaagcttgcc | 540 |
| ttgagtgcta taagtagtgt gtgcccatct gttatatgga gtctggtaac tagagatccc | 600 |
| tcaggccctt ttggtagtga ggaaaatctc tagcagtggc gcccgaacag ggacttgaaa | 660 |
| gcgaaagtaa gaccagagga gggctctcga cgcaggactc ggcttgctga agtgcactcg | 720 |
| gcaagaggcg aggggcggcg actggtgagt acgccaaatt ttatttgact agcggaggct | 780 |
| agaaggagag agatgggtgc gagagcgtca atattaagag ggggaaattt agatacatgg | 840 |
| gaaaaaatta ggttaaggcc aggggggaaag aaacactata tgctaaaaca cctagtatgg | 900 |
| gcaagcaggg agctggaaag atttgcactt aaccctggcc ttttagagac atcagaaggc | 960 |
| tgtaaacaaa taatgcaaca gcttcaacca gctcttcaga caggaacaga ggaacttaga | 1020 |
| tcattattca acacagtagc aactctctat tgtgtacata aaggaataaa ggtacaagac | 1080 |
| accaaggaag ccctagacaa gatagaggaa gaacaaaaca aaagtcagca aaaaacacag | 1140 |
| caggcagaag cagctgccgg aaaagtcagt caaaattatc ctatagtgca gaatcttcaa | 1200 |
| gggcaaatgg tacaccagcc catatcacct agaactttga atgcatgggt aaaagtaata | 1260 |
| gaggagaaag gttttagtcc cgaggtaata cccatgttta cagcattatc agaaggagcc | 1320 |
| accccacaag atttaaacac catgttaaat acagtagggg gacatcaagc agccatgcaa | 1380 |
| atgttaaagg ataccatcaa tgaggaggct gcagaatggg atagattaca tccagtacaa | 1440 |
| gcagggcctg ttgcaccagg ccaaatgaga gacccaaggg gaagtgacat agcaggaact | 1500 |
| actagtaccc ttcaggaaca aataggatgg atgacacaca tccacctat cccagtggga | 1560 |
| gacatctata aaagatggat aattctgggg ttaaataaaa tagtaagaat gtatagccct | 1620 |
| gtcagcattt tggacataaa acaagggcca aaagaatcct ttagagacta tgtagatcgg | 1680 |

-continued

```
ttctttaaaa ctctaagagc tgaacaatgt acacaagatg taaagaattg gatgacagac    1740
accttgttgg tccaaaatgc gaacccagat tgtaagacca ttttaagagc attaggacca    1800
ggggctacat tagaagaaat gatgacagca tgtcagggag tgggaggacc cagccacaaa    1860
gcaagagtat tggctgaggc aatgagccaa gcaaacagta caagtatact gatgcagaga    1920
ggcaacttca aaggccctaa aagaattatt aaatgtttca actgtggcaa ggaagggcac    1980
atagccaaaa actgcagggc ccctaggaaa aagggctgtt ggaaatgtgg aaaggaagga    2040
caccaaatga aagactgtac tgagaggcag gctaattttt tagggaaaat ctggccttcc    2100
cacaaagggg ggaggccagg gaatttcctt cagagcaggc cagagccaac agccccacca    2160
gcagagagct tcagattcga ggagacaacc ccgctttga agcaggaacc aaaagacaag    2220
gaacccttaa cttccctcaa atcacccttt ggcagcgacc ccttgtctca ataaaagtag    2280
ggggccaaat aaaggaggct cttttagaca caggagcaga tgatacagta ttagaagaaa    2340
tgagtttgtc aggaaaatgg aaaccaaaaa tgataggagg aattggaggt tttattaaag    2400
taagacagta tgatcaaata cctatagaaa tttgtggaaa aaaggctata ggtacagtgt    2460
taataggacc tactcctgtc aacataattg gaagaaatat gttgactcag cttggctgca    2520
ctctaaattt tccaatcagt cctattgaaa ctgtaccagt aaaattaaag ccaggcatgg    2580 atggcccctaa ggttaaacaa tggccattga cagaagaaaa aataaaagca ttaacagaaa    2640
tttgtgcaga aatggaaaag gaaggaaaaa ttacaaaaat tgggcctgaa aatccatata    2700
atactccagt atttgcaata aaaaagaaag acagtactaa gtggagaaaa ttagtagact    2760
tcagggaact taataaaaga actcaagact tttgggaggt tcaattagga ataccgcacc    2820
cagcagggtt aaaaaagaaa aaatcagtaa cagtattaga tgtgggggat gcatattttt    2880
cagttccttt agatgaaggc ttcaggaaat acactgcatt caccatacct agtataaaca    2940
atgaaacacc agggattaca tatcaatata atgtgcttcc acagggatgg aaaggatcac    3000
cagcaatatt ccagagtagc atgacaagaa tcttagagcc ctttaggaca caaaatccag    3060
aaatagtcat ctatcaatat atggatgatt tgtatgtagg atctgattta gaaatagggc    3120
aacatagagc aaaaatagag gaattaagaa accatctatt aaagtgggga tttaccacac    3180
cagacaagaa acatcagaaa gaaccccat ttctttggat ggggtatgaa ctccatcctg    3240
ataaatggac agtacagcct atacagctgc caacaaagga tagctggact gtcaatgata    3300
tacagaagtt agtgggaaaa ttaaactggg caagtcagat ttacccaggg attaaagtaa    3360
ggcaactttg taaactcctt aggggggacca aagcattaac agacgtagta ccactaaatg    3420
aagaagcaga attagaattg gcagaaaaca gggaaattct aaaagaacca gtacatggag    3480
tatattatga cccatcaaaa gacttgatag ctgaaataca gaaacaggga caggatcaat    3540
ggacatatca aatttaccaa gaaccattca aaaatctgaa aacagggaag tatgcaaaaa    3600
tgaggactgc ccacactaat gatgtaaaac agttaacaga ggcagtgcaa aaaatagcca    3660
tggaaagcat agtaatatgg ggaaagactc ctaaatttag actacccatc caaaaagaaa    3720
tatgggaaac atggtggaca gactattggc aagccacctg gattcctgag tgggagtttg    3780 ttaataccc tcccctagta aaattatggt accagttgga gaaagaaccc ataatgggag    3840
cagaaacttt ctatgtagat ggagcagcta atagggaaac taaagcagga aaagcaggat    3900
atgttactga tagaggaagg cagaaagtta tttctctaac tgaaacaaca aatcagaaga    3960
ctgaattaca agcaattcag ctagctttgc aagattcagg attagaagta aacatagtaa    4020
cagactcaca gtatgcatta ggaatcattc aagcacagcc agataagagt gaatcagagt    4080
```

```
tagtcaacca aataatagaa caattaataa acaaggaaag ggtctacctg tcatgggtac    4140
cagcacataa aggaattgga ggaaatgaac aagtagataa attagtaagt aatggaatta    4200
ggaaagtgct atttctagat ggaatagata aggctcaaga agagcatgaa aggtatcata    4260
gcaattggag agcaatggct agtgagttta atctgccacc catagtagca aaagaaatag    4320
tagctagctg tgataagtgt cagtcaaaag gggaagccat gcatggacaa gtagactgta    4380
gcccaggaat atggcaatta gattgtacac atttagaagg aaaagtcatc ctggtagcag    4440
tccatgtagc cagtggctat atagaagcag aggttatccc agcagaaaca ggacaagaca    4500
cggcatacta tatactaaaa ttagcaggaa gatggccagt caaagtaata catacagaca    4560
atggcagtaa tttcaccagt gctgcagtca aggcagcctg ttggtgggca ggtatccaac    4620
aggaatttgg gattccctac aatccccaaa gtcaggagt agtagaatcc atgaataaag    4680
aattaaagaa aatcataggg caggtaagag atcaagctga gcaccttaag acagcagtac    4740
aaatggcagt attcattcac aattttaaaa gaaaaggggg gattgggga tacagtgcag    4800 gggaaagaat aatagatata atagcaacag atatacaaac taaagaatta caaaaacaaa    4860
ttacaaatat tcaaaaattt cgggtttatt acagagacag cagagaccct atttggaaag    4920
gaccagccaa actactctgg aaaggtgaag gggcagtagt aatacaagat aatagtgaca    4980
taaaggtagt accaaggagg aaagtaaaga tcattaagga ctatggaaaa cagatggcag    5040
gtgctgattg tgtggcaagt agacaggatg aagattagaa catggaatag tctagtaaag    5100
catcatatgt atatctcaaa gagagctaat ggatggtttt acagacatca ttatgaaagc    5160
agacatccaa aagtaagttc agaagtacac atcccattag gggatgctag attagtaata    5220
acaacatatt ggggcttgca acaggagaaa agagagtggc atttgggtca tggagtctcc    5280
atagaatgga gattgagaag atatagcaca caagtagacc caggcctggc agaccaacta    5340
attcatatgt attattttga ttgttttgca gactctgcca taaggaaagc catattagga    5400
cacatagtta atcctaggtg tgactatcaa gcaggacata taaggtagg atctctacag    5460 tacttggcac tgacagcatt aataaaacca aaaaagagaa agccacctct gcctagtatt    5520
agtaaattag tagaggatag atggaacaag ccccagagga ccaggggccg cagagggaac    5580
catacaatga atggacacta gagattttag aggaactcaa gcaggaagct gtcagacact    5640
ttcctccacc atggctccat agcttaggac aatatatcta tgaaacctat ggggatactt    5700
ggacaggagt cgaaactata ataagaatac tgcaacaact gctgtttatt catttcagaa    5760
ttgggtgcca gcatagcaga ataggcattt tgcaacagag aagagcaaga aatggagcca    5820
gtagacccta aactagagcc ctggaaccat ccgggaggtc agcctaaaac tccttgtaat    5880
acatgctatt gtaaaaatg cagctatcat tgtttagttt gctttcagaa aaaggcttta    5940
ggcatttact atggcaggaa gaagcggaga cagcgacgaa gcgctccttc aagcagtgag    6000
gatcatcaag atcctatatc aaagcagtaa gtatctaata gtagatgtaa tgatagattt    6060
actagcaaga gtagattata gaataggact agcagctttt gtagtagcat tactcatagc    6120
aataattgtg tggaccatag tatatctaga atataggaaa cttgtaagac aaagaaagat    6180
agactggtta attaaaagaa ttagggaaag agcagaagac agtggcaatg agagtgaagg    6240
ggataccgag gaattggcaa caatggtgga tatgggcag cttaggcttt tggataattt    6300
gtagtgtgat ggggaacttg tgggtcacag tctattatgg ggtacctgtg tggagagaag    6360
caaaaactac tctattttgt gcatcagatg ctaaagcata tgaggcagaa gtgcataatg    6420
tctgggctac acatgcctgt gtacccacag accccaaccc acaagaaata gagttaaaaa    6480
```

```
atgtaacaga aaattttaac atgtgggaaa atgacatggt ggatcagatg catgaggata      6540
taatcagttt atgggatcaa agcctaaagc catgtgtaaa gttgacccca ctctgtgtca      6600
ctttaaactg taagaatgtt accagtaagg atatcaatat taccagcaat gcagaaatga      6660
aagcagaaat gaaaaattgc tctttcaata taaccacaga actaagagat aagaaaaagc      6720
aggaatatgc actttttat aaacttgata tagtaccact tactaatgac aatgccagtg       6780
agaatgccag tgagtataga ttaataaatt gtgatacctc aaccataaca cagtcttgtc      6840
caaaggtcac ttttgaccca attcctatac attattgtgc tccagctggt tatgtgatcc      6900
taaagtgtaa taataagaca ttcaatggaa caggaccatg caataatgtc agcactgtac      6960
aatgtacaca tggaattaag ccagtagtgt caactcaact actgttaaat ggtagtctag      7020 cagaaaaga gataataatt agatctaaaa atataacaga caatgtcaaa acaataatag       7080
tacatcttaa tgaatctgta gagattgagt gtacaaggcc tggcaataat acaagaagaa      7140
gtgtgaggat aggaccagga caagcattct atgcaacagg agacataata ggagatataa      7200
gagcagcaca ttgtaacatt agtgaaagta aatggaataa aatttttatac agggtaagtg     7260 aaaaattaaa agaacacttc cctaataaaa caatacaatt tgaccaaccc ataggagggg      7320
acttagaaat tacaacacat agctttaatt gtagaggaga ttttttctat tgtaatacat      7380
caaagctgtt taatggtaca tacaacagta caggagatac ttcaaattca acaatcacac      7440
tctcatgcag aataaaacaa attataaaca tgtggcaggg ggtaggacga gcaatgtatg      7500
cctctcccat tgcaggaaac ataacatgta aatcaaatat cacaggacta ctattgacac      7560
gtgatggagg aaatgagaca agtgggattg agatattcag acctgcagga ggagatatga      7620
gggacaattg gagaagtgaa ttatataaat ataaagtggt agaaattaag ccattaggat      7680
tagcacccac taagtcaaaa cggagagtgg tggagagaga aaaagagca gtgacattcg       7740 gagctatgtt ccttgggttc ttgggagcag caggaagcac tatgggcgcg gcgtccatga      7800
cgctgacggt acaggccaga caactgttgt ctggtatagt gcaacagcaa agcaatttgc      7860
tgagggctat agaggcgcaa cagcatatgt tgcaactcac ggtctggggc attaagcaac      7920
tccagacaag agtcctggct gtagaaagat acctaaggga tcaacagctc ctaggaattt      7980
ggggctgctc tggaaaactc atctgcacca ctgctgtgcc ttggaatagt agttggagta      8040
ataaatctca acatgatatt tgggacaacc tgacctggat gcagtgggat agagagatta      8100
gtaattacac agacacaata taggttgc ttgaggaatc gcaaaaccag caggaaagaa        8160
atgaaaagga tttactagca ttggacagtt ggaaaactct gtggagttgg tttgacatat      8220
caaactggct gtggtacata aaaatattca taatgatagt aggaagcttg ataggttaa       8280 ggataatttt tgctgtgcta tctatagtaa atagagttag gcaggatac tcaccttttgt      8340 cattccagac ccttacccca aacccgaggg gacccgacag gctcgaagga atcgaagaag      8400
aaggtggaga gcaagacaaa gacagatcaa ttcgattagt gaacggatcc ttagcacttg      8460
cctgggacga tctgcggagc ctgtgccttt tcagttacca ccaattgaga gacttcatat      8520
tggtggtagc gagagcggtg gaacttctgg gacgcagcag tctcagggc ctacagaggg       8580 ggtgggaagc ccttaagtat ttgggaagtc ttatacagta ttggggtctg gaactaaaaa      8640
ggagtactat tagtctgctt gataccgtag caatagcagt agctgaagga acagatagga      8700
ttatagaatt aatacaaaga atttggaggg ctatctgcaa tatacctaga agaataagac      8760
agggctttga agcagctttg ctataaaatg ggggcaagt ggtcaaaaag cagtatagtt       8820
ggatggcctg ctgtaagaga aagaataaga acaactgagc cagcggcaga gggagtagga      8880
```

-continued

```
gcagcatctc aagacttaga taaacatgga gcacttacaa gcagcaacac agccgccaat      8940
aatgctgacg ttgcctggct ggaaccgcaa gaggaggaag gggcggtagg ctttccagtc      9000
agacctcaag tacctttaaa accaatgact tataagggag cggtggatct aggcttcttt      9060
ttaaaagaaa aggggggact ggaagggtta atttactcta agaaaaggca agagatcctt      9120
gatttgtggg tctatcacac acaaggctac ttccctgact ggcaaaacta cacaccggga      9180
ccagggatca catacccact gacctttgga tggccattca agctagtgcc agttgaccca      9240
agggaagtag aagaggccaa caatggagag aacaactgtt tgctacatcc tatgagccag      9300
catggaatgg atgatgaaga agagaagta ttaacatgga gtttgacag tcacctagta       9360
cacagaccca tggcccgcga gatacatccg gagtattaca agactgctg acacagaagg      9420
gactttccgc tgggactttc cactggggcg ggtcaggagg tgtggtctgg gcggacggg      9480
gagtggtcag ccctcagatg ctgcatataa gcagctgctt ttcgcctgta ctgggtctct      9540
ctaggtagac cagatctgag cccgggagct ttctggctat ctgggaacc cactgcttaa      9600
gcctcaataa agcttgcctt gagtgctcta agtagtgtgt gcccatctgt tatatggact      9660
ctggtaacta gagatccctc agaccctttt ggtagtgagg aaaatctcta gcagtggcgc      9720
ccgaacaggg acttgaaagc gaaagtaaga ccagaggaga gctctcgacg caggactcgg      9780
cttgctgaag tgcactcggc aagaggcgag gggcggcgac tggtgagtac gccaaatttt      9840
atttgactag cggaggctag aaggagagag atgggtgcgc ggccgccgcg gatccgcgaa      9900
gggcgaattc gat                                                          9913

<210> SEQ ID NO 12
<211> LENGTH: 9737
<212> TYPE: DNA
<213> ORGANISM: HIV isolate ARV-2/SF2

<400> SEQUENCE: 12
ctggaagggc taatttggtc ccaaagaaga caagagatcc ttgatctgtg gatctaccac        60
acacaaggct acttccctga ttggcagaat tacacaccag ggccaggat cagatatcca       120
ctgacctttg gatggtgctt caagctagta ccagttgagc cagagaaggt agaagaggcc       180
aatgaaggag agaacaacag cttgttacac cctatgagcc tgcatgggat ggaggacgcg       240
gagaaagaag tgttagtgtg gaggtttgac agcaaactag catttcatca catggcccga       300
gagctgcatc cggagtacta caaagactgc tgacatcgag cttttctacaa gggactttcc       360
gctggggact ttccagggag gcgtggcctg ggcgggactg gggagtggcg tccctcagat       420
gctgcatata agcagctgct ttttgcctgt actgggtctc tctggttaga ccagatctga       480
gcctgggagc tctctggcta actagggaac ccactgctta agcctcaata aagcttgcct       540
tgagtgcttc aagtagtgtg tgcccgtctg ttgtgtgact ctggtaacta gagatccctc       600
agaccctttt agtcagtgtg aaaaatctct agcagtggc gcccgaacag gacgcgaaa        660
gcgaaagtag aaccagagga gctctctcga cgcaggactc ggcttgctga agcgcgcaca       720
gcaagaggcg aggggcggcg actggtgagt acgccaattt ttgactagcg gaggctagaa       780
ggagagagag atgggtgcga gagcgtcggt attaagcggg ggagaattag ataaatggga       840
aaaaattcgg ttaaggccag ggggaaagaa aaaatataag ttaaaacata tagtatgggc       900
aagcagggag ctagaacgat tcgcagtcaa tcctggcctg ttagaaacat cagaaggctg       960
cagacaaata ttgggacagc tacagccatc ccttcagaca ggatcagaag aacttagatc      1020
attatataat acagtagcaa ccctctattg tgtacatcaa aggatagatg taaaagacac      1080
```

-continued

```
caaggaagct ttagagaaga tagaggaaga gcaaaacaaa agtaagaaaa aggcacagca    1140
agcagcagct gcagctggca caggaaacag cagccaggtc agccaaaatt accctatagt    1200
gcagaaccta caggggcaaa tggtacatca ggccatatca cctagaactt taaatgcatg    1260
ggtaaaagta gtagaagaaa aggctttcag cccagaagta atacccatgt tttcagcatt    1320
atcagaagga gccaccccac aagatttaaa caccatgcta aacacagtgg ggggacatca    1380
agcagccatg caaatgttaa aagagactat caatgaggaa gctgcagaat gggatagagt    1440
gcatccagtg catgcagggc ctattgcacc aggccaaatg agagaaccaa ggggaagtga    1500
catagcagga actactagta cccttcagga acaaatagga tggatgacaa ataatccacc    1560
tatcccagta ggagaaatct ataaaagatg gataatcctg ggattaaata aaatagtaag    1620
aatgtatagc cctaccagca ttctggacat aagacaagga ccaaaggaac cctttagaga    1680
ttatgtagac cggttctata aaactctaag agccgaacaa gcttcacagg atgtaaaaaa    1740
ttggatgaca gaaaccttgt tggtccaaaa tgcaaaccca gattgtaaga ctatttaaa    1800 agcattggga ccagcagcta cactagaaga aatgatgaca gcatgtcagg gagtgggggg    1860
acccggccat aaagcaagag ttttggctga agccatgagc caagtaacaa atccagctaa    1920
cataatgatg cagagaggca attttaggaa ccaaagaaag actgttaagt gtttcaattg    1980
tggcaaagaa gggcacatag ccaaaaattg cagggcccct aggaaaaagg gctgttggag    2040
atgtggaagg gaaggacacc aaatgaaaga ttgcactgag agacaggcta atttttagg     2100 gaagatctgg ccttcctaca agggaaggcc agggaatttt cttcagcaga gaccagagcc    2160
aacagcccca ccagaagaga gcttcaggtt tggggaggag aaaacaactc cctctcagaa    2220
gcaggagccg atagacaagg aactgtatcc tttaacttcc ctcagatcac tctttggcaa    2280 cgaccctcg tcacaataag gatagggggg caactaaagg aagctctatt agatacagga     2340
gcagatgata cagtattaga agaaatgaat ttgccaggaa atggaaaacc aaaaatgata    2400
gggggaattg gaggttttat caaagtaaga cagtacgatc agatacctgt agaaatctgt    2460
ggacataaag ctataggtac agtattagta ggacctacac ctgtcaacat aattggaaga    2520
aatctgttga ctcagattgg ttgtacttta aatttcccca ttagtcctat tgaaactgta    2580
ccagtaaaat taaagccagg aatggatggc ccaaaagtta agcaatggcc attgacagaa    2640
gaaaaaataa aagcattagt agagatatgt acagaaatgg aaaaggaagg gaaaatttca    2700
aaaattgggc ctgaaaatcc atacaatact ccagtatttg ctataaagaa aaaagacagt    2760
actaaatgga gaaaactagt agatttcaga gaacttaata aaagaactca agacttctgg    2820
gaagttcagt taggaatacc acaccccgca gggttaaaaa agaaaaaatc agtaacagta    2880
ttggatgtgg gtgatgcata cttttcagtt cccttagata aagactttag aaagtatact    2940
gcatttacca tacctagtat aaacaatgag acaccaggga ttagatatca gtacaatgtg    3000
ctgccacagg gatggaaagg atcaccagca atattccaaa gtagcatgac aaaaatctta    3060 gagccttta gaaaacagaa tccagacata gttatctatc aatacatgga tgatttgtat    3120
gtaggatctg acttagaaat agggcagcat agaacaaaaa tagaggaact gagacagcat    3180
ctgttgaggt ggggatttac cacaccagac aaaaaacatc agaaagaacc tccattcctt    3240
tggatgggtt atgaactcca tcctgataaa tggacagtac agcctataat gctgccagaa    3300
aaagacagct ggactgtcaa tgacatacag aagttagtgg gaaaattgaa ttgggcaagt    3360
cagatttatg cagggattaa agtaaagcag ttatgtaaac tccttagagg aaccaaagca    3420
ctaacagaag taataccact aacagaagaa gcagagctag aactggcaga aaacagggag    3480
```

```
attctaaaag aaccagtaca tgaagtatat tatgacccat caaaagactt agtagcagaa    3540
atacagaagc aggggcaagg ccaatggaca tatcaaattt atcaagagcc atttaaaaat    3600
ctgaaaacag gaaagtatgc aaggatgagg ggtgcccaca ctaatgatgt aaaacagtta    3660
acagaggcag tgcaaaaagt atccacagaa agcatagtaa tatggggaaa gattcctaaa    3720
tttaaactac ccatacaaaa ggaaacatgg gaagcatggt ggatggagta ttggcaagct    3780
acctggattc ctgagtggga gtttgtcaat acccctccct tagtgaaatt atggtaccag    3840
ttagagaaag aacccatagt aggagcagaa actttctatg tagatggggc agctaatagg    3900
gagactaaat taggaaaagc aggatatgtt actgacagag gaagacaaaa agttgtctcc    3960
atagctgaca caacaaatca gaagactgaa ttacaagcaa ttcatctagc tttgcaggat    4020
tcgggattag aagtaaacat agtaacagac tcacaatatg cattaggaat cattcaagca    4080
caaccagata gagtgaatc agagttagtc agtcaaataa tagagcagtt aataaaaaag    4140
gaaaaggtct acctggcatg ggtaccagca cacaaaggaa ttggaggaaa tgaacaagta    4200
gataaattag tcagtgctgg aatcaggaaa gtactatttt tgaatggaat agataaggcc    4260
caagaagaac atgagaaata tcacagtaat tggagagcaa tggctagtga ttttaacctg    4320
ccacctgtag tagcaaaaga aatagtagcc agctgtgata atgtcagct aaaaggagaa    4380 gccatgcatg gacaagtaga ctgtagtcca ggaatatggc aactagattg tacacatcta    4440
gaaggaaaaa ttatcctggt agcagttcat gtagccagtg gatatataga agcagaagtt    4500
attccagcag agacagggca ggaaacagca tattttctct taaaattagc aggaagatgg    4560
ccagtaaaaa caatacatac agacaatggc agcaatttca ccagtactac ggttaaggcc    4620
gcctgttggt gggcagggat caagcaggaa tttggcattc cctacaatcc ccaaagtcaa    4680
ggagtagtag aatctatgaa taatgaatta aagaaaatta taggacaggt aagagatcag    4740
gctgaacacc ttaagacagc agtacaaatg gcagtattca tccacaattt taaaagaaaa    4800
ggggggattg ggggatacag tgcaggggaa agaatagtag acataatagc aacagacata    4860
caaactaaag aactacaaaa gcaaattaca aaaattcaaa attttcgggt ttattacagg    4920
gacaacaaag atcccctttg gaaaggacca gcaaagcttc tctggaaagg tgaaggggca    4980
gtagtaatac aagataatag tgacataaaa gtagtgccaa gagaaaagc aaaaatcatt    5040 agggattatg gaaaacagat ggcaggtgat gattgtgtgg caagtagaca ggatgaggat    5100
tagaacatgg aaaagtttag taaaacacca tatgtatatt tcaaagaaag ctaaggatg     5160 gttttataga catcactatg aaagtactca tccaagagta agttcagaag tacacatccc    5220
cctaggggat gctaaattgg taataacaac atattggggt ctgcatacag gagaaagaga    5280
atggcatttg ggccagggag tcgccataga atggaggaaa agaaatata gcacacaagt    5340 agaccctggc ctagcagacc aactaattca tctgcattat tttgattgtt tttcagaatc    5400
tgctataaaa aatgccatat taggatatag agttagtcct aggtgtgaat atcaagcagg    5460
acataacaag gtaggatctc tacaatactt ggcactagca gcattaataa caccaaaaaa    5520
gacaaagcca ccttttgccta gtgttaagaa actgacagag gatagatgga acaagcccca    5580
gaagaccaag ggccacagag ggagccatac aatgaatgga cactagagct tttagaggag    5640
cttaagagag aagctgttag acattttcct aggccatggc tccatagctt aggacaatat    5700
atctatgaaa cttatgggga tacttgggca ggagtggaag ccataataag aattctgcaa    5760
caactgctgt ttattcattt cagaattggg tgtcaacata gcagaatagg cattattcaa    5820
cagaggagag caagaagaaa tggagccagt agatcctaat ctagagccct ggaagcatcc    5880
```

```
aggaagtcag cctaggactg cttgtaacaa ttgctattgt aaaaagtgtt gctttcattg    5940
ctacgcgtgt ttcacaagaa aaggcttagg catctcctat ggcaggaaga agcggagaca    6000
gcgacgaaga gctcctcagg acagtcagac tcatcaagct tctctatcaa agcagtaagt    6060
agtaaatgta atgcaatctt tacaaatatt agcaatagta tcattagtag tagtagcaat    6120
aatagcaata gttgtgtgga ccatagtact catagaatat aggaaaatat aagacaaag     6180 aaaatagaca gattaattga tagaataaga gaaaagcag aagacagtgg caatgaaagt     6240 gaagggacc aggaggaatt atcagcactt gtggagatgg ggcaccttgc tccttgggat     6300
gttgatgatc tgtagtgcta cagaaaaatt gtgggtcaca gtttattatg gagtacctgt    6360
gtggaaagaa gcaactacca ctctattttg tgcatcagat gctagagcat atgatacaga    6420
ggtacataat gtttgggcca cacatgcctg tgtacccaca gaccccaacc cacaagaagt    6480
agtattggga aatgtgacag aaaattttaa catgtggaaa ataacatgg tagaacagat     6540 gcaggaggat ataatcagtt tatgggatca agcctaaag ccatgtgtaa aattaacccc     6600
actctgtgtt actttaaatt gcactgattt ggggaaggct actaatacca atagtagtaa    6660
ttggaaagaa gaaataaaag gagaaataaa aaactgctct ttcaatatca ccacaagcat    6720
aagagataag attcagaaag aaaatgcact ttttcgtaac cttgatgtag taccaataga    6780
taatgctagt actactacca actataccaa ctataggttg atacattgta acagatcagt    6840
cattacacag gcctgtccaa aggtatcatt tgagccaatt cccatacatt attgtacccc    6900
ggctggtttt gcgattctaa agtgtaataa taaaacgttc aatggaaaag gaccatgtac    6960
aaatgtcagc acagtacaat gtacacatgg aattaggcca atagtgtcaa ctcaactgct    7020
gttaaatggc agtctagcag aagaagaggt agtaattaga tctgacaatt tcacgaacaa    7080
tgctaaaacc ataatagtac agctgaatga atctgtagca attaactgta caagacccaa    7140
caacaataca agaaaagta tctatatagg accaggaga gcatttcata caacaggaag      7200
aataatagga gatataagaa aagcacattg taacattagt agagcacaat ggaataacac    7260
tttagaacag atagttaaaa aattaagaga acagtttggg aataataaaa caatagtctt    7320
taatcaatcc tcaggagggg acccagaaat tgtaatgcac agttttaatt gtagagggga    7380 attttttctac tgtaatacaa cacaactgtt aataatacaa tggaggttaa atcacactga    7440
aggaactaaa ggaaatgaca caatcatact cccatgtaga ataaaacaaa ttataaacat    7500
gtggcaggaa gtaggaaaag caatgtatgc ccctcccatt ggaggacaaa ttagttgttc    7560
atcaaatatt acagggctgc tattaacaag agatggtggt acaaatgtaa ctaatgacac    7620
cgaggtcttc agacctggag gaggagatat gagggacaat tggagaagtg aattatataa    7680
atataaagta ataaaaattg aaccattagg aatagcaccc accaaggcaa agagaagagt    7740
ggtgcagaga gaaaaaagag cagtgggaat agtaggagct atgttccttg ggttcttggg    7800
agcagcagga agcactatgg gcgcagtgtc attgacgctg acggtacagg ccagacaatt    7860
attgtctggt atagtgcaac agcagaacaa tttgctgagg gctattgagg cgcaacaaca    7920
tctgttgcaa ctcacagtct ggggcatcaa gcagctccag gcaagagtcc tggctgtgga    7980
aagataccta agggatcaac agctcctagg gatttggggt tgctctggaa aactcatttg    8040
caccactgct gtgccttgga atgctagttg gagtaataaa tctctggaag acatttggga    8100
taacatgacc tggatgcagt gggaaagaga aattgacaat tacacaaaca caatatacac    8160
cttacttgaa gaatcgcaga accaacaaga aaagaatgaa caagaattat tagaattgga    8220
taagtgggca agtttgtgga attggtttag cataacaaac tggctgtggt atataaagat    8280
```

-continued

```
attcataatg atagtaggag gcttggtagg tttaagaata gttttgctg tgctttctat        8340 agtgaataga gttaggcagg gatactcacc attgtcattt cagacccgcc tcccagtccc        8400
gaggggaccc gacaggcccg acggaatcga agaagaaggt ggagagagag acagagacag        8460
atccgttcga ttagtggatg gattcttagc acttatctgg gaagatctgc ggagcctgtg        8520
cctcttcagc taccgccgct tgagagactt actcttgatt gcagcgagga ctgtggaaat        8580 tctgggcac aggggtggg aagccctcaa atattggtgg agtctcctgc agtattggat         8640
tcaggaacta agaatagtg ctgttagctg gctcaacgcc acagctatag cagtaactga         8700
ggggacagat agggttatag aagtagcaca aagagcttat agagctattc tccacataca        8760
tagaagaatt agacagggct tggaaaggct tttgctataa gatgggtggc aagtggtcaa        8820
aacgtagtat gggtggatgg tctgctataa gggaaagaat gagacgagct gagccacgag        8880
ctgagccagc agcagatggg gtgggagcag tatctcgaga cctggaaaaa catggagcaa        8940
tcacaagtag caatacagca gctactaatg ctgattgtgc ctggctagaa gcacaagagg        9000
aggaagaggt gggttttcca gtcagacctc aggtaccttt aagaccaatg acttacaagg        9060
cagctttaga tattagccac ttttaaaag aaaggggg actggaaggg ctaatttggt           9120
cccaaagaag acaagagatc cttgatctgt ggatctacca cacacaaggc tacttccctg        9180
attggcagaa ttacacacca gggcaggga tcagatatcc actgaccttt ggatggtgct         9240
tcaagctagt accagttgag ccagagaagg tagaagaggc caatgaagga gagaacaaca        9300
gcttgttaca ccctatgagc ctgcatggga tggaggacgc ggagaaagaa gtgttagtgt        9360
ggaggtttga cagcaaacta gcatttcatc acatggcccg agagctgcat ccggagtact        9420
acaaagactg ctgacatcga gctttctaca agggactttc cgctggggac tttccaggga        9480
ggcgtggcct gggcgggact ggggagtggc gtccctcaga tgctgcatat aagcagctgc        9540
tttttgcctg tactgggtct ctctggttag accagatctg agcctgggag ctctctggct        9600
aactagggaa cccactgctt aagcctcaat aaagcttgcc ttgagtgctt caagtagtgt        9660
gtgcccgtct gttgtgtgac tctggtaact agagatccct cagacccttt tagtcagtgt        9720
ggaaaaatct ctagcag                                                       9737
```

<210> SEQ ID NO 13
<211> LENGTH: 492
<212> TYPE: DNA
<213> ORGANISM: HGH(Human Growth Hormone)

<400> SEQUENCE: 13

```
atggctacag gctcccggac gtccctgctc ctggcttttg cctgctctg cctgccctgg          60 cttcaagagg gcagtgcctt cccaaccatt cccttatcca ggcttttga caacgctatg         120 ctccgcgccc atcgtctgca ccagctggcc tttgacacct accaggagtt tgaagaagcc        180
tatatcccaa aggaacagaa gtattcattc ctgcagaacc cccagacctc cctctgtttc        240
tcagagtcta ttccgacacc ctccaacagg gaggaaacac aacagaaatc caacctagag        300
ctgctccgca tctccctgct gctcatccag tcgtggctgg agcccgtgca gttcctcagg        360
agtgtcttcg ccaacagcct ggtgtacggc gcctctgaca gcaacgtcta tgacctccta        420
aaggacctag aggaaggcat ccaaacgctg atggggaggc tggaagatgg cagccccgg         480 actgggcaga tc                                                            492
```